United States Patent
Hasty et al.

(10) Patent No.: US 11,896,626 B2
(45) Date of Patent: Feb. 13, 2024

(54) MULTISTRAIN POPULATION CONTROL SYSTEMS AND METHODS

(71) Applicant: The Regents of the University of California, Oakland, CA (US)

(72) Inventors: Jeff Hasty, Encinitas, CA (US); Michael Julius Liao, San Diego, CA (US); Muhammad Omar Din, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 289 days.

(21) Appl. No.: 16/972,405

(22) PCT Filed: Jun. 7, 2019

(86) PCT No.: PCT/US2019/036179
§ 371 (c)(1),
(2) Date: Dec. 4, 2020

(87) PCT Pub. No.: WO2019/237083
PCT Pub. Date: Dec. 12, 2019

(65) Prior Publication Data
US 2021/0169941 A1 Jun. 10, 2021

Related U.S. Application Data

(60) Provisional application No. 62/682,755, filed on Jun. 8, 2018.

(51) Int. Cl.
*A61K 35/74* (2015.01)
*C07K 14/245* (2006.01)
*C12N 1/20* (2006.01)
*A61K 35/00* (2006.01)

(52) U.S. Cl.
CPC ............ *A61K 35/74* (2013.01); *C07K 14/245* (2013.01); *C12N 1/20* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 5,196,318 A | 3/1993 | Baldwin | |
| 8,293,478 B2* | 10/2012 | Souno | C12Q 1/025 435/6.15 |
| 9,593,339 B1 | 3/2017 | Bermudes | |
| 11,174,486 B2 | 11/2021 | Hasty et al. | |
| 11,613,758 B2 | 3/2023 | Hasty et al. | |
| 2004/0180829 A1* | 9/2004 | Bassler | A61K 31/00 514/2.7 |
| 2008/0286310 A1* | 11/2008 | Zhu | C12N 1/36 424/257.1 |
| 2010/0104607 A1 | 4/2010 | Engelberg-Kulka et al. | |
| 2010/0217282 A1 | 8/2010 | Cabrera et al. | |
| 2011/0217282 A1 | 9/2011 | Inouye et al. | |
| 2012/0069914 A1 | 3/2012 | Shental et al. | |
| 2013/0023035 A1 | 1/2013 | Bielinski et al. | |
| 2013/0052164 A1 | 2/2013 | Chang et al. | |
| 2013/0209405 A1 | 8/2013 | Curtiss | |
| 2015/0209393 A1 | 7/2015 | Chang et al. | |
| 2017/0037363 A1 | 2/2017 | Whitlock et al. | |
| 2018/0148729 A1 | 5/2018 | Hasty | |
| 2021/0284953 A1 | 9/2021 | Hasty et al. | |
| 2022/0251579 A1 | 8/2022 | Hasty et al. | |
| 2023/0044530 A1 | 2/2023 | Hasty et al. | |
| 2023/0126966 A1 | 4/2023 | Hasty et al. | |

FOREIGN PATENT DOCUMENTS

| | | |
|---|---|---|
| CN | 201362719 | 12/2009 |
| CN | 103635571 | 3/2014 |
| CN | 104131018 | 11/2014 |
| EP | 2182068 | 5/2010 |
| JP | 2008519002 | 6/2008 |
| KR | 20160000979 | 1/2016 |
| WO | WO 2013/003597 | 1/2013 |
| WO | WO 2014/043593 | 3/2014 |
| WO | WO 2014/046593 | 3/2014 |
| WO | WO 2014/098767 | 6/2014 |
| WO | WO 2016/164636 | 10/2016 |
| WO | WO 2017/203533 | 11/2017 |
| WO | WO 2018/213815 | 11/2018 |

OTHER PUBLICATIONS

Borek et al., "Turing patterning using gene circuits with gas-induced degradation of quorum sensing molecules," PloS one, May 5, 2016, 11(5):e0153679, 13 pages.
Newcombe, "Origin of bacterial variant," Nature, Jul. 1949, 164(4160):150-151.
Andersen et al., "New unstable Variants of Green Fluorescent Protein for Studies of Transient Gene Expression in Bacteria," Appl. Environ. Microbiol., Jun. 1, 1998, 64(6):2240-2246.
Baban et al., "Bacteria as vectors for gene therapy of cancer," Bioengineered bugs, Nov. 1, 2010, 1(6):385-394.
Begley et al., "Raise standards for preclinical cancer research," Nature, Mar. 2012, 4839(7391):531-533.
Bernardes et al., "Engineering of bacterial strains and their products for cancer therapy," Applied microbiology and biotechnology, Jun. 2013, 97(12):5189-5199.
Buchler et al., "Molecular titration and ultrasensitivity in regulatory networks," Journal of molecular biology, Dec. 31, 2008, 384(5):1106-1119.

(Continued)

*Primary Examiner* — Blaine Lankford
(74) *Attorney, Agent, or Firm* — Fish & Richardson P.C.

(57) ABSTRACT

Provided herein are multi-strain population control systems, methods, kits, and compositions. Also provided are methods, systems, kits, and compositions for culturing bacterial cells in multi-strain ecosystems, and temporally arranged multi-strain ecosystems or cultures using a synchronized lysis circuit in combination with multiple toxin/antitoxin systems to cycle continuously over a long period of time.

16 Claims, 51 Drawing Sheets

(56) References Cited

OTHER PUBLICATIONS

Burger et al., "Abduction and asylum in the lives of transcription factors," Proceedings of the National Academy of Sciences, Mar. 2, 2010, 107(9):4016-4021.
Cann et al., "Dr William Coley and Tumour Regression: A Place in History or in the Future," Postgraduate medical journal, Dec. 1, 2003, 79(938):672-680.
Chen et al., "Application of a Proapoptotic Peptide to Intratumorally Spreading Cancer Therapy Intratumorally Spreading Tumor Therapy," Cancer research, Feb. 15, 2013, 73(4):1352-1361.
Cheong et al., "A bacterial protein enhances the release and efficacy of liposomal cancer drugs," Science, Nov. 24, 2006, 314(5803):1308-1311.
Chlebina et al., "Continuous protein production and release via oscillatory suicidal lysis circuits," Dissertation Thesis, Department of Biomedical Engineering, Duke University, Published 2012, 50 pages.
Cho et al., "The human microbiome: at the interface of health and disease," Nature Reviews Genetics, Apr. 2012, 13(4):260-270.
Coley, "The Treatment of Inoperable Sarcoma by Bacterial Toxins (the mixed toxins of the *Streptococcus erysipelas* and the Bacillus prodigiosus)," Proceedings of the Royal Society of Medicine, Jun. 1910, (Surg_Sect): 48 pages.
Cookson et al., "Queueing up for enzymatic processing: correlated signaling through coupled degradation," Molecular systems biology, 2011, 7(1): 9 pages.
Cummins et al., "Bacteria and tumours: causative agents or opportunistic inhabitants?," Infectious agents and cancer, Dec. 2013, 8(1):1-8.
Dai et al., "Construction of an inducible cell-communication system that amplifies *Salmonella* gene expression in tumor tissue," Biotechnology and Bioengineering, Jun. 2013, 110(6):1769-1781.
Dang et al., "Combination bacteriolytic therapy for the treatment of experimental tumors," Proceedings of the National Academy of Sciences, Dec. 18, 2001, 98(26):15155-15160.
Danino et al., "Measuring Growth and Gene Expression Dynamics of Tumor-Targeted S. Typhimurium Bacteria," Jo VE (Journal of Visualized Experiments), Jul. 6, 2013, 6(77):e50540, 7 pages.
Danino et al., In vivo gene expression dynamics of tumor targeted bacteria, ACS synthetic biology, Oct. 19, 2012, 1(10):465-470.
Davila et al., "Efficacy and Toxicity Management of 1 9-28z CAR T Cell Therapy in B Cell Acute Lymphoblastic Leukemia." Science Translational Medicine, Feb. 19, 2014, 6(224): 23 pages.
De Boer et al., "The Tac Promoter: A Functional Hybrid Derived from the TRP and LAC Promoters," Proceedings of the National Academy of Sciences, Jan. 1983, 80(1):21-25.
Del Vecchio et al., "Modular Cell Biology• Retroactivity and Insulation," Molecular systems biology, 2008, 4(1): 16 pages.
Derman et al., "Phylogenetic analysis identifies many uncharacterized actin-like proteins (Alps) in bacteria: regulated polymerization, dynamic instability and treadmilling in Alp7A," Molecular microbiology, Aug. 2009, 73(4):534-552.
Extended European Search Report in U.S. Appl. No. 16/777,310, dated Oct. 17, 2018, 13 pages.
Ferry et al., "Microfluidics for Synthetic Bioiogy from Design to Execution.", Methods Enzymol, 2011, 497: 295-372.
Folcher et al., "Synthetic biology advancing clinical applications," Current opinion in chemical biology, Aug. 1, 2012, 16(3-4):345-354.
Forbes, Engineering the perfect (bacterial) cancer therapy, Nature Reviews Cancer, Nov. 2010, 10(11):785-794.
Fredriksson et al., "Decline in ribosomal fidelity contributes to the accumulation and stabilization of the master stress response regulator σS upon carbon starvation," Genes & development, Apr. 2007, 21(7):862-874.
Garrett et al., "Cancer and the Microbiota," Science, Apr. 3, 2015, 348(6230):80-86.

Goldbeter et al., An Amplified Sensitivity Arising from Covalent Modification in Biological Systems, Proceedings of the National Academy of Sciences, Nov. 1981, 78(11):6840-6844.
Griffith et al., "Inducible protein degradation in Bacillus subtilis using heterologous peptide tags and adaptor proteins to target substrates to the protease C1lpx'P," Molecular microbiology, Nov. 2008, 70(4):1012-1025.
Grunberg et al., "Strategies for protein synthetic biology," Nucleic acids research, May 1, 2010, 38(8):2663-2675.
Higashikuni et al., "Advancing therapeutic applications of synthetic gene circuits," Current opinion in biotechnology, Oct. 1, 2017, 47:133-141.
Hohmann et al., "Evaluation of a Phop/Phoq-Deleted, Aroa-Deleted Live Oral *Salmonella typhi* Vaccine Strain in Human Volunteers," Vaccine, Jan. 1, 1996, 14(1):19-24.
Hooshangi et al., "Ultrasensitivity and Noise Propagation in a Synthetic Transcriptional Cascade," Proceedings of the National Academy of Sciences, Mar. 8, 2005, 102(10):3581-3586.
International Preliminary Report on Patentability in International Application No. PCT/US2016/26518, dated Oct. 10, 2017, 7 pages.
International Search Report and Written Opinion in International Application No. PCT/US2016/26518, dated Apr. 7, 2016, 9 pages.
International Search Report and Written Opinion in International Appln. PCT/US2020/064525, dated Mar. 10, 2021, 18 pages.
International Preliminary Report on Patentability in International Appln. No. PCT/US2020/064525, dated Jun. 23, 2022 7 pages.
Isaacs et al., "Prediction and measurement of an autoregulatory genetic module," PNAS, 2003, 100(13):7714-7719.
Jeong et al., "Anti-Tumoral Effect of the Mitochondrial Target Domain of Noxa Delivered by an Engineered *Salmonella typhimurium*," PloS one, Jan. 8, 2014, 9(1):e80050, 11 pages.
Jiang et al., "Inhibition of Tumor Growth and Metastasis by a Combination of *Escherichia coli*- mediated Cytolytic Therapy and Radiotherapy," Molecular therapy, Mar. 1, 2010, 18(3):635-642.
June, CH et al., "Engineered t Cells for Cancer Therapy," Cancer Immunology, Immunotherapy, Sep. 2014, 63(9):969-975.
Keiler et al., "Role of a Peptide Tagging System in Degradation of Proteins Synthesized from Damaged Messenger RNA," Science, Feb. 16, 1996, 271(5251):990-993.
Kolnik et al., "Vacuum-Assisted Cell Loading Enables Shear-Free Mammalian Microfluidic Culture," Lab on a chip, 2012,12(22):4732-4737.
Leone V. et al., "Effects of diurnal variation of gut microbes and high-fat feeding on host circadian clock function and metabolism," Cell host & microbe, May 13, 2015, 17(5):681-689.
Lien et al., "Low-Dose Metronomic Chemotherapy: A Systematic Literature Analysis," European Journal of Cancer, Nov. 1, 2013, 49(16):3387-3395.
Loeffler et al., "*Salmonella typhimurium* engineered to produce CCL21 inhibit tumor growth," Cancer immunology, immunotherapy, May 2009, 58(5):769-775.
Loessner et al., "Remote Control of Tumour-Targeted *Salmonella enterica* Serovar Typhimuriurn by the Use of 1-Arabinose as Inducer of Bacterial Gene Expression in vivo," Cellular microbiology, Jun. 2007, 9(6):1529-1537.
Mather et al., "Delay-induced degrade-and-fire oscillations in small genetic circuits," Physical review letters, Feb. 13, 2009, 102(6):068105, 4 pages.
McGinness et al., "Engineering controllable protein degradation," Molecular cell, Jun. 9, 2006, 22(5):701-707.
Meighen, E. A., "Genetics of bacterial bioluminescence", Annual review of genetics, 1994, 28(1):117-139.
Merrikh et al., "A DNA Damage Response in *Escherichia coli* Involving the Alternative Sigma Factor, RpoS," Proceedings of the National Academy of Sciences, Jan. 13, 2009, 106(2):611-616.
Miest et al., "New Viruses for Cancer Therapy: Meeting Clinical Needs," Nature reviews microbiology, Jan. 1, 2014, 12(1):23-34.
Mika, et al., "A Two-Component Phosphotransfer Network Involving ArcB, Arc.A, and RssB Coordinates Synthesis and Proteolysis of crS (RpoS) in *E coli*," Genes & development, Nov. 15, 2005, 19(22):2770-2781.
Moon et al., "Genetic Programs Constructed From Layered Logic Gates in Single Cells," Nature, Nov. 2012, 491(7423):249-253.
Mukherji et al., "MicroRNAs can generate thresholds in target gene expression," Nature genetics, Sep. 2011, 43(9):854-859.

(56) References Cited

OTHER PUBLICATIONS

Muller et al., "Cell-cell communication by quorum sensing and dimension-reduction," Journal of mathematical biology, Oct. 2006, 53(4):672-702.
Nandagopal et al., "Synthetic Biology: Integrated Gene Circuits," Science, Sep. 2, 2011, 333(6047): 6 pages.
Nguyen et al., Genetically Engineered *Salmonella* Typhirnurium as an Imageable Therapeutic Probe for Cancer, Cancer research, Jan. 1, 2010, 70(1):18-23.
O'Shea, CC., "Viruses Seeking and Destroying the Tumor Program," Oncogene, Nov. 2005, 24(52):7640-7655.
Parsek et al., "Acyl-homoserine lactone quorum sensing in gram-negative bacteria: a signaling mechanism involved in associations with higher organisms, " Proceedings of the National Academy of Sciences, Aug. 1, 2000, 97(16):8789-8793.
Paton et al., "Bioengineered microbes in disease therapy", Trends in molecular medicine, 18, 7, pp. 417-425, 2012.
Pawelek et al., "Tumor-Targeted *Salmonella* as a Novel Anticancer Vector," Cancer research, Oct. 15, 1997, 57(20):4537-4544.
Press, WH in Numerical Recipes: The Art of Scientific Computing 3rd ed. Cambridge Univ. Press), 2007, 1262 pages.
Prindle et al., "Genetic Circuits in *Salmonella typhimurium*," ACS synthetic biology, Oct. 19, 2012, 1(10):458-464.
Prindle et al., "Rapid and Tunable Post-Translational Coupling of Genetic Circuits," Nature, Apr. 2014, 508(7496):387-391.
Pruteanu et al., "The Cellular Level of the Recognition Factor RssB is Transduction in aS Turnover in scherichia coli," Molecular microbiology, Sep. 2002, 45(6):1701-1713.
Purcell et al., "Temperature Dependence of Ssra-Tag Mediated Protein Degradation," Journal of biological engineering, Dec. 2012, 6(1):1-3.
Riedel et al., "Construction of p16slux, a novel vector for improved bioluminescent labeling of gram-negative bacteria," Applied and environmental microbiology, Nov. 1, 2007, 73(21):7092-7095.
Roberts et al., "Intratumornl injection of Clostridium novyi-NT spores induces antitumor responses," Science translational medicine, Aug. 13, 2014, 6(249): 12 pages.
Rosenfeld et al., "Response Delays and the Structure of Transcription Networks," Journal of molecular biology, Jun. 13, 2003, 329(4):645-654.
Ryan et al., "Bacterial Delivery of a Novel Cytolysin to Hypoxic Areas of Solid Tumors," Gene Therapy, Mar. 2009, 16(3):329-339.
Sausville et al., "Contributions of human tumor xenografts to anticancer drug development," Cancer research, Apr. 1, 2006, 66(7):3351-3354.
Schaefer et al., "A New Class of Homoserine Lactone Quorum-Sensing Signals," Nature, Jul. 2008, 454(7204):595-599.
Shaked et al., "Low-Dose Metronomic Combined With Intermittent Bolus-Dose Cydophosphamide is an Effective Long-Term Chemotherapy Treatment Strategy," Cancer research, Aug. 15, 2005, 65(16):7045-7051.
Stecher et al., "Flagella and Chemotaxis are Required for Efficient Induction of *Salmonella enterica* Serovar *Typhimurium* Colitis in Streptomycin-Pretreated Mice," Infection and immunity, Jul. 2004, 72(7):4138-4150.
Stricker et al., "A Fast, Robust and Tunable Synthetic Gene oscillator," Nature, Nov. 2008, 456(7221):516-519.
Strogatz S., "Nonlinear Dynamics and Chaos: with Applications to Physics, Biology, Chemistry and Engineering" (Perseus Books), 2001, 505 pages.
Swofford et al., "Quorum-sensing *Salmonella* Selectively Trigger Protein Expression within Tumors," Proceedings of the National Academy of Sciences, Match 17, 2015, 112(11):3457-3462.
Thaiss et al., "Chronobiomics: The biological clock as a new principle in host-microbial interactions," PLoS pathogens, Oct. 8, 2015, 11(10):e1005113, 5 pages.
Thakur et al., "Modelling Vemurafenib Resistance in Melanoma Reveals a Strategy to Forestall Drug Resistance", Nature, 494, pp. 251-255, 2013.

Tigges et al., "A Tunable Synthetic Mammalian Oscillator," Nature, Jan. 2009, 457(7227):309-312.
Unger et al., "Monolithic Microfabricated Valves and Pumps by Multilayer Soft Lithography," Science, Apr. 7, 2000, 288(5463):113-116.
Waters et al., "Quorum Sensing: Cell-to-Cell Communication in Bacteria," Annual review of cell and developmental biology, Nov. 10, 2005, 21(1): 32 pages.
Weber et al.,"Emerging Biomedical Applications of Synthetic Biology," Nature Reviews Genetics, Jan. 2012, 13(1):21-35.
Wood et al., "Enhanced Plasmid Stability Through Post-Segregational Killing of Plasmid-Free cells," Biotechnology techniques, Jan. 1990, 4(1):39-44.
Xie et al., "Multi-input RNAi-based Logic Circuit for Identification of Specific Cancer Cells," Science, Sep. 2, 2011, 333(6047): 7 pages.
Xuan et al., "Microbial Dysbiosis is Associated with Human Breast Cancer," PloS one, Jan. 8, 2014, 9(1):e83744, 7 pages.
Young et al., "Lytic Action of Cloned Phi x174 Gene e," Journal of virology, Dec. 1982, 44(3):993-1002.
Anderson et al. "Environmentally controlled invasion of cancer cells by engineered bacteria," J Mol Biol, 2005, 355(4):619-627.
Balagadde et al., "Long-term monitoring of bacteria undergoing programmed population control in a microchemostat," Science, Jul. 1, 2005, 309(5731):137-140.
Balagadde, F. K. et al., "A synthetic *Escherichia coli* predator-prey ecosystem," Molecular systems biology, 2008, 4:187.
Bittihn et al., "Suppression of beneficial mutations in dynamic microbial populations," Physical Review Letters, 2017, 118:028102.
Boyer et al., "Characterization of the cvaaand cvi promoters of the colicin v export system: Iron-dependent transcription of cvaa is modulated by downstream sequences," Journal of bacteriology, Apr. 1, 1998, 180(7):1662-1672.
Brenner et al., "Engineered bidirectional communication mediates a consensus in a microbial biofilm consortium," Proceedings of the National Academy of Sciences, Oct. 30, 2007, 104(44):17300-17304.
Brenner et al., "Engineering microbial consortia: a new frontier in synthetic biology," Trends in biotechnology, Sep. 1, 2008, 26(9):483-489.
Cascales et al., "Colicin biology," Microbiology and molecular biology reviews, Mar. 1, 2007, 71(1):158-229.
Chen et al., "Emergent genetic oscillations in a synthetic microbial consortium," Science, 2015, 349(6251):986-989.
Chen, "Development and application of co-culture for ethanol production by cofermentation of glucose and xylose: a systematic review," Journal of industrial microbiology & biotechnology, 2011, 38:581-597.
Danino et al., "A synchronized quorum of genetic clocks," Nature, 2010, 463:326-330.
Danino, T. et al., "Programmable probiotics for detection of cancer in urine," Science translational medicine, 2015, 7:289ra84-289ra84.
De Roy et al., "Synthetic microbial ecosystems: an exciting tool to understand and apply microbial communities," Environmental microbiology, Jun. 2014, 16(6):1472-1481.
De Roy et al., "Environmental conditions and community evenness determine the outcome of biological invasion," Nature communications, Jan. 22, 2013, 4(1):1-5.
Dejonghe et al., "Synergistic degradation oflinuron by a bacterial consortium and isolation of a single linuron-degrading variovorax strain," Applied and Environmental Microbiology, 2003, 69(3):1532-1541.
Din et al., "Synchronized cycles of bacterial lysis for in vivo delivery," Nature, Aug. 2016, 536(7614): 12 Pages.
Elowitz et al., "A synthetic oscillatory network of transcriptional regulators," Nature, Jan. 2000, 403(6767):335-338.
Endy et al., "Foundations for engineering biology," Nature, Nov. 2005, 438(7067):449-453.
Faust et al., "Microbial interactions: from networks to models," Nature Reviews Microbiology, 2012, 10:538-550.
Fischbach et al., "Cell-based therapeutics: the next pillar of medicine," Science translational medicine, Apr. 3, 2013, 5(179):179ps7, 7 Pages.

(56) References Cited

OTHER PUBLICATIONS

Foster et al., "Competition, not cooperation, dominates interactions among culturable microbial species," Current biology, 2012, 22(19):1845-1850.
Fulget et al., "Melissa: global control strategy of the artificial ecosystem by using first principles models of the compartments," Advances in Space Research, 1999, 24(3):397-405.
Gardner et al., "Construction of a genetic toggle switch in *Escherichia coli*," Nature, Jan. 2000, 403(6767):339-342.
Gerdes et al.,"The parB (hok/sok) locus of plasmid R1: a general purpose plasmid stabilization system," Bio/Technology, Dec. 1988, 6(12):1402-1405.
Gravel et al., "Experimental niche evolution alters the strength of the diversity-productivity relationship," Nature, Jan. 2011, 469(7328):89-92.
Großkopf et al., "Synthetic microbial communities," Current opinion in microbiology, Apr. 1, 2014, 18:72-77.
Hasty et al., "Engineered gene circuits," Nature, Nov. 2002, 420(6912):224-230.
Kaur et al., "Bacteriocins as potential anticancer agents," Frontiers in pharmacology, Nov. 10, 2015, 6: 11 Pages.
Kerr et al., "Local dispersal promotes biodiversity in a real-life game of rock-paper-scissors," Nature, Jul. 2002, 418(6894):171-174.
Kirkup et al., "Antibiotic-mediated antagonism leads to a bacterial game of rock-paper-scissors in vivo," Nature, Mar. 1, 2004, 428(6981):412-414.
Klitgord et al., "Environments that induce synthetic microbial ecosystems," PLoS Comput Biol., Nov. 18, 2010, 6(11):e1001002, 17 Pages.
Little et al., "Rules of engagement: interspecies interactions that regulate microbial communities," Annu. Rev. Microbiol., Oct. 13, 2008, 62: 29 Pages.
Lutz et al., "Independent and tight regulation of transcriptional units in *Escherichia coli* via the lacr/o, the tetr/o and arac/il-i2 regulatory elements," Nucleic acids research, 1997, 25(6):1203-1210.
Lynd et al., "How biotech can transform biofuels," Nature biotechnology, Feb. 2008, 26(2):169-172.
Mandell et al., "Biocontainment of genetically modified organisms by synthetic protein design," Nature, Feb. 2015, 518(7537): 20 Pages.
Marguet et al., "Oscillations by minimal bacterial suicide circuits reveal hidden facets of host-circuit physiology," PloS one, 2010, 5(7):e11909.
Mather et al., "Streaming instability in growing cell populations," Physical review letters, 2010, 104(20):208101.
Mondragno-Palomino et al. "Entrainment of a population of synthetic genetic oscillators," Science, 2011, 333(6047):1315-1319.
Ostrov et al., "Design, synthesis, and testing toward a 57-codon genome," Science, Aug. 19, 2016, 353(6301): 5 Pages.
PCT International Preliminary Report on Patentability in International Appln. No. PCT/US2018/033555, dated Feb. 25, 2020, 7 pages.
PCT International Preliminary Report on Patentability in International Appln. No. PCT/US2019/036179, dated Dec. 17, 2020 8 Pages.
PCT International Search Report and Written Opinion in Appln. No. PCT/US/2018/033555, dated Aug. 13, 2018, 10 pages.
PCT International Search Report and Written Opinion in International Appln. PCT/US2019/036179, dated Sep. 23, 2019, 14 Pages.
Pedelacq et al., "Engineering and characterization of a superfolder green fluorescent protein," Nature biotechnology, 2006, 2(1)4:79-88.
Peredelchuk et al., "A method for construction of *E. coli* strains with multiple DNA insertions in the chromosome," Gene, Mar. 18, 1997, 187(2):231-238.
Petrof et al., "Stool substitute transplant therapy for the eradication of clostridium difficile infection:"repoopulating" the gut," Microbiome, 2013, 1:3.

Prindle et al., "A sensing array of radically coupled genetic 'biopixels'," Nature, Jan. 2012, 481(7379):39-44.
Purnick et al., "The second wave of synthetic biology: from modules to systems," Nature reviews Molecular cell biology, Jun. 2009, 10(6):410-422.
Quan et al., "Circular polymerase extension cloning of complex gene libraries and pathways," PloS one, 2009, 4(7):e6441.
Renda et al., "Engineering reduced evolutionary potential for synthetic biology," Molecular BioSystems, 2014, 10:1668-1678.
Riglar et al., "Engineering bacteria for diagnostic and therapeutic applications," Nature Reviews Microbiology, Apr. 2018, 16(4): 12 Pages.
Rovner et al., "Recoded organisms engineered to depend on synthetic amino acids," Nature, Feb. 2015, 518(7537): 17 Pages.
Ruder et al., Synthetic biology moving into the clinic, Science, Sep. 2, 2011, 333(6047):1248-1252.
Scott et al. "A stabilized microbial ecosystem of self-limiting bacteria using synthetic quorum-regulated lysis," Nat Microbiol, 2017, 2(17083):1-9.
Scott et al., "Quorum sensing communication modules for microbial consortia," ACS synthetic biology, 2016, 5(9):969-977.
Scott, "Communication and Coexistence: Engineering Tools for Synthetic Microbial Ecosystems," Thesis, University of California, San Diego, Jan. 1, 2016, pp. 1-102.
Segall-Shapiro et al., "Engineered promoters enable constant gene expression at any copy number in bacteria," Nature biotechnology, Apr. 2018, 36(4): 11 Pages.
Shong et al., "Towards synthetic microbial consortia for bioprocessing," Current Opinion in Biotechnology, Oct. 1, 2012, 23(5):798-802.
Shou et al., "Synthetic cooperation in engineered yeast populations," Proceedings of the National Academy of Sciences, 2007, 104:1877-1882.
Siuti et al., "Synthetic circuits integrating logic and memory in living cells," Nature biotechnology, May 2013, 31(5): 6 Pages.
Tanouchi et al., "Engineering microbial systems to explore ecological and evolutionary dynamics," Current opinion in biotechnology, Oct. 1, 2012, 23(5):791-797.
Teixeira et al., "Synthetic biology-inspired therapies for metabolic diseases," Current Opinion in Biotechnology, Oct. 1, 2017, 47:59-66.
Volfson et al., "Biomechanical ordering of dense cell populations," Proceedings of the National Academy of Sciences, 2008, 105(40):15346-15351.
Wang et al., "Programming cells by multiplex genome engineering and accelerated evolution," Nature, Aug. 2009, 460(7257):894-898.
Wintermute et al., "Emergent cooperation in microbial metabolism," Molecular systems biology, 2010, 6(1): 7 Pages.
You et al., "Programmed population control by cell-cell communication and regulated killing," Nature, Apr. 2004, 428(6985): 4 Pages.
Zambrano et al., "Microbial competition: *Escherichia coli* mutants that take over stationary phase cultures," Science, Mar. 19, 1993, 259(5102):1757-1760.
Zemke et al., "Microbiology: Social suicide for a good cause," Current Biology, 2016, 26(2):R80-R82.
Zhou et al., "Distributing a metabolic pathway among a microbial consortium enhances production of natural products," Nature biotechnology, Apr. 2015, 33(4): 9 Pages.
Escholarship.org [online], "Communication and Coexistence: Engineering Tools for Synthetic Microbial Ecosystems," Jan. 2016, retrieved on May 4, 2021, retrieved from URL <https://escholarship.org/uc/item/5qs3q001>, 102 pages.
Extended European Search Report in European Appln. No. 18801861.8, dated May 3, 2021, 8 pages.
Mangwani et al., "Bacterial quorum sensing: functional features and potential applications in biotechnology," Journal of molecular microbiology and biotechnology, 2012, 22(4):215-227.
Extended European Search Report in European Appln. No. 19815732.3, dated Jun. 3, 2022, 11 pages.
Ausländer et al., "Programmable single-cell mammalian biocomputers," Nature, Jul. 2012, 487(7405):123-127.

(56) References Cited

OTHER PUBLICATIONS

Chan et al., "'Deadman'and'Passcode'microbial kill switches for bacterial containment," Nature chemical biology, Feb. 2016, 12(2): 19 Pages.

Landry et al., "Engineering diagnostic and therapeutic gut bacteria. Bugs as Drugs: Therapeutic Microbes for the Prevention and Treatment of Disease," Oct. 20, 2017, 1: 22 pages.

Lee et al., "Next-generation biocontainment systems for engineered organisms," Nature chemical biology, Jun. 2018, 14(6):530-537.

Zhou, "Bacteria synchronized for drug delivery," Nature, Aug. 2016, 536(7614):33-34.

European Search Report and Written Opinion in European Appln. No. 21189319.3, dated Sep. 13, 2022, 10 pages.

\* cited by examiner

| Toxin # | Toxin Type | Immunity Protein | Cytotoxic Activity | OM Receptor | Translocation Proteins |
|---|---|---|---|---|---|
| 1 | Colicin E3 | Im3 | 16s rRNase | BtuB | OmpF/TolQRAB |
| 2 | Colicin E7 | Im7 | DNase | BtuB | OmpF/TolQRAB |
| 3 | Colicin V | Cvi | Disruption of membrane potential | Cir | TonB, ExbB |

Fig. 4

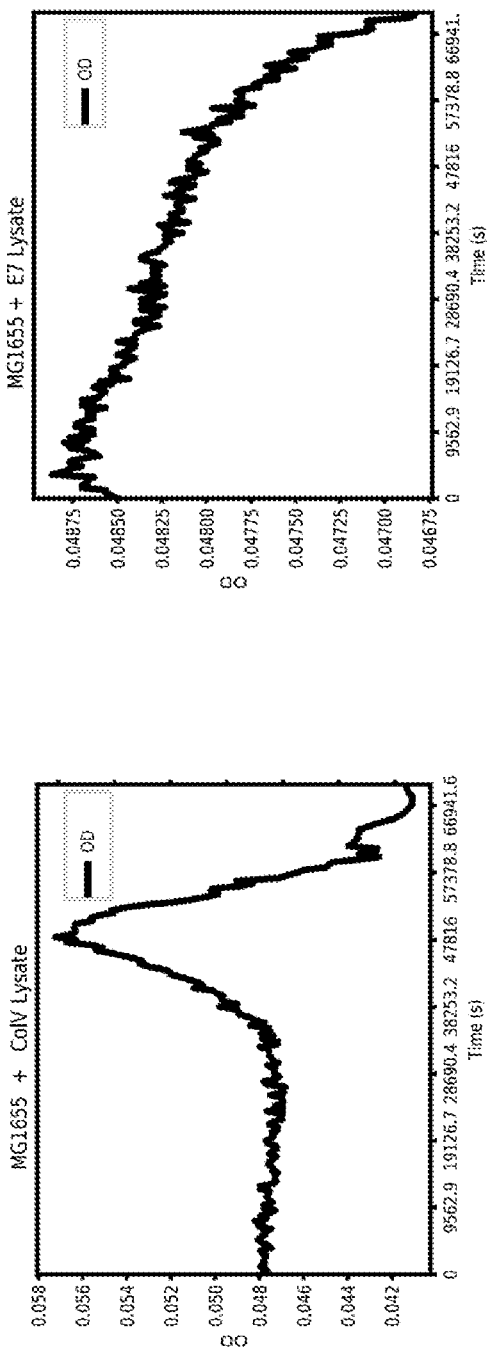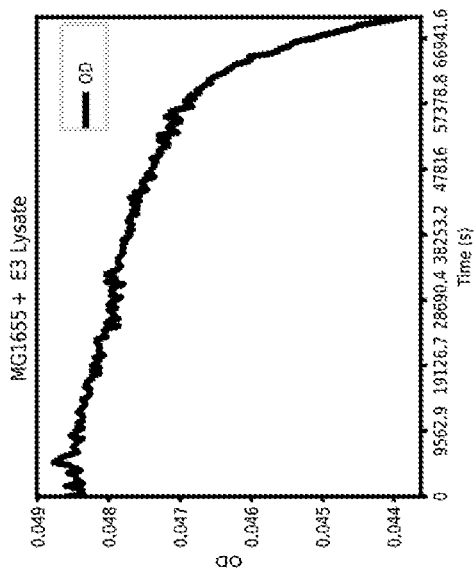
Fig. 5I Fig. 5J Fig. 5K

| Strain Name | Strain # | Host Bacterium | Plasmids | Referenced in Figure |
|---|---|---|---|---|
| MJL004 | A | MG1655 | pML001 - Colicin E3 + E3 immunity + E7 immunity + ColE1 Lysis + sfGFP | 1a, 1b, 1c, 1e |
| MJL006 | B | MG1655 | pML004 - Colicin E7 + E7 immunity + V immunity + ColE1 Lysis + mCherry | 1a, 1b, 1c, 1e |
| MJL035 | C | MG1655 | pML002 - Colicin E7 + E3 immunity + E3 immunity + ColE1 Lysis + mCherry | Supplementary |
| MJL046 | 1 | MG1655 | pML046 - Colicin V + V immunity + E3 immunity + X174E (+LuxR) pTD103 sfGFP luxI (+LAA) | 1e, 2a-d, 2g, 2i, 2j, 3c-e |
| MJL044 | 2 | MG1655 | pML044 - Colicin E3 + E3 immunity + E7 immunity + X174E (+LuxR) pTD103 CFP luxI (+LAA) | 1e, 2a-d, 2h, 2i, 3c-e |
| MJL042 | 3 | MG1655 | pML042 - Colicin E7 + E7 immunity + V immunity + X174E (+LuxR) pTD103 mKate2 luxI (+LAA) | 2a-d, 2f, 2g, 2i, 2j, 3c-e |

Fig. 10

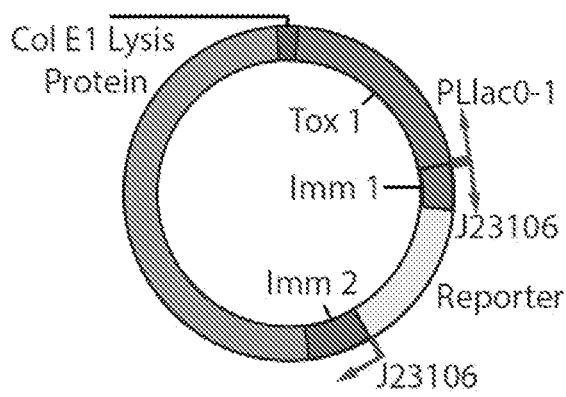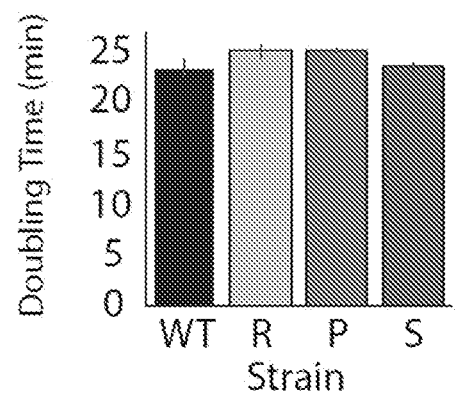
Fig. 12C
Fig. 12D
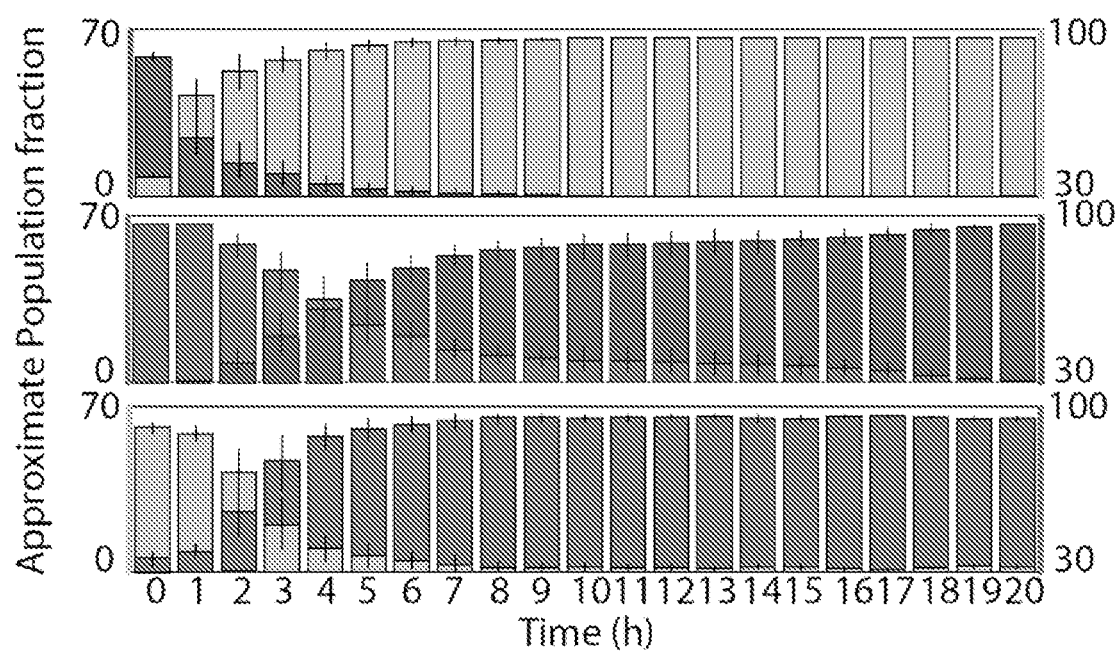
Fig. 12E

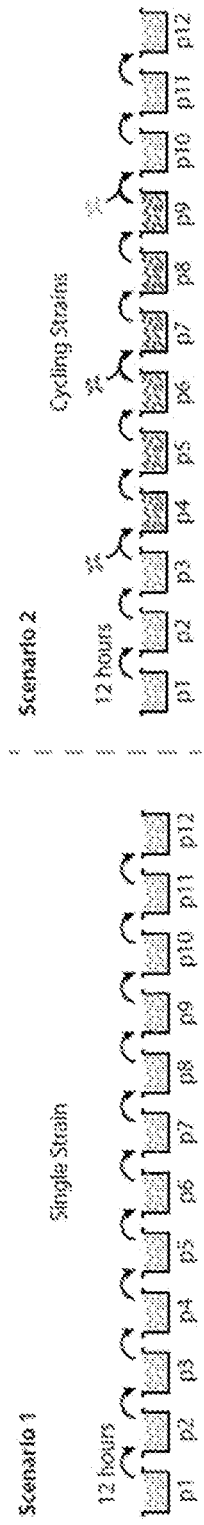
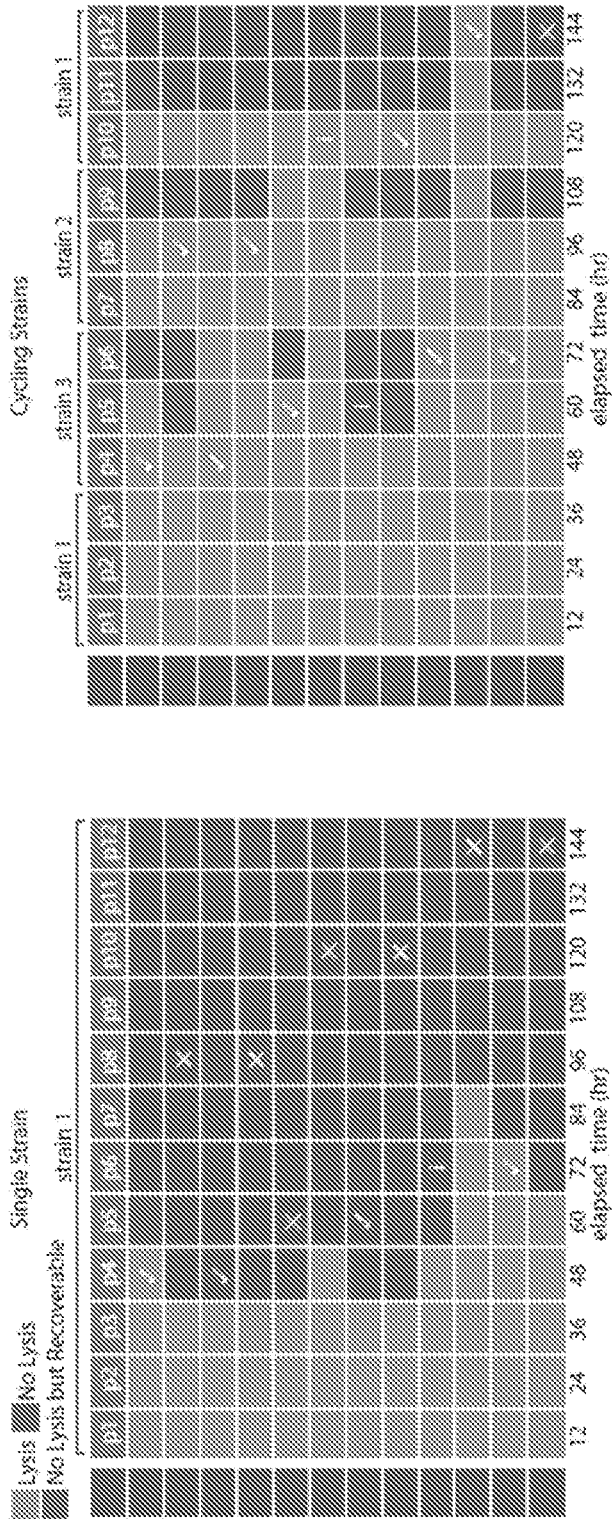
Fig. 15A
Fig. 15B

| Toxin Type | Immunity Protein | Cytotoxic Activity | OM Receptor | Translocation Proteins |
|---|---|---|---|---|
| Colicin E3 | Col E3 Immunity (Im3) | 16s rRNase | BtuB | OmpF/TolQRAB |
| Colicin E7 | Col E3 Immunity (Im7) | DNase | BtuB | OmpF/TolQRAB |
| Colicin V (Cvac) | Col V Immunity (Cvi) | Disruption of membrane potential | Cir | TonB, ExbB |

Fig. 22

| Strain Name | Strain # | Host Bacterium | Plasmids | Referenced in Figure |
|---|---|---|---|---|
| MJL003 | R | MG1655 | pML003 – Colicin E7 + Col E7 Immunity + sfGFP + Col V Immunity + Col E1 Lysis Protein | 1b-f |
| MJL002 | P | MG1655 | pML002 – Colicin E3 + Col E3 Immunity + mKate2 + Col E7 Immunity + Col E1 Lysis Protein | 1b-f |
| MJL107 | S | MG1655 | pML107 – Colicin V + Col V Immunity + CFP + Col E3 Immunity + Col E1 Lysis Protein | 1b-f |
| MJL046 | 1 | MG1655 | pML046 – Colicin V + Col V Immunity + Col E3 Immunity + X174E (+LuxR) pTD103 sfGFP luxI (+LAA) | 2b-h, 3b-d, 4b, S2, S3 |
| MJL044 | 2 | MG1655 | pML044 – Colicin E3 + Col E3 Immunity + Col E7 Immunity + X174E (+LuxR) pTD103 CFP luxI (+LAA) | 2b-h, 3b-d, 4b, S2, S3 |
| MJL042 | 3 | MG1655 | pML042 – Colicin E7 + Col E7 Immunity + Col V Immunity + X174E (+LuxR) pTD103 mKate2 luxI (+LAA) | 2b-h, 3b-d, 4b, S2, S3 |

Fig. 23

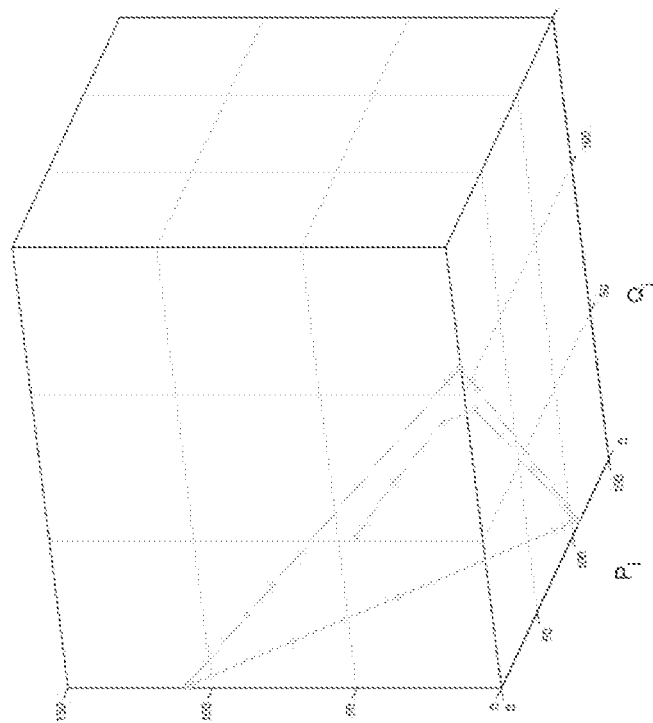
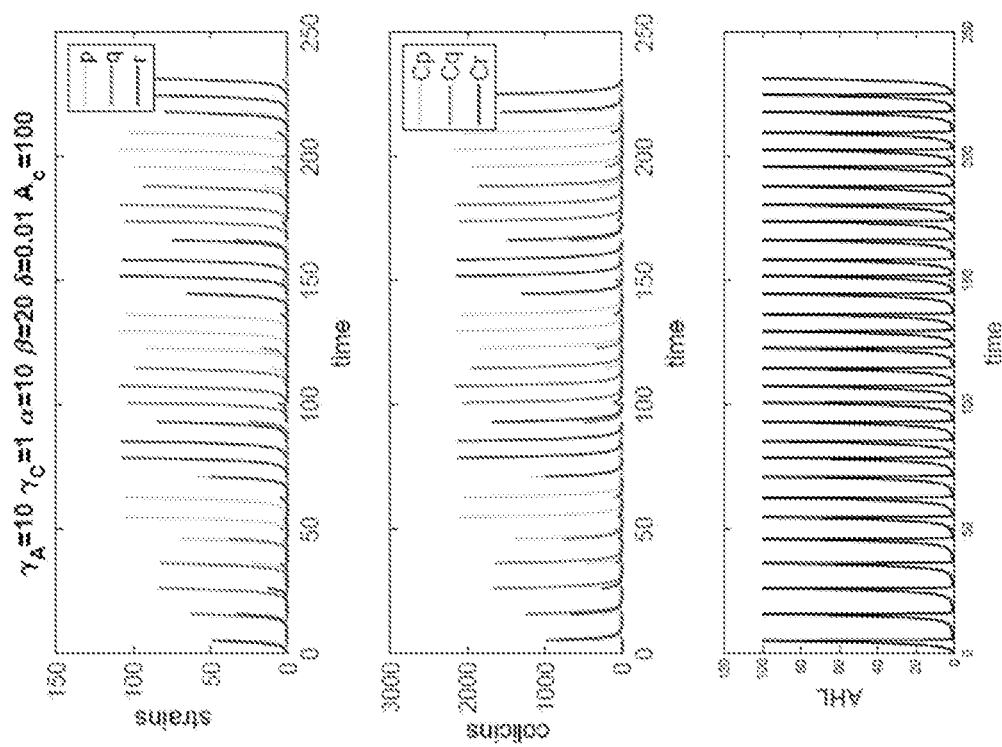
Fig. 26A
Fig. 26B

MULTISTRAIN POPULATION CONTROL SYSTEMS AND METHODS

CLAIM OF PRIORITY

This application is a National Stage Application under 35 U.S.C. 071 and claims the benefit of International Application No. PCT/US2019/036179, filed Jun. 7, 2019, which claims the benefit of U.S. Provisional Patent Application Ser. No. 62/682,755, filed Jun. 8, 2018, the entire contents of which are hereby incorporated by reference.

FEDERALLY SPONSORED RESEARCH OR DEVELOPMENT

This invention was made with Government support under Grant Nos. RO1 GM069811 awarded by the National Institutes of Health. The Government has certain rights in the invention.

TECHNICAL FIELD

This disclosure relates to methods, systems, kits, and compositions for culturing bacterial cells, and more particularly to methods, systems, kits, and compositions for multi-strain ecosystems, including a quorum-regulated multi-lysis system.

BACKGROUND

Microbial ecologists are increasingly turning to small, synthesized ecosystems[1-5] as a reductionist tool to probe the complexity of native microbiomes[6,7]. Concurrently, synthetic biologists have gone from single-cell gene circuits[8-11] to controlling whole populations using intercellular signaling[12-16].

SUMMARY

Without wishing to be bound by theory, the present inventors disclose a tri-lysis or multi-lysis system that can be used to engineer multi-strain ecosystems and/or enable cyclical delivery of one or more payloads, such as therapeutic agents. Each strain can deliver, e.g., a payload of a single therapeutic protein or multiple therapeutic proteins, while excluding previously administered strains, or previously existing strains, in the site of disease. For example, there may be at least three strains that comprise this system, wherein each strain produces a toxin, which kills one of the other two strains, and an antitoxin to protect itself, and the other strains not targeted by the toxin. For example, in an exemplary system comprising strains labeled strain A, strain B, and strain C, strain A can produce a toxin that kills strain B; strain B, in turn, can produce a toxin that kills strain C, and strain C can produce a toxin that kills strain A. More strains can be present in the system, and may or may not participate in the cyclical toxin system. The system is not limited to a three strain system, it can potentially be composed of more than three strains (e.g., 4, 5, 6, 7, 8, 9, 10, 11 or 12 strains), where each strain produces a toxin with the ability to kill another strain in the system which does not have the anti-toxin, thereby allowing a cyclical system (composed of four, five, six, seven, eight, nine, ten, eleven, twelve or more strains). Additionally, it is possible that the system is composed of more than three strains (e.g., 4, 5, 6, 7, 8, 9, 10, 11 or 12 strains), wherein each of at least three of the strains produces a toxin with the ability to kill another strain in the system which does not have the anti-toxin, thereby allowing a cyclical system among at least three of the strains while other strains of the system are not controlled according to the tri-lysis or multi-lysis circuit. In one aspect, such a system can provide specific delivery of a therapeutic agent(s) via engineered strains for a certain amount of time until a subsequent strain in the system is administered, thereby separating the delivery of certain therapeutic agent(s) in space and time, as desired.

In some embodiments, each of the strains can produce a therapeutic protein or a suite of therapeutic proteins, the expression of which can be controlled by a genetic circuit such as a Synchronized Lysis Circuit (SLC). In some embodiments, exemplary SLC's can include those described in International Application No. PCT/US18/33555, which is incorporated herein by reference in its entirety.

In some embodiments, a tri-lysis or multi-lysis system utilizes a well characterized *E. coli* specific toxin-antitoxin system, combined with a Lux AHL quorum sensing lysis circuit, to not only provide self-limiting control of bacterial population size, but also enable the precise removal of unwanted strains in a cyclic "rock paper scissors" fashion that enables long term continuous culture. A tri-lysis or multi-lysis system ensures specific delivery of a therapeutic protein(s) via engineered strains for a certain amount of time until a subsequent strain in the system is administered, thereby separating the delivery of certain therapeutic protein(s) in space and time. A tri-lysis or multi-lysis system may also be engineered to output specific profiles of therapeutic proteins to the disease site.

In another aspect, the tri-lysis or multi-lysis system can also be applicable to engineering 'division of labor' ecosystems where multiple strains may metabolize or produce certain intermediates with the goal of synthesizing a commercially valuable compound. Additional similar applications the tri-lysis or multi-lysis system can include remediation and sensing applications.

Additionally, the use of the tri-lysis or multi-lysis system as a method to ensure circuit stability is not necessarily limited to therapeutic applications, it may be applicable to any application where the stability of engineered genetic constructs in bacteria are necessary.

Provided herein are methods of maintaining a co-culture by quorum sensing that include: co-culturing at least three (e.g., 3, 4, 5, 6, 7, 8, 9, 10) bacterial strains at certain ratios (e.g., 1:1:1) during a period of time; wherein each of the at least three bacterial strains comprises a lysis plasmid and an activator plasmid.

Also provided herein are methods of maintaining a co-culture by quorum sensing that include: co-culturing at least three (e.g., 3, 4, 5, 6, 7, 8, 9, 10) bacterial strains at certain ratios (e.g., 1:1:1) during a period of time; wherein each of the at least three bacterial strains comprises a toxin system.

Also provided herein are methods of maintaining a co-culture that include: co-culturing at least three (e.g., 3, 4, 5, 6, 7, 8, 9, 10) bacterial strains at certain ratios (e.g., 1:1:1) during a period of time; wherein each of the at least three bacterial strains comprises a toxin system.

In some embodiments, the at least three bacterial strains are *E. coli, S. typhimurium*, or a bacterial variant thereof. In some embodiments, the at least three bacterial strains are Gram-negative bacterial strains, e.g., a *Salmonella* strain, an *Acetobacter* strain, an *Enterobacter* strain, a *Fusobacterium* strain, a *Helicobacter* strain, a *Klebsiella* strain, or an *E. coli* strain. In some embodiments, the at least three bacterial strains are Gram-positive bacterial strains, e.g., a *Actinomyces* strain, a *Bacillus* strain, a *Clostridium* strain, an *Entero-* coccus strain, or a *Lactobacillus* strain. In some embodiments, the at least three bacterial strains are all Gram negative bacterial strains or all Gram positive strains. In some embodiments, at least one of the at least three bacterial strains is a Gram negative bacterial strain. In some embodiments, at least one of the at least three bacterial strains is a Gram positive bacterial strain.

In some embodiments, the lysis plasmid comprises a lysis gene, an activatable promoter, and optionally a reporter gene; and the activator plasmid comprises an activator gene, a degradation tag, and optionally a reporter gene. In some embodiments, the lysis gene is E from a bacteriophage ΦX174. In some embodiments, the activatable promoter is a LuxR-N-acyl homoserine lactone (AHL) activatable luxI promoter and the activator gene is a LuxI. In some embodiments, the activatable promoter is a RpaR-N-acyl homoserine lactone (AHL) activatable RpaI promoter and the activator gene is a RpaI. In some embodiments, the reporter gene is green fluorescent protein (GFP), cyan fluorescent protein (CFP), red fluorescent protein (RFP) or a variant thereof. In some embodiments, the degradation tag is an ssrA-LAA degradation tag. In some embodiments, each of the at least three bacterial stains comprises the lysis plasmid and the activator plasmid. In some embodiments, each of the at least three bacterial strains comprises a different reporter gene.

In some embodiments, the co-culture is inoculated at a ratio of 1:1:1. In some embodiments one or more bacterial strains can be co-cultured. In some embodiments, the co-culture is inoculated at certain ratios (e.g., 1:1, 1:5, 1:10, 1:1:1, 1:5:1, and the like) based on the strains used, the desired characteristics of the system, the outcome goals, and the like. In some embodiments, one or more strain in a system may have a growth advantage over one or more other strains in the system.

In some embodiments, the plasmid is integrated into a genome of the at least one of the at least three bacterial strains.

In some embodiments, the co-culturing occurs in a microfluidic device. In some embodiments, the co-culturing occurs in a cell culture vessel (e.g., a cell culture plate, a bioreactor).

In some embodiments, the period of time is 0 to 72 hours (e.g., 0 to 72; 0 to 60 hours; 0 to 48 hours; 0 to 36 hours; 0 to 24 hours; 0 to 16 hours; 0 to 14 hours; 0 to 12 hours; 0 to 10 hours; 0 to 8 hours; 0 to 6 hours; 0 to 4 hours; 0 to 2 hours; 2 to 72 hours; 2 to 60 hours; 2 to 48 hours; 2 to 36 hours; 2 to 24 hours; 2 to 16 hours; 2 to 14 hours; 2 to 12 hours; 2 to 10 hours; 2 to 8 hours; 2 to 6 hours; 2 to 4 hours; 4 to 72 hours; 4 to 60 hours; 4 to 48 hours; 4 to 36 hours; 4 to 24 hours; 4 to 16 hours; 4 to 14 hours; 4 to 12 hours; 4 to 10 hours; 4 to 8 hours; 4 to 6 hours; 6 to 8 hours; 6 to 10 hours; 6 to 12 hours; 6 to 14 hours; 6 to 16 hours; 6 to 18 hours; 6 to 20 hours; 6 to 22 hours 6 to 24 hours; 8 to 10 hours; 8 to 12 hours; 8 to 16 hours; 8 to 24 hours; 8 to 36 hours; 8 to 48 hours; 8 to 60 hours; 8 to 72 hours; 1 to 2 hours; 1 to 3 hours; 1 to 4 hours; 1 to 6 hours; 1 to 8 hours; 1 to 10 hours; 1 to 12 hours; 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 or 72 hours).

In some embodiments, the co-culturing of the at least three bacterial strains is in a constant lysis state; wherein the constant lysis state is characterized by a steady-state balance of growth and lysis of the at least three bacterial strains.

Provided herein are bacterial strains including a lysis plasmid and an activator plasmid; wherein the lysis plasmid comprises a lysis gene, an activatable promoter, and optionally a reporter gene; and the activator plasmid comprises an activator gene, a degradation tag, and optionally a reporter gene.

In some embodiments, the lysis gene is E from a bacteriophage ΦX174.

In some embodiments, the activatable promoter is a LuxR-N-acyl homoserine lactone (AHL) activatable luxI promoter and the activator gene is a LuxI.

Also provided herein are pharmaceutical composition that include any of the bacterial strains described herein. In some embodiments, the pharmaceutical composition is formulated for in situ drug delivery. A pharmaceutical composition is formulated to be compatible with its intended route of administration. Examples of routes of administration include oral or parenteral, e.g., intravenous, intradermal, subcutaneous, inhalation, transdermal (topical), transmucosal, and rectal administration. As used herein the language "pharmaceutically acceptable carrier" includes solvents, dispersion media, coatings, isotonic and absorption delaying agents, and the like, compatible with pharmaceutical administration. Supplementary active compounds can also be incorporated into the compositions.

Provided herein are systems including: a co-culture of at least three bacterial strains as described herein.

Provided herein are drug delivery systems including any of the systems described herein. Provided herein are periodic drug delivery systems including any of the systems described herein.

Provided herein are methods for treating a disease in a subject, comprising: administering to a subject in need therapeutically effective amounts of at least three bacterial strains as described herein, or a pharmaceutical composition as described herein, to treat the disease in the subject. In some embodiments, the administering comprises administering sequentially each of the at least three bacterial strains to the subject. In some embodiments, the administering comprises administering each of the at least three bacterial strains simultaneously. In some embodiments, each of the at least three bacterial strains expresses a different therapeutic agent. In some embodiments, the disease is cancer or an infection.

Provided herein are microfluidic sample traps including any of the systems described herein.

Provided herein are microfluidic devices including one or more microfluidic sample traps. In some embodiments, the microfluidic system further includes at least one channel in fluid communication with the microfluidic sample trap.

Provided herein is a method including culturing a first bacterial strain for a first period of time in a growth environment, adding a second bacterial strain to the growth environment and culturing the second bacterial strain for a second period of time, adding a third bacterial strain to the growth environment and culturing the third bacterial strain for a third period of time, wherein each of the first, second, and third bacterial strains includes a toxin system, wherein the toxin system of the first bacterial strain produces a first toxin/first antitoxin pair and a third antitoxin from a third toxin/third antitoxin pair wherein the first bacterial strain does not produce the third toxin, wherein the toxin system of the second bacterial strain produces a second toxin/second antitoxin pair and the first antitoxin from the first toxin/first antitoxin pair wherein the second bacterial strain does not produce the first toxin, and wherein the toxin system of the third bacterial strain produces a third toxin/ third antitoxin pair and the second antitoxin from the second toxin/second antitoxin pair wherein the third bacterial strain does not produce the second toxin, and optionally wherein each of the first, second, and third bacterial strains includes a lysis plasmid having a lysis gene under the control of an activatable promoter, and an activator plasmid having an activator gene, the expression of which promotes the accumulation of a quorum-sensing molecule, wherein both the activatable promoter of the lysis gene and the expression of the activator gene can be activated by the quorum-sensing molecule.

Implementations can include one or more of the following features. The quorum-sensing molecule can be different in each of the first, second, and third bacterial strains. Each quorum-sensing molecule of each of the first, second, and third bacterial strains can have no or substantially no effect on the activatable promoter of the lysis gene of another strain. The quorum-sensing molecule can be the same in each of the first, second, and third bacterial strains. The method can further include culturing or co-culturing one or more additional bacterial strains in the growth environment. Each of the one or more additional bacterial strains can include a lysis plasmid having a lysis gene under the control of an activatable promoter, and an activator plasmid having an activator gene, the expression of which promotes the accumulation of a quorum-sensing molecule, wherein both the activatable promoter of the lysis gene and the expression of the activator gene can be activated by the quorum-sensing molecule. The quorum-sensing molecule can be different in each of the first, second, third, and one or more additional bacterial strains. Each quorum-sensing molecule of each of the first, second, third, and one or more additional bacterial strains can have no or substantially no effect on the activatable promoter of the lysis gene of another bacterial strain used in the growth environment. The quorum sensing molecule can be the same in each of the first, second, third, and one or more additional bacterial strains. Each of the one or more additional bacterial strains can include a toxin system. The toxin system of the first bacterial strain, the second bacterial strain, the third bacterial strain, and each of the one or more additional bacterial strains can be independently encoded in the genome, on a plasmid, on multiple plasmids, or a combination thereof. The lysis plasmid and activator plasmid of each of the at least first, second, and third bacterial strains can be copies of the same plasmid. The lysis plasmid and activator plasmid of each of the at least the first, second, and third bacterial strains can be different plasmids. At least the first, second, and third bacterial strains can be metabolically competitive. At least the first, second, and third bacterial strains can be selected from *E. coli, S. typhimurium*, or a bacterial variant thereof. Each of the at least the first, second, and third bacterial strains can not have a growth advantage compared to another strain in the growth environment. In each of the at least the first, second, and third bacterial strains, the lysis plasmid can include a lysis gene, an activatable promoter, and optionally a reporter gene, and the activator plasmid includes an activator gene, optionally a degradation tag, and optionally a reporter gene. The lysis gene in each of the at least the first, second, and third bacterial strains can be E from a bacteriophage ΦX174. The activatable promoter in each of the at least the first, second, and third bacterial strains can be a LuxR-AHL activatable luxI promoter and the activator gene can be a LuxI. At least one reporter gene can be selected from a gene encoding a green fluorescent protein (GFP), cyan fluorescent protein (CFP), red fluorescent protein (RFP), or a variant thereof. The degradation tag can be an ssrA-LAA degradation tag. At least one of the plasmids can be integrated into a genome of at least one of the first, second, and third bacterial strains. The culturing can occur in a microfluidic device. The culturing can occur in a bioreactor. The culturing can occur in vivo. Each of the first, second, and third periods of time can range from about 12 to about 72 hours. Each of the first, second, and third periods of time can be selected from at least 24 hours, at least 48 hours, at least 72 hours, and at least 96 hours. Each of the first, second, and third periods of time can be selected from 12 hours, 24 hours, 48 hours, 72 hours, and 96 hours. Each of the first, second, and third periods of time independently can range from about 1 hours to about 72 hours. Each of the first, second, and third periods of time independently can range from about 1 hours to about 48 hours. Each of the first, second, and third periods of time independently can range from about 1 hours to about 24 hours. Each of the first, second, and third periods of time independently can range from about 1 hours to about 18 hours. Each of the first, second, and third periods of time independently can range from about 1 hours to about 12 hours. Each of the first, second, and third periods of time independently can range from about 1 hours to about 6 hours. Each of the first, second, and third periods of time independently can range from about 1 hours to about 3 hours. The first, second, and third periods of time can occur sequentially. The first and second, second and third, or first and third periods of time can partially or completely overlap. One or more of the first, second, and third bacterial strains can encode a heterologous nucleic acid and/or a heterologous protein operably linked to a promoter. The promoter can be an activatable promoter. The promoter can be activated by the quorum sensing molecule. The promoter can be a constitutive promoter. The heterologous nucleic acid and/or heterologous protein can be a therapeutic agent. The therapeutic agent can be selected from the group consisting of: an inhibitory nucleic acid, a cytokine, an enzyme, a peptide hormone, a fusion protein, a clotting factor, a toxin, an antimicrobial peptide, and an antibody or antigen-binding fragment thereof. The inhibitory nucleic acid can be siRNA, shRNA, miRNA, or antisense.

Also provided herein is a method including providing n bacterial strains including at least a first bacterial strain, a second bacterial strain, and an nth bacterial strain, co-culturing each of the bacterial strains sequentially for an independent period of time in a growth environment, wherein each of the second bacterial strain to the $n^{th}$ bacterial strain has a previous bacterial strain, wherein n can be at least 3, wherein each of the n strains includes a lysis plasmid having a lysis gene under the control of an activatable promoter, and an activator plasmid having an activator gene, the expression of which promotes the accumulation of a quorum sensing molecule, wherein both the activatable promoter of the lysis gene and the expression of the activator gene can be activated by the quorum sensing molecule, wherein each of the n bacterial strains includes a toxin system, wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain, wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Implementations can include one or more of the following features. In each of the n bacterial strains, the lysis plasmid can include a lysis gene, an activatable promoter, and optionally a reporter gene, and the activator plasmid includes an activator gene, optionally a degradation tag, and optionally a reporter gene. The lysis gene in each of the n bacterial strains can be E from a bacteriophage ΦX174. The activatable promoter in each of the n bacterial strains can be a LuxR-AHL activatable luxI promoter and the activator gene can be a LuxI. At least one reporter gene can be selected from a gene encoding a green fluorescent protein (GFP), cyan fluorescent protein (CFP), red fluorescent protein (RFP), or a variant thereof. The degradation tag can be an ssrA-LAA degradation tag. At least one of the plasmids can be integrated into a genome of at least one of the n bacterial strains. The quorum-sensing molecule can be different in each of the n bacterial strains. Each quorum-sensing molecule of each of then bacterial strains has no or substantially no effect on the activatable promoter of the lysis gene of another strain. The quorum-sensing molecule can be the same in each of then bacterial strains. The lysis plasmid and activator plasmid of each of the n bacterial strains can be copies of the same plasmid. The lysis plasmid and activator plasmid of each of the n bacterial strains are different plasmids.

Also provided herein is a method including providing n bacterial strains including at least a first bacterial strain, a second bacterial strain, and an nth bacterial strain, co-culturing each of the bacterial strains sequentially for an independent period of time in a growth environment, wherein each of the second bacterial strain to the $n^{th}$ bacterial strain has a previous bacterial strain, wherein n can be at least 3, wherein each of the n bacterial strains includes a toxin system, wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain, wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain. The n bacterial strains can be metabolically competitive. Each of the n bacterial strains can be selected from E. coli, S. typhimurium, or a bacterial variant thereof. Each of the n bacterial strains can not have a growth advantage compared to another strain in the growth environment. The toxin system of the n bacterial strains can be independently encoded in the genome, on a plasmid, on multiple plasmids, or a combination thereof. The culturing can occur in a microfluidic device. The culturing can occur in a bioreactor. The culturing can occur in vivo. Each of the independent periods of time can range from about 12 to about 72 hours. Each of the independent periods of time can be selected from at least 24 hours, at least 48 hours, at least 72 hours, and at least 96 hours. Each of the independent periods of time can be selected from 12 hours, 24 hours, 48 hours, 72 hours, and 96 hours. Each of the periods of time independently can range from about 1 hours to about 72 hours. Each of the periods of time independently can range from about 1 hours to about 48 hours. Each of the periods of time independently can range from about 1 hours to about 24 hours. Each of the periods of time independently can range from about 1 hours to about 18 hours. Each of the periods of time independently can range from about 1 hours to about 12 hours. Each of the periods of time independently can range from about 1 hours to about 6 hours. Each of the periods of time independently can range from about 1 hours to about 3 hours. One or more of the periods of time can partially or completely overlap. One or more of the n bacterial strains can encode a heterologous nucleic acid and/or a heterologous protein operably linked to a promoter. The promoter can be an activatable promoter. The activatable promoter can be activated by a quorum-sensing molecule. The promoter can be a constitutive promoter. The heterologous nucleic acid and/or heterologous protein can be a therapeutic agent. The therapeutic agent can be selected from the group consisting of: an inhibitory nucleic acid, a cytokine, an enzyme, a peptide hormone, a fusion protein, a clotting factor, a toxin, an antimicrobial peptide, and an antibody or antigen-binding fragment thereof. The inhibitory nucleic acid can be siRNA, shRNA, miRNA, or antisense. Each of the second bacterial strain through the nth bacterial strain can not produce the second toxin of the toxin system of the previous strain, and the first bacterial strain can not produce the fourth toxin of the toxin system of the nth bacterial strain.

Also provided herein is a bacterial strain including a lysis plasmid and an activator plasmid, wherein the lysis plasmid includes a lysis gene, an activatable promoter, and optionally a reporter gene, and the activator plasmid includes an activator gene, optionally a degradation tag, and optionally a reporter gene, wherein the bacterial strain further includes a toxin system, wherein the toxin system produces a first toxin/first antitoxin pair and a second antitoxin from a second toxin/second antitoxin pair wherein the bacterial strain does not produce the second toxin.

Implementations can include one or more of the following features. The lysis gene can be E from a bacteriophage ΦX174. The activatable promoter can be a LuxR-AHL activatable luxI promoter and the activator gene can be a LuxI. The activator gene can encode a molecule that activates, directly or indirectly, the activatable promoter. The molecule that activates, directly or indirectly, the activatable promoter can be a quorum-sensing molecule. The lysis gene can be operably linked to the activatable promoter. The reporter gene on the lysis plasmid can be operably linked to the activatable promoter. The activator plasmid can further include an activatable promoter. The activatable promoter of the activator plasmid can be a copy of the activatable promoter of the lysis plasmid. The activator gene can be operably linked to the activatable promoter of the activator plasmid. The reporter gene of the activator plasmid can be operably linked to the activatable promoter of the activator plasmid. The degradation tag can be operably linked to the activatable promoter of the activator plasmid. The toxin system can be operably linked to the activatable promoter of the lysis plasmid. The degradation tag can be an ssrA-LAA degradation tag. The reporter gene of the lysis plasmid, the reporter gene of the activator plasmid, or both, can be fluorescent proteins. The reporter gene of the lysis plasmid and the reporter gene of the activator plasmid can be different genes.

Also provided herein is bacterial strain including a toxin system, wherein the toxin system produces a first toxin/first antitoxin pair and a second antitoxin from a second toxin/second antitoxin pair wherein the bacterial strain does not produce the second toxin.

Implementations can include one or more of the following features. The bacterial strain can encode a heterologous nucleic acid and/or a heterologous protein operably linked to a promoter. The promoter can be an activatable promoter. The activatable promoter can be activated by a quorum-sensing molecule. The promoter can be a constitutive promoter. The heterologous nucleic acid and/or heterologous protein can be a therapeutic agent. The toxin system can be encoded in the genome, on a plasmid, on multiple plasmids, or a combination thereof. The bacterial strain can further include a nucleic acid encoding a therapeutic agent. The therapeutic agent can be selected from the group consisting of: an inhibitory nucleic acid, a cytokine, an enzyme, a peptide hormone, a fusion protein, a clotting factor, a toxin, an antimicrobial peptide, and an antibody or antigen-binding fragment thereof. The therapeutic agent can be a therapeutic polypeptide. The therapeutic agent can be cytotoxic or cytostatic to a target cell. The target cell can be a cancer cell or an infected cell.

Also provided herein is a pharmaceutical composition including any one or more of the bacterial strains described herein. The pharmaceutical composition can be formulated for in situ drug delivery.

Also provided herein is a system including a first bacterial strain including a first lysis plasmid and a first activator plasmid, wherein the first lysis plasmid includes a first lysis gene, a first activatable promoter, and optionally a first reporter gene, and the first activator plasmid includes a first activator gene, optionally a first degradation tag, and optionally a first reporter gene, wherein the first bacterial strain further includes a first toxin system, wherein the first toxin system produces a first toxin/first antitoxin pair and a third antitoxin from a third toxin/third antitoxin pair wherein the first bacterial strain does not produce the third toxin, a second bacterial strain including a second lysis plasmid and a second activator plasmid, wherein the second lysis plasmid includes a second lysis gene, a second activatable promoter, and optionally a second reporter gene, and the second activator plasmid includes a second activator gene, optionally a second degradation tag, and optionally a second reporter gene, wherein the second bacterial strain further includes a second toxin system, wherein the second toxin system produces a second toxin/second antitoxin pair and the first antitoxin from the first toxin/first antitoxin pair wherein the second bacterial strain does not produce the first toxin, and a third bacterial strain including a third lysis plasmid and a third activator plasmid, wherein the third lysis plasmid includes a third lysis gene, a third activatable promoter, and optionally a third reporter gene, and the third activator plasmid includes a third activator gene, optionally a third degradation tag, and optionally a third reporter gene, wherein the third bacterial strain further includes a third toxin system, wherein the third toxin system produces a third toxin/third antitoxin pair and a second antitoxin from a second toxin/second antitoxin pair wherein the third bacterial strain does not produce the second toxin.

Also provided herein is a system including first bacterial strain including a first toxin system, wherein the first toxin system produces a first toxin/first antitoxin pair and a third antitoxin from a third toxin/third antitoxin pair wherein the first bacterial strain does not produce the third toxin, wherein the first bacterial strain optionally further includes a first lysis plasmid and a first activator plasmid, wherein the first lysis plasmid includes a first lysis gene, a first activatable promoter, and optionally a first reporter gene, and the first activator plasmid includes a first activator gene, optionally a first degradation tag, and optionally a first reporter gene, a second bacterial strain including a second toxin system, wherein the second toxin system produces a second toxin/second antitoxin pair and the first antitoxin from the first toxin/first antitoxin pair wherein the second bacterial strain does not produce the first toxin, wherein the second bacterial strain optionally further includes a second lysis plasmid and a second activator plasmid, wherein the second lysis plasmid includes a second lysis gene, a second activatable promoter, and optionally a second reporter gene, and the second activator plasmid includes a second activator gene, optionally a second degradation tag, and optionally a second reporter gene, and a third bacterial strain including a third toxin system produces a third toxin/third antitoxin pair and a second antitoxin from a second toxin/second antitoxin pair wherein the third bacterial strain does not produce the second toxin, wherein the third bacterial strain optionally further includes a third lysis plasmid and a third activator plasmid, wherein the third lysis plasmid includes a third lysis gene, a third activatable promoter, and optionally a third reporter gene, and the third activator plasmid includes a third activator gene, optionally a third degradation tag, and optionally a third reporter gene.

Implementations of some systems can include one or more of the following features. The system can further include one or more additional bacterial strains. The first toxin system, the second toxin system, and the third toxin system can be independently encoded in the genome, on a plasmid, on multiple plasmids, or a combination thereof.

Also provided herein is a system including n bacterial strains including at least a first bacterial strain, a second bacterial strain, and an nth bacterial strain, wherein each of the second bacterial strain to the $n^{th}$ bacterial strain has a previous bacterial strain, wherein n can be at least 3, wherein each of the n strains includes a toxin system, wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain, wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Also provided herein is a system including n bacterial strains including at least a first bacterial strain, a second bacterial strain, and an $n^{th}$ bacterial strain, wherein each of the second bacterial strain to the $n^{th}$ bacterial strain has a previous bacterial strain, wherein n can be at least 3, wherein each of the n strains includes a lysis plasmid having a lysis gene under the control of an activatable promoter, and an activator plasmid having an activator gene, the expression of which promotes the accumulation of a quorum sensing molecule, wherein both the activatable promoter of the lysis gene and the expression of the activator gene can be activated by the quorum sensing molecule, wherein each of the n bacterial strains includes a toxin system, wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain, wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Implementations of some systems can include one or more of the following features. The value of n can be 3. The value of n can be 4, 5, 6, 7, 8, 9, or 10. Each of the toxin systems can be independently encoded in the genome, on a plasmid, on multiple plasmids, or a combination thereof. Each of the second bacterial strain through the nth bacterial strain can not produce the second toxin of the toxin system of the previous strain, and the first bacterial strain does not produce the fourth toxin of the toxin system of the nth bacterial strain.

Also provided herein is a kit including a first pharmaceutical composition including a first bacterial strain including a first lysis plasmid and a first activator plasmid, wherein the first lysis plasmid includes a first lysis gene, a first activatable promoter, and optionally a first reporter gene, and the first activator plasmid includes a first activator gene, a first degradation tag, and optionally a first reporter gene, wherein the first bacterial strain further includes a first toxin system, wherein the first toxin system produces a first toxin/first antitoxin pair and a third antitoxin from a third toxin/third antitoxin pair wherein the first bacterial strain does not produce the third toxin, a second pharmaceutical composition including a second bacterial strain including a second lysis plasmid and a second activator plasmid, wherein the second lysis plasmid includes a second lysis gene, a second activatable promoter, and optionally a second reporter gene, and the second activator plasmid includes a second activator gene, a second degradation tag, and optionally a second reporter gene, wherein the second bacterial strain further includes a second toxin system, wherein the second toxin system produces a second toxin/second antitoxin pair and the first antitoxin from the first toxin/first antitoxin pair wherein the second bacterial strain does not produce the first toxin, and a third pharmaceutical composition including a third bacterial strain including a third lysis plasmid and a third activator plasmid, wherein the third lysis plasmid includes a third lysis gene, a third activatable promoter, and optionally a third reporter gene, and the third activator plasmid includes a third activator gene, a third degradation tag, and optionally a third reporter gene, wherein the third bacterial strain further includes a third toxin system, wherein the third toxin system produces a third toxin/third antitoxin pair and a second antitoxin from a second toxin/second antitoxin pair wherein the third bacterial strain does not produce the second toxin.

Also provided here is a kit including a first pharmaceutical composition including a first bacterial strain including a first toxin system, wherein the first toxin system produces a first toxin/first antitoxin pair and a third antitoxin from a third toxin/third antitoxin pair wherein the first bacterial strain does not produce the third toxin, wherein the first bacterial strain optionally further includes a first lysis plasmid and a first activator plasmid, wherein the first lysis plasmid includes a first lysis gene, a first activatable promoter, and optionally a first reporter gene, and the first activator plasmid includes a first activator gene, optionally a first degradation tag, and optionally a first reporter gene, a second pharmaceutical composition including second bacterial strain including a second toxin system, wherein the second toxin system produces a second toxin/second antitoxin pair and the first antitoxin from the first toxin/first antitoxin pair wherein the second bacterial strain does not produce the first toxin, wherein the second bacterial strain optionally further includes a second lysis plasmid and a second activator plasmid, wherein the second lysis plasmid includes a second lysis gene, a second activatable promoter, and optionally a second reporter gene, and the second activator plasmid includes a second activator gene, optionally a second degradation tag, and optionally a second reporter gene, and a third pharmaceutical composition including a third bacterial strain including a third toxin system produces a third toxin/third antitoxin pair and a second antitoxin from a second toxin/second antitoxin pair wherein the third bacterial strain does not produce the second toxin, wherein the third bacterial strain optionally further includes a third lysis plasmid and a third activator plasmid, wherein the third lysis plasmid includes a third lysis gene, a third activatable promoter, and optionally a third reporter gene, and the third activator plasmid includes a third activator gene, optionally a third degradation tag, and optionally a third reporter gene.

Implementations of some kits can include one or more of the following features. The first toxin system, the second toxin system, and the third toxin system can independently encoded in the genome, on a plasmid, on multiple plasmids, or a combination thereof. The kit can further include one or more additional bacterial strains in the first, second, third, and/or one or more additional pharmaceutical compositions.

Also provided herein is a kit including n bacterial strains including at least a first bacterial strain, a second bacterial strain, and an nth bacterial strain, wherein each of the second bacterial strain to the $n^{th}$ bacterial strain has a previous bacterial strain, wherein n can be at least 3, wherein each of the n strains includes a toxin system, wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain, wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Also provided herein is a kit including n bacterial strains including at least a first bacterial strain, a second bacterial strain, and an nth bacterial strain, wherein each of the second bacterial strain to the $n^{th}$ bacterial strain has a previous bacterial strain, wherein n can be at least 3, wherein each of the n strains includes a lysis plasmid having a lysis gene under the control of an activatable promoter, and an activator plasmid having an activator gene, the expression of which promotes the accumulation of a quorum sensing molecule, wherein both the activatable promoter of the lysis gene and the expression of the activator gene can be activated by the quorum sensing molecule, wherein the lysis plasmid of each of the n bacterial strains includes a toxin system, wherein the toxin system of the lysis plasmid of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain, wherein the toxin system of the lysis plasmid of the first bacterial strain produces a third toxin/third antitoxin pair, wherein the third toxin is effective against the $n^{th}$ bacterial strain, and a fourth antitoxin from a fourth toxin/antitoxin pair produced by the $n^{th}$ bacterial strain.

Implementations of some kits can include one or more of the following features. The value of n can be 3. The value of n can be 4, 5, 6, 7, 8, 9, or 10.

Also provided herein is a drug delivery system including any one or more of the systems or kits provided herein.

Also provided herein is a periodic drug delivery system including any one or more of the systems or kits provided herein.

Also provided herein is a method for treating a disease in a subject in need thereof, including administering to the subject a therapeutically effective amount of each of a first bacterial strain including a first lysis plasmid and a first activator plasmid, wherein the first lysis plasmid includes a first lysis gene, a first activatable promoter, and optionally a first reporter gene, and the first activator plasmid includes a first activator gene, optionally a first degradation tag, and optionally a first reporter gene, wherein the first bacterial strain further includes a first toxin system, wherein the first toxin system produces a first toxin/first antitoxin pair and a third antitoxin from a third toxin/third antitoxin pair wherein the first bacterial strain does not produce the third toxin, a second bacterial strain including a second lysis plasmid and a second activator plasmid, wherein the second lysis plasmid includes a second lysis gene, a second activatable promoter, and optionally a second reporter gene, and the second activator plasmid includes a second activator gene, optionally a second degradation tag, and optionally a second reporter gene, wherein the second bacterial strain further includes a second toxin system, wherein the second toxin system produces a second toxin/second antitoxin pair and the first antitoxin from the first toxin/first antitoxin pair wherein the second bacterial strain does not produce the first toxin, and a third bacterial strain including a third lysis plasmid and a third activator plasmid, wherein the third lysis plasmid includes a third lysis gene, a third activatable promoter, and optionally a third reporter gene, and the third activator plasmid includes a third activator gene, optionally a third degradation tag, and optionally a third reporter gene, wherein the third bacterial strain further includes a third toxin system, wherein the third toxin system produces a third toxin/third antitoxin pair and a second antitoxin from a second toxin/second antitoxin pair wherein the third bacterial strain does not produce the second toxin.

Also provided herein is a method for treating a disease in a subject in need thereof, including administering to the subject a therapeutically effective amount of each of: a first pharmaceutical including a first bacterial strain including a first lysis plasmid and a first activator plasmid, wherein the first lysis plasmid includes a first lysis gene, a first activatable promoter, and optionally a first reporter gene, and the first activator plasmid includes a first activator gene, optionally a first degradation tag, and optionally a first reporter gene, wherein the first bacterial strain further includes a first toxin system, wherein the first toxin system produces a first toxin/first antitoxin pair and a third antitoxin from a third toxin/third antitoxin pair wherein the first bacterial strain does not produce the third toxin, a second pharmaceutical including a second bacterial strain including a second lysis plasmid and a second activator plasmid, wherein the second lysis plasmid includes a second lysis gene, optionally a second activatable promoter, and optionally a second reporter gene, and the second activator plasmid includes a second activator gene, a second degradation tag, and optionally a second reporter gene, wherein the second bacterial strain further includes a second toxin system, wherein the second toxin system produces a second toxin/second antitoxin pair and the first antitoxin from the first toxin/first antitoxin pair wherein the second bacterial strain does not produce the first toxin, and a third pharmaceutical including a third bacterial strain including a third lysis plasmid and a third activator plasmid, wherein the third lysis plasmid includes a third lysis gene, a third activatable promoter, and optionally a third reporter gene, and the third activator plasmid includes a third activator gene, optionally a third degradation tag, and optionally a third reporter gene, wherein the third bacterial strain further includes a third toxin system, wherein the third toxin system produces a third toxin/third antitoxin pair and a second antitoxin from a second toxin/second antitoxin pair wherein the third bacterial strain does not produce the second toxin.

Also provided herein is a method for treating a disease in a subject in need thereof, including administering to the subject a therapeutically effective amount of each of: a first bacterial strain including a first toxin system, wherein the first toxin system produces a first toxin/first antitoxin pair and a third antitoxin from a third toxin/third antitoxin pair wherein the first bacterial strain does not produce the third toxin, wherein the first bacterial strain optionally further includes a first lysis plasmid and a first activator plasmid, wherein the first lysis plasmid includes a first lysis gene, a first activatable promoter, and optionally a first reporter gene, and the first activator plasmid includes a first activator gene, optionally a first degradation tag, and optionally a first reporter gene, a second bacterial strain including a second toxin system, wherein the second toxin system produces a second toxin/second antitoxin pair and the first antitoxin from the first toxin/first antitoxin pair wherein the second bacterial strain does not produce the first toxin, wherein the second bacterial strain optionally further includes a second lysis plasmid and a second activator plasmid, wherein the second lysis plasmid includes a second lysis gene, a second activatable promoter, and optionally a second reporter gene, and the second activator plasmid includes a second activator gene, optionally a second degradation tag, and optionally a second reporter gene, and a third bacterial strain including a third toxin system produces a third toxin/third antitoxin pair and a second antitoxin from a second toxin/second antitoxin pair wherein the third bacterial strain does not produce the second toxin, wherein the third bacterial strain optionally further includes a third lysis plasmid and a third activator plasmid, wherein the third lysis plasmid includes a third lysis gene, a third activatable promoter, and optionally a third reporter gene, and the third activator plasmid includes a third activator gene, optionally a third degradation tag, and optionally a third reporter gene.

Also provided herein is a method for treating a disease in a subject in need thereof, including administering to the subject a therapeutically effective amount of each of: a first pharmaceutical composition including a first bacterial strain including a first toxin system, wherein the first toxin system produces a first toxin/first antitoxin pair and a third antitoxin from a third toxin/third antitoxin pair wherein the first bacterial strain does not produce the third toxin, wherein the first bacterial strain optionally further includes a first lysis plasmid and a first activator plasmid, wherein the first lysis plasmid includes a first lysis gene, a first activatable promoter, and optionally a first reporter gene, and the first activator plasmid includes a first activator gene, optionally a first degradation tag, and optionally a first reporter gene, a second pharmaceutical composition including second bacterial strain including a second toxin system, wherein the second toxin system produces a second toxin/second antitoxin pair and the first antitoxin from the first toxin/first antitoxin pair wherein the second bacterial strain does not produce the first toxin, wherein the second bacterial strain optionally further includes a second lysis plasmid and a second activator plasmid, wherein the second lysis plasmid includes a second lysis gene, a second activatable promoter, and optionally a second reporter gene, and the second activator plasmid includes a second activator gene, optionally a second degradation tag, and optionally a second reporter gene, and a third pharmaceutical composition including a third bacterial strain including a third toxin system produces a third toxin/third antitoxin pair and a second antitoxin from a second toxin/second antitoxin pair wherein the third bacterial strain does not produce the second toxin, wherein the third bacterial strain optionally further includes a third lysis plasmid and a third activator plasmid, wherein the third lysis plasmid includes a third lysis gene, a third activatable promoter, and optionally a third reporter gene, and the third activator plasmid includes a third activator gene, optionally a third degradation tag, and optionally a third reporter gene.

Implementations of some methods can include one or more of the following features. Administering can include administering sequentially each of the first, second, and third bacterial strains or first second and third pharmaceutical compositions to the subject. Administering can include administering each of the first, second, and third pharmaceutical compositions simultaneously and wherein each of the first, second, and third pharmaceutical compositions has a different release profile for releasing the first second and third bacterial strains. Each of the first, second, and third bacterial strains can express a different therapeutic agent.

Also provided herein is a method for treating a disease in a subject in need thereof, including administering to the subject a therapeutically effective amount of each of n bacterial strains including at least a first bacterial strain, a second bacterial strain, and an nth bacterial strain, wherein each of the second bacterial strain to the $n^{th}$ bacterial strain has a previous bacterial strain, wherein n can be at least 3, wherein each of the n strains includes a toxin system, wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain, wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Also provided herein is a method for treating a disease in a subject in need thereof, including administering to the subject a therapeutically effective amount of each of n bacterial strains including at least first bacterial strain, a second bacterial strain, and an nth bacterial strain, wherein each of the second bacterial strain to the $n^{th}$ bacterial strain has a previous bacterial strain, wherein n can be at least 3, wherein each of the n strains includes a lysis plasmid having a lysis gene under the control of an activatable promoter, and an activator plasmid having an activator gene, the expression of which promotes the accumulation of a quorum sensing molecule, wherein both the activatable promoter of the lysis gene and the expression of the activator gene can be activated by the quorum sensing molecule, wherein the lysis plasmid of each of the n bacterial strains includes a toxin system, wherein the toxin system of the lysis plasmid of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain, wherein the toxin system of the lysis plasmid of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Implementations of some methods can include one or more of the following features. The value of n can be 3. The value of n can be 4, 5, 6, 7, 8, 9, or 10.

Also provided herein is a method for treating a disease in a subject in need thereof, including administering to the subject a therapeutically effective amount of each of m pharmaceutical compositions, each including at least one of n bacterial strains, wherein the n bacterial strains comprise at least a first bacterial strain, a second bacterial strain, and an nth bacterial strain, wherein each of the second bacterial strain to the $n^{th}$ bacterial strain has a previous bacterial strain, wherein n can be at least 3, wherein each of the n strains includes a toxin system, wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain, wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Also provided herein is a method for treating a disease in a subject in need thereof, including administering to the subject a therapeutically effective amount of each of m pharmaceutical compositions, each including at least one of n bacterial strains, wherein the n bacterial strains comprise at least a first bacterial strain, a second bacterial strain, and an nth bacterial strain, wherein each of the second bacterial strain to the $n^{th}$ bacterial strain has a previous bacterial strain, wherein n can be at least 3, wherein each of the n strains includes a lysis plasmid having a lysis gene under the control of an activatable promoter, and an activator plasmid having an activator gene, the expression of which promotes the accumulation of a quorum sensing molecule, wherein both the activatable promoter of the lysis gene and the expression of the activator gene can be activated by the quorum sensing molecule, wherein the lysis plasmid of each of the n bacterial strains includes a toxin system, wherein the toxin system of the lysis plasmid of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain, wherein the toxin system of the lysis plasmid of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Implementations of some methods can include one or more of the following features. The value n can be 3. The value of n can be 4, 5, 6, 7, 8, 9, or 10. The value m=n. Each of the toxin systems can be independently encoded in the genome, on a plasmid, on multiple plasmids, or a combination thereof. Each of the second bacterial strain through the nth bacterial strain does not produce the second toxin of the toxin system of the previous strain, and the first bacterial strain does not produce the fourth toxin of the toxin system of the nth bacterial strain. Administering can include administering sequentially each of the n bacterial strains or m pharmaceutical compositions to the subject. Administering can include administering each of the m pharmaceutical compositions simultaneously and wherein each of the m pharmaceutical compositions has a different release profile for releasing the first second and third bacterial strains. Each of the first, second, and third bacterial strains can express a different therapeutic agent. The disease can be cancer or an infection. The infection can be caused by an infectious agent selected from the group consisting of: *Camphylobacter jejuni, Clostridium botulinium, Escherichia coli, Listeria monocytogenes* and *Salmonella*. The cancer can be selected from the group consisting of: glioblastoma, squamous cell carcinoma, breast cancer, colon cancer, hepatocellular cancer, melanoma, neuroblastoma, pancreatic cancer, and prostate cancer.

In some implementations of any one or more of the methods, bacterial strains, pharmaceutical compositions, systems, or kits described herein, one or more of the bacterial strains can express a therapeutic agent. In some implementations of any one or more of the methods, bacterial strains, pharmaceutical compositions, systems, or kits described herein, one or more of the bacterial strains expresses a therapeutic agent selected from the group consisting of: an inhibitory nucleic acid, a cytokine, an enzyme, a peptide hormone, a fusion protein, a clotting factor, a toxin, an antimicrobial peptide, and an antibody or antigen-binding fragment thereof.

Also provided herein is a method including culturing a first bacterial strain for a first period of time in a growth environment, adding a second bacterial strain to the growth environment and culturing the second bacterial strain for a second period of time, adding a third bacterial strain to the growth environment and culturing the third bacterial strain for a second period of time, wherein each of the first, second, and third bacterial strains includes a toxin system, wherein the toxin system of the first bacterial strain produces a first toxin/first antitoxin pair and a third antitoxin from a third toxin/third antitoxin pair wherein the first bacterial strain does not produce the third toxin, wherein the toxin system of the second bacterial strain produces a second toxin/second antitoxin pair and the first antitoxin from the first toxin/first antitoxin pair wherein the second bacterial strain does not produce the first toxin, and wherein the toxin system of the third bacterial strain produces a third toxin/third antitoxin pair and the second antitoxin from the second toxin/second antitoxin pair wherein the third bacterial strain does not produce the second toxin, wherein the toxin system can be encoded on a plasmid, multiple plasmids, integrated into the host genome, or a combination thereof.

Implementations can include one or more of the following features. Each of the first, second, and third bacterial strains can include a lysis plasmid having a lysis gene under the control of an activatable promoter, and an activator plasmid having an activator gene, the expression of which promotes the accumulation of a quorum sensing molecule, wherein both the activatable promoter of the lysis gene and the expression of the activator gene can be activated by the quorum sensing molecule, wherein the quorum sensing molecule may or may not be different in each of the first, second, and third bacterial strains, wherein each quorum-sensing molecule of each of the first, second, and third bacterial strains may or may not have any effect on the activatable promoter of the lysis gene of another strain. Each of the lysis plasmids of the first, second, and third bacterial strains can be the plasmid containing the toxin system for such bacterial strain, or wherein each of the activator plasmids of the first, second, and third bacterial strains can be the plasmid containing the toxin system for such bacterial strain, or wherein the toxin system for each bacterial strain can be integrated into the genome.

Also provided herein is a method of culturing n bacterial strains including culturing a first bacterial strain of n bacterial strains for a first period of time in a culture, adding a second bacterial strain of the n bacterial strains to the culture and culturing the second bacterial strain for a second period of time, adding each of the other of then bacterial strains to the culture and culturing each such bacterial strain for a period of time, wherein n can be three or a greater whole number and wherein a plasmid of each of the n bacterial strains includes a toxin system, wherein the toxin system of the plasmid of the first bacterial strain produces a first toxin/first antitoxin pair and a nth antitoxin from an nth toxin/nth antitoxin pair wherein the first bacterial strain does not produce the nth toxin, wherein the toxin system of the plasmid of each mth, where m can be an element of the set $\{2, 3, \ldots, n\}$, of the other bacterial strains in the n bacterial strains produces a mth toxin/mth antitoxin pair and the $(m-1)$th antitoxin from the $(m-1)$th toxin/$(m-1)$th antitoxin pair.

Implementations of some methods described herein can include one or more of the following features. Each of the n bacterial strains can include a lysis plasmid having a lysis gene under the control of an activatable promoter, and an activator plasmid having an activator gene, the expression of which promotes the accumulation of a quorum sensing molecule, wherein both the activatable promoter of the lysis gene and the expression of the activator gene can be activated by the quorum sensing molecule, wherein the quorum sensing molecule may or may not be different in each of the n bacterial strains, wherein each quorum-sensing molecule of each of the n bacterial strains may or may not have an effect on the activatable promoter of the lysis gene of another strain of then bacterial strains. Each of the lysis plasmids of the n strains can be the plasmid containing the toxin system for such bacterial strain. Each of the n bacterial strains can produce a payload. Each of the n bacterial strains can produce a different payload. Each of the n bacterial strains can produce the same payload. Each payload can be a therapeutic. The payload of the mth bacterial strain produces an mth substrate by directly or indirectly acting upon the substrate of the $(m-1)$th bacterial strain, and wherein the payload of the first bacterial strain acts upon a substrate present in the environment where the n bacterial strains are cultured. The value of n can be four. The value of n can be five. The value of n can be six. The method can further include culturing or co-culturing one or more additional bacterial strains in the culture. Each of the one or more additional bacterial strains can include a lysis plasmid having a lysis gene under the control of an activatable promoter, and an activator plasmid having an activator gene, the expression of which promotes the accumulation of a quorum sensing molecule, wherein both the activatable promoter of the lysis gene and the expression of the activator gene can be activated by the quorum sensing molecule, wherein the quorum sensing molecule can be different in each of the first, second, third, and one or more additional bacterial strains, wherein each quorum-sensing molecule of each of the first, second, third, and one or more additional bacterial strains can have no or substantially no effect on the activatable promoter of the lysis gene of another bacterial strain used in the culture. The lysis plasmid of each of the one or more additional bacterial strains can include a toxin system. The lysis plasmid and activator plasmid of each of the at least first, second, and third bacterial strains can be the same plasmid. The lysis plasmid and activator plasmid of each of the at least the first, second, and third bacterial strains can be separate plasmids. At least the first, second, and third bacterial strains can be metabolically competitive. At least the first, second, and third bacterial strains can be selected from *E. coli, S. typhimurium*, or a bacterial variant thereof. Each of the at least the first, second, and third bacterial strains can not have a growth advantage compared to another strain in the culture. In each of the at least the first, second, and third bacterial strains, the lysis plasmid includes a lysis gene, an activatable promoter, and optionally a reporter gene, and the activator plasmid includes an activator gene, a degradation tag, and optionally a reporter gene. The lysis gene in each of the at least the first, second, and third bacterial strains can be E from a bacteriophage ΦX174. The activatable promoter in each of the at least the first, second, and third bacterial strains can be a LuxR-AHL activatable luxI promoter and the activator gene can be a LuxI. At least one reporter gene can be selected from a gene encoding a green fluorescent protein (GFP), cyan fluorescent protein (CFP), red fluorescent protein (RFP), or a variant thereof. The degradation tag can be an ssrA-LAA degradation tag. At least one of the plasmids can be integrated into a genome of at least one of the first, second, and third bacterial strains. The culturing can occur in a designated growth environment. The culturing can occur in a microfluidic device. The culturing can occur in a bio reactor. The culturing can occur in vivo. Each of the bacterial strains can produce therapeutic payloads and the culturing can occur in a human or animal patient in need of the therapeutic payloads. Each of the first, second, and third periods of time can range from about 12 to about 72 hours. Each of the first, second, and third periods of time can range from about 1 hours to about n hours. Each of the first, second, and third periods of time can be selected from at least 24 hours, at least 48 hours, at least 72 hours, and at least 96 hours. Each of the n periods of time can partially or completely overlap. The n bacterial strains can be cultured together. Each of the n bacterial strains are added to the culture sequentially such that each mth bacterial strain can be added to the culture after the passage of the (m−1)th period of time. The first, second, and third periods of time can be selected from 12 hours, 24 hours, 48 hours, 72 hours, and 96 hours.

Also provided herein is a method of maintaining a co-culture, the method including co-culturing at least three bacterial strains, wherein each of the at least three bacterial strains includes a lysis plasmid having a lysis gene under the control of an activatable promoter, and an activator plasmid having an activator gene, the expression of which promotes the accumulation of a quorum sensing molecule, wherein both the activatable promoter of the lysis gene and the expression of the activator gene can be activated by the quorum sensing molecule, wherein the quorum sensing molecule can be different in each of the at least three bacterial strains, wherein each quorum-sensing molecule of each of the at least three bacterial strains has no or substantially no effect on the activatable promoter of the lysis gene of another strain, wherein the lysis plasmid includes a toxin/antitoxin system.

Implementations of some methods described herein can have one or more of the following features. The toxin/antitoxin system can produce a toxin/antitoxin pair and a different antitoxin of another strain. The lysis plasmid and activator plasmid of each of the at least three bacterial strains can be the same plasmid. The lysis plasmid and activator plasmid of each of the at least three bacterial strains can be separate plasmids. The at least the three strains can be metabolically competitive. The at least three strains can be selected from *E. coli, S. typhimurium*, or a bacterial variant thereof. Each of the at least three strains does not have a growth advantage compared to another strain. In each of the at least three strains, the lysis plasmid can include a lysis gene, an activatable promoter, and optionally a reporter gene, and the activator plasmid can include an activator gene, optionally a degradation tag, and optionally a reporter gene. The lysis gene in the at least three strains can be E from a bacteriophage ΦX174. The activatable promoter can be a LuxR-AHL activatable luxI promoter and the activator gene can be a LuxI. At least one reporter gene can be selected from a gene encoding a green fluorescent protein (GFP), cyan fluorescent protein (CFP), red fluorescent protein (RFP), or a variant thereof. The degradation tag can be an ssrA-LAA degradation tag. The co-culture can be inoculated at a ratio of 1:1:1 of each of the at least three bacterial strains. At least one of the plasmids can be integrated into a genome of at least one of the at least three strains. The culturing occurs can occur a microfluidic device. The period of time can be 12 to 72 hours. The period of time can be selected from at least 24 hours, at least 48 hours, at least 72 hours, and at least 96 hours. The period of time can be selected from 12 hours, 24 hours, 48 hours, 72 hours, and 96 hours. The co-culturing of the at least three strains can be in a constant lysis state; wherein the constant lysis state is characterized by a steady-state balance of growth and lysis of the at least three bacterial strains.

The methods, systems, kits, bacterial strain, and compositions described herein can provide several advantages. First, a tri-lysis or multi-lysis system can ensure specific delivery of a therapeutic protein(s) via engineered strains for a certain amount of time until a subsequent strain in the system is administered, thereby separating the delivery of certain therapeutic protein(s) in space and time, as desired. This capability would not otherwise be available with the engineered bacteria approach to therapy since they colonize the sites of disease for extended periods of time, potentially resulting in a single therapeutic being delivered regardless of whether or not another strain has been introduced into the disease environment, as well as decreasing the colonization ability of future strains due to decreased resources in the disease environment used up by the strain that has been introduced earlier.

Second, the tri-lysis or multi-lysis system can also be engineered to output specific profiles of therapeutic proteins to the disease site. For example, the proteins produced by the three strains and the time in which they are allowed to colonize the site of disease may be adjusted depending on the context of the application.

Third, the tri-lysis or multi-lysis system can ensure the stability of the circuit components in the strains. This can be accomplished because subsequent strains in the tri-lysis cycle are able to kill off and remove the previous strain populating the site of disease, even if members of that population have mutated the circuit machinery. For example, strain A is administered and allowed to colonize the site of disease for a desired period of time, where members of the population have mutated the lysis gene (or any other gene critical to the function of the circuit). Then the introduction of strain B to the site of disease will allow for the de-population of strain A from the environment, including the mutated members of the population, since they do not carry an immunity for the toxin released by strain B.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 1 shows a strategy to provide rapid and reliable control over active populations in a continuous culture.

FIG. 2 shows an exemplary diagram of a three strain system that cycles between engineered strains unidirectionally. In FIG. 2H, arrows 1 and 2 indicate the GFP and CFP peaks, respectively. In FIG. 2I, arrows 2 and 3 indicate the CFP and RFP peaks, respectively. In FIG. 2J, arrows 1 and 3 indicate the GFP and RFP peaks, respectively. Fluorescent reporters for the synchronized lysis strains are driven by production of AHL and are only expressed when quorum threshold is reached.

FIG. 3 shows three-strain co-culture dynamics, model and experimental results. FIG. 3D shows time series dynamics of the colicin model demonstrate that when three-strains are simultaneously co-cultured and under estimated parameters, given constant seeding, the three strains should cycle indefinitely.

FIG. 4 shows exemplary toxins that can be used according to some embodiments.

FIG. 5 shows exemplary verification of colicin and immunity activity in non-lysis strains in 96-well plate reader experiments.

Strain 2 with Colicin E7. Time course traces of OD600 and GFP fluorescence (RFU) expression verify that Strain 1 is able to grow in the presence of Colicin E7. FIGS. 5I, 5J, and 5K show co-incubation of Colicin E3, E7 and V with MG1655 wild type control strains demonstrate effectiveness of Colicins in inhibiting MG1655 wild type growth. Time course traces of OD600, GFP and RFP fluorescence (AU).

FIG. 6 shows video stills taken from exemplary microfluidic experiments to show growth inhibition of one strain by toxin production of the other strain. In this experiment, Strain 1 produces toxin 1, antitoxin 1, and antitoxin 3. Strain 3 produces toxin 3, antitoxin 3, and antitoxin 2. The inhibition of growth by toxins released by strain 1 is evident when comparing normal growth of Strain 3 (scenario 2) with the growth rate when Strain 1 is nearby (scenario 3). It is demonstrated that toxin activity is dependent on proximity, as shown in (Scenario 4), when the two strains are not in close proximity, growth of Strain 3 is not affected.

FIG. 7 shows exemplary characterization of lysis strains in both plate reader and microfluidic experiments. Amplitude of oscillations of transmitted light in microfluidic experiments can vary due to phenotypic differences in the lysis event. For example, lysis events for strain 1 occur with more force, expelling cell lysate from the trap. However, lysis events for Strain 3 result in more buildup of cell lysate within the microfluidic trap.

FIG. 8 shows deterministic modeling of an exemplary three-strain tri-lysis system.

FIG. 9 shows roughly 1600 individual exemplary microfluidic traps from 4 separate 3-strain co-culture experiments that were analyzed. Microfluidic devices were simultaneously loaded with all 3 engineered strains, resulting in varying initial seeding cell concentrations of each microfluidic trap. Traps that demonstrate transitions between strains were recorded and shown in the above chart. The colors (gray, black, light gray) correspond to Strain 1, Strain 2, and Strain 3 respectively, and represent the dominant strain in the trap at the given time of the experiment.

FIG. 10 shows exemplary strains and gene expression constructs found on each plasmid that can be used according to some embodiments.

FIG. 12 shows exemplary expansion of the function of plasmid stabilizing Toxin-antitoxin modules in multi-strain populations. FIG. 12C is a general plasmid diagram of the RPS strains. FIG. 12D is a plot of batch culture growth rates of the engineered RPS and wild type *E. coli* MG1655 strains (n=3). All strains were started from the same diluted density and under the same growth conditions. FIG. 12E is a set of bar plots depicting the approximate population fractions over time for strain co-cultures seeded at an initial ratio of 1:2 dominant to susceptible (n=8). From top to bottom: (1) strain R (light gray) inhibits strain S (black); (2) strain S (black) inhibits strain P (gray); (3) strain P (gray) inhibits strain R (light gray).

FIG. 13 shows exemplary development of an engineered rock-paper-scissors ecology.

FIG. 14 shows exemplary prolonging of circuit function in the absence of antibiotics.

FIG. 15 shows exemplary RPS effect on a mutable genetic circuit. FIG. 15A illustrates Scenario 1, which depicts a system in which strain 1 was cultured in a 96 well plate for the duration of a single lysis event and passaged every 12 hours. Scenario 2 depicts a system in which strain 1 was cultured in a 96 well plate for the duration of a single lysis event and passaged every 12 hours. On every third passage the next strain of the RPS system is simultaneously added to the culture. FIG. 15B illustrates side-by-side comparison of each scenario (n=12) from FIG. 15A for a duration of 12 passages. Light gray squares represent functioning synchronized population lysis. Gray squares represent loss of synchronized population lysis. Dark gray squares represent loss of synchronized population lysis that was later recovered. Additionally, 12 corresponding samples from each scenario were Sanger sequenced across a 1000 base pair region containing the X174E lysis protein and Lux cassette. A check mark represents a correct sequence, (X) represents an incorrect sequence, and (i) represents an inconclusive sequencing read. All strains were started from the same diluted density and under the same growth conditions.

FIG. 16 shows exemplary verification of Colicin activity in non-lysis strains in 96-well plate reader experiments.

FIG. 17 shows exemplary characterization of strains in both plate reader and microfluidic experiments.

FIG. 18 shows exemplary co-culture incubation of strain pairs in microfluidic devices.

FIG. 20 shows exemplary three-strain co-culture dynamics.

FIG. 22 shows exemplary toxins that can be used according to some embodiments.

FIG. 23 shows exemplary strains that can be used according to some embodiments.

FIG. 24 shows exemplary dynamics of the colicin model for $\gamma_A=1$, $\gamma_C=0.2$, $\alpha=1$, $\beta=1$, $\delta=0.02$, $A_c=1$, $\varepsilon=0.001$.

FIG. 25 shows exemplary dynamics of the colicin model for $\gamma_A=10$, $\gamma_C=1$, $\alpha=10$, $\beta=1$, $\delta=0.02$, $A_c=100$, $\varepsilon=0.001$.

FIG. 26 shows exemplary dynamics of the colicin model for $\gamma_A=10$, $\gamma_C=1$, $\alpha=10$, $\beta=20$, $\delta=0.01$, $A_c=100$, $\varepsilon=0.02$. FIG. 26A shows an exemplary time series. FIG. 26B shows an exemplary map of $P_i$, $Q_i$, $R_i$.

DETAILED DESCRIPTION

Figure 1A:
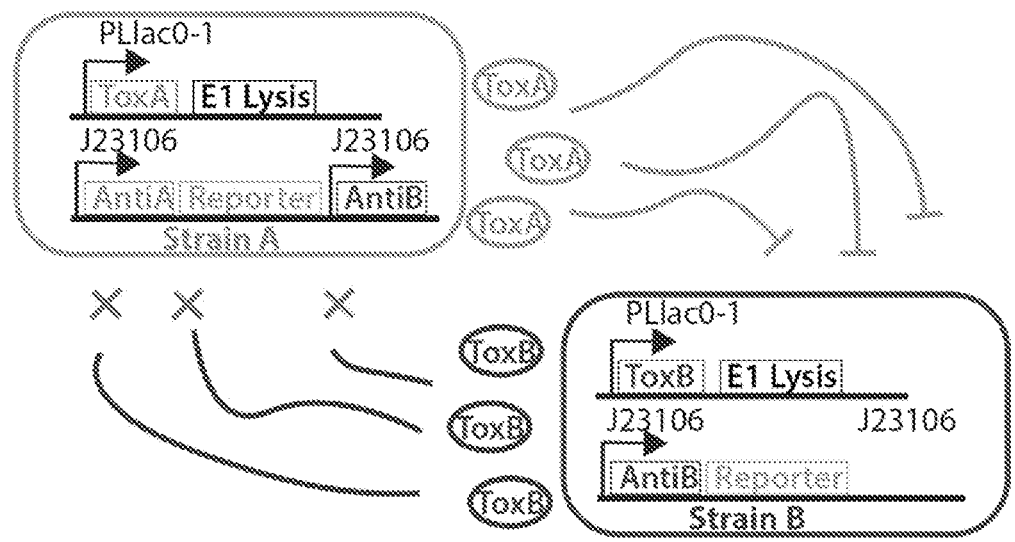
FIG. 1A is a schematic of a two strain system in which strain A has an engineered selective advantage over strain B using a paired toxin antitoxin system. Strain A produces toxin A, antitoxin A, and antitoxin B, while Strain B only produces toxin B and antitoxin B.

Population control is a powerful tool in synthetic biology. Control of microbial communities has been achieved in a few systems over the last decade. Until now, population control can be categorized as two systems. The first, involves a single strain community that exhibits self-limiting population density. The mechanisms behind these systems utilize bacterial quorum sensing systems such as the LuxI/LuxR AHL systems. When cells grow to a certain density and reach 'quorum' they drive the production of a toxic or lysis inducing protein. A second category can be classified as two strain populations in which the strains exhibit predator-prey behavior, oscillatory behavior, or maintain a constant ratio between the two strains. Two strain systems, much like single strain systems rely on quorum sensing in order to drive production of a toxin or lysis protein in either strain. For example, in a predator prey model, a two-way quorum sensing system is used in order to drive production of toxic proteins in the prey, only when the predator is present. Other mechanisms of two strain systems include the use of orthogonal quorum sensing systems such as Lux and Las, to drive oscillating lysis events between two strains, which then oscillate in population density over a duration of time.

Advances in synthetic biology have led to an arsenal of proof-of-principle bacterial circuits that can be leveraged for applications ranging from therapeutics to bio-production. A unifying challenge for most applications is the presence of selective pressures that lead to high mutation rates for engineered bacteria. A common strategy is to develop cloning technologies aimed to increase the fixation time for deleterious mutations in single cells. Provided herein is a complimentary approach that is guided by ecological interactions, whereby cyclical population control is engineered to stabilize the functionality of intracellular gene circuits.

Over the past two decades, synthetic biologists have developed sophisticated molecular circuitry to control the activity of individual cells (see, e.g., M. B. Elowitz, S. Leibler, *Nature* 403, 335 (2000); T. S. Gardner, C. R. Cantor, J. J. Collins, *Nature* 403, 339 (2000); J. Hasty, D. McMillen, J. J. Collins, *Nature* 420, 224 (2002); L. You, R. S. Cox III, R. Weiss, F. H. Arnold, *Nature* 428, 868 (2004); P. E. Purnick, R. Weiss, *Nature reviews Molecular cell biology* 10, 410 (2009); H. H. Wang, et al., *Nature* 460, 894 (2009); S. Ausländer, D. Ausländer, M. Müller, M. Wieland, M. Fussenegger, *Nature* 487, 123 (2012); P. Siuti, J. Yazbek, T. K. Lu, *Nature biotechnology* 31, 448 (2013); T. H. Segall-Shapiro, E. D. Sontag, C. A. Voigt, *Nature biotechnology* 36, 352 (2018)). Over time, such systems inevitably lose function due to evolutionary selection pressures that lead to runaway mutations (see, e.g., F. K. Balagaddé, L. You, C. L. Hansen, F. H. Arnold, S. R. Quake, *Science* 309, 137 (2005)). Approaches to this challenge include the integration of recombinant elements into the host genome (see, e.g., M. Y. Peredelchuk, G. N. Bennett, *Gene* 187, 231 (1997)), or use of plasmid stabilizing elements (see, e.g., K. Gerdes, *Nature Biotechnology* 6, 1402 (1988)), synthetic "kill switches" (see, e.g., C. T. Chan, J. W. Lee, D. E. Cameron, C. J. Bashor, J. J. Collins, *Nature chemical biology* 12, 82 (2016)), or synthetic amino acids (see, e.g., D. J. Mandell, et al., *Nature* 518, 55 (2015); A. J. Rovner, et al., *Nature* 518, 89 (2015); N. Ostrov, et al., *Science* 353, 819 (2016); J. W. Lee, C. T. Chan, S. Slomovic, J. J. Collins, *Nature chemical biology* p. 1 (2018)). Although stabilizing elements can prolong the march to mutation, evolution will inevitably render stabilizing elements ineffective (see, e.g., F. K. Balagaddé, L. You, C. L. Hansen, F. H. Arnold, S. R. Quake, *Science* 309, 137 (2005)). This is particularly true in the case of in vivo applications where delivery of antibiotics is difficult (see, e.g., W. C. Ruder, T. Lu, J. J. Collins, *Science* 333, 1248 (2011); M. A. Fischbach, J. A. Bluestone, W. A. Lim, *Science translational medicine* 5, 179ps7 (2013); D. T. Riglar, P. A. Silver, *Nature Reviews Microbiology* 16, 214 (2018); M. O. Din, et al., *Nature* 536, 81 (2016); A. P. Teixeira, M. Fussenegger, *Current opinion in biotechnology* 47, 59 (2017); B. P. Landry, J. J. Tabor, *Microbiology spectrum* 5 (2017)), or where the interruption of plasmid function is particularly problematic (see, e.g., J. Shong, M. R. J. Diaz, C. H. Collins, *Current Opinion in Biotechnology* 23, 798 (2012)). Described herein is how a small ecology can be engineered to stabilize gene circuit functionality in a manner that complements genetic engineering at the single cell level. Rather than housing stabilizing elements within a single strain, the components of stability are decoupled to different subpopulations of an ecological system such that a runaway mutation in one strain would not cause the stabilizing ecology to fail.

Over the past decade, the field of synthetic biology has advanced from engineering single cells to engineering whole populations. Described herein are three-strain (or more) population control systems and methods that can cycle continuously over a long period of time, which has not previously been achieved. Now, the tri-lysis or multi-lysis system presents a new paradigm of multi-population dynamic control (circuitry within an ecology instead of circuitry within a cell) that opens exciting new possibilities for engineered synthetic systems. These multi-strain systems may enable scientists to achieve complex interactions that may not have been possible previously through the engineering of single cells or single populations.

Disclosed herein are methods, materials and circuits/devices/systems that pertain to a multi-strain 'tri-lysis' or 'multi-lysis' microbial system. A "rock paper scissors" system provides a unique solution to the synthetic biology problems of plasmid loss or mutation of burdensome circuits caused by selective pressures. For example, three strains of *E. coli* can be designed such that each strain could kill, or be killed by one of the other two strains. The resulting "rock-paper-scissors" ecology demonstrates rapid cycling of strains in microfluidic devices and leads to a significant increase in the stability of gene circuit functionality in cell culture. This can be accomplished by the tri-lysis or multi-lysis system because subsequent strains in the tri-lysis or multi-lysis cycle are able to kill off and remove the previous strain population, even if members of that population have mutated the circuit machinery. A 'tri-lysis' or 'multi-lysis' system uses at least three strains of bacteria to complementarily kill off each strain in a cyclical or time-specific manner. For example, strain A is administered and allowed to colonize a region, over a period of time the population may begin to mutate a lysis gene (or any other gene critical to the function of the circuit). As another example, strain A is administered and allowed to colonize a region, over a period of time, the population may begin to mutate a gene of interest (e.g., a gene encoding a heterologous nucleic acid and/or protein, such as, e.g., a therapeutic agent or a payload). Then the introduction of strain B to the ecosystem will allow for the de-population of strain A from the environment, including the mutated members of the population, since they do not carry an immunity for the toxin released by strain B. The use of a system as provided herein as a method to ensure circuit stability has many broadened applications in the fields of therapeutics, production, and sensing applications. As used herein, 'lysis' includes the process of breaking down a cell in a manner that compromises its integrity, as well as any process that kills a cell. Exemplary processes of cellular death encompassed by 'lysis' include, e.g., expression of a lysis gene, the action of a toxin, and the like. In some exemplary embodiments, cell death by toxin can occur through the process of breaking down a cell in a manner that compromises its integrity. In some embodiments, a toxin can initiate cell death without the process of breaking down a cell.

Any of the toxin systems described herein can be replaced by an appropriate cell death system. In some cases, a cell death system can include different pairs of materials (e.g., analogous to a toxin an antitoxin). In yet other cases, the different characteristics of adjacent or sequential bacterial strains can be specific to the prior strain (e.g., a strain can produce a material specific and detrimental for the prior strain, but it is not harmed by such material itself because of some different characteristic in comparison with the prior strain). Additional exemplary pairs of materials that can be used herein are as follows: (i) antibiotic peptides or antimicrobial peptides and host defense peptides (e.g., derived from bacterial, fungal, or animal sources); (ii) systems that include bacteriophages that are specific to a particular to a prior strain that is earlier in the cycle, e.g., sequential delivery of bacteriophages by the bacteria to clear out the previous strain, where the bacteriophages are specific to that previous strain; (iii) systems that include delivery of prodrugs that kill the previous strain upon enzymatic activation by a bacterial protein specific to that previous strain; (iv) systems that include use of different bacterial strains in the cycle where each bacterial strain is a natural predator of the prior strain in the cycle, (for example, *Acinetobacter* (predator) and *E. coli* (prey); (v) a system where each strain produces the same single toxin, but orthogonal quorum sensing is used to activate toxin expression in the previous strain, (e.g., where production of such toxin the prior strain is activated by the presence of another strain (via that other strain's quorum sensing molecules) such as an orthogonal quorum system that initiates production of toxin or lysis protein in the n−1 strain when the n strain is added). Moreover, in some embodiments, instead of an expressed antitoxin, the toxin system can use toxins (or other types of cell death systems, such as those described herein) that are specific to certain bacterial species and not to other strains. In such cases, instead of expressing an antitoxin, the toxin (or other types of cell death systems, such as those described herein)-expressing bacteria can have characteristics that render it insensitive to the toxin (or other types of cell death systems, such as those described herein) it produces that is specific to other strains. For example, one could use different bacterial species that can be targeted with different species-specific toxins (for example, *E coli* followed by *Salmonella*) where the *Salmonella* produces an antimicrobial peptide specific to the *E coli* (for example, colicins only kill *E. coli* and not *Salmonella*). In such systems the analog of the antitoxin is a subsequent strain's inherent insensitivity to the toxin it expresses that is specific to the species of the prior strain. Similarly, other characteristics of a bacterial strain can constitute an appropriate cell death system, such as where one strain is a gram positive bacterium followed by a gram negative bacterial strain that produces as a toxin (or other types of cell death systems, such as those described herein) that is specific to gram positive bacteria, and the analog of the antitoxin in gram negative bacterial is its status of not being a gram positive bacterial strain. In yet other cases, an analog of a bacterial strain's antitoxin may be the presence or absence of certain surface receptors or cellular import/export systems in comparison with other bacterial strains, e.g., an *E. coli* strain could have a receptor necessary for the toxicity of a toxin (or other types of cell death systems, such as those described herein) expressed by the following *E. coli* strain that lacks that receptor, such as *E. coli* expressing SdaC/DcrA receptor (which is necessary for colicin V to be toxic) followed by an *E. coli* strain that does not express SdaC/DcrA receptor but does express colicin V (in such case the non-expression of the SdaC/DcrA receptor in the second strain would be analogous to an antitoxin. In certain embodiments, the foregoing variations on the concept of a toxin system may be combined such that not all bacterial strains in the cycle of the invention need to use the same type of toxin system or combination of toxin/antitoxin pairs. It will be appreciated that any appropriate combination of toxin systems and cell death systems can be used.

Additionally, the tri-lysis or multi-lysis system also ensures specific delivery of a therapeutic protein(s) via engineered strains for a certain amount of time until a subsequent strain in the system is administered, thereby separating the delivery of certain therapeutic protein(s) in space and time, as desired. This capability would not otherwise be available with the engineered bacteria approach to therapy since they colonize the sites of disease for extended periods of time, potentially resulting in a single therapeutic being delivered regardless of whether or not another strain has been introduced into the disease environment, as well as decreasing the colonization ability of future strains due to decreased resources in the disease environment used up by the strain that has been introduced earlier.

As used herein the term "co-culture" or "co-culturing" refers to growing or culturing two or more (e.g., three or more) distinct cell types (e.g., at least two distinct bacterial strains or at least three bacterial strains) within a single recipient or environment (e.g., a single cell culture vessel, a single cell culture plate, a single bioreactor, a single microfluidic device, or a single subject (e.g., in vivo)). In some cases, co-culturing can include growing or culturing two or more (e.g., three or more) distinct cell types at the same time. In some cases, co-culturing can include growing or culturing two or more (e.g., three or more) distinct cell types within a single recipient over a period of time (e.g., growing a first cell type, followed by growing a second cell type, followed by growing a third cell type, where the growing periods may or may not overlap). In some embodiments, co-culturing can include growing or culturing two or more (e.g., three or more) distinct cell types within a single recipient over a period of time, wherein the growing periods of each of the distinct cell types partially overlap.

A variety of different methods known in the art can be used to introduce any of the plasmids disclosed herein into a bacterial cell (e.g., a Gram negative bacterial cell, a Gram positive bacterial cell). Non-limiting examples of methods for introducing nucleic acid into a cell include: transformation, microinjection, electroporation, cell squeezing, sonoporation. Skilled practitioners will appreciate that the plasmids described herein can be introduced into any cell provided herein.

The term "treat(ment)," is used herein to denote delaying the onset of, inhibiting, alleviating the effects of, or prolonging the life of a subject suffering from disease, e.g., a cancer, an infection.

The terms "effective amount" and "amount effective to treat" as used herein, refer to an amount or concentration of a composition or treatment described herein, at least three bacterial strains, utilized for a period of time (including acute or chronic administration and periodic or continuous administration) that is effective within the context of its administration for causing an intended effect or physiological outcome. For example, effective amounts of at least three bacterial strains that express and/or secrete a therapeutic agent (e.g., any of the therapeutic agents described herein)

for use in the present disclosure include, for example, amounts that inhibit the growth of a cancer, e.g., tumor cells and/or tumor-associated immune cells, improve or delay tumor growth, improve survival for a subject suffering from or at risk of developing cancer, and improving the outcome of other cancer treatments. As another example, effective amounts of at least three bacterial strains that express and/or secrete a therapeutic agent (e.g., any of the therapeutic agents described herein) can include amounts that advantageously affect a tumor microenvironment.

The term "subject" (used interchangeably with "patient") is used throughout the specification to describe an animal, human or non-human, to whom treatment according to the methods of the present disclosure is provided. Veterinary applications are clearly anticipated by the present disclosure. The term includes but is not limited to birds, reptiles, amphibians, and mammals, e.g., humans, other primates, pigs, rodents, such as mice and rats, rabbits, guinea pigs, hamsters, horses, cows, cats, dogs, sheep and goats. Preferred subjects are humans, farm animals, and domestic pets such as cats and dogs. In some embodiments, the subject is a human. For example, in any of the methods described herein, the subject can be at least 2 years or older (e.g., 4 years or older, 6 years or older, 10 years or older, 13 years or older, 16 years or older, 18 years or older, 21 years or older, 25 years or older, 30 years or older, 35 years or older, 40 years or older, 45 years or older, 50 years or older, 60 years or older, 65 years or older, 70 years or older, 75 years or older, 80 years or older, 85 years or older, 90 years or older, or 2, 3, 4, 5, 6, 7, 8, 9, 10, 12, 13, 14, 15, 16, 18, 20, 21, 24, 25, 27, 28, 30, 33, 35, 37, 39, 40, 42, 44, 45, 48, 50, 52, 55, 60, 65, 70, 75, 80, 85, 90, 95, 96, 97, 98, 99, 100, 101, 102, 103, or 104 years old).

The term "population" when used before a noun means two more of the specific noun. For example, the phrase "a population of bacterial strains" can mean three or more bacterial strains.

The term "cancer" refers to cells having the capacity for unlimited autonomous growth. Examples of such cells includes cells having an abnormal state or condition characterized by rapidly proliferating cell growth. The term is meant to include cancerous growths, e.g., tumors, oncogenic processes, metastatic tissues, malignantly transformed cells.

A metastatic tumor can arise from a multitude of primary tumor types, including but not limited to those of prostate, colon, lung, breast, bone and liver origin. Metastases develop, e.g., when tumor cells shed, detach or migrate from a primary tumor, enter the vascular system, penetrate into surrounding tissues, and grow to form tumors at distinct anatomical sites, e.g., sites separate from a primary tumor.

Individuals considered at risk for developing cancer may benefit from the present disclosure, e.g., because prophylactic treatment can begin before there is any evidence and/or diagnosis of the disorder. Individuals "at risk" include, e.g., individuals exposed to carcinogens, e.g., by consumption (e.g., by inhalation and/or ingestion), at levels that have been shown statistically to promote cancer in susceptible individuals. Also included are individuals at risk due to exposure to ultraviolet radiation, or their environment, occupation, and/or heredity, as well as those who show signs of a precancerous condition such as polyps. Similarly, individuals in very early stages of cancer or development of metastases (i.e., only one or a few aberrant cells are present in the individual's body or at a particular site in an individual's tissue) may benefit from such prophylactic treatment.

Skilled practitioners will appreciate that a subject can be diagnosed, e.g., by a medical professional, e.g., a physician or nurse (or veterinarian, as appropriate for the subject being diagnosed), as suffering from or at risk for a condition described herein, e.g., cancer, using any method known in the art, e.g., by assessing a subject's medical history, performing diagnostic tests, and/or by employing imaging techniques.

Skilled practitioners will also appreciate that treatment need not be administered to a subject by the same individual who diagnosed the subject (or the same individual who prescribed the treatment for the subject). Treatment can be administered (and/or administration can be supervised), e.g., by the diagnosing and/or prescribing individual, and/or any other individual, including the subject her/himself (e.g., where the subject is capable of self-administration).

Also provided herein are methods of generating a recombinant bacterial cell that can express and/or secrete a therapeutic agent (e.g., any of the therapeutic agents described herein) that include: a nucleic acid encoding the therapeutic agent to be produced in the recombinant bacterial cell, and optionally, a plasmid-stabilizing element, wherein the plasmid-stabilizing element is a toxin/antitoxin system; and culturing the recombinant bacterial cell under conditions sufficient for the expression and/or secretion of the toxin, antitoxin and therapeutic agent. Also provided herein are methods of generating a recombinant bacterial cell that can express and/or secrete a therapeutic agent (e.g., any of the therapeutic agents described herein) that include: introducing into a bacterial cell a lysis plasmid, an activator plasmid, a nucleic acid encoding the therapeutic agent to be produced in the recombinant bacterial cell, and a plasmid-stabilizing element; and culturing the recombinant bacterial cell under conditions sufficient for the expression and/or secretion of the toxin, antitoxin and therapeutic agent. In some embodiments, the plasmid stabilizing element is a toxin/antitoxin system. In some embodiments, the plasmid stabilizing element may be expressed in the lysis plasmid. In some embodiments, the toxin/antitoxin system may produce a toxin/antitoxin pair and a different antitoxin of another strain. In some embodiments, the introducing step can include introducing into a recombinant bacterial cell an expression vector including a nucleic acid encoding the therapeutic agent to be produced into a recombinant bacterial cell. In some embodiments, the bacterial cell is an *E. coli* cell, a *S. typhimurium* cell, or a bacterial variant thereof. In some embodiments, the bacterial strain is a Gram-negative bacterial strains, e.g., a *Salmonella* strain, an *Acetobacter* strain, an *Enterobacter* strain, a *Fusobacterium* strain, a *Helicobacter* strain, a *Klebsiella* strain, or an *E. coli* strain. In some embodiments, the bacterial strain is a Gram-positive bacterial strain, e.g., a *Actinomyces* strain, a *Bacillus* strain, a *Clostridium* strain, an *Enterococcus* strain, or a *Lactobacillus* strain. In some embodiments, the at least three bacterial strains are all Gram negative bacterial strains or all Gram positive strains. In some embodiments, at least one of the at least three bacterial strains is a Gram negative bacterial strain. In some embodiments, at least one of the at least three bacterial strains is a Gram positive bacterial strain.

Methods of culturing bacterial cells are well known in the art, and examples of such methods are provided in the Examples. Bacterial cells can be maintained in vitro under conditions that favor proliferation and growth. Briefly, bacterial cells can be cultured by contacting a bacterial cell (e.g., any bacterial cell described herein) with a cell culture medium that includes the necessary growth factors and supplements to support cell viability and growth.

Methods of introducing nucleic acids and expression vectors into a bacterial cell are known in the art. For example, transformation can be used to introduce a nucleic acid into a bacterial cell. In some embodiments, the bacterial cell can include any of the plasmids described herein.

Provided herein is a bacterial strain comprising a toxin system (also called a toxin/antitoxin system) including a toxin/antitoxin pair (e.g., the antitoxin is effective against the toxin). In some embodiments, the toxin system can produce a toxin/antitoxin pair and a different antitoxin of another strain. A toxin system can be included (e.g., encoded) in any appropriate location. In some embodiments, a toxin system can be included in the genome of a bacterial strain. In some embodiments, a toxin system can be included in one or more plasmids. In some embodiments, a toxin system can be partially included in the genome and partially included in one or more plasmids. In some embodiments, a toxin system can be included on a lysis plasmid. In some embodiments, a toxin system can be included on an activator plasmid. In some embodiments, a toxin system can be included on a third plasmid. A third plasmid can be any appropriate plasmid. In some embodiments, a toxin system can be genetically engineered, or naturally occurring in a bacterial strain. In some embodiments, the toxin system can be inserted into a bacterial strain.

The toxin system can be any appropriate toxin system. In some embodiments, a toxin system includes a first toxin/first antitoxin pair (e.g., the first antitoxin is effective against the first toxin) and a second antitoxin. In some embodiments, a bacterial strain encoding such a toxin system does not encode a second toxin against which the second antitoxin is effective.

In some embodiments, the toxin/antitoxin system may be type I toxin/antitoxin system, type II toxin/antitoxin system, type III toxin/antitoxin system, type IV toxin/antitoxin system, type V toxin/antitoxin system, or type VI toxin/antitoxin system. Non-limiting examples of type I toxin/antitoxins include Hok and Sok, Fst and RNAII, TisB and IstR, LdrB and RdlD, FlmA and FlmB, Ibs and Sib, TxpA/BrnT and RatA, SymE and SymR, and XXCV2162 and ptaRNA1. Non-limiting examples of type II toxin/antitoxins include CcdB and CcdA; ParE and ParD; MaxF and MazE; yafO and yafN; HicA and HicB; Kid and Kis; Zeta and Epsilon; DarT and DarG. For example, type III toxin/antitoxin systems include interactions between a toxic protein and an RNA antitoxin, e.g., ToxN and ToxI. For example, type IV toxin/antitoxin systems include toxin/antitoxin systems that counteract the activity of the toxin and the two proteins do not directly interact. An example of a type V toxin/antitoxin system is GoT and GoS. An example of a type VI toxin/antitoxin system is SocA and SocB.

In some embodiments, the toxin/antitoxin system may be replaced by a bacteriocin/immunity protein system. As used herein, the term "toxin/antitoxin" includes both the toxin/antitoxin systems described herein above, including bacteriocin/immunity protein systems. Bacteriocins are ribosomally-synthesized peptides that are produced by bacteria. Bacteriocins are non-toxic to bacteria that produce the bacteriocins and are generally toxic to other bacteria. Typically, a bacterium that produces a bacteriocin also produces an immunity protein that can inhibit or prevent the toxic effect of the bacteriocin. Accordingly, a bacteriocin and a corresponding immunity protein can be used in an analogous fashion to a toxin/antitoxin system as described herein. Most bacteriocins are extremely potent, and exhibit antimicrobial activity at nanomolar concentrations. By way of example, eukaryotic produced microbials have $10^2$ to $10^3$ lower activities (Kaur and Kaur (2015) Front. Pharmacol. doi: 10.3389/fphar.2015.00272).

Non-limiting examples of bacteriocins that can be included in any of the bacteria strains, systems and methods described herein include: acidocin, actagardine, agrocin, alveicin, aureocin, aureocin A53, aureocin A70, bisin, carnocin, carnocyclin, caseicin, cerein, circularin A, colicin, curvaticin, divercin, duramycin, enterocin, enterolysin, epidermin/gallidermin, erwiniocin, gardimycin, gassericin A, glycinecin, halocin, klebicin, lactosin S, lactococcin, lacticin, leucoccin, lysostaphin, macedocin, mersacidin, mesentericin, microbisporicin, microcin S, mutacin, nisin, paenibacillin, planosporicin, pediocin, pentocin, plantaricin, pneumocyclicin, pyocin, reutericin 6, sakacin, salivaricin, sublancin, subtilin, sulfolobicin, tasmancin, thuricin 17, trifolitoxin, variacin, vibriocin, warnericin, cytolisin, pyocyn S2, colicin A, colicin E1, microcin MccE492, and warnerin.

In some embodiments, the bacteriocin is obtained from a Gram negative bacteria (e.g., microcins (e.g., microcin V of E coli, subtilosin A from B. subtillis), colicins (E.g., colicin produced by and toxic to certain strains of E. coli (e.g., colicin A, colicin B, colicin E1, colicin E3, colicin E5, and colicin E7), tailocins (e.g., R-type pyocins, F-type pyocins)).

In some embodiments, the bacteriocin is obtained from a Gram positive bacteria (e.g., class I bacteriocins (e.g., Nisin, lantibiotics), class II bacteriocins (e.g., IIa pediocin-like bacteriocins, IIb bacteriocins (e.g., lactococcin G), IIc cyclic peptides (e.g., enterocin AS-48), IId single peptide bacteriocins (e.g., aureocin A53), class III bacteriocins (e.g., Ma (e.g., bacteriolysins), and IIIb (which kill the target by disrupting the membrane potential), or class IV bacteriocins (e.g., complex bacteriocins containing lipid or carbohydrate moieties)).

Any of the bacterial systems described herein can further include a lysis plasmid and an activator plasmid. The lysis plasmid and activator plasmid can each independently include any appropriate components. The lysis plasmid and the activator plasmid can be based on any appropriate existing plasmid.

The lysis plasmid can include a lysis gene, an activatable promoter, and optionally a reporter gene. In some embodiments, the lysis gene can be operably linked to the activatable promoter. In some embodiments, the reporter gene can be operably linked to the activatable promoter. In some embodiments, both the lysis gene and the reporter gene can be operably linked to a single copy of the activatable promoter. In some embodiments, both the lysis gene and the reporter gene can be independently operably linked to separate copies of the activatable promoter.

The activator plasmid can include an activator gene, optionally a degradation tag, and optionally a reporter gene. In some embodiments, the activatable promoter in the activator plasmid is the same activatable promoter as in the lysis plasmid. In some embodiments, the activatable promoter in the activator plasmid is activated by the same mechanism as the activatable promoter in the lysis plasmid (e.g., by the same quorum-sensing molecule, directly or indirectly). The activator gene can, in some embodiments, promote the accumulation of a quorum-sensing molecule (e.g., the activator gene can encode a protein in the biosynthetic pathway of the quorum-sensing molecule). In some embodiments, the activator gene is operatively linked to an activatable promoter.

A quorum-sensing molecule can be any appropriate quorum-sensing molecule. In some embodiments, the quorum-sensing molecule can be an N-acyl homoserine lactone (AHL). In some embodiments, the quorum-sensing molecule can be a homoserine lactone (HSL) or a homolog thereof. In some embodiments, a quorum-sensing molecule can be an auto-inducing peptide (AIP) from a Gram-positive bacteria. Other quorum-sensing molecules are known in the art.

An activatable promoter can be any appropriate activatable promoter. In some embodiments, the activatable promoter can be activated, directly or indirectly, by the quorum-sensing molecule. In this way, in some embodiments, a feedback loop can be set up such that the presence of the quorum-sensing molecule drives accumulation of the quorum-sensing molecule. In some embodiments of any of the bacterial strains described herein, the activatable promoter is an AHL-activatable promoter. In some embodiments of any of the bacterial strains described herein, the activatable promoter is a LuxR-AHL activatable luxI promoter. In some embodiments, the activatable promoter is a RpaR-AHL activatable RpaI promoter. In some embodiments, the activatable promoter is a TraR-HSL activatable traI promoter. Other activatable promoters are known in the art.

A lysis gene can be any appropriate lysis gene. In some embodiments of any of the bacterial strains described herein, the lysis gene is E from a bacteriophage ΦX174. In some embodiments, the lysis gene is the col E1 Lysis protein. Other lysis genes are known in the art.

An activator gene can be any appropriate activator gene. In some embodiments, the activator gene is a LuxI. In some embodiments, the activator gene is a RpaI. In some embodiments, the activator gene is TraI Other activator genes are known in the art.

In some embodiments, the quorum-sensing molecule is an AHL, the activatable promoter is a LuxR-AHL activatable luxI promoter, and the activator gene is a LuxI.

In some embodiments, the quorum-sensing molecule is an AHL, the activatable promoter is a RpaR-AHL activatable RpaI promoter, and the activator gene is a RpaI.

In some embodiments, the quorum-sensing molecule is a HSL, the activatable promoter is a TraR-HSL activatable traI promoter, and the activator gene is a TraI.

A reporter gene can be any appropriate reporter gene. In some embodiments, the reporter gene can be a fluorescent protein (e.g., green fluorescent protein (GFP), cyan fluorescent protein (CFP), red fluorescent protein (RFP) or a variant thereof). In some embodiments, the reporter gene can be an enzyme (e.g., β-galactosidase). Other reporter genes are known in the art.

A degradation tag can be any appropriate degradation tag. In some embodiments, the degradation tag is an ssrA-LAA degradation tag. Other degradation tags are known in the art.

In some embodiments, a bacterial strain can encode an additional nucleic acid and/or protein (e.g., a heterologous nucleic acid and/or protein (e.g., a payload)) operably linked to a promoter. In some embodiments, the additional nucleic acid and/or protein (e.g., a heterologous nucleic acid and/or protein) operably linked to a promoter is encoded on a plasmid. The plasmid can be any appropriate plasmid. In some embodiments, the plasmid be a lysis plasmid or an activator plasmid. An additional nucleic acid and/or protein can be any appropriate nucleic acid and/or protein. For example, an additional nucleic acid and/or protein can be a therapeutic agent. Any appropriate promoter can be used. In some embodiments, the promoter can be an activatable promoter. In some embodiments, the promoter can be a promoter that is activated, directly or indirectly, by the quorum sensing molecule. In some embodiments, the promoter can be an activatable promoter as described above. In some embodiments, the promoter can be a constitutive promoter. Many constitutive promoters are known in the art. A therapeutic agent can be any appropriate therapeutic agent. In some embodiments, a therapeutic agent can be any of the therapeutic agents described herein. For example, in some embodiments, a therapeutic agent can be selected from the group consisting of: an inhibitory nucleic acid (e.g., siRNA, shRNA, miRNA, or antisense (e.g., antisense DNA, antisense RNA, or a synthetic analog)), a cytokine, an enzyme, a peptide hormone, a fusion protein, a clotting factor, and an antibody or antigen-binding fragment thereof. In some embodiments, an additional nucleic acid and/or protein (e.g., a heterologous nucleic acid and/or protein) may be secreted, exocytosed, or otherwise exported from a bacterial strain as described herein. In some embodiments, an additional nucleic acid and/or protein (e.g., a heterologous nucleic acid and/or protein) may be released upon lysis of a bacterial strain as described herein. In some embodiments, an additional nucleic acid and/or protein (e.g., a heterologous nucleic acid and/or protein) may be displayed on the surface a bacterial strain as described herein.

In some embodiments, an additional nucleic acid and/or protein (e.g., payload) encoded by a bacterial strain can act upon an additional nucleic acid and/or protein (or a product thereof) encoded by a previous (e.g., immediately previous) bacterial strain in a tri-lysis or multi-lysis system. In some embodiments, a payload of an $m^{th}$ bacterial strain (e.g., one of the n bacterial strains) can produce an $m^{th}$ substrate by directly or indirectly acting upon the substrate of the $(m-1)^{th}$ bacterial strain, and the payload of the first bacterial strain can act upon a substrate present in the environment where the n bacterial strains are cultured.

Provided herein are systems that include two or more (e.g., three or more) bacterial strains as described herein. In some embodiments, a system as described can be a multi-lysis system. In some embodiments, such systems can include 3 bacterial strains. In some embodiments, such systems can include 4, 5, 6, 7, 8, 9, 10, or more bacterial strains.

In some embodiments, when an activator plasmid/lysis plasmid system is used, the quorum-sensing molecule of each of the bacterial strains in the system can be different. In some embodiments, the quorum-sensing molecule of each of the bacterial strains in the system can have no or substantially no effect on the activatable promoter of the lysis gene of another strain. In some embodiments, the quorum sensing molecule can be the same in each of the bacterial strains. In some embodiments, the lysis plasmid of each of the bacterial strains can be copies of the same plasmid. In some embodiments, activator plasmid of each of the bacterial strains can be copies of the same plasmid. In some embodiments, the lysis plasmid of each of the bacterial strains can be different plasmids. In some embodiments, the activator plasmid of each of the bacterial strains can be different plasmids. In some embodiments, two or more (e.g., 3, 4, 5, 6, 7, 8, 9, 10, or more) of bacterial strains can be metabolically competitive. In some embodiments, the bacterial strains can be selected from E. coli, S. typhimurium, or a bacterial variant thereof. In some embodiments none of the bacterial strains have a growth advantage compared to another strain in the system.

In some systems that include more than one bacterial strain, all bacterial strains can encode an additional nucleic acid and/or protein (e.g., a heterologous nucleic acid and/or protein). In some systems that include more than one bacterial strain, no bacterial strains can encode an additional nucleic acid and/or protein (e.g., a heterologous nucleic acid and/or protein). In some systems that include more than one bacterial strain, some bacterial strains can encode an additional nucleic acid and/or protein (e.g., a heterologous nucleic acid and/or protein), while some do not. In systems that include more than one bacterial strain encoding an additional nucleic acid and/or protein (e.g., a heterologous nucleic acid and/or protein), the encoded additional nucleic acid and/or protein of each such bacterial strain is independently selected (e.g., all such bacterial strains can encode a different additional nucleic acid and/or protein, all such bacterial strains can encode the same additional nucleic acid and/or protein, or some such bacterial strains can encode the same additional nucleic acid and/or protein, while others encode one or more different additional nucleic acids and/or proteins).

Figure 12A:
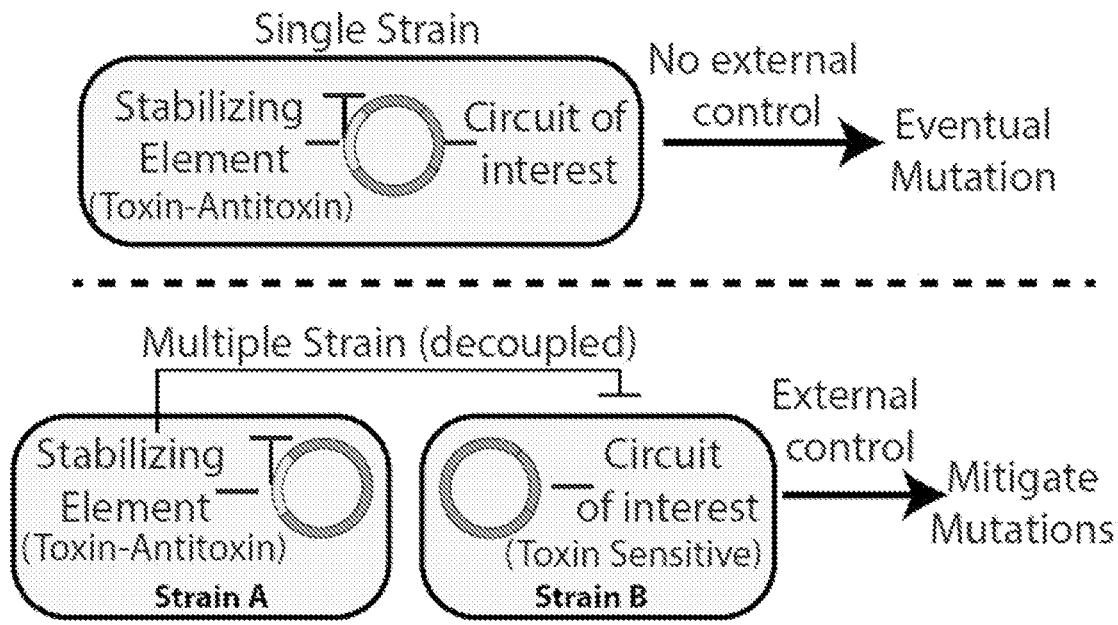
FIG. 12A shows that in monoclonal populations, plasmid stabilizing toxin-antitoxin modules enable the killing of progeny cells that have mutated or lost the antitoxin gene. When expanded to a system of n>1 strains, the strain that contains the TA module maintains self-stabilizing function, while gaining the added ability to kill any strain that does not have the antitoxin.
Figure 12B:
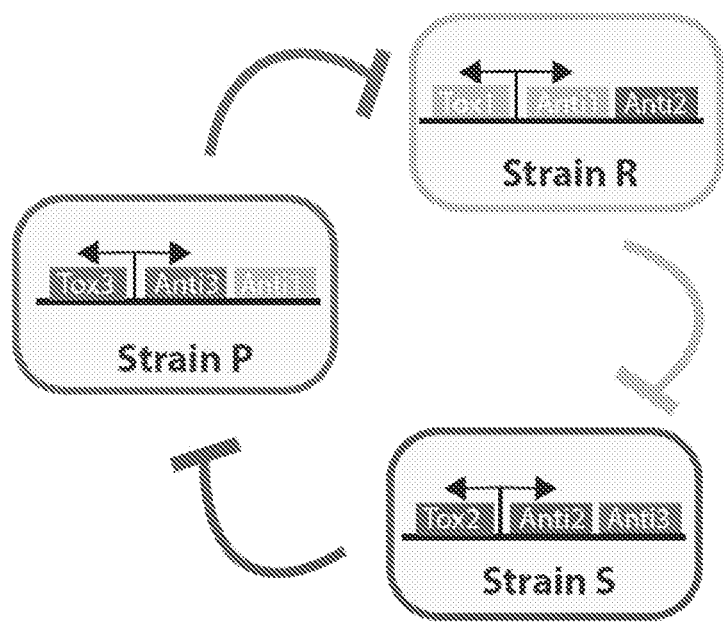
FIG. 12B is a diagram showing that each strain produced its own toxin-antitoxin pair, while also producing the antitoxin of the following strain enabling sequential strain inhibition. Strain R contained toxin 1, antitoxin 1, and antitoxin 2. Strain P contained toxin 3, antitoxin 3, and antitoxin 1. Strain S contained toxin 2, antitoxin 2, and antitoxin 3.

A multi-lysis system can have include appropriate number of strains. A tri-lysis system can include three strains (this can also be called a "rock, paper, scissors" (RPS) ecology). In such a system, each strain can encode a toxin/antitoxin pair and a secondary antitoxin, such that the strain can kill a previous strain in the cycle (e.g., the secondary antitoxin encoded by the previous strain is not effective against the toxin of the instant strain, and the secondary antitoxin encoded by the instant strain is effective against the toxin of the previous strain) and be killed by a subsequent strain in a cycle (e.g., the secondary antitoxin encoded by the instant strain is not effective against the toxin of the subsequent strain, and the secondary antitoxin encoded by the subsequent strain is effective against the secondary toxin of the instant strain. An exemplary tri-lysis system is shown in FIG. 12B.

In some embodiments, a multi-lysis system can include at least three strains (e.g., at least four, five, six, or more strains). In some embodiments, a multi-lysis system can have n strains, including a first strain, a second strain, and an $n^{th}$ strain. In some such cases, the second strain to the $n^{th}$ strain can each have a previous strain, based on the numbering of the strains (e.g., the previous strain for the second strain is the first strain). In some such cases, each of the second through $n-1^{th}$ strains have a subsequent strain (e.g., the subsequent strain of the $n-1^{th}$ strain is the $n^{th}$ strain). In some such cases, each of the second strain through the $n^{th}$ strain encodes a first toxin that is effective against the previous strain, a first antitoxin to the first toxin, and a second antitoxin to the toxin produced by the previous strain. In some such cases, the first strain encodes a first toxin that is effective against the $n^{th}$ strain, a first antitoxin to the first toxin, and a second antitoxin to the toxin produced by the $n^{th}$ strain. The value of n can be any appropriate value. In some embodiments, n can be at least 3 (e.g., 3, 4, 5, 6, 7, 8, 9, 10, 11, 12, or more).

Also provided herein are methods of co-culturing at least three (e.g., at least four, at least five, at least six, at least seven, at least eight, at least nine, at least ten, at least eleven, at least twelve, 2, 3, 4, 5, 6, 7, 8, 9, 10, 11 or 12) bacterial strains (e.g., any of the bacterial strains described herein). In some embodiments, co-culturing can include inoculating a culture with at least two (e.g., at least three, at least four, at least five, at least six, at least seven, at least eight, at least nine, at least ten, at least eleven, at least twelve, 2, 3, 4, 5, 6, 7, 8, 9, 10, 11 or 12) bacterial strains (e.g., any of the bacterial strains described herein), initially inoculated at a ratio of inoculation. A ratio of inoculation can be any appropriate ratio. In some embodiments, a ratio of inoculation of at least one bacterial strain to at least one other bacterial strain can be 1:1 (e.g., for three strains, the ratio can be 1:1:1). In some embodiments, a ratio of inoculation of at least one bacterial strain to at least one other bacterial strain can be 1:2 (e.g., for three strains, the ratio can be 1:2:m, 2:1:m, 1:m:2, 2:m:1, m:1:2, m:2:1). In some embodiments, a ratio of inoculation of at least one bacterial strain to at least one other bacterial strain can be 1:5 (e.g., for three strains, the ratio can be 1:5:m, 5:1:m, 1:m:5, 5:m:1, m:1:5, m:5:1). In some embodiments, a ratio of inoculation of at least one bacterial strain to at least one other bacterial strain can be 1:10 (e.g., for three strains, the ratio can be 1:10:m, 10:1:m, 1:m:10, 10:m:1, m:1:10, m:10:1). The value of m can be any appropriate value. For example, in some embodiments, m can be 1, 2, 3, 4, 5, 6, 7, 8, 9, 10, or more.

In some embodiments, co-culturing can include, sequentially, beginning a culture with a first bacterial strain, culturing for a period of time, adding a second bacterial strain, and culturing for a period of time. As used herein, sequentially can include a particular order of culturing two or more strains. In some embodiments, sequentially can include completely overlapping periods of time (e.g., growth periods), partially overlapping periods of time, and/or non-overlapping periods of time. In some embodiments, one or more growth periods can overlap while other growth periods in the same system can be non-overlapping. In some embodiments, all growth periods in a given system can be overlapping or non-overlapping. In some embodiments, one or more additional bacterial strains can be sequentially cultured in the same manner as the second bacterial strain. In this way, a sequential co-culture can be performed with partially overlapping growth periods. In some embodiments, the first bacterial strain can be added to the culture containing the second bacterial strain and cultured for a period of time, and optionally followed, in an alternating fashion, by the second bacterial strain and the first bacterial strain. In this way, an alternating co-culture can be performed with partially overlapping growth periods. Additions of bacterial strains can be performed at any appropriate inoculation ratio, where the inoculation ratio is based on the population(s) of cells in the culture. For example, in some embodiments, the inoculation ratio can be any of the inoculation ratios described herein.

In some embodiments, co-culturing can include, sequentially, beginning a culture with a first bacterial strain, culturing for a period of time, adding a second bacterial strain, culturing for a period of time, adding a third bacterial strain, and culturing for a period of time. In some embodiments, one or more additional bacterial strains can be sequentially cultured in the same manner as the second and bacterial strains. In this way, a sequential co-culture can be performed with partially overlapping growth periods. In some embodiments, a cyclical co-culture with partially overlapping growth periods can be performed by adding the first bacterial strain to the culture containing the third (or the one or more additional bacterial strains), cultured for a period of time, followed by the sequential addition and culturing of the second bacterial strain, the third bacterial strain, and the one or more additional bacterial strains, in the same order as was carried out initially. Additions of bacterial strains can be performed at any appropriate inoculation ratio, where the inoculation ratio is based on the population(s) of cells in the culture. For example, in some embodiments, the inoculation ratio can be any of the inoculation ratios described herein.

In some embodiments, a bacterial strain that is added to a culture can reduce the population of or eliminate one or more bacterial strains present in the culture. For example, a second bacterial strain can, in some embodiments, reduce the population of or eliminate the first bacterial culture.

In some embodiments, a period of time for the culture (e.g., a growth period) of any of the bacterial strains described herein can be between 1 hour to 35 days (e.g., 1 hour to 30 days, 1 hour to 28 days, 1 hour to 26 days, 1 hour to 25 days, 1 hour to 24 days, 1 hour to 22 days, 1 hour to 20 days, 1 hour to 18 days, 1 hour to 16 days, 1 hour to 14 days, 1 hour to 12 days, 1 hour to 10 days, 1 hour to 8 days, 1 hour to 7 days, 1 hour to 6 days, 1 hour to 5 days, 1 hour to 4 days, 1 hour to 72 hours, 1 hour to 70 hours, 1 hour to 68 hours, 1 hour to 66 hours 1 hour to 64 hours, 1 hour to 62 hours, 1 hour to 60 hours, 1 hour to 58 hours, 1 hour to 56 hours, 1 hour to 54 hours, 1 hour to 52 hours, 1 hour to 50 hours, 1 hour to 48 hours, 1 hour to 46 hours, 1 hour to 44 hours, 1 hour to 40 hours, 1 hour to 38 hours, 1 hour to 36 hours, 1 hour to 34 hours, 1 hour to 32 hours, 1 hour to 30 hours, 1 hour to 28 hours, 1 hour to 26 hours, 1 hour to 24 hours, 1 hour to 22 hours, 1 hour to 20 hours, 1 hour to 18 hours, 1 hour to 16 hours, 1 hour to 14 hours, 1 hour to 12 hours, 1 hour to 10 hours, 1 hour to 8 hours, 1 hour to 6 hours, 1 hour to 4 hours, 1 hour to 2 hours, 2 hours to 35 days, 2 hours to 30 days, 2 hours to 28 days, 2 hours to 26 days, 2 hours to 25 days, 2 hours to 24 days, 2 hours to 22 days, 2 hours to 20 days, 2 hours to 18 days, 2 hours to 16 days, 2 hours to 14 days, 2 hours to 12 days, 2 hours to 10 days, 2 hours to 8 days, 2 hours to 7 days, 2 hours to 6 days, 2 hours to 5 days, 2 hours to 4 days, 2 hours to 72 hours, 2 hours to 70 hours, 2 hours to 68 hours, 2 hours to 66 hours 2 hours to 64 hours, 2 hours to 62 hours, 2 hours to 60 hours, 2 hours to 58 hours, 2 hours to 56 hours, 2 hours to 54 hours, 2 hours to 52 hours, 2 hours to 50 hours, 2 hours to 48 hours, 2 hours to 46 hours, 2 hours to 44 hours, 2 hours to 40 hours, 2 hours to 38 hours, 2 hours to 36 hours, 2 hours to 34 hours, 2 hours to 32 hours, 2 hours to 30 hours, 2 hours to 28 hours, 2 hours to 26 hours, 2 hours to 24 hours, 2 hours to 22 hours, 2 hours to 20 hours, 2 hours to 18 hours, 2 hours to 16 hours, 2 hours to 14 hours, 2 hours to 12 hours, 2 hours to 10 hours, 2 hours to 8 hours, 2 hours to 6 hours, 2 hours to 4 hours, 4 hours to 35 days, 4 hours to 30 days, 4 hours to 28 days, 4 hours to 26 days, 4 hours to 25 days, 4 hours to 24 days, 4 hours to 22 days, 4 hours to 20 days, 4 hours to 18 days, 4 hours to 16 days, 4 hours to 14 days, 4 hours to 12 days, 4 hours to 10 days, 4 hours to 8 days, 4 hours to 7 days, 4 hours to 6 days, 4 hours to 5 days, 4 hours to 4 days, 4 hours to 74 hours, 4 hours to 70 hours, 4 hours to 68 hours, 4 hours to 66 hours 4 hours to 64 hours, 4 hours to 64 hours, 4 hours to 60 hours, 4 hours to 58 hours, 4 hour to 56 hours, 4 hours to 54 hours, 4 hours to 54 hours, 4 hours to 50 hours, 4 hours to 48 hours, 4 hours to 46 hours, 4 hours to 44 hours, 4 hours to 40 hours, 4 hours to 38 hours, 4 hours to 36 hours, 4 hours to 34 hours, 4 hours to 34 hours, 4 hours to 30 hours, 4 hours to 28 hours, 4 hours to 26 hours, 4 hours to 24 hours, 4 hours to 24 hours, 4 hours to 20 hours, 4 hours to 18 hours, 4 hours to 16 hours, 4 hours to 14 hours, 4 hours to 14 hours, 4 hours to 10 hours, 4 hours to 8 hours, 4 hours to 6 hours, 6 hours to 35 days, 6 hours to 30 days, 6 hours to 28 days, 6 hours to 26 days, 6 hours to 25 days, 6 hours to 24 days, 6 hours to 22 days, 6 hours to 20 days, 6 hours to 18 days, 6 hours to 16 days, 6 hours to 14 days, 6 hours to 12 days, 6 hours to 10 days, 6 hours to 8 days, 6 hours to 7 days, 6 hours to 6 days, 6 hours to 5 days, 6 hours to 4 days, 6 hours to 76 hours, 6 hours to 70 hours, 6 hours to 68 hours, 6 hours to 66 hours 6 hours to 64 hours, 6 hours to 66 hours, 6 hours to 60 hours, 6 hours to 58 hours, 6 hours to 56 hours, 6 hours to 54 hours, 6 hours to 56 hours, 6 hours to 50 hours, 6 hours to 48 hours, 6 hours to 46 hours, 6 hours to 44 hours, 6 hours to 40 hours, 6 hours to 38 hours, 6 hours to 36 hours, 6 hours to 34 hours, 6 hours to 36 hours, 6 hours to 30 hours, 6 hours to 28 hours, 6 hours to 26 hours, 6 hours to 24 hours, 6 hours to 26 hours, 6 hours to 20 hours, 6 hours to 18 hours, 6 hours to 16 hours, 6 hours to 14 hours, 6 hours to 16 hours, 6 hours to 10 hours, 6 hours to 8 hours, 12 hours to 35 days, 12 hours to 30 days, 12 hours to 28 days, 12 hours to 26 days, 12 hours to 25 days, 12 hours to 24 days, 12 hours to 22 days, 12 hours to 20 days, 12 hours to 18 days, 12 hours to 16 days, 12 hours to 14 days, 12 hours to 12 days, 12 hours to 10 days, 12 hours to 8 days, 12 hours to 7 days, 12 hours to 6 days, 12 hours to 5 days, 12 hours to 4 days, 12 hours to 72 hours, 12 hours to 70 hours, 12 hours to 68 hours, 12 hours to 66 hours 12 hours to 64 hours, 12 hours to 62 hours, 12 hours to 60 hours, 12 hours to 58 hours, 12 hours to 56 hours, 12 hours to 54 hours, 12 hours to 512 hours, 12 hours to 50 hours, 12 hours to 48 hours, 12 hours to 46 hours, 12 hours to 44 hours, 12 hours to 40 hours, 12 hours to 38 hours, 12 hours to 36 hours, 12 hours to 34 hours, 12 hours to 312 hours, 12 hours to 30 hours, 12 hours to 28 hours, 12 hours to 26 hours, 12 hours to 24 hours, 12 hours to 22 hours, 12 hours to 20 hours, 12 hours to 18 hours, 12 hours to 16 hours, 12 hours to 14 hours, 1 day to 35 days, 1 day to 30 days, 1 day to 28 days, 1 day to 26 days, 1 day to 25 days, 1 day to 24 days, 1 day to 22 days, 1 day to 20 days, 1 day to 18 days, 1 day to 16 days, 1 day to 14 days, 1 day to 12 days, 1 day to 10 days, 1 day to 8 days, 1 day to 6 days, 1 day to 5 days, 1 day to 4 days, 1 day to 3 days, 1 day to 2 days, 2 days to 35 days, 2 days to 30 days, 2 days to 28 days, 2 days to 26 days, 2 days to 25 days, 2 days to 24 days, 2 days to 22 days, 2 days to 20 days, 2 days to 18 days, 2 days to 16 days, 2 days to 15 days, 2 days to 14 days, 2 days to 12 days, 2 days to 10 days, 2 days to 8 days, 2 days to 6 days, 2 days to 4 days, 2 days to 3 days, 4 days to 35 days, 4 days to 30 days, 4 days to 28 days, 4 days to 26 days, 4 days to 25 days, 4 days to 24 days, 4 days to 22 days, 4 days to 20 days, 4 days to 18 days, 4 days to 16 days, 4 days to 15 days, 4 days to 14 days, 4 days to 12 days, 4 days to 10 days, 4 days to 8 days, 4 days to 6 days, 7 days to 35 days, 7 days to 30 days, 7 days to 28 days, 7 days to 26 days, 7 days to 25 days, 7 days to 24 days, 7 days to 22 days, 7 days to 20 days, 7 days to 18 days, 7 days to 16 days, 7 days to 15 days, 7 days to 14 days, 7 days to 12 days, 7 days to 10 days, 7 days to 8 days, 14 days to 35 days, 14 days to 30 days, 14 days to 28 days, 14 days to 26 days, 14 days to 25 days, 14 days to 24 days, 14 days to 22 days, 14 days to 20 days, 14 days to 18 days, 14 days to 16 days, 14 days to 15 days, 21 days to 35 days, 21 days to 30 days, 21 days to 28 days, 21 days to 26 days, 21 days to 25 days, 21 days to 24 days, 21 days to 22 days, 28 days to 35 days, or 28 days to 30 days; 1 hour, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 6 days, 7 days, 8 days, 10 days, 12 days, 14 days, 16 days, 18 days, 20 days, 21 days, 22 days, 24 days, 25 days, 26 days, 28 days, 30 days, 32 days, 34 days or 35 days).

The length of a cycle can be modulated by an appropriate method. For example, the length of a cycle can be regulated by using strains that lyse at different ODs. Cell lysis can also be regulated by tuning the internal circuitry of the quorum sensing components, e.g., tuning of AHL degradation, tuning lysis of protein degradation, tuning of promoters to increase or decrease expression of molecules involved in the quorum sensing circuitry.

Various methods known in the art can be used to determine whether the quorum threshold is reached. For example, the quorum threshold can be measured using traditional protein quantification methods to measure the level of AHL expression in the culture medium. The quorum threshold can also be measured using reporter proteins driven by the luxI promoter. In some embodiments, the reporter protein is a fluorescent protein, a bioluminescent luciferase reporter, a secreted blood/serum or urine reporter (e.g., secreted alkaline phosphatase, soluble peptides, Gaussian luciferase).

Various methods are known in the art to determine and/or measure cell lysis. For example, cell lysis can be determined phenotypically using a microscopy by the change in intensity of transmitted light and/or absorbance at various wavelengths including 600 nm light. In some embodiments, bacterial cell lysis is synchronized. In other embodiments, bacterial cell lysis is not synchronized. Synchronized lysis can be measured via optical density at 600 nm absorbance ($OD_{600}$) in a plate reader or other quantitative instruments.

In some embodiments of any of the bacterial strains described herein, the therapeutic agent is selected from the group consisting of: an inhibitory nucleic acid (e.g., siRNA, shRNA, miRNA, or antisense), a cytokine, an enzyme, a peptide hormone, a fusion protein, a clotting factor, a toxin (e.g., a diphtheria toxin, a gelonin toxin, anthrax toxin), an antimicrobial peptide, and an antibody or antigen-binding fragment thereof. Non-limiting examples of cytokines include filgrastim, an interleukin, an interferon (e.g., IFNb-1b), and a transforming growth factor beta. Non-limiting examples of enzymes include asparaginase, glucarpidase, β-glucocerebrosidase, elosulfase alfa, asfotase-alfa, and sebelipase alfa. Non-limiting examples of peptide hormones include metreleptin, parathyroid hormone, and insulin. Non-limiting examples of fusion proteins include albiglutide, dulaglutide, a factor IX Fc-fusion, and a factor VIII Fc-fusion. Non-limiting examples of clotting factors include factor IX, factor VIII, and factor XIII A subunit. Non-limiting examples of antibodies or antigen-binding fragments thereof include belimumab, ipilimumab, belatacept, brentuximab, afilbercept, pertuzumab, raxibacumab, trastuzumab, golimumab, bevacizumab, obinutuzumab, ramucirumab, siltuximab, rituximab, adalimumab, vedolizumab, pembrolizumab, blintumomab, nivolumab, secukinumab, dinutuximab, alirocumab, evolocumab, idarucizumab, mepolizumab, daratumumab, necitumumab, elotuzumab, obiltoxaximab, ixekizumab, reslizumab, infliximab, atezolizumab, daclizumab, ustekinumab and etanercept. In some embodiments, the therapeutic agent can be a C1 esterase inhibitor. In some embodiments, the therapeutic agent can be a von Willebrand factor.

Provided herein are pharmaceutical compositions comprising any one or more of the bacterial strains as described herein. In some embodiments, the pharmaceutical composition is formulated for in situ drug delivery.

Provided herein is also a system that can include a co-culture of at least two bacterial strains as described herein (e.g., at least three, at least four, at least five, at least six, at least seven, at least eight, at least nine, at least ten, at least eleven, at least twelve, 2, 3, 4, 5, 6, 7, 8, 9, 10, 11, 12).

Provided herein is also a drug system comprising one or more systems as described herein.

Provided herein is also a periodic drug system comprising one or more systems as described herein.

Provided herein is also a kit comprising one or more bacterial strains as described herein.

Provided herein is also a kit comprising one or more systems as described herein.

Provided herein are methods of treating a disease in a subject (e.g., a cancer, an infectious disease, an autoimmune disorder, a genetic disorder, a metabolic disorder). Exemplary methods include administering to a subject in need of treatment therapeutically effective amounts of any one or more of the bacterial strains described herein, or any one or more of the pharmaceutical compositions described herein, or any one or more of the systems described herein to thereby treat the disease in the subject. For example, provided herein is a method of treating a disease in a subject comprising administering to the subject a therapeutically effective amount of each of n bacterial strains including at least a first bacterial strain, a second bacterial strain, and an nth bacterial strain. Each of the second bacterial strain to the $n^{th}$ bacterial strain can have a previous bacterial strain. The value of n can be at least 3. Each of then strains can include a toxin system as described herein. In some cases, the toxin system each of the second through $n^{th}$ bacterial strains independently produces a first toxin/first antitoxin pair, wherein the first toxin is effective against the previous bacterial strain, and a second antitoxin from a second toxin/second antitoxin pair produced by the previous bacterial strain. The toxin system of the first bacterial strain can produce a third toxin/third antitoxin pair, wherein the third toxin is effective against the nth bacterial strain, and a fourth antitoxin from a fourth toxin/antitoxin pair produced by the $n^{th}$ bacterial strain. In some embodiments, one or more of the n strains can include lysis plasmid described herein and/or an activator plasmid as described herein. The value of n can be any appropriate value. In some embodiments, n can be at least 3 (e.g., 3, 4, 5, 6, 7, 8, 9, 10, 11, 12, or more).

Provided herein are methods of treating a disease in a subject (e.g., a cancer, an infectious disease, an autoimmune disorder, a genetic disorder, a metabolic disorder). Exemplary methods include administering to a subject in need of treatment therapeutically effective amounts of a pharmaceutical composition including any one or more of the bacterial strains described herein, or any one or more of the pharmaceutical compositions described herein, or any one or more of the systems described herein to thereby treat the disease in the subject. For example, provided herein is a method of treating a disease in a subject comprising administering to the subject a therapeutically effective amount of m pharmaceutical compositions, each comprising one or more of n bacterial strains including at least a first bacterial strain, a second bacterial strain, and an nth bacterial strain. Each of the second bacterial strain to the $n^{th}$ bacterial strain can have a previous bacterial strain. The value of n can be at least 3. The value of m can be at least 3. The value of m can be equal to the value of n. Each of the n strains can include a toxin system as described herein. In some cases, the toxin system each of the second through $n^{th}$ bacterial strains independently produces a first toxin/first antitoxin pair, wherein the first toxin is effective against the previous bacterial strain, and a second antitoxin from a second toxin/second antitoxin pair produced by the previous bacterial strain. The toxin system of the first bacterial strain can produce a third toxin/third antitoxin pair, wherein the third toxin is effective against the nth bacterial strain, and a fourth antitoxin from a fourth toxin/antitoxin pair produced by the $n^{th}$ bacterial strain. In some embodiments, one or more of the n strains can include lysis plasmid described herein and/or an activator plasmid as described herein. The value of n can be any appropriate value. In some embodiments, n can be at least 3 (e.g., 3, 4, 5, 6, 7, 8, 9, 10, 11, 12, or more). The value of m can be any appropriate value. In some embodiments, m can be at least 3 (e.g., 3, 4, 5, 6, 7, 8, 9, 10, 11, 12, or more).

Administering can include any appropriate schedule. For example, administering can include a schedule that is effective for co-culturing as described herein. In some embodiments, administering can include a schedule that is effective for co-culturing including partially overlapping growth periods, as described herein. In methods described herein, administering can include administering at least two (e.g., at least three) bacterial strains to the subject.

Also provided herein are methods of treating a disease in a subject (e.g., a cancer, an infectious disease, an autoimmune disorder, a genetic disorder, a metabolic disorder) that include administering to a subject in need of treatment therapeutically effective amounts of a first bacterial strain (e.g., any of the bacterial strains described herein) for a first period of time, administering therapeutically effective amounts of a second bacterial strain (e.g., any of the bacterial strains described herein) for a second period of time, and administering therapeutically effective amounts of a third bacterial strain (e.g., any of the bacterial strains described herein) for a third period of time.

In some embodiments of any of the methods described herein, the n bacterial strains (e.g., the first, the second and the third bacterial strains) are different bacterial strains that each express and/or secrete a different therapeutic agent (e.g., any of the therapeutic agents described herein). In some embodiments of any of the methods described herein, the n bacterial strains (e.g., the first, the second and the third bacterial strains) are different bacterial strains that each express and/or secrete the same therapeutic agent (e.g., any of the therapeutic agents described herein). In some embodiments of any of the methods described herein, the n bacterial strains (e.g., the first, the second and the third bacterial strains) are different bacterial strains that may or may not each express and/or secrete the same or a different therapeutic agent (e.g., any of the therapeutic agents described herein) (e.g., two strains can express and/or secrete one therapeutic agent, and a third strain can express and/or secrete a different therapeutic agent). The value of n can be any appropriate value. In some embodiments, n can be at least 3 (e.g., 3, 4, 5, 6, 7, 8, 9, 10, 11, 12, or more).

In some embodiments of any of the methods described herein, the n bacterial strains (e.g., the first, the second and the third bacterial strains) do not express or secrete a therapeutic agent (e.g., any of the therapeutic agents described herein). In some embodiments of any of the methods described herein, then bacterial strains (e.g., the first, the second and the third bacterial strains) produce a bacteriocin (e.g., any of the bacteriocins described herein). The value of n can be any appropriate value. In some embodiments, n can be at least 3 (e.g., 3, 4, 5, 6, 7, 8, 9, 10, 11, 12, or more).

In some embodiments of any of the methods described herein, administering includes a cycle of treatment, and the cycle of treatment is repeated at least two times (e.g., at least 3 times, at least 4 times, at least 5 times, at least 6 times, at least 7 times, at least 8 times, at least 9 times, at least 10 times, at least 11 times, at least 12 times).

In some embodiments of any of the methods described herein, the first, the second, and the third time period can be between 1 hour and 35 days (e.g., between 1 hour and 28 days, between 1 hour and 21 days, between 1 hour and 14 days, between 1 hour and 7 days, between 1 hour and 5 days, between 1 hour and 3 days, between 1 hour and 2 days, between 1 hour and 1 day, between 1 day and 35 days, between 1 day and 28 days, between 1 day and 21 days, between 1 day and 14 days, between 1 day and 7 days, between 1 day and 5 days, between 1 day and 3 days, between 1 day and 2 days, between 7 days and 35 days, between 7 days and 28 days, between 7 days and 14 days, between 7 days and 10 days, between 14 days and 35 days, between 14 days and 28 days, between 14 days and 21 days, between 21 days and 35 days, between 21 days and 28 days, between 21 days and 24 days, or between 28 days and 35 days).

In some aspects of any of the methods described herein, the first, the second and the third time period of time are similar in length, e.g., the same length of time.

In other aspects of any of the methods described herein, the first, the second and the third time period of time are not the same length of time. In some aspects, the first and the third period of times are the same. In some aspects, the first and the third period of times are not the same. In some aspects, the first and the second period of times are the same. In some aspects, the first and the second period of times are not the same. In some aspects, the second and the third period of times are the same. In some aspects, the second and the third period of times are not the same.

In some embodiments of any of the methods described herein, a growth period can be between 1 hour and 35 days (e.g., between 1 hour and 28 days, between 1 hour and 21 days, between 1 hour and 14 days, between 1 hour and 7 days, between 1 hour and 5 days, between 1 hour and 3 days, between 1 hour and 2 days, between 1 hour and 1 day, between 1 day and 35 days, between 1 day and 28 days, between 1 day and 21 days, between 1 day and 14 days, between 1 day and 7 days, between 1 day and 5 days, between 1 day and 3 days, between 1 day and 2 days, between 7 days and 35 days, between 7 days and 28 days, between 7 days and 14 days, between 7 days and 10 days, between 14 days and 35 days, between 14 days and 28 days, between 14 days and 21 days, between 21 days and 35 days, between 21 days and 28 days, between 21 days and 24 days, or between 28 days and 35 days).

In some aspects of any of the methods described herein, the growth period of each of the n bacterial strains is about the same. In some embodiments of any of the methods described herein, the growth period of one or more of the n bacterial strains is different from one or more of the other bacterial strains.

In some embodiments of any of the methods described herein, administering includes administering sequentially each of the at least three bacterial strains to the subject. In some embodiments of any of the methods described herein, administering includes administering sequentially each of the n bacterial strains to the subject.

In some embodiments of any of the methods described herein, administering includes administering each of the at least three bacterial strains simultaneously. In some embodiments of any of the methods described herein, administering includes administering each of the n bacterial strains simultaneously.

In some embodiments of any of the methods described herein, the subject has a cancer or an infection.

In some embodiments wherein the subject has a cancer, the cancer can be, e.g., a primary tumor, or a metastatic tumor.

In some embodiments, the cancer is a non-T-cell-infiltrating tumor.

In some embodiments of any of the methods described herein, the cancer is selected from the group consisting of: glioblastoma, squamous cell carcinoma, breast cancer, colon cancer, hepatocellular cancer, melanoma, neuroblastoma, pancreatic cancer, and prostate cancer. Treatment of multiple cancer types at the same time is contemplated by and within the present disclosure.

In some instances, the subject having the cancer may have previously received cancer treatment (e.g., any of the cancer treatments described herein).

In some embodiments of any of the methods described herein, the subject has an infection (e.g., an infectious disease). In some embodiments of any of the methods described herein, the infection is caused by an infectious agent selected from the group consisting of: *Camphylobacter jejuni, Clostridium botulinium, Escherichia coli, Listeria monocytogenes* and *Salmonella*.

In some embodiments, strain A, or a first strain, is first introduced to the site of culture or colonization, for a specified period of time, to deliver its payload of therapeutic protein(s). Then a second strain, strain B, can be introduced, which produces a toxin to kill and remove strain A, and then Strain B can deliver its payload of therapeutic protein(s) for a specified period of time. Then a third strain, strain C, can be introduced, which will kill and remove strain B, and then deliver its payload of therapeutic protein(s) for a specified period of time. Then strain A can be re-introduced to repeat the cycle. This system is not limited to a three strain system, it can potentially be composed of more than three strains where each strain produces a toxin with the ability to kill another strain in the system which does not have the anti-toxin, thereby allowing a cyclical system (composed of four, five, six, or more strains).

Administering may be performed, e.g., at least once (e.g., at least 2-times, at least 3-times, at least 4-times, at least 5-times, at least 6-times, at least 7-times, at least 8-times, at least 9-times, at least 10-times, at least 11-times, at least 12-times, at least 13-times, or at least 14-times) a week. Also contemplated are monthly treatments, e.g., administering at least once per month for at least 1 month (e.g., at least two, three, four, five, or six or more months, e.g., 12 or more months), and yearly treatments (e.g., administration once a year for one or more years). Administration can be via any art-known means, e.g., intravenous, subcutaneous, intraperitoneal, oral, topical, and/or rectal administration, or any combination of known administration methods.

As used herein, treating includes "prophylactic treatment", which means reducing the incidence of or preventing (or reducing the risk of) a sign or symptom of a disease (e.g., a cancer, an infection) in a subject at risk of developing a disease (e.g., a cancer, an infection). The term "therapeutic treatment" refers to reducing signs or symptoms of a disease, e.g., reducing cancer progression, reducing severity of a cancer, and/or re-occurrence in a subject having cancer, reducing inflammation in a subject, reducing the spread of an infection in a subject.

The methods described herein can be used in cancer treatments. Non-limiting examples of cancer include: acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, Burkitt Lymphoma, carcinoma of unknown primary origin, cardiac tumor, cervical cancer, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hairy cell leukemia, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, leukemia, lip and oral cavity cancer, liver cancer, lobular carcinoma in situ, lung cancer, lymphoma, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and para-nasal sinus cancer, nasopharyngeal cancer, neuroblastoma, non-Hodgkin lymphoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms' tumor.

For example, any of the methods described herein can be used to treat a cancer selected from the group consisting of: glioblastoma, squamous cell carcinoma, breast cancer, colon cancer, hepatocellular cancer, melanoma, neuroblastoma, pancreatic cancer, and prostate cancer.

The term "therapeutic agent" refers to a therapeutic treatment that involves administering to a subject a therapeutic agent that is known to be useful in the treatment of a disease, e.g., a cancer, an infection. For example, a cancer therapeutic agent can decrease the size or rate of tumor growth. In other instances, a cancer therapeutic agent can affect the tumor microenvironment.

Non-limiting examples of therapeutic agents that can be expressed and/or secreted in any of the bacterial strains described herein include: an inhibitory nucleic acid (e.g., a microRNA (miRNA), a short hairpin RNA (shRNA), a small interfering RNA (siRNA), an antisense), a cytokine, an enzyme, a peptide hormone, a fusion protein, a clotting factor, a toxin (e.g., a diphtheria toxin, a gelonin toxin, anthrax toxin), an antimicrobial peptide, and an antibody or antigen-binding fragment thereof.

In some instances, the therapeutic agent is a therapeutic polypeptide. In some instances, the therapeutic polypeptide includes one or more polypeptides (e.g., 2, 3, 4, 5, or 6). In some instances, the therapeutic polypeptide is conjugated to a toxin, a radioisotope, or a drug via a linker (e.g., a cleavable linker, a non-cleavable linker).

In some instances, the therapeutic agent is cytotoxic or cytostatic to a target cell.

The phrase "cytotoxic to a target cell" refers to the inducement, directly or indirectly, in the death (e.g., necrosis or apoptosis) of the target cell. For example, a target cell can be a cancer cell (e.g., a cancerous cell or a tumor-associated immune cell (e.g., macrophage) or an infected cell.

The phrase "cytostatic to a target cell" refers to direct or indirect decrease in the proliferation (cell division) of a target cell in vivo or in vitro. When a therapeutic agent is cytostatic to a target cell, the therapeutic agent can, e.g., directly or indirectly result in cell cycle arrest of the target cell. In some examples, the therapeutic agent that is cytostatic can reduce the number of target cells in a population of cells that are in S phase (as compared to the number of target cells in a population of cells that are in S phase prior to contact with the therapeutic agent). In some instances, the therapeutic agent that is cytostatic can reduce the percentage of target cells in S phase by at least 20% (e.g., at least 40%, at least 60%, at least 80%) as compared to the percentage of target cells in a population of cells that in S phase prior to contact with the therapeutic agent.

Also provided herein are pharmaceutical compositions that include at least three (e.g., 3, 4, 5, 6, 7, 8, 9, or 10) of any of the bacterial strains described herein that express and/or secrete at least one of any of the therapeutic agents described herein.

The pharmaceutical compositions can be formulated in any matter known in the art. The pharmaceutical compositions are formulated to be compatible with their intended route of administration (e.g., intravenous, subcutaneous, intraperitoneal, rectal, topical, or oral). In some embodiments, the pharmaceutical composition is administered directly into the site of disease or diseased tissue, e.g., administered into the tumor, administered into the infected tissue. In some embodiments, administering is targeting, e.g., the pharmaceutical composition includes a targeting moiety (e.g., a targeting protein or peptide).

In some embodiments, the pharmaceutical compositions can include a pharmaceutically acceptable carrier (e.g., phosphate buffered saline). Pharmaceutical compositions can include any appropriate additional agents, for example, excipients, fillers, disintegrants, lubricants, glidants, binders, solubilizers, bulking agents, buffers, surfactants, chelating agents, adjuvants, and the like, as are known in the art. Single or multiple administrations of formulations can be given depending on for example: the dosage (i.e., number of bacterial cells per mL) and the frequency as required and tolerated by the subject. The dosage, frequency and timing required to effectively treat a subject may be influenced by the age of the subject, the general health of the subject, the severity of the disease, previous treatments, and the presence of comorbidities (e.g., diabetes, cardiovascular disease). The formulation should provide a sufficient quantity of active agent to effectively treat, prevent or ameliorate conditions, diseases or symptoms. Toxicity and therapeutic efficacy of compositions can be determined using conventional procedures in cell cultures, pre-clinical models (e.g., mice, rats, or monkeys), and humans. Data obtained from in vitro assays and pre-clinical studies can be used to formulate the appropriate dosage of any compositions described herein (e.g., pharmaceutical compositions described herein).

Efficacy of any of the compositions described herein can be determined using methods known in the art, such as by the observation of the clinical signs of a disease (e.g., tumor size, presence of metastasis).

Also provided herein are kits that include at least three of any of the bacterial strains described herein that express and/or secrete at least one of any of the therapeutic agents described herein. In some instances, the kits can include instructions for performing any of the methods described herein. In some embodiments, the kits can include at least one dose of any of the pharmaceutical compositions described herein. The kits described herein are not so limited; other variations will be apparent to one of ordinary skill in the art.

EXAMPLES

The invention is further described in the following examples, which do not limit the scope of the invention described in the claims.

Materials and Methods
Strains and Plasmids.

Circuit strains were cultured in lysogeny broth (LB) media with 50 µg ml$^{-1}$ kanamycin and 34 µg ml$^{-1}$ chloramphenicol for strains containing ColE1 origin and p15A origin plasmids respectively, along with 0.2% glucose, or 50 µg ml$^{-1}$ spectinomycin for non-lysis colicin strains in a 37° shaking incubator. Exemplary toxins are shown in FIG. 4 and FIG. 22. Exemplary strains are shown in FIG. 5 and FIG. 23. Exemplary plasmids used in this study are described in FIG. 11 and FIG. 21. Colicin E3 and E5 genes were assembled with overlapping PCR of gene blocks (IDT). Colicin V genes were obtained from PCR off of wild-type Colicin V *E. coli* (obtained from Dr. Joe Pogliano and Dr. Roberto Kolter). All plasmids were constructed by Gibson assembly followed by transformation into DH5α (Thermofisher) chemically competent *E. coli*. Plasmids were verified by Sanger sequencing before transformation into *E. coli* strain MG1655.

For toxin co-culture experiments, wild type MG1655 *E. coli* strains were seeded from a −80° glycerol stock into 2 ml LB and incubated in a 37° C. shaking incubator. After cells reached an OD600 between 0.2-0.4, 5 µl culture was added to 200 µl fresh media in a standard Falcon tissue culture 96-well flat bottom plate. Additionally, 5 µl of the purified colicin lysate was added to each well. Cultures were grown at 37° shaking for 19 hours and their optical density at 600 nm absorbance was measured every 5 min with a Tecan Infinite M200 Pro. Fluorescence measurements were taken every 5 min at 485 nm excitation 520 nm emission, 433 nm excitation 475 nm emission, and 590 nm excitation 630 nm emission, for GFP, CFP, and RFP respectively.

Microfluidics and Microscopy.

The microfluidic devices and experiment preparation protocols used in this study are similar to those reported elsewhere (see, e.g., Prindle, et al. A sensing array of radically coupled genetic biopixels. Nature, 481(7379):39-44, 2012.). All microfluidic experiments were performed in a side-trap array device with bacteria growth chambers approximately 100×80 µm in area and approximately 1.2 µm in height. The appropriate *E. coli* strain was seeded from a −80° glycerol stock into 5 ml LB with the appropriate antibiotics. For lysis strain, 0.2% glucose was added to the media. After growth for 8-12 h at 37° in a shaking incubator, the culture was diluted 100-fold into 25 ml of the same medium in a 50 ml Erlenmeyer flask and grown until reaching an OD between 0.4-0.6 (Plastibrand 1.5 ml cuvettes were used). Once the above OD was reached cells were concentrated by centrifugation at 5,000 g for 1 min and resuspended in 10 µl of LB media with 0.75% Tween-20 and the appropriate antibiotics. This concentrate was used to vacuum-load the cells for single-strain experiments. For multi-strain experiments, cultures were first normalized to the same OD$_{600}$ prior to centrifugation and mixed at either 1:1, 1:2, 4:6, or 1:5 ratio for 2 strain experiments, or mixed at a 1:1:1 ratio for 3 strain experiments prior to vacuum loading. The control of media flow into the microfluidic device was gravity driven. Chip temperatures were maintained at 37□ with a plexiglass incubation chamber encompassing the entire microscope.

For sequential loading experiments the initial two strains were prepared as described for 2 strain experiments. Subsequent strains were then seeded from a −80° glycerol stock into 5 ml LB with 0.2% glucose and the appropriate antibiotics. After growth for 8-12 h at 37° in a shaking incubator, the culture was diluted 100-fold into 100 ml of the same medium in a 500 ml Erlenmeyer flask and grown until reaching an OD between 0.1-0.4 (Plastibrand 1.5 ml cuvettes were used). Once the above OD was reached cells were concentrated by centrifugation at 5,000 g for 5 min and resuspended in 1 ml of LB media with 0.075% Tween-20 and the appropriate antibiotics. Cells were then loaded into a second or third inlet port of the microfluidic device, and introduced into the traps by flick loading. Flick loading was done by flicking the tygon tubing leading to the inlet of the microfluidic device, in order to disturb the laminar flow within the device to allow cells to be washed into the microfluidic traps. The control of media flow into the microfluidic device was gravity driven. For the duration of the experiment LB media containing 34 μg ml$^{-1}$ chloramphenicol was used. Chip temperatures were maintained at 37° C. with a plexiglass incubation chamber encompassing the entire microscope.

For microscopy a Nikon Eclipse TI epifluorescent microscope with phase-contrast-based imaging was used. Image acquisition was performed with a Photometrics CoolSnap cooled CCD camera and Nikon Elements software. For 10× magnification experiments, phase-contrast images were taken with 50-100 μs exposure times. Fluorescence exposure times were 100 μs at 30% intensity, 300 μs at 30% intensity and 100 μs at 30% intensity for gfp, rfp, and cfp respectively. Images were taken either every 3 minutes or every 6 minutes for the duration of the experiment (1-4 days). For 60× magnification experiments, phase-contrast images were taken with 20-50 μs exposure times. Fluorescence exposure times were 50 μs at 30% intensity, 200 μs at 30% intensity and 50 μs at 30% intensity for gfp, rfp, and cfp respectively. Images were taken either every 3 minutes or every 6 minutes for the duration of the experiment (1-4 days). For sequential loading experiments, imaging was paused for the duration of strain loading.

Population Estimates and Growth Rate of RPS Strains.

Population estimates for the approximate population fractions in the co-culture mixtures were made in the following way. Fluorescence channel image stacks from the dominant strain were converted to 8-bit in ImageJ (Process>Binary>Make Binary). Z-axis profiles were then taken for the cell incubating region (Image>Stacks Plot Z-axis Profile) and the values were normalized to 1 by dividing by the max value. The max-value of the fluorescence time-series trace for the dominant strain was used as a standard for accumulated fluorescence of a culture with 100% dominant strain alone. Susceptible strain fractions were estimated by subtracting the normalized dominant strain values from 1. The values were then normalized to the initial cell fractions corresponding to roughly 70% dominant strain and 30% susceptible strain. Initial cell fractions were counted manually using the ImageJ cell counter plugin.

For growth rate experiments, the appropriate *E. coli* strains were seeded from a −80° glycerol stock into 2 ml LB and the appropriate antibiotics and incubated in a 37° C. shaking incubator. After cells reached an OD$_{600}$ of 0.1, 1 ml culture was added to a 125 ml Erlenmeyer flask containing 25 ml fresh media with appropriate antibiotics and left shaking at 270 rpm. Once the samples reached an OD$_{600}$ of 0.1 samples were taken every 10 minutes and measured at OD$_{600}$ using a DU 740 Life Science Uv/vis spectrophotometer.

Passage and Plate Reader Experiments.

For passage experiments, the appropriate *E. coli* strains were seeded from a −80° glycerol stock into 2 ml LB with 0.2% glucose with the appropriate antibiotics and incubated in a 37° C. shaking incubator. At an OD$_{600}$ of 0.2, 10 μl culture was added to 190 μl fresh media containing appropriate antibiotics in a standard Falcon tissue culture 96-well flat bottom plate. Cells were incubated at 37° shaking in a Tecan Infinite M200 Pro, each passage was grown for 12 hours and the optical density at 600 nm absorbance was measured every 10 min. Fluorescence measurements were taken every 10 min at 485 nm excitation 520 nm emission, 433 nm excitation 475 nm emission, and 590 nm excitation 630 nm emission for GFP, CFP, and RFP respectively. After 12 hours, the OD$_{600}$ of each sample was diluted to 0.2 and 10 μl of each sample was passaged into 190 μl of fresh media containing appropriate antibiotics in a new culture plate. For cycling strains, the appropriate *E. coli* strains were grown immediately before the appropriate passage from a −80° glycerol stock, as described before, to an OD$_{600}$ of 0.2, and 10 μl of the culture containing the new strain was then added to the appropriate passage before measurements were taken. Samples for Sanger sequencing were collected at the end of each passage. For analysis, a successful lysis event was defined as an OD$_{600}$ growth curve that had a defined peak followed by a drop in OD.

Plate Reader Fluorescence.

For well-plate experiments, the appropriate *E. coli* strains were seeded from a −80° glycerol stock into 2 ml LB with 0.2% g glucose and the appropriate antibiotics and incubated in a 37□ shaking incubator. After cells reached an OD600 between 0.2-0.6, 5 μl culture was added to 200 μl fresh media containing appropriate antibiotics in a standard Falcon tissue culture 96-well flat bottom plate. Cells were incubated at 37° shaking and imaged every 5 min in a Tecan Infinite M200 Pro. Dilutions were grown for 19 hours and their optical density at 600 nm absorbance was measured every 5 min. Fluorescence measurements were taken every 5 min at 485 nm excitation 520 nm emission, 433 nm excitation 475 nm emission, and 590 nm excitation 630 nm emission, for GFP, CFP, and RFP respectively. The resulting curves were used to estimate OD600 of lysis and growth dynamics of each strain.

Example 1—Two Strain System

The first stage of development consisted of engineering a selective advantage. A strategy to give one strain a selective advantage over the other was initially investigated.

Figure 1B:
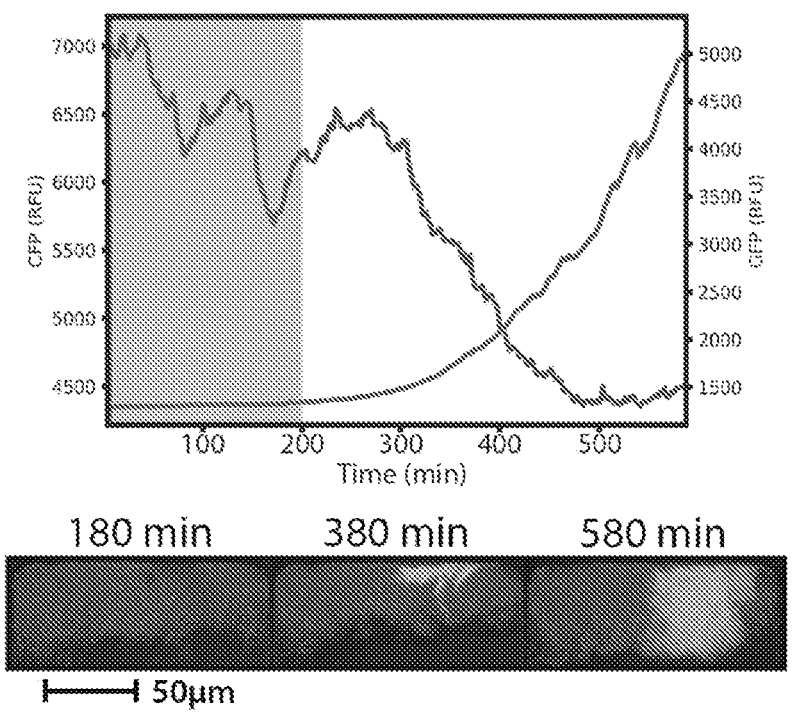
FIG. 1B shows exemplary growth of strain B from FIG. 1A in a microfluidic cell chamber. After introduction of strain A via pulse loading (grey shaded region), fraction of Strain A increases exponentially while fraction of strain B decays. The images below the plot show a composite of phase contrast and fluorescence at the indicated time points. AU, arbitrary fluorescence units (background subtracted).
Figure 11:
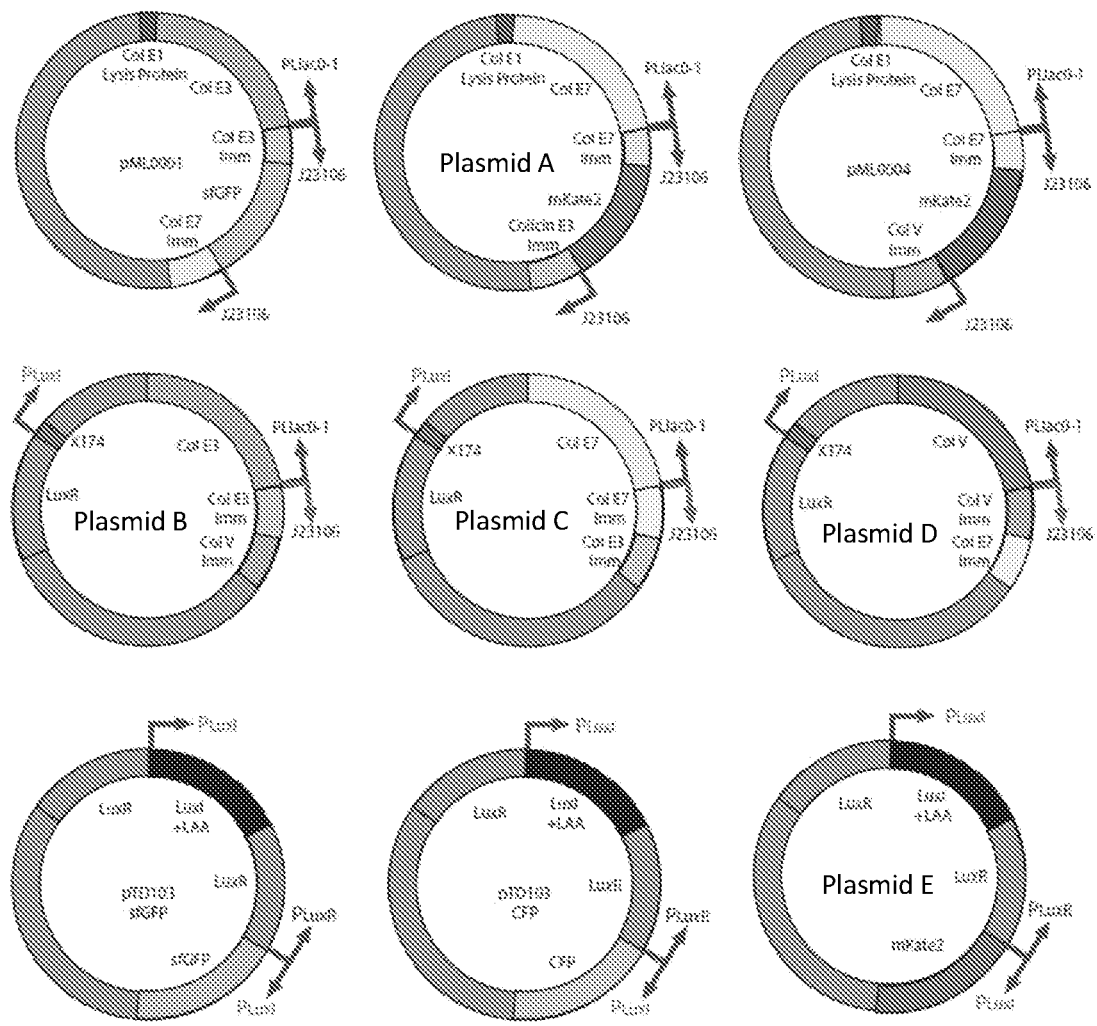
FIG. 11 shows exemplary plasmids that can be used according to some embodiments.
Figure 21:
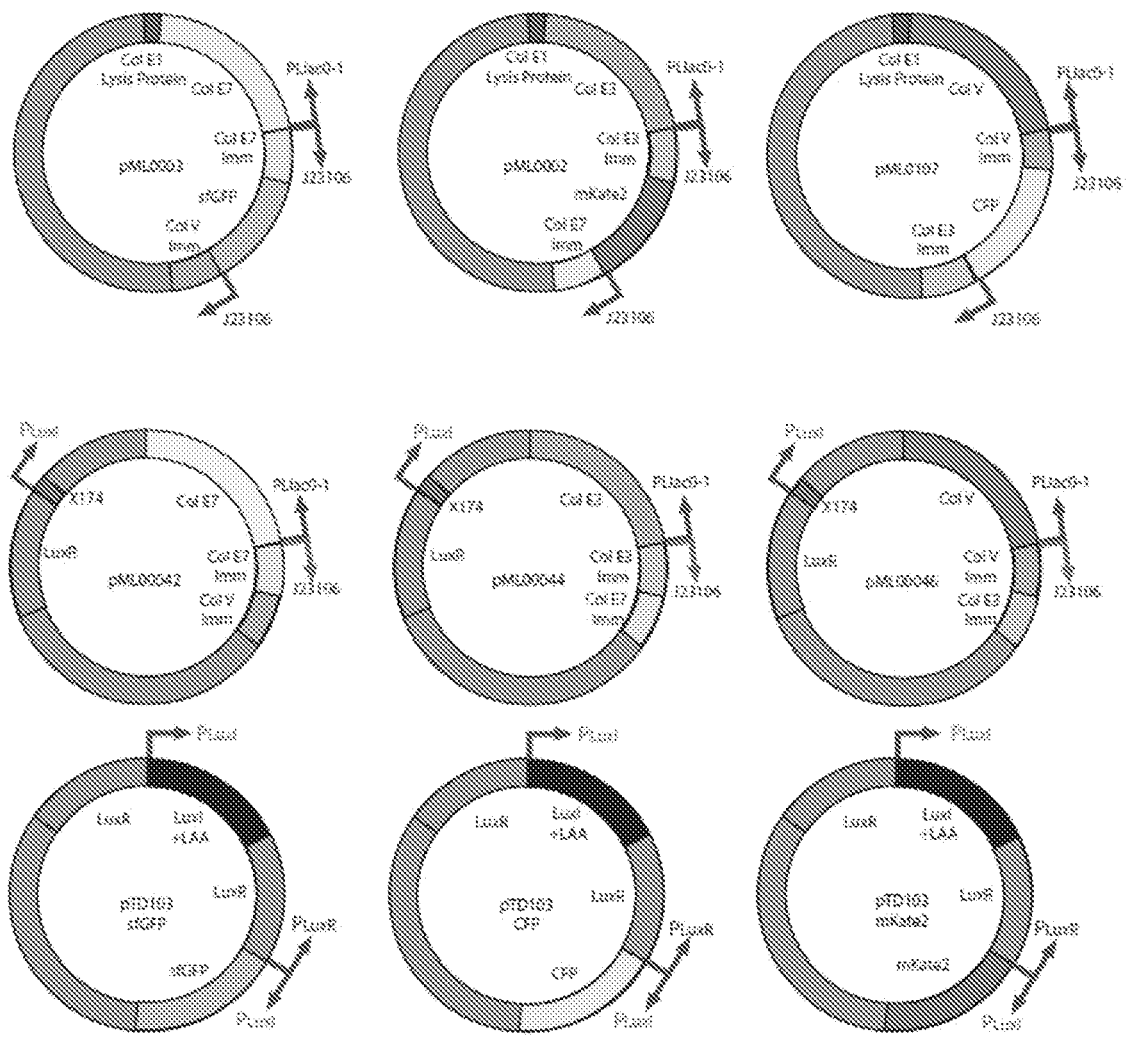
FIG. 21 shows exemplary plasmids that can be used according to some embodiments.
Figure 24B:
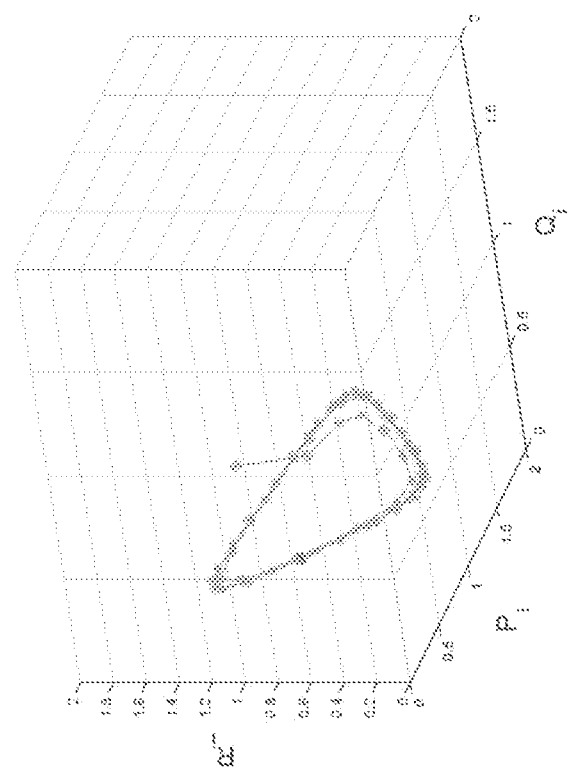
FIG. 24B shows an exemplary map of $P_i$, $Q_i$, $R_i$.
Figure 24A:
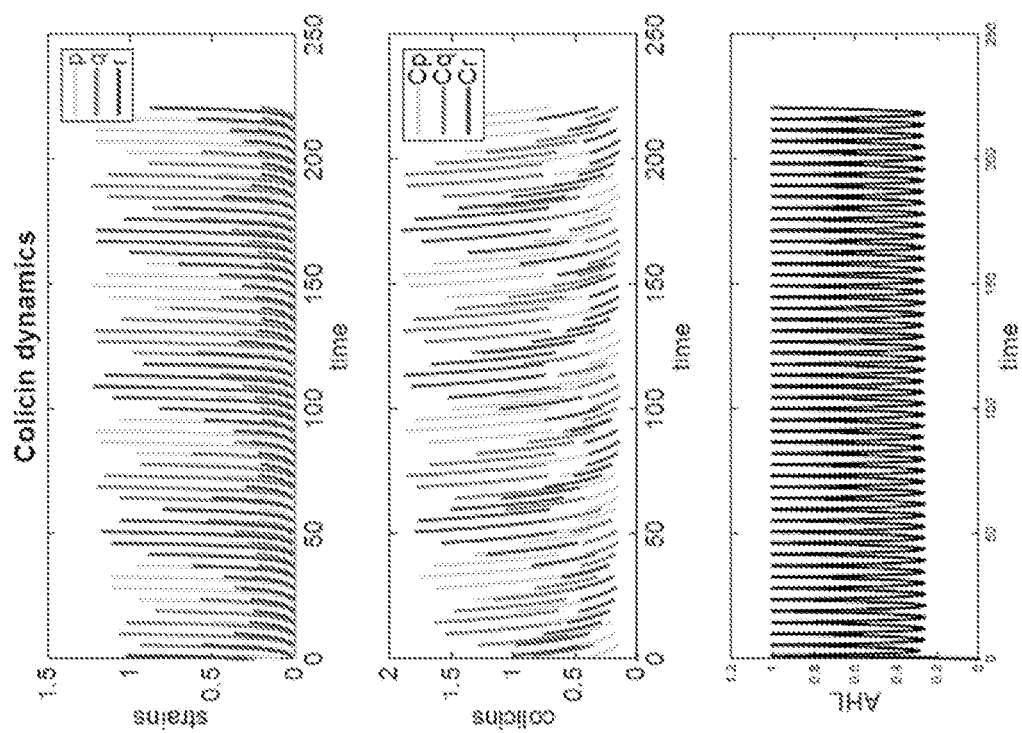
FIG. 24A shows an exemplary time series.
Figure 25B:
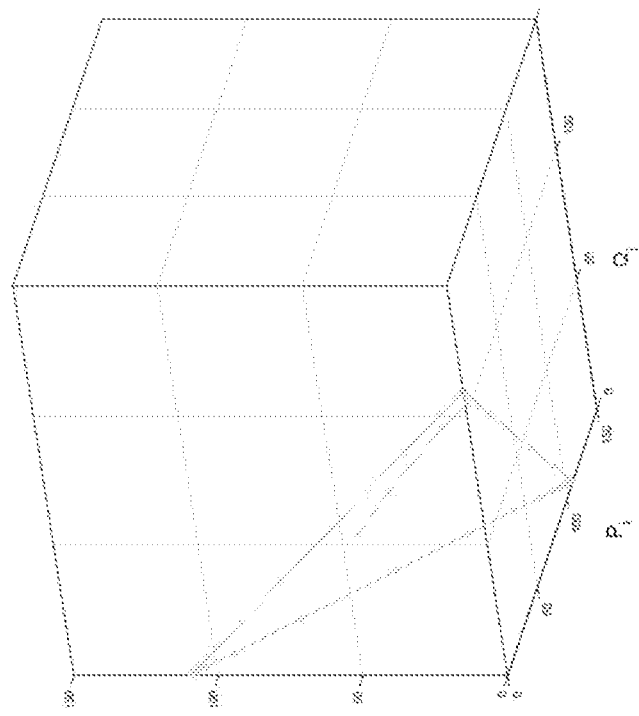
FIG. 25B shows an exemplary map of $P_i$, $Q_i$, $R_i$.
Figure 25A:
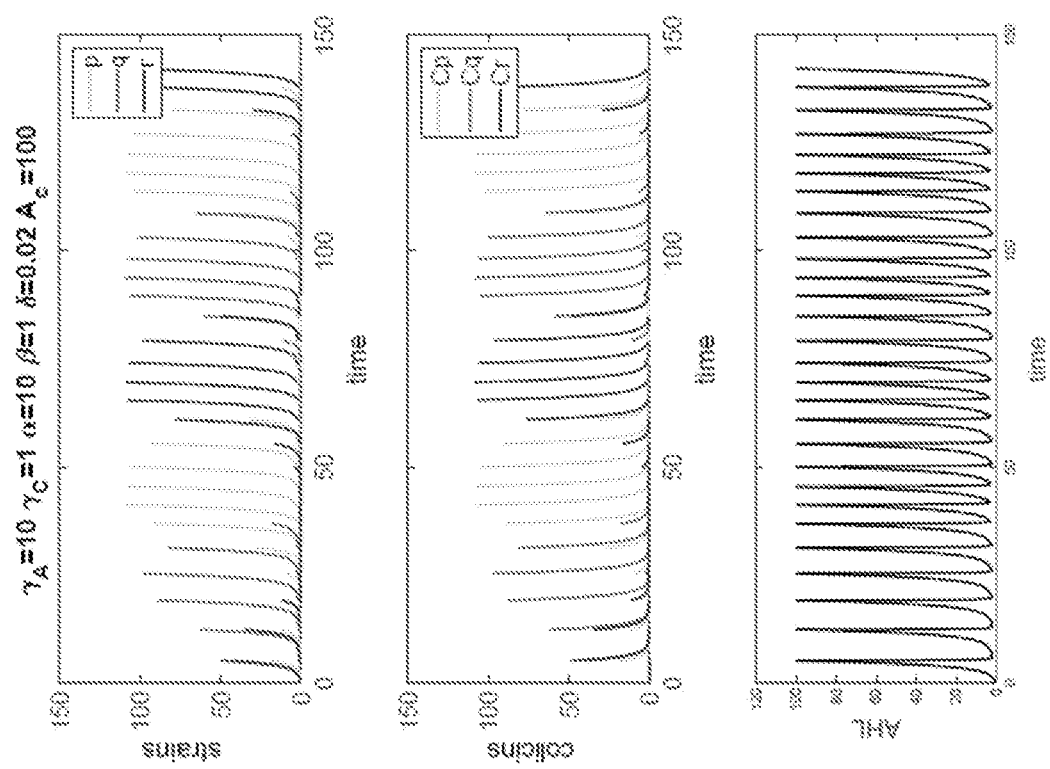
FIG. 25A shows an exemplary time series.

A strategy to give one strain a selective advantage over the other was initially investigated. From the range of possible colicins, two (colicin E3, colicin E7) were identified which are lethal through DNase and rRNase activity (see, e.g., FIG. 4 and FIG. 22). Toxin effects were verified in microfluidic and plate reader experiments (FIG. 5, FIG. 6). To characterize this effect, a p15A origin plasmid was constructed with a weak constitutive promoter driving colicin and Col E1 lysis protein. In addition, the plasmid included a constitutive promoter driving the immunity protein linked to a fluorescence reporter protein. A second identical constitutive promoter drives a secondary immunity protein (exemplary plasmid diagrams are shown in FIG. 11 and FIG. 21). Each of the plasmid constructs was expressed in MG1655 *E. coli*. The initial strains, addressed as "Strain A" and "Strain B", produce colicin E3+E3 immunity+E7 Immunity+sfGFP, and colicin E7+E7 immunity+mCherry, respectively (FIG. 1A). To study the dynamics of our engineered strains, microfluidic devices were used containing rectangular traps of dimension 100 μm×80 μm×1 μm. Strain B, named the 'disadvantaged strain', was initially seeded into the microfluidic device and allowed to fully colonize the traps. At this point, Strain A, called the 'dominant strain', was introduced into the microfluidic device. Following the introduction of Strain A, an exponential increase of the dominant strain and decay of the disadvantaged strain was observed (FIG. 1B). These experiments demonstrate that colicins can be used to control population dynamics. However, a possible outcome of this experiment could be mutation of the 'disadvantaged strain' against the dominant strain due to long term exposure to a low concentration of colicin.

Figure 1C:
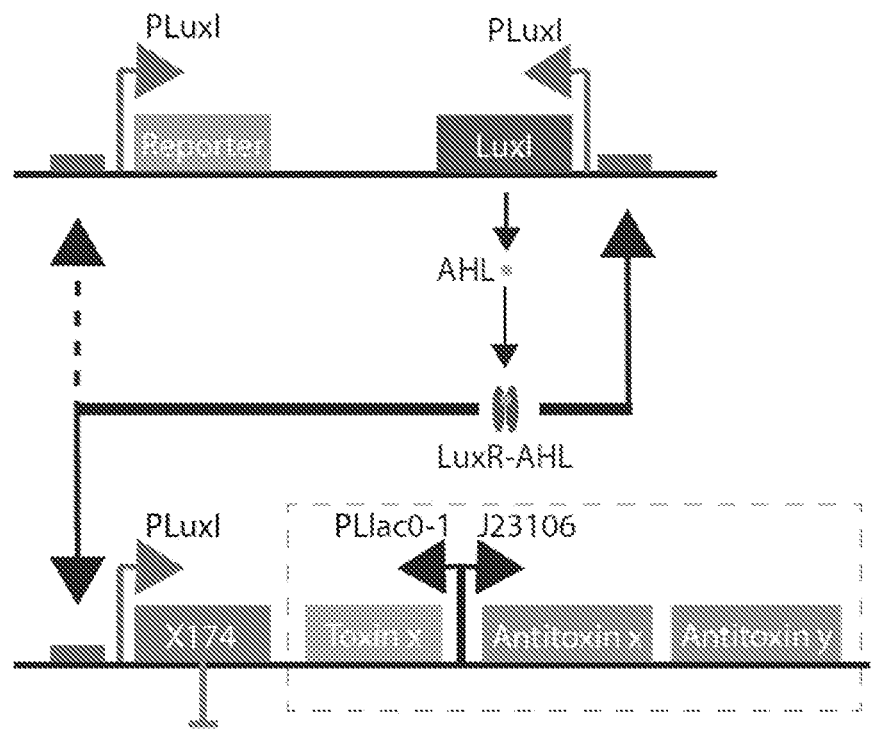
FIG. 1C is an exemplary genetic diagram of a toxin antitoxin system integrated with the quorum sensing synchronized lysis circuit. The circuit contains a lysis plasmid containing the toxin, antitoxin system, and an activator/reporter plasmid. Transient production of LuxI eventually leads to an accumulation of AHL above the quorum threshold needed to activate LuxR, which begins a positive feedback loop by driving transcription off the PluxI promoters that control production of LuxI, reporter fluorescence protein (sfGFP, CFP or mKAte2) and the lysis gene X174E. LuxR in this system is driven by the native LuxR promoter.
Figure 1D:
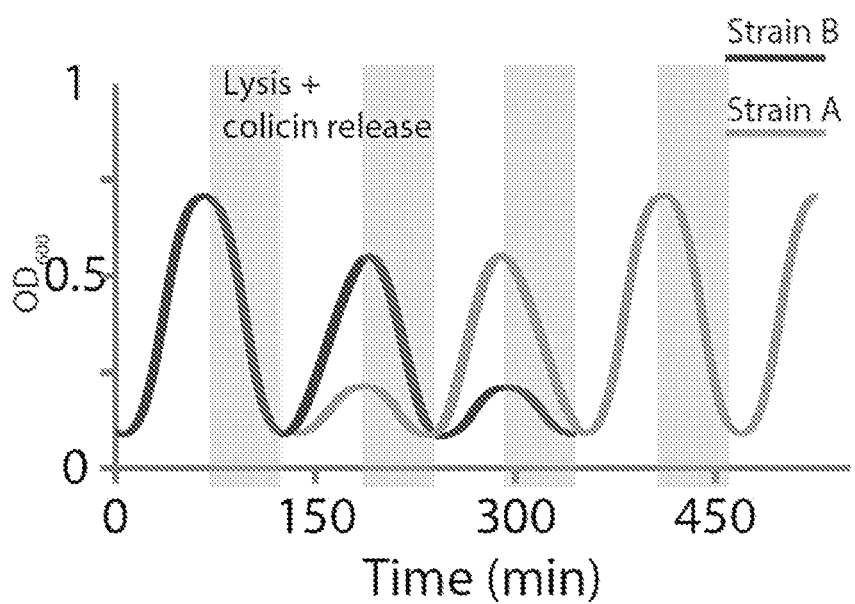
FIG. 1D is schematic of an exemplary two strain population dynamics with the integration of the synchronized lysis circuit to control population size. The self-limiting behavior of the synchronized lysis circuit, as well as the synchronization of toxin release when the primary strain is at its lowest population should enable more rapid strain takeover.
Figure 1E:
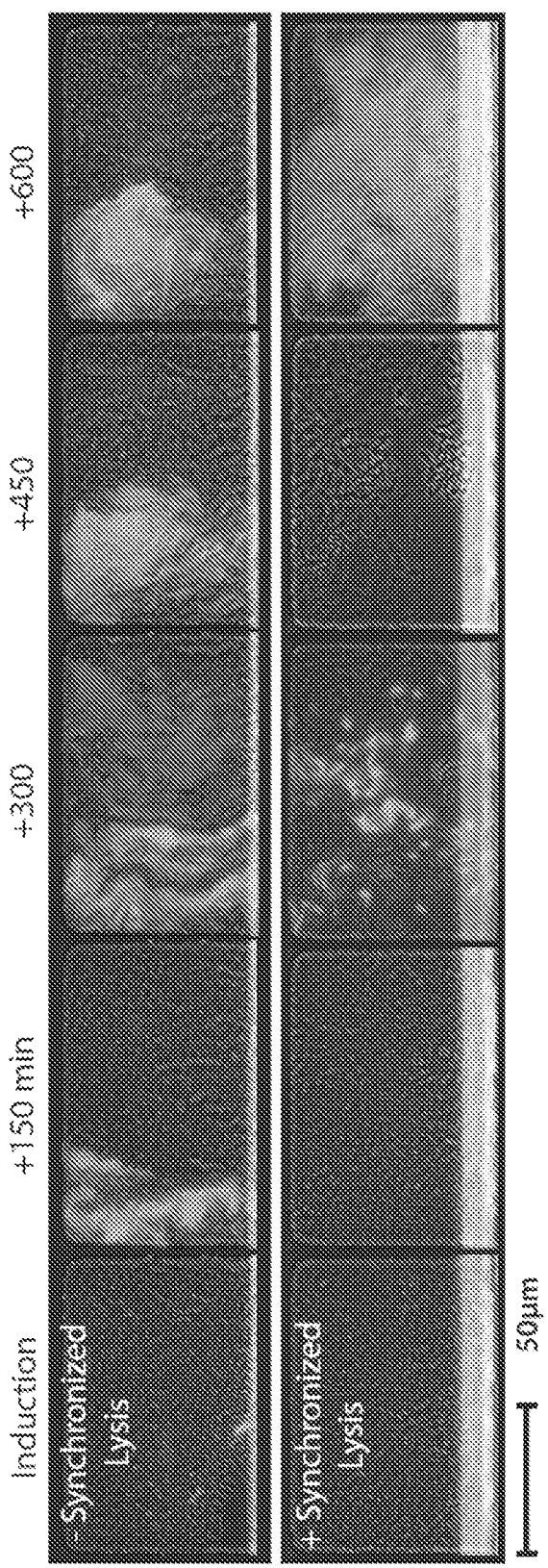
FIG. 1E shows film strips showing a composite of phase contrast, GFP and CFP fluorescence produced by the oscillator circuit. The integration of the synchronized lysis circuit (bottom strip) reduces the time needed to achieve full takeover of the microfluidic trap compared to the non-synchronized lysis circuit strain (top strip). Note the sfGFP and CFP fluorescence reporters for the synchronized lysis strains are driven by production of AHL and are only expressed when quorum threshold is reached.

To address this concern, it was reasoned that synchronized release of colicin would enable the simultaneous release of a more lethal concentration of colicin, while also limiting the exposure time to low concentrations of colicin. To test this hypothesis, p15A origin plasmids were constructed in which the initial col E1 Lysis protein was removed and replaced with the X174 E lysis protein under control of the luxI promoter (FIG. 1C). A second plasmid, from a synthetic oscillator reported elsewhere (Danino, et al. A synchronized quorum of genetic clocks. Nature, 463(7279):326-330, 2010), contains luxI and luxR driven by their native bidirectional promoter on the ColE1 origin plasmid ('activator plasmid'). In addition, a second lux promoter drives the production of a fluorescent reporter protein. In this two plasmid architecture, the lux quorum-sensing system from *Aliivbrio fischeri* was used to create a positive feedback loop driving quorum lysis. In short, LuxI catalyzes the production of the diffusible quorum-sensing molecule N-acyl homoserine lactone (AHL). This molecule binds to the constitutively produced luxR transcription factor, forming a complex which acts as a transcriptional activator of the luxI promoter. It was expected that the different strains would synchronously lyse resulting in simultaneous release of colicin when both populations are at their lowest (FIG. 1D). To test this idea, *E. coli* containing both these plasmids were grown in the microfluidic device previously described. The dominant and disadvantaged strains were loaded at a ratio of 1:5 respectively and co-cultured for a duration of 600 minutes. It was observed that both strains lysed synchronously within each chamber and drastically improved strain takeover rate compared to strains lacking synchronized lysis (FIG. 1E). This synthetic colicin-based circuit demonstrates that, when combined with an engineered selective advantage, lysis mediated population control is a powerful tool for controlling populations.

Example 2—Three Strain System

During the second stage of development the system was expanded to three-strains.

Figure 2A:
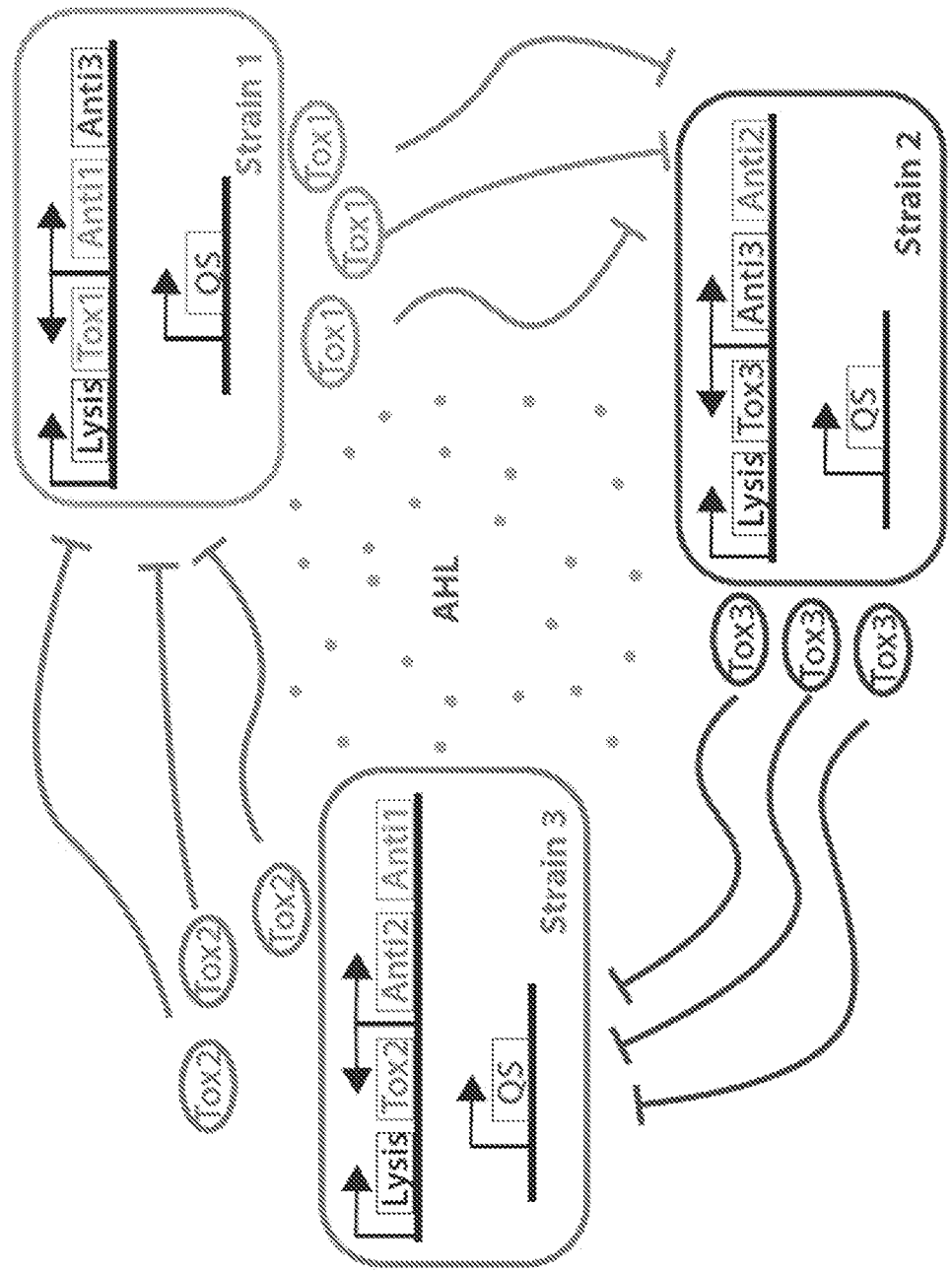
FIG. 2A is an exemplary schematic of a three-strain system of self-lysing *E. coli*. Each strain produces its own toxin-antitoxin pair, while also producing the antitoxin of the following strain. All three strains utilize the same Lux AHL quorum sensing system to drive fluorescent reporter protein expression, as well as self-limiting synchronized lysis.

Since a two strain population control system would only enable the switching from one strain to another, the design was expanded to a three strain system that could be cycled in a "rock paper scissors" approach. To explore this, a third toxin was identified, colicin V, which acts by disrupting the membrane potential. Each strain contains the same two plasmid architecture described in FIG. 1C but with orthogonal sets of colicins. The three strains, now referred to as strain 1, strain 2 and strain 3, contain colicin E3, colicin E7 and colicin V respectively. In this system, each strain produces a colicin lethal to the preceding strain and two immunity proteins (FIG. 2A). The first immunity protein gives the current strain protection to its own colicin production. In addition, a second immunity protein protects the current strain to the toxicity of the colicin produced by the preceding strain.

Three *E. coli* strains were engineered in which each strain contains a unique toxin and antitoxin system (TA module). In monoclonal populations, TA modules aid in plasmid stabilization because mutation or loss of the antitoxin results in cell death either due to the presence of extracellular toxin produced by the healthy bacteria or killing of newborn plasmid-free cells through the prolonged persistence of toxin producing mRNA (see, e.g. K. Gerdes, *Nature Biotechnology* 6, 1402 (1988)). By expanding the mechanism of the TA module to a multi-strain ecology, each TA module gives its host strain the added ability to kill any other strain that does not have the corresponding antitoxin, enabling external control over displacement of the existing population (FIG. 12A). A synthetic "rock, paper, scissors" (RPS) ecology was created by adding a secondary antitoxin into each strain so that each strain can be killed by a subsequent strain in a cycle (FIG. 12B). This RPS system can be coupled with any circuit of interest to increase stabilization. In this combined system, a circuit that has mutated in one strain can be replaced by the introduction of a fresh batch of the next RPS housing strain. Thus, rather than attempting to "beat Darwin," an engineering strategy was developed that enabled external control over the evolution and composition of the ecology.

Figure 2B:
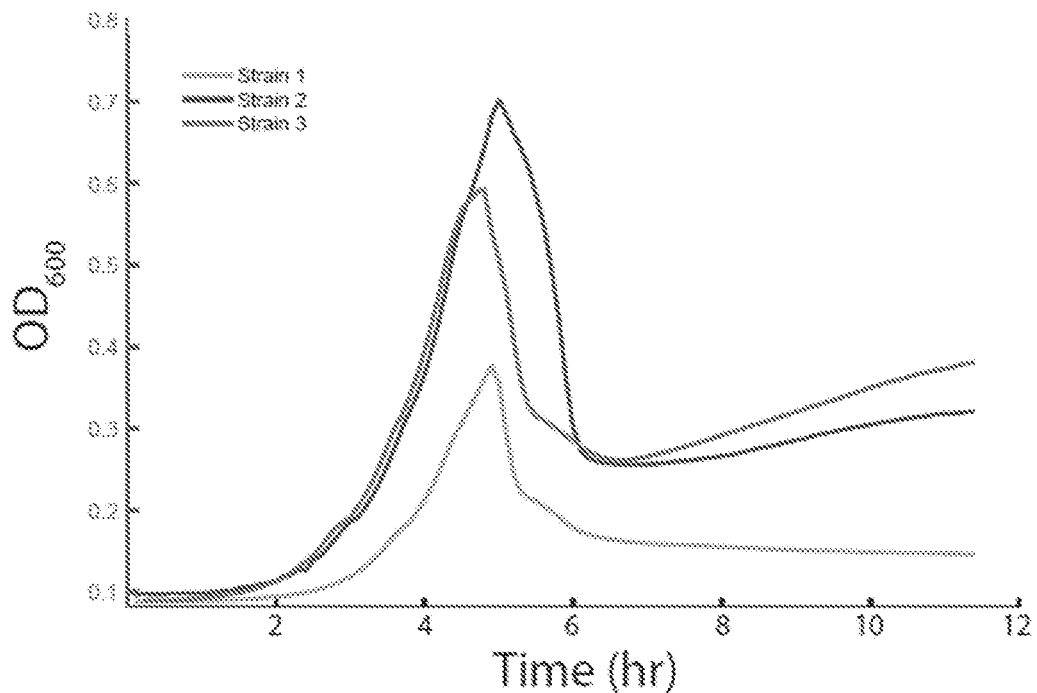
FIG. 2B shows exemplary batch culture growth curves of the 3 strains shows the lysis OD600 of each strain. All strains were started from the same diluted density and under the same growth conditions (n=3).

Because multi-strain competition dynamics are typically dictated by differences in growth rate, the dynamics of the three strains were characterized first individually. Growth rates of the three lysis strains and the wild-type MG1655 *E. coli* were compared by using fluorescence microplate reader absorbance experiments. Before the lysis event occurred, it was found that the addition of engineered circuits had little effect on the growth compared to the wild-type control. The threshold $OD_{600}$ was recorded at which each of the three strains lysis (FIG. 2B).

Figure 2C:
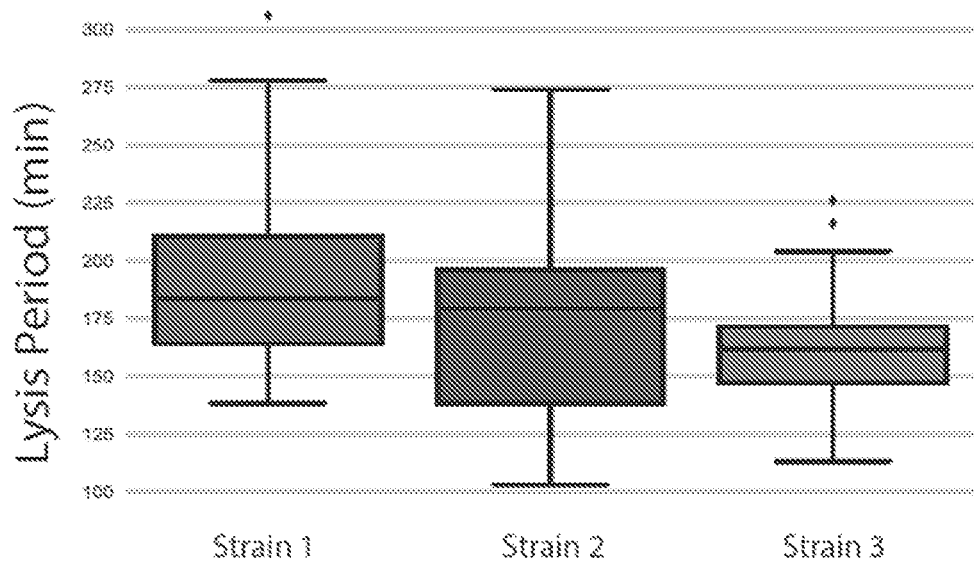
FIG. 2C shows exemplary lysis periods for the three strain system as measured in bilayer microfluidic chambers under the same growth conditions (n=15).

Next, the effect of differences in $OD_{600}$ of lysis on the period of lysis was explored in the microfluidic devices. The microfluidic device was loaded with each individual strain and imaged every six minutes. The period of lysis between the three strains was found to be relatively uniform in spite of different $OD_{600}$ thresholds of lysis (FIG. 2C).

Without wishing to be bound by theory, it was hypothesized that this may be due to a lower post-lysis survival fraction of Strain 1 cells in comparison to survivor cells belonging to Strain 2 and Strain 3. Phenotypic differences in the lysis dynamics of the three strains were noticed. The lysis event of Strain 1 results in a more explosive lysis event, which leaves a smaller fraction of surviving cells and expels more lysate from the trap. Alternatively, strain 3 has a very mild lysis event resulting in a higher fraction of surviving cells and more cell lysate buildup in the microfluidic trap (FIG. 7).

In any environment, once engineered cells have mutated they cannot be reverted back to the non-mutated state. They must be removed and replaced by healthy cells. Such a 'system reboot' interrupts dynamic circuit function in the environment. A multi-strain RPS ecology should in theory enable the removal of mutated, or mutation prone, cells without interrupting the dynamics of the circuit of interest. After validating the expanded function of the TA module in a RPS system, the utility of the stabilizing RPS elements with a genetic circuit that is subject to high selective pressure was tested. The quorum driven synchronized lysis circuit (SLC) was chosen, which has been investigated for microbial therapeutics such as drug delivery to tumors in vivo (see, e.g., M. O. Din, et al., *Nature* 536, 81 (2016); T. Danino, O. Mondragón-Palomino, L. Tsimring, J. Hasty, Nature 463, 326 (2010)). With the SLC circuit, a quorum sensing molecule (AHL), gradually accumulates in the growth environment in proportion to population density. When the population reaches a threshold density, synchronized lysis eliminates around 90% of the bacteria, leaving about 10% to reseed population growth. The resulting dynamics of the cell population are cycles of cell growth and synchronized lysis. However, when employed in in vivo environments where selective media cannot be used, plasmid loss or mutations are expected to result in loss of function over long time periods.

Figure 13A:
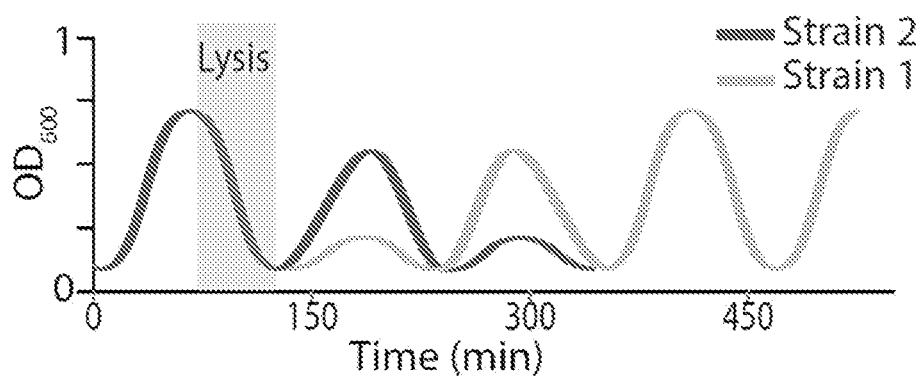
FIG. 13A is a schematic of an exemplary two strain population dynamics with the integration of the SLC. Depicted is continuous synchronized population lysis during a strain takeover event.
Figure 13B:
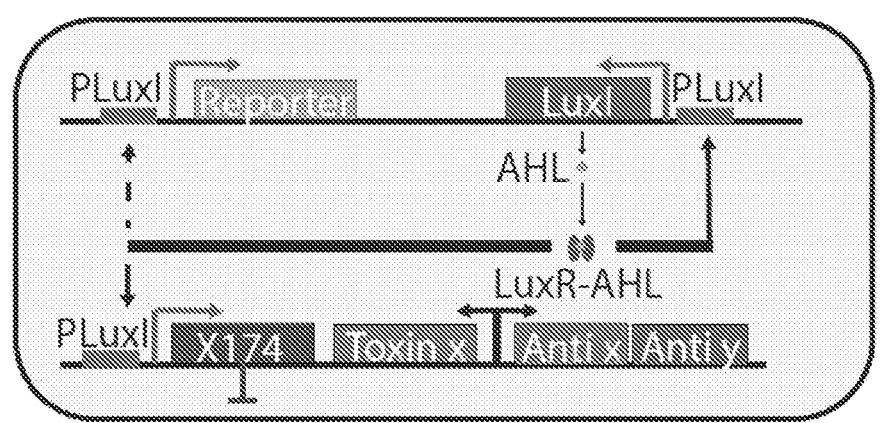
FIG. 13B is an exemplary genetic diagram of the quorum sensing synchronized lysis circuit and TA module. The first plasmid contained the X174E lysis protein driven by the luxI promoter, and corresponding toxin/antitoxin/antitoxin gene. A second 'activator' plasmid contained the luxI and LuxR genes driven by their native promoter pLuxI.

It was investigated whether successful plasmid stabilization from the RPS system would result in strain takeover without any interruption of the oscillatory dynamics (FIG. 13A). The SLC and TA modules were integrated into a two-plasmid system with one plasmid containing the lysis gene, E, from the phage ϕX174 (X174E), a TA module, immunity proteins, and an activator-reporter plasmid (FIG. 13B). To investigate how the different dynamics of the strains would impact the interactions between them, each of the strain pairs were tested in microfluidic devices. Due to the difference in lysis threshold, it was expected that strain 1 would lyse before strain 2 and strain 3, causing a problem in strain takeover. A three strain RPS system was developed in which each strain contained a distinct toxin-antitoxin pair as well as a secondary antitoxin to one other strain (FIG. 12C). To achieve this, used colicins were used, which are naturally occurring toxin-antitoxin systems that are lethal to certain *E. coli* strains and are effective antagonistic agents within *E. coli* populations in vivo (FIG. 16A-D) (see, e.g., B. C. Kirkup, M. A. Riley, *Nature* 428, 412 (2004), A. E. Boyer, P. C. Tai, *Journal of bacteriology* 180, 1662 (1998); E. Cascales, et al., *Microbiology and molecular biology reviews* 71, 158 (2007); M. M. Zambrano, D. A. Siegele, M. Almiron, A. Tormo, R. Kolter, *Science* 259, 1757 (1993)).

To test this, each strain pair was co-cultured in the microfluidic device at an initial seeding ratio of 1:5 advantaged to susceptible. Each of the three strains were monitored via fluorescence reporter proteins sfGFP, CFP and mKate2. Production of the fluorescent reporter is driven by the luxI promoter. Strain 3 contains a plasmid producing colicin E7 and E7 immunity protein, and a colicin V immunity protein. Strain 2 contains a plasmid producing colicin E3 and E3 immunity protein, and an E7 immunity protein. Strain 1 contains a plasmid producing colicin V and V immunity protein and an E3 immunity protein. Thus, each pair of strains has one 'dominant strain', immune to the toxin produced by the other strain, and a 'susceptible' strain, vulnerable to the toxin produced by the other. Therefore, the reporter protein is only produced after initiation of the AHL quorum based positive feedback loop.

Figure 12F:
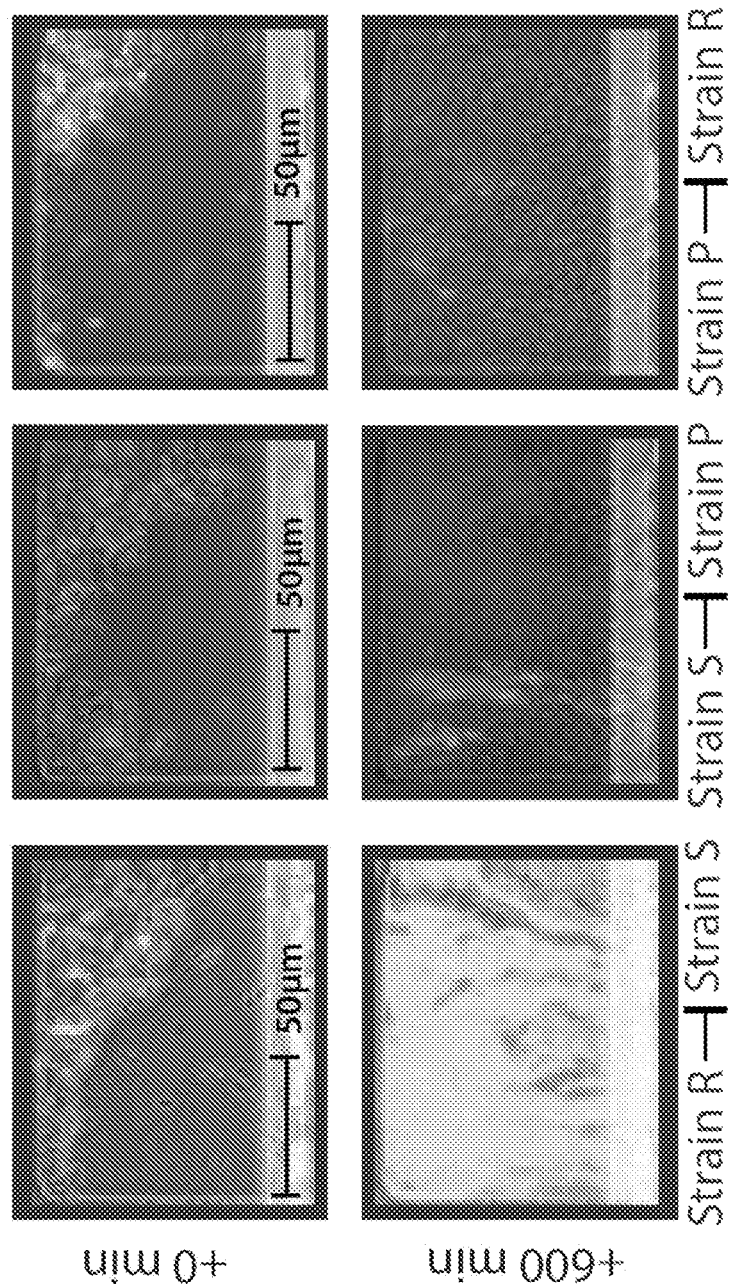
FIG. 12F is fluorescence microscopy images showing a composite of phase contrast, GFP, CFP, and RFP fluorescence. From left to right: (1) strain R (light gray) inhibits strain S (dark gray); (2) strain S (dark gray) inhibits strain P (gray); (3) strain P (gray) inhibits strain R (light gray).

Since displacement within microbial co-cultures are typically dominated by differences in growth rate, growth rate of each RPS strain was measured (FIG. 12D). The efficacy of the engineered colicin kill circuits in microfluidic devices by co-culturing the strain pairs at a 1:2 ratio of dominant to susceptible was also determined. In each case, it was observed that a rapid increase of the dominant strain and decay of the susceptible strain, confirming that the colicin produced by the dominant strain was effective against the susceptible strain, but not vice versa (FIG. 12E, 12F).

Figure 2D:
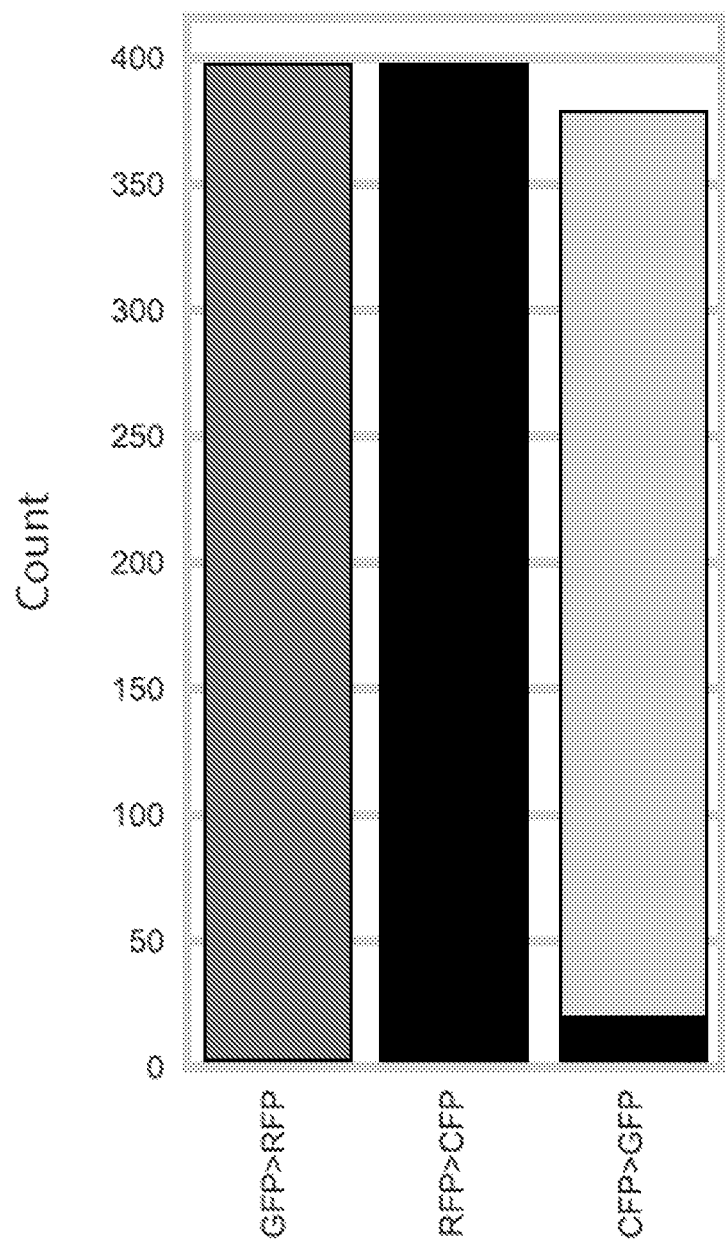
FIG. 2D shows co-culture incubation of two strains seeded in microfluidic devices at initial concentrations of 20 percent dominant strain 80 percent susceptible strain. Strain takeover proceeds unidirectionally with the dominant strain taking over the microfluidic chamber.
Figure 2F:
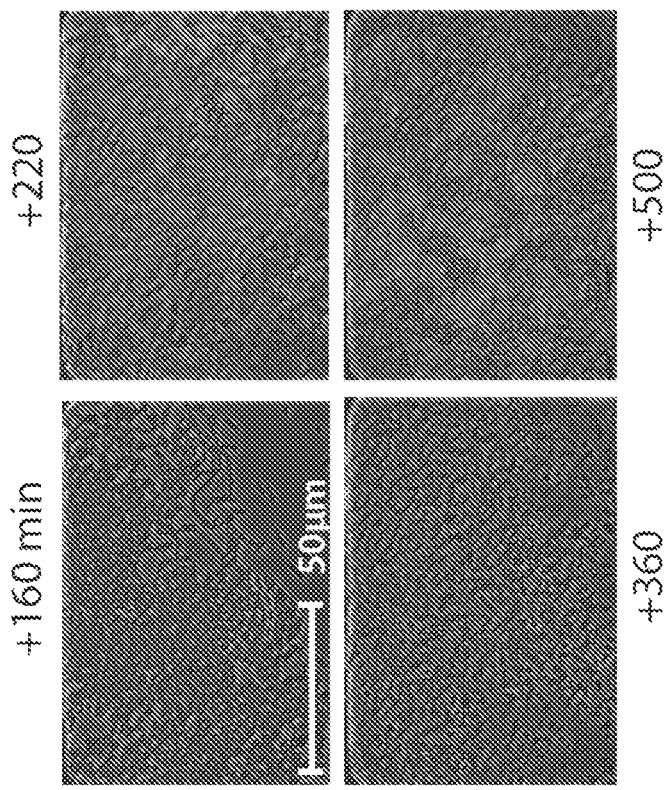
FIG. 2F shows Video stills of a co-culture seeded at initial densities of 40 percent strain 2, 60 percent strain 3, exhibiting strain takeover by strain 2 in a bilayer microfluidic chamber.
Figure 2E:
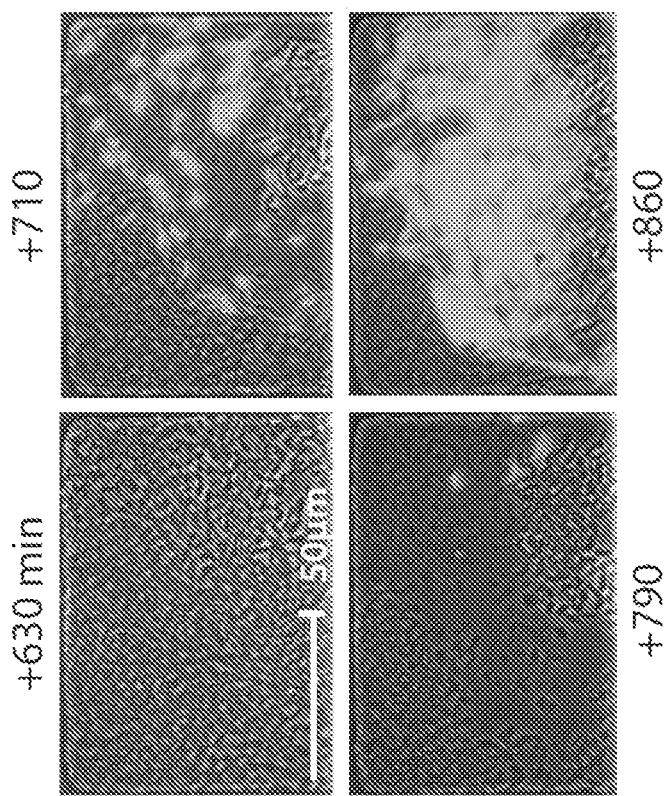
FIG. 2E shows video stills of a co-culture seeded at initial densities of 40 percent strain 1, 60 percent strain 2, exhibiting strain takeover by strain 1 in a bilayer microfluidic chamber.
Figure 2G:
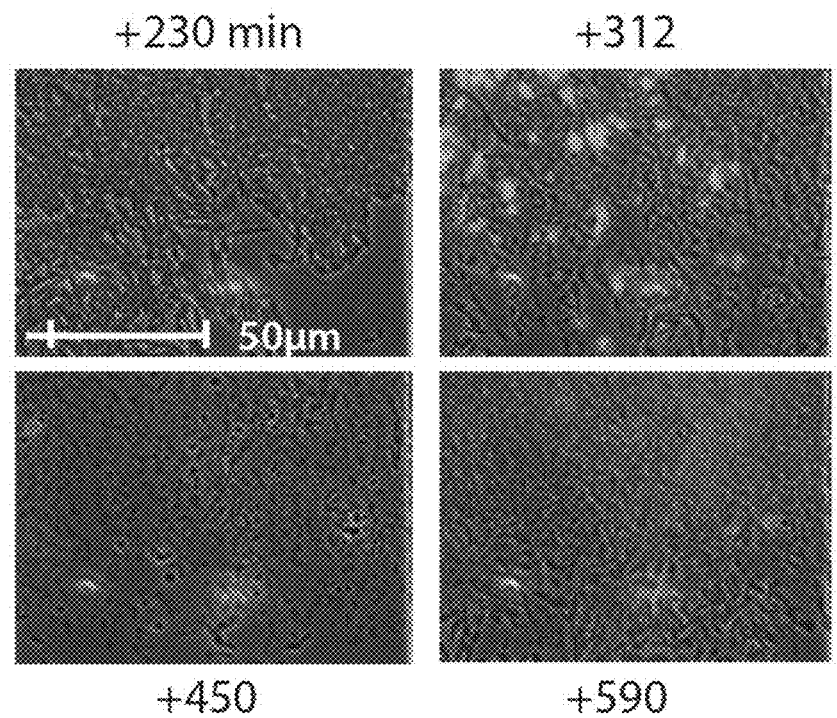
FIG. 2G shows video stills of a co-culture seeded at initial densities of 40 percent strain 3, 60 percent strain 1, exhibiting strain takeover by strain 3 in a bilayer microfluidic chamber.
Figure 2H:
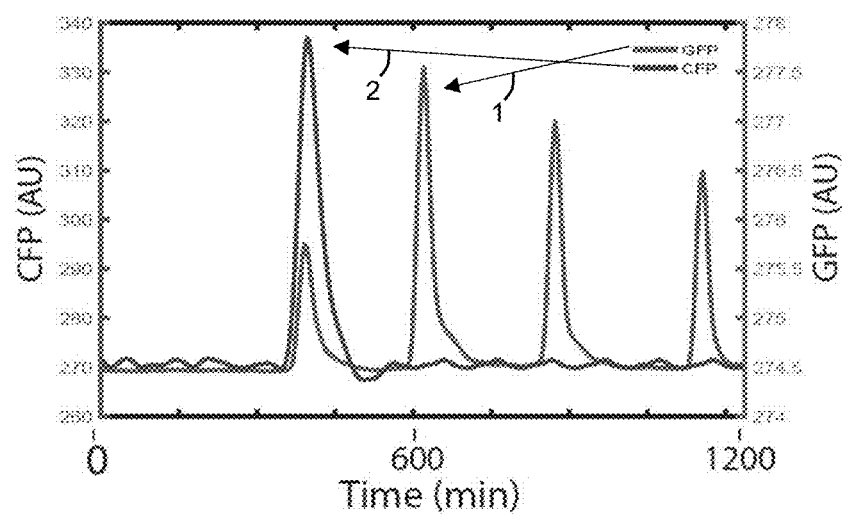
FIGS. 2H, 2I, and 2J each show time series of fluorescence expression for the microfluidic experiments depicted in FIGS. E-G demonstrating synchronized lysis of both strains and strain takeover within the microfluidic chamber.
Figure 2I:
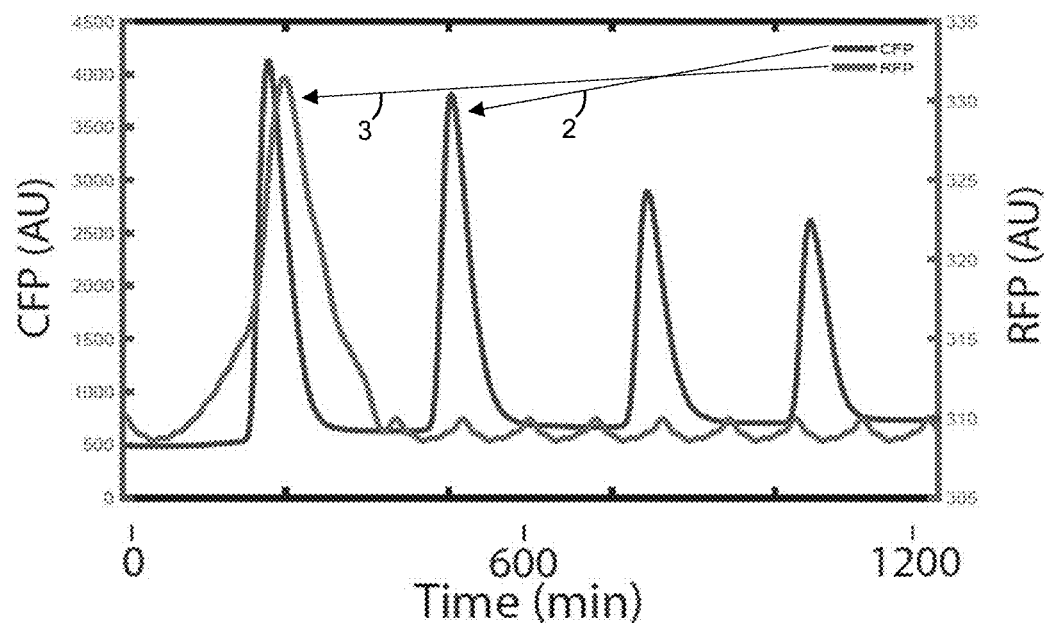
Figure 2J:
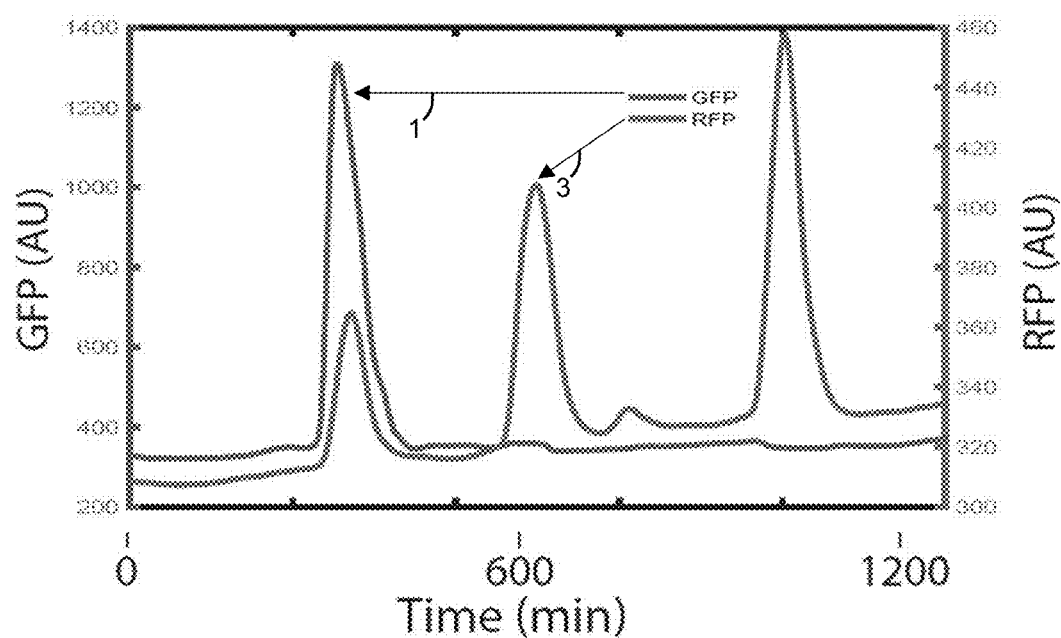
Figure 13C:
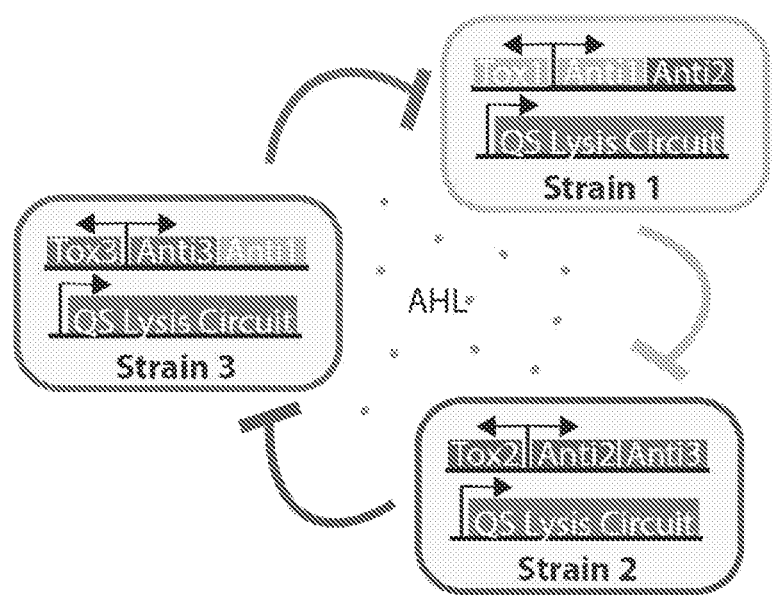
FIG. 13C is a schematic showing that each strain produced its own toxin-antitoxin pair, while also producing the antitoxin of the following strain. All three strains utilized the same Lux-AHL quorum sensing system to drive fluorescent reporter protein expression, as well as self-limiting synchronized lysis.
Figure 13D:
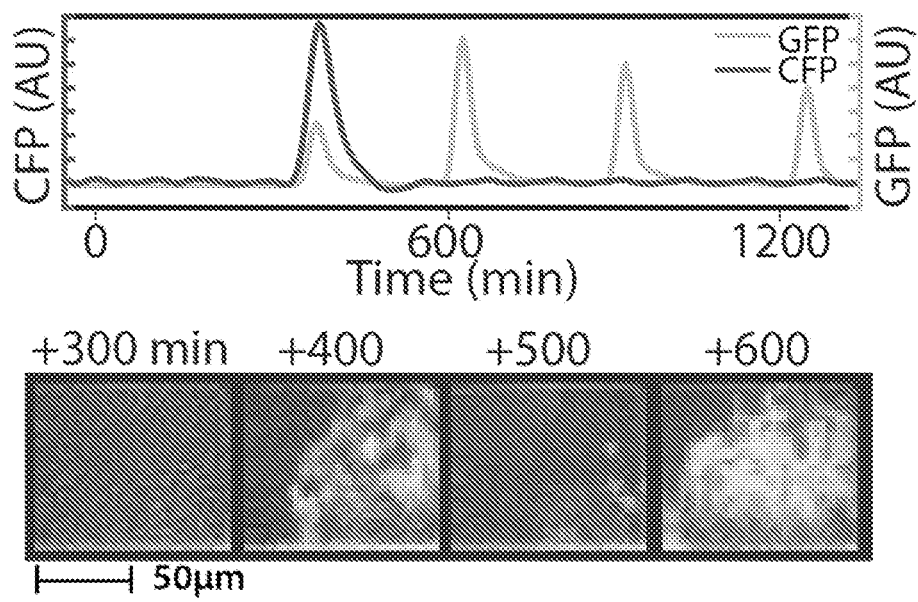
FIG. 13D shows a time series of fluorescence expression and video stills of a co-culture seeded at a 1:1 ratio strain 1 to strain 2, exhibiting strain takeover by strain 1 in a microfluidic chamber.
Figure 13E:
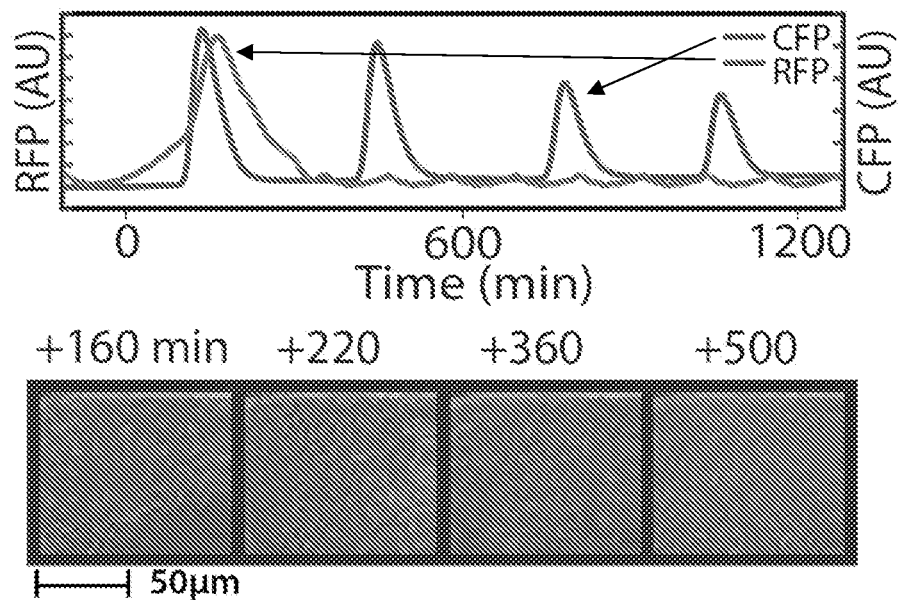
FIG. 13E shows a time series of fluorescence expression and video stills of a co-culture seeded at a 1:1 ratio strain 2 to strain 3, exhibiting strain takeover by strain 2 in a microfluidic chamber.
Figure 13F:
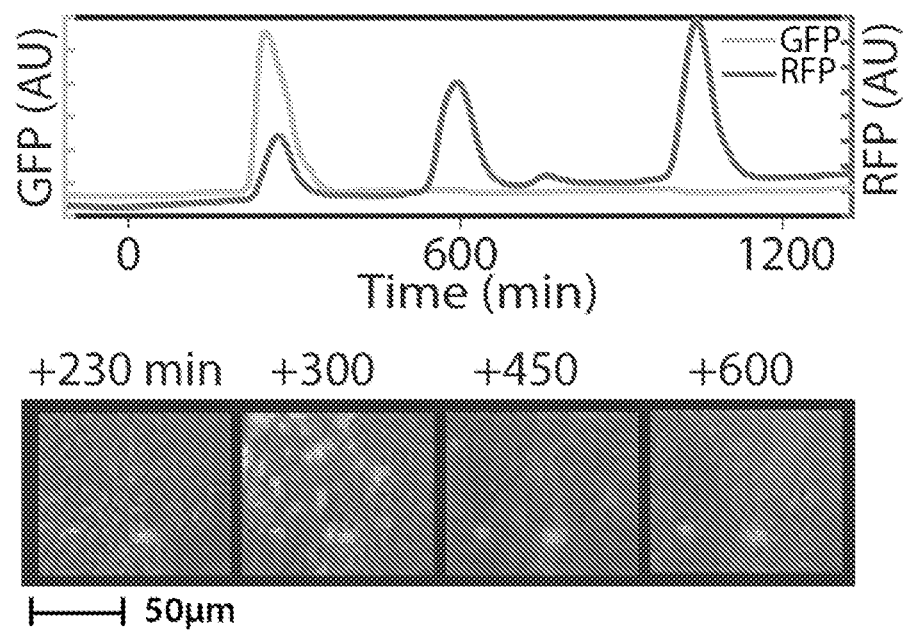
FIG. 13F shows a time series of fluorescence expression and video stills of a co-culture seeded at a 1:1 ratio strain 3 to strain 1, exhibiting strain takeover by strain 3 in a microfluidic chamber.
Figure 18A:
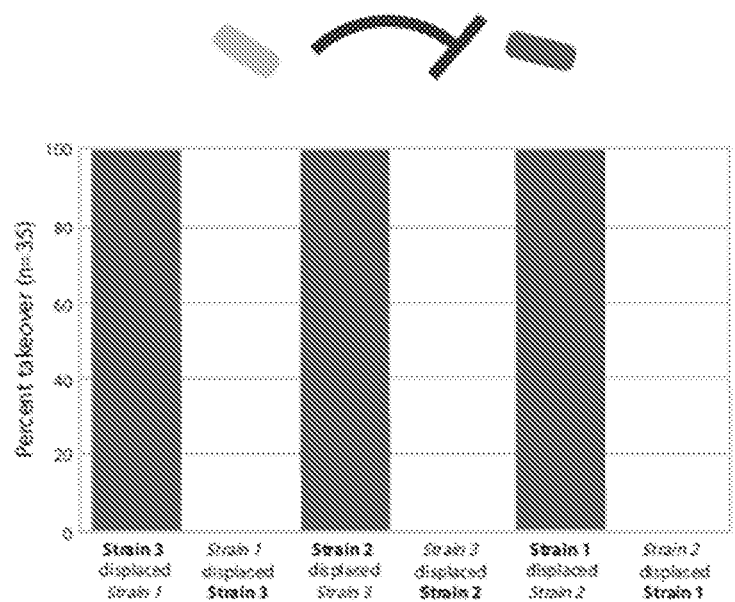
FIG. 18A is a bar plot showing that each pair of strains was co-cultured at a 1:1 ratio dominant (bold) to susceptible (italic) (n=35). For each strain pair, the dominant strain displaced the susceptible strain in 100% of culture regions.
Figure 18B:
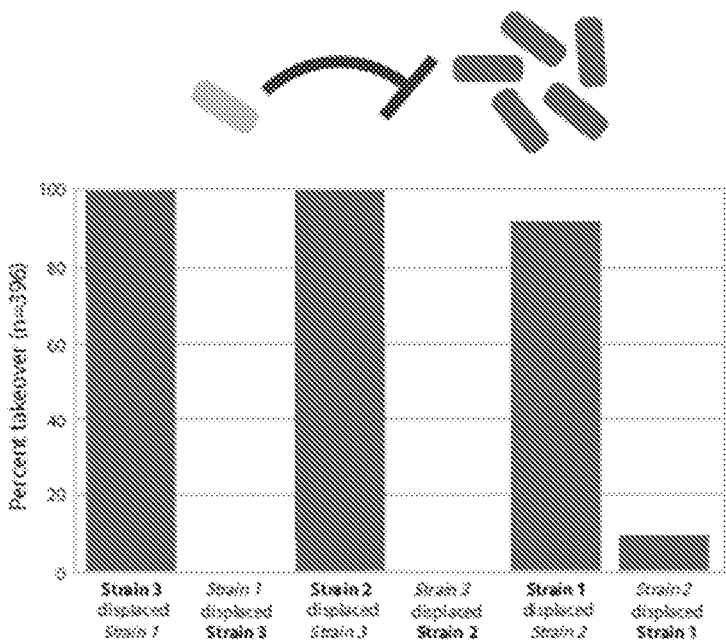
FIG. 18B is a bar plot showing that each pair of strains was co-cultured at a 1:5 ratio dominant (bold) to susceptible (italic) (n=396). For each strain pair the dominant strain displaced the susceptible strain in 100%, 100%, and 92% of culture regions.

Using this architecture, three strains were created that exhibited simultaneous cycles of synchronized lysis and constant RPS competition (FIG. 13C). Each RPS lysis strain was characterized individually (FIGS. 17A-D), and each strain pair was validated in microfluidic devices with initial seeding ratios of both 1:1, and 1:5, dominant to susceptible. It was observed that in addition to successful strain displacement, the function of the synchronized lysis circuit remained unaffected, as all strains lysed synchronously within each chamber. At 1:1 dominant to susceptible, take-over occurred in 100% of cultures (n=35) for each strain pair and a single lysis event was sufficient to complete strain take-over (FIG. 18A). For the three pairings at a 1:5 ratio (strain 1 and 3, 3 and 2, 2 and 1) dominant strain take-over occurred in 100%, 100%, and 92% of the cultures (n=396), respectively (FIG. 2D, FIG. 18B). For co-cultures consisting of strain 1 and strain 2, a small fraction (<8%) of strain 2 was able to out-compete strain 1 to colonize the trap. In all cases, the function of the SLC circuit was not interrupted during strain changeovers (FIG. 13D-13F).

Without wishing to be bound by theory, it was hypothesized that this may be caused by the lower lysis threshold which characterizes strain 1. Strain 1 began lysis prior to strain 2. As a result, the released colicin has a lower relative concentration to target strain 2. Additionally, while the two strains were initially loaded at a ratio of 1:5 dominant to disadvantaged, in most cases the observed ratio at the time of the first lysis event was different.

To investigate this further, a microfluidic experiment was conducted in which both strains were loaded at an equal ratio 1:1. In the majority of cases, before the occurrence of the first lysis event the dominant strain had already completely taken over the microfluidic trap. In a few cases, the traps still had both strains present. However, the dominant strain had a larger population size, leading to a single lysis event being sufficient for trap takeover (see, e.g., FIG. 2E-2G, FIG. 13D-13F).

Microscopy at single cell resolution (60× magnification) visually confirmed that the disadvantaged cells started dying prior to synchronized lysis. Without wishing to be bound by theory, this may suggest that there is some level of 'leaky expression' of lysis protein which leads to the release of a small amount of colicin during exponential growth phase.

Example 3—Population Dynamics

Figure 3A:
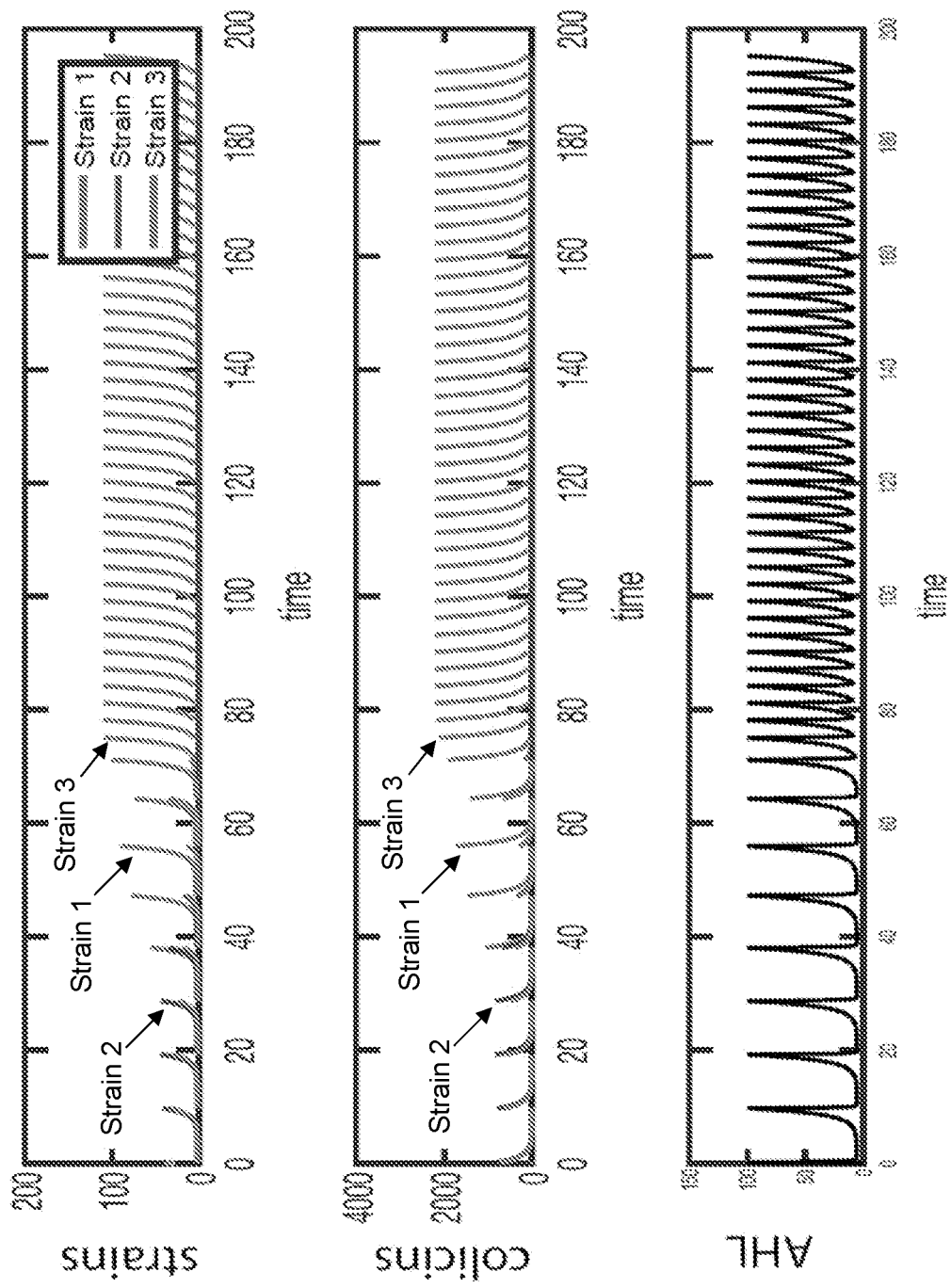
FIG. 3A shows time series dynamics of the colicin model demonstrate that when three-strains are simultaneously co-cultured and under estimated parameters, the three strains should each cycle once until a single strain overtakes the trap. The three graphs show the concentrations of the strains, colicins, and AHL over time.
Figure 3B:
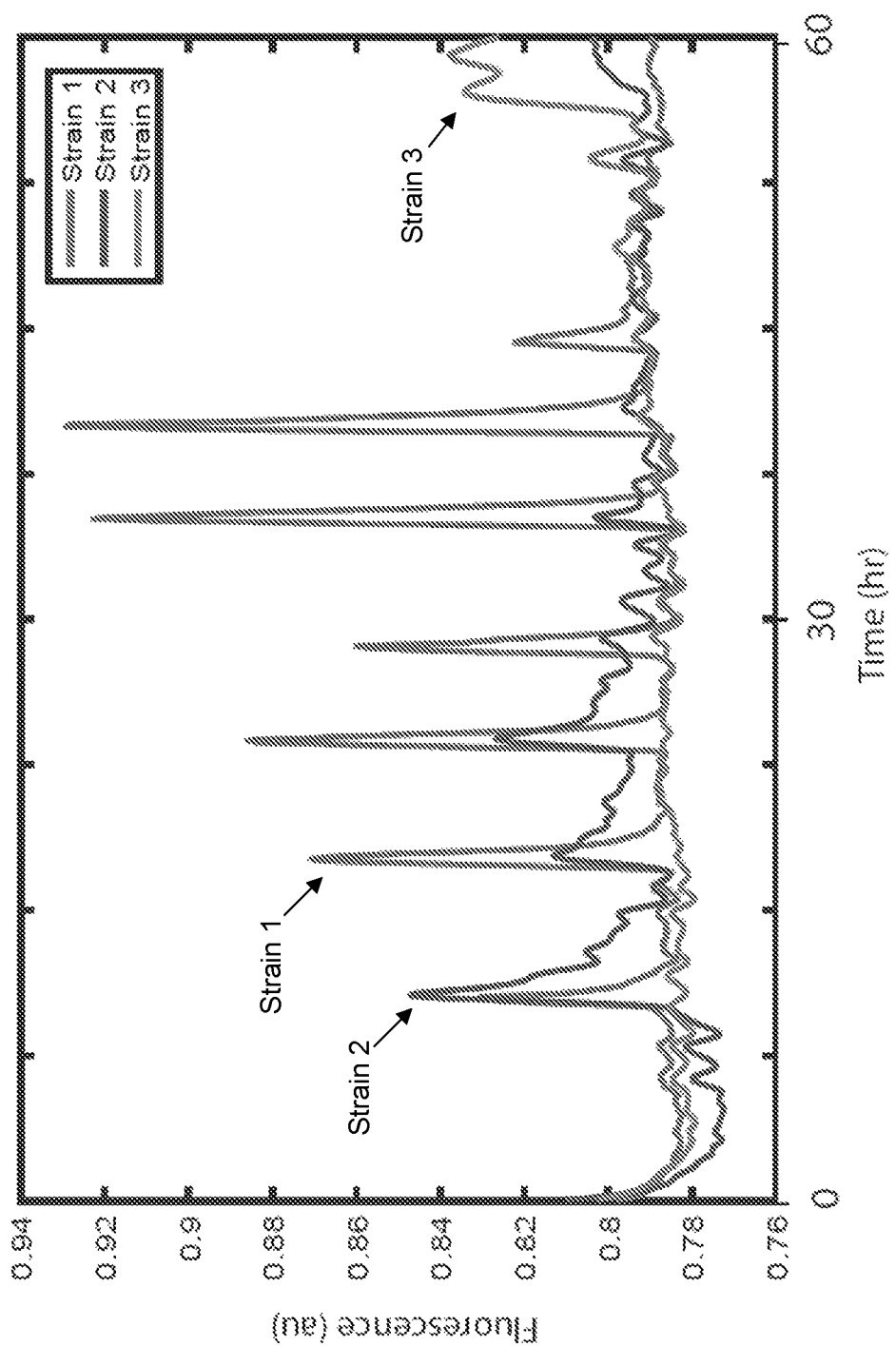
FIG. 3B shows time trace of GFP, CFP, and RFP fluorescence expression of a single trap from a 3-strain co-culture experiment in which all three strains are loaded at roughly equal ratios.
Figure 3C:
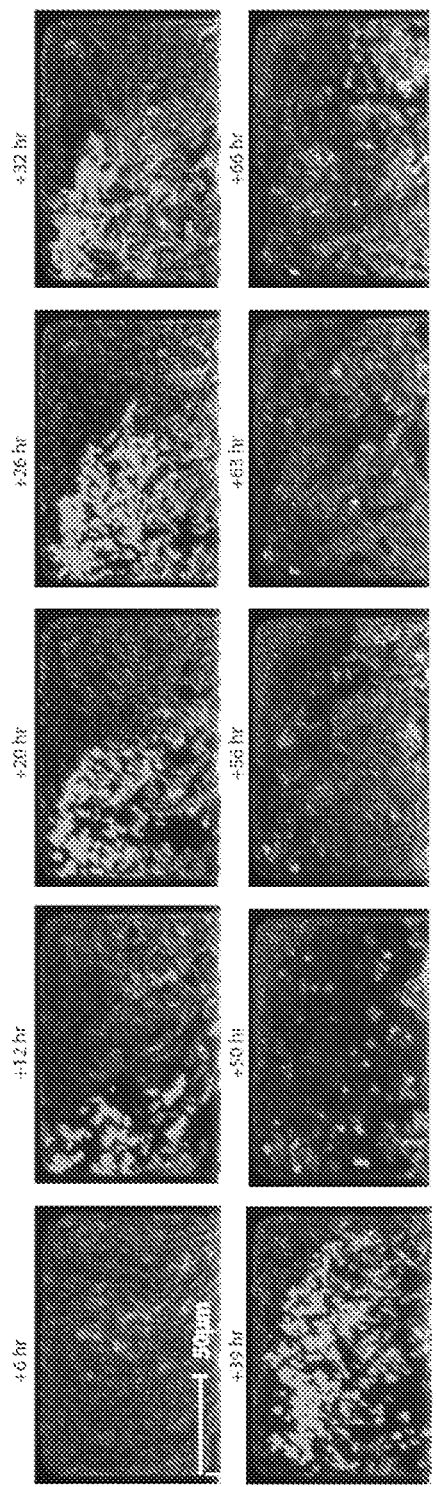
FIG. 3C shows video stills of phase contrast, GFP, CFP, and RFP for the microfluidic chamber shown in FIG. 3B.
Figure 3D:
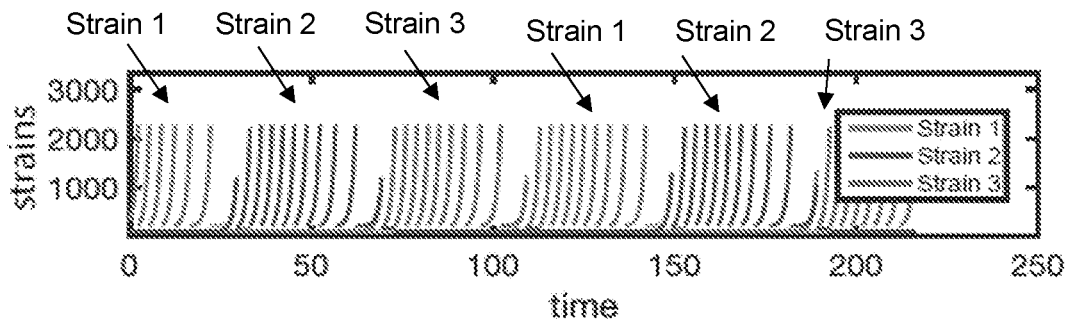
FIG. 3D shows time trace of GFP, CFP, and RFP fluorescence expression of a single trap from the experiment in FIG. 3C that demonstrates cycling through all 3 strains in a single continuous uninterrupted run.
Figure 3E:
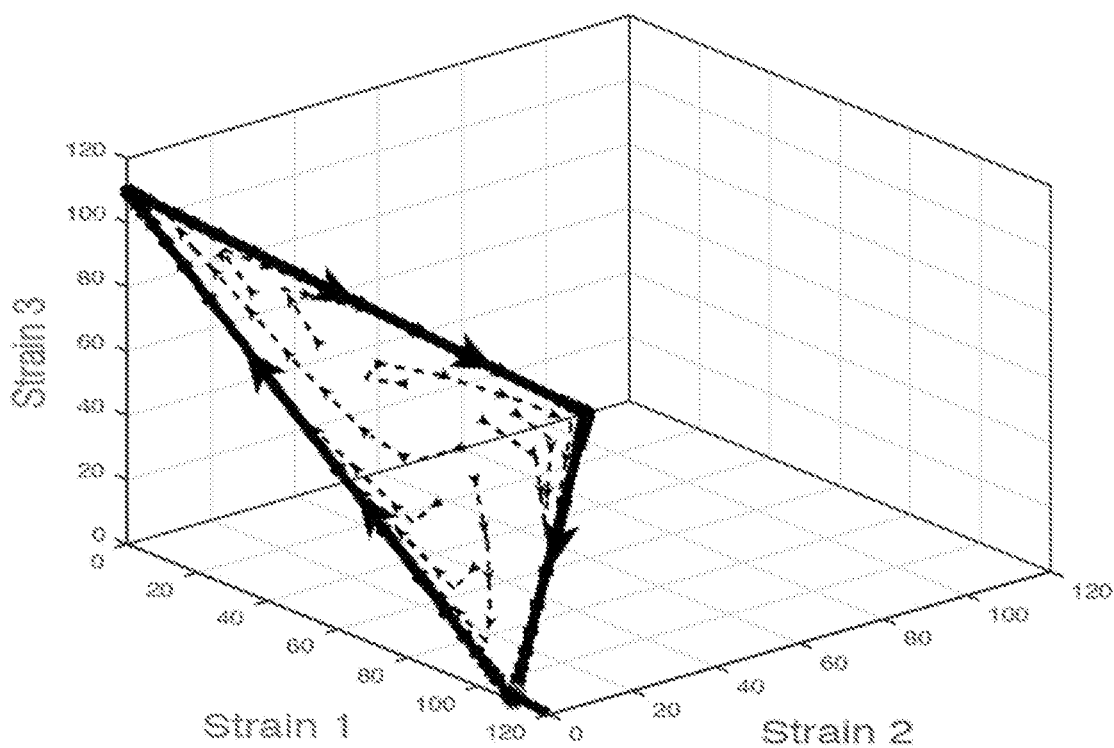
FIG. 3E shows limit cycle of the three-strain system demonstrates stable transitions between the three strains. Additionally, all input parameters of reasonable value result in convergence towards the stable limit cycle.
Figure 13G:
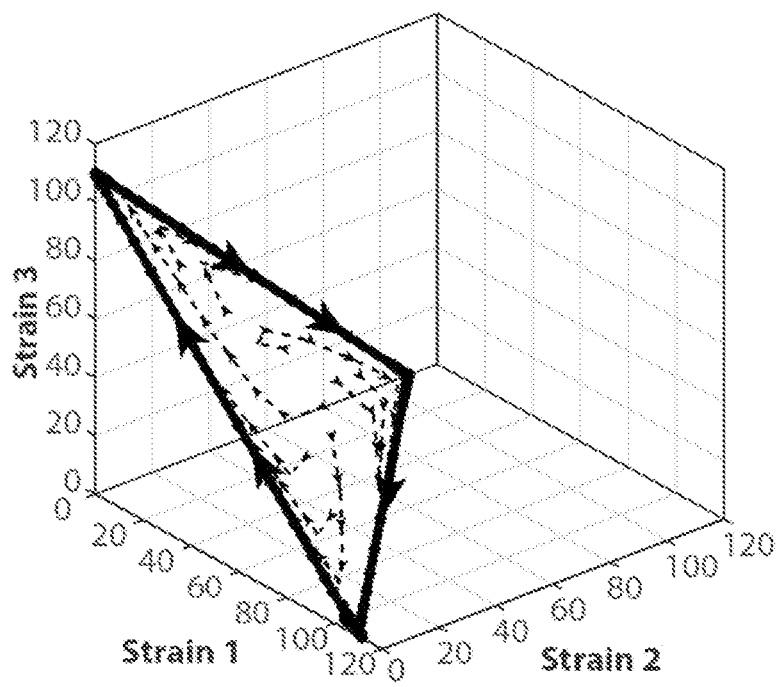
FIG. 13G is a plot illustrating the limit cycle of the three-strain system demonstrates convergence to stable transitions between the three strains regardless of initial strain ratios.
Figure 19:
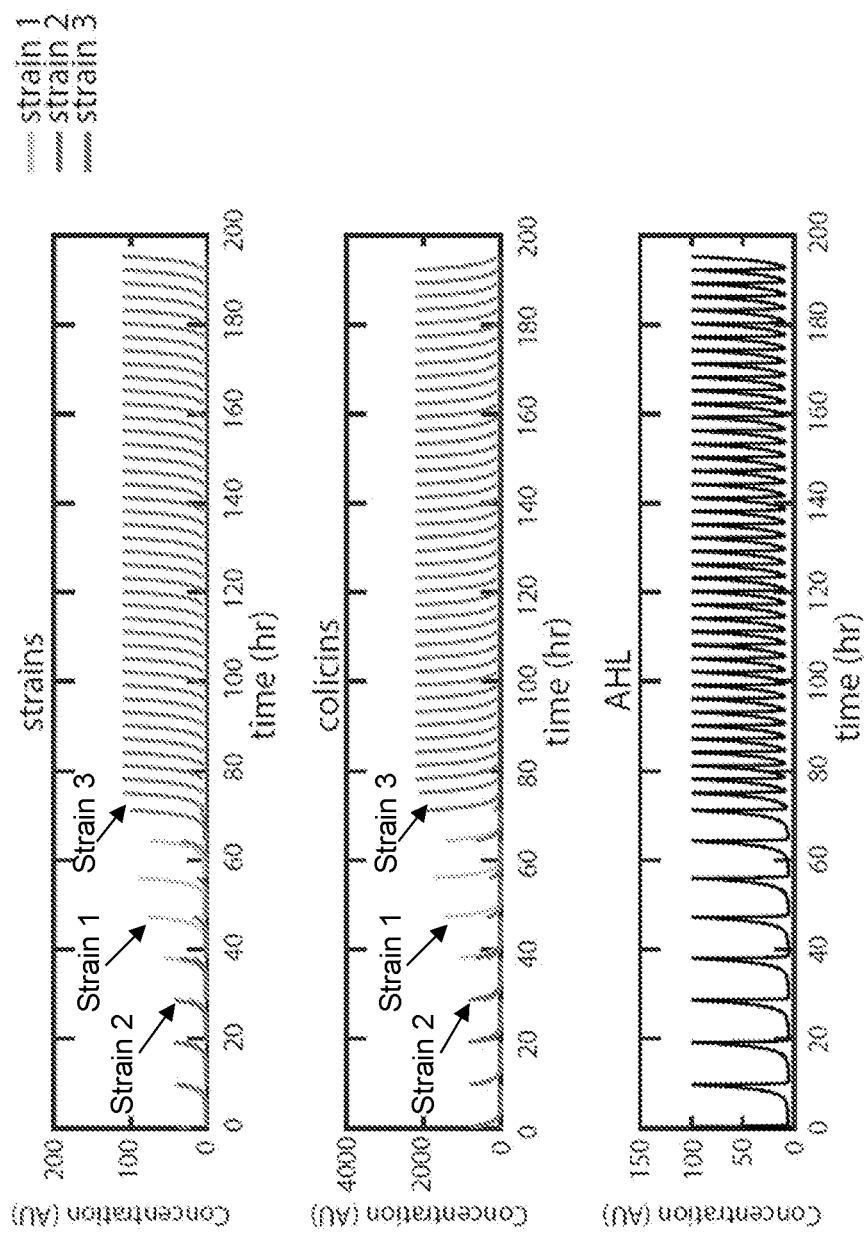
FIG. 19 shows exemplary time series dynamics of the colicin model assuming the system is closed to the introduction of new cells. The three graphs show the concentrations of the strains, colicins, and AHL over time when strain 3 initially starts at a higher concentration and there is no introduction of new cells.

Although co-culture of dominant-susceptible strain pairs enabled consistent strain displacement, an ecology consisting of three antagonistic strains may introduce novel emergent properties when cultured simultaneously. A mathematical model was developed that described the switching population dynamics and reduced it to a discrete-time map that permitted analytical predictions for the switching frequency and interval duration (See Example 5). It was found that when all three strains were present simultaneously, cycles of population dominance between the three strains was an emergent property of the system. Under the assumption that the system was closed to the introduction of fresh cells, the strain that initially started at a higher concentration subsequently dominated the trap (FIG. 19). Alternatively, given a small constant supply of each strain, the trajectory of the three-strain system converged to a stable limit cycle regardless of the initial ratios between the three strains (FIG. 3E, FIG. 13G).

To test this emergent property, all three strains were simultaneously loaded into a single microfluidic device. The same experimental setup described above was used to test the theoretical robustness of the system. The only difference in the protocol consisted in applying a high flow rate following the cell loading in the microfluidic device. This procedure was meant to flush the majority of the cells out of the traps, leaving only roughly 1 to 10 cells in each trap. Using this method, a wide range of relative ratios between the three strains in the various traps were obtained, allowing testing a large distribution of initial concentrations.

Figure 3F:
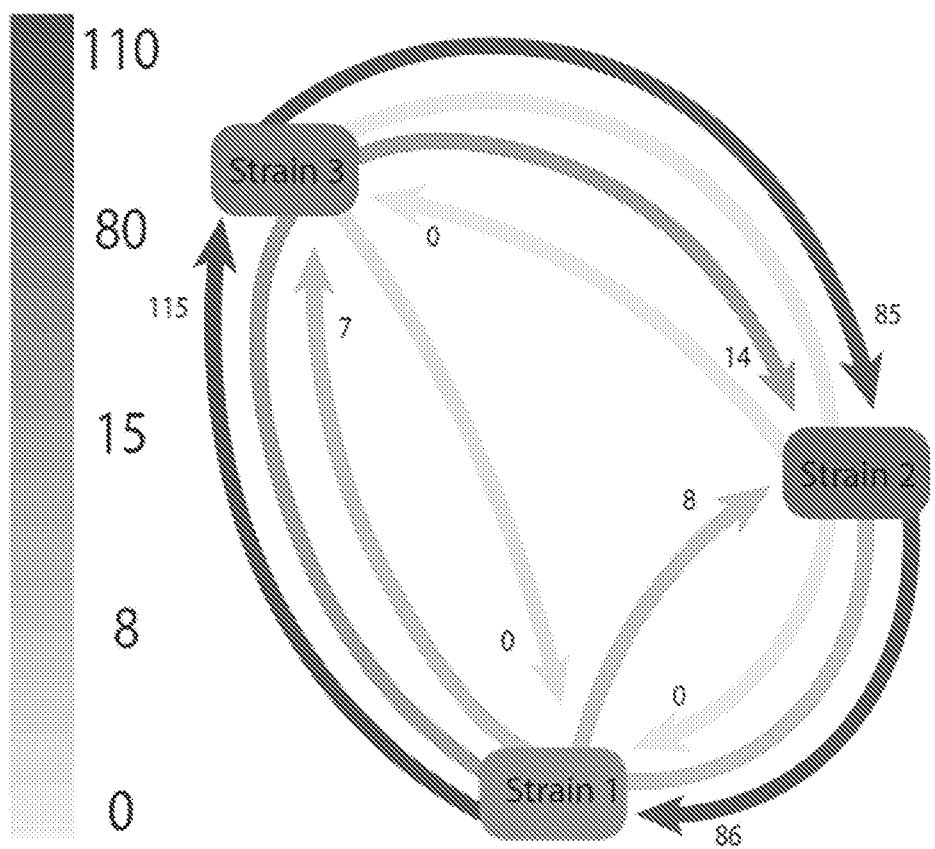
FIG. 3F shows diagram representing strain takeover events observed across 1600 microfluidic traps in which all three engineered strains are loaded simultaneously at approximately equal ratios. Arrows represent each possible transition event between the three strains, arrow colors indicate the number of observed transitions for each arrow.
Figure 5B:
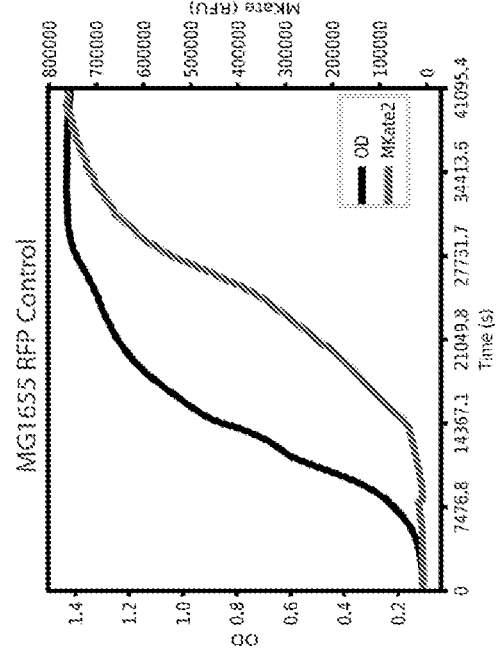
FIG. 5B shows MG1655 wild-type control strain with a GFP expression plasmid. Time course traces of OD600 and GFP fluorescence expression (RFU).
Figure 5D:
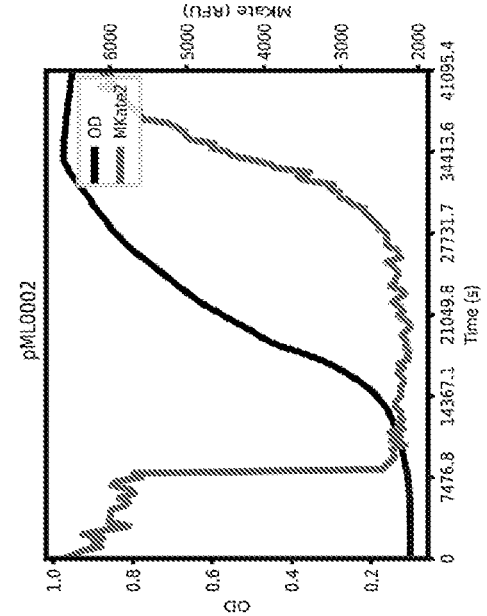
FIG. 5D shows MG1655 Strain 2 time course traces of OD600 and RFP fluorescence expression.
Figure 5A:
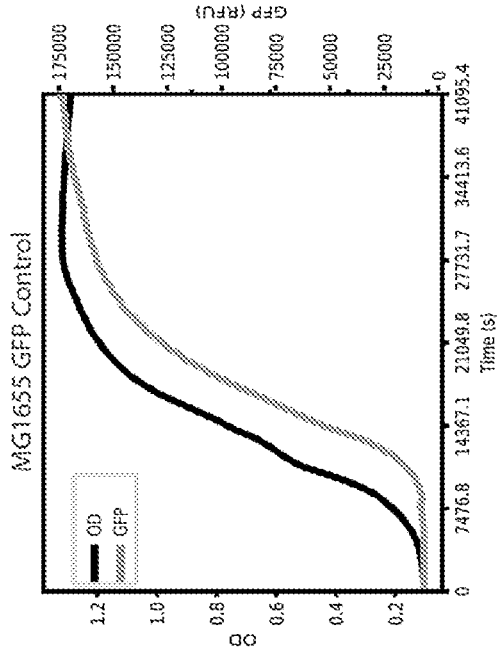
FIG. 5A shows MG1655 wild-type control strain with a mKate2 expression plasmid. Time course traces of OD600 and RFP fluorescence expression.
Figure 5C:
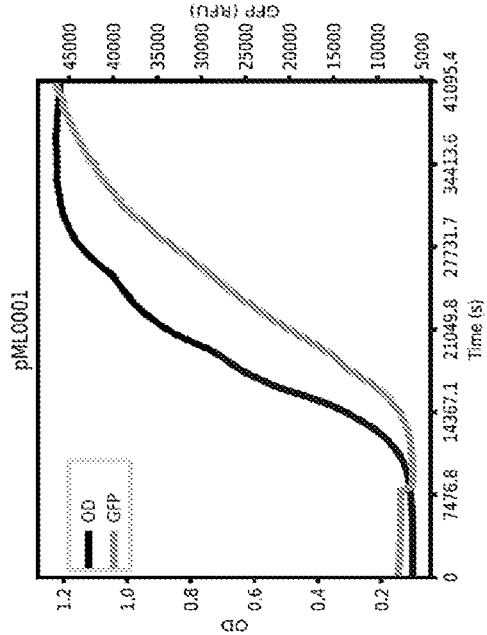
FIG. 5C shows MG1655 Strain 1 (pML0001) time course traces of OD600 and GFP fluorescence expression.
Figure 5E:
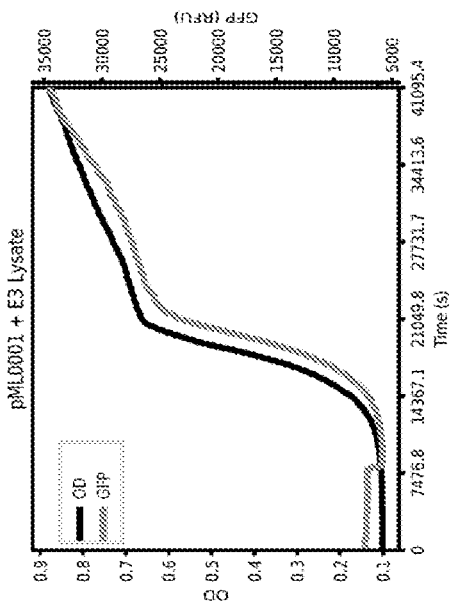
FIG. 5E shows MG1655 Strain 3 time course traces of OD600 and RFP fluorescence expression.
Figure 5F:
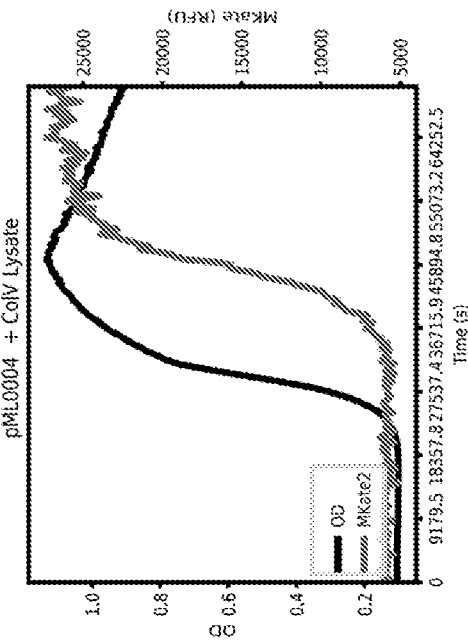
FIG. 5F shows co-incubation of MG1655 Strain 1 with Colicin E3. Time course traces of OD600, GFP and RFP fluorescence (RFU) expression verify that Strain 1 is able to grow in the presence of Colicin E3.
Figure 5G:
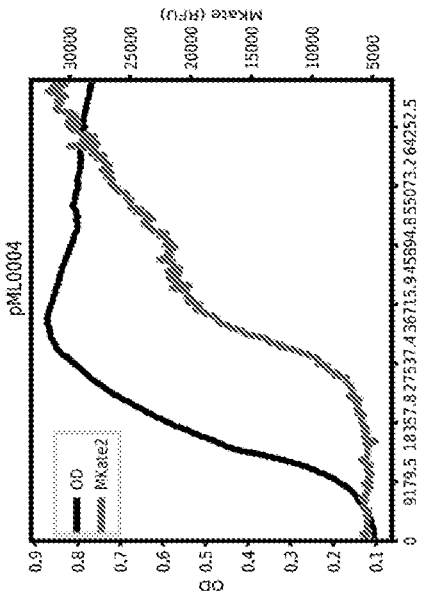
FIG. 5G shows co-incubation of MG1655
Figure 5H:
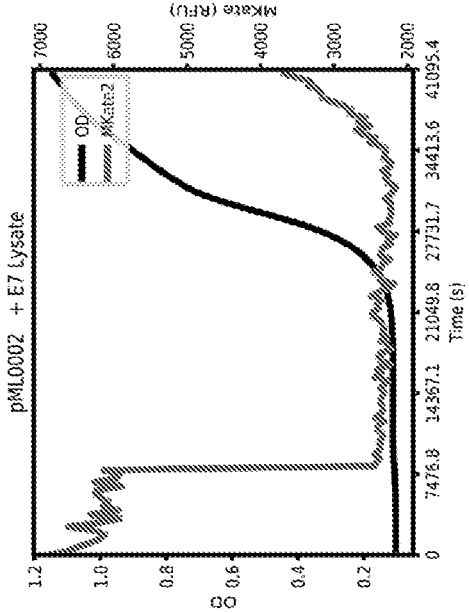
FIG. 5H shows co-incubation of MG1655 Strain 3 (pML0004) with Colicin V. Time course traces of OD600 and RFP fluorescence expression verify that Strain 3 is able to grow in the presence of Colicin V.
Figure 6A:
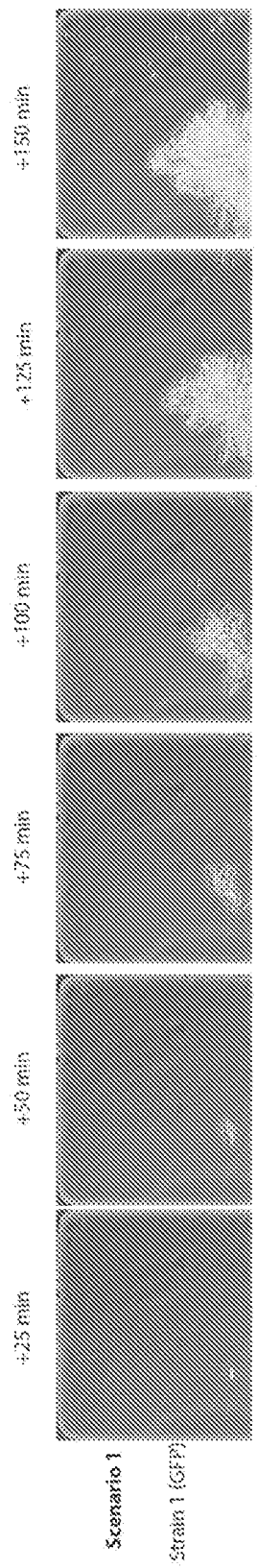
FIG. 6A is scenario 1 showing the growth of Strain 1 alone in a microfluidic trap.
Figure 6B:
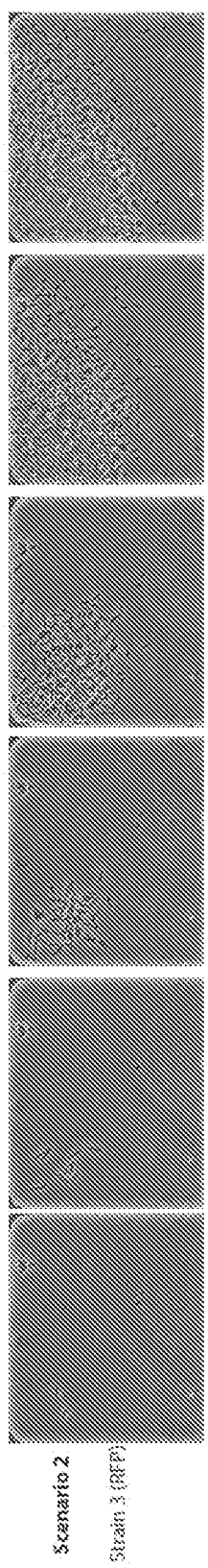
FIG. 6B is scenario 2 showing the growth of Strain 3 alone in a microfluidic trap.
Figure 6C:
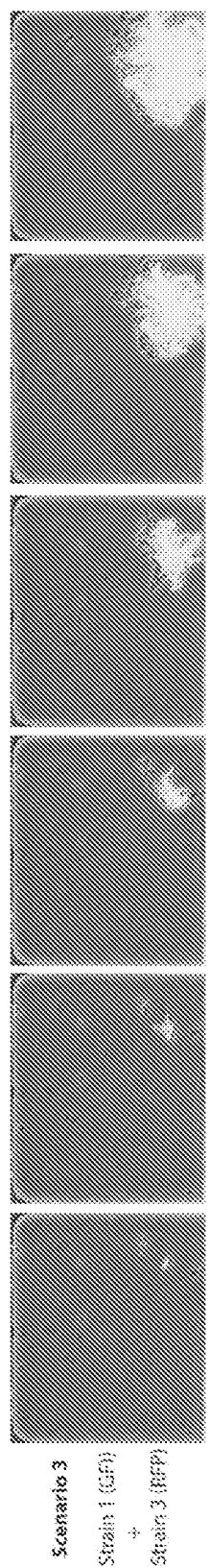
FIG. 6C is scenario 3 showing the growth and Strain 1 and Strain 3 when they are in close proximity with each other. Growth of Strain 3 is inhibited by Strain 1.
Figure 6D:
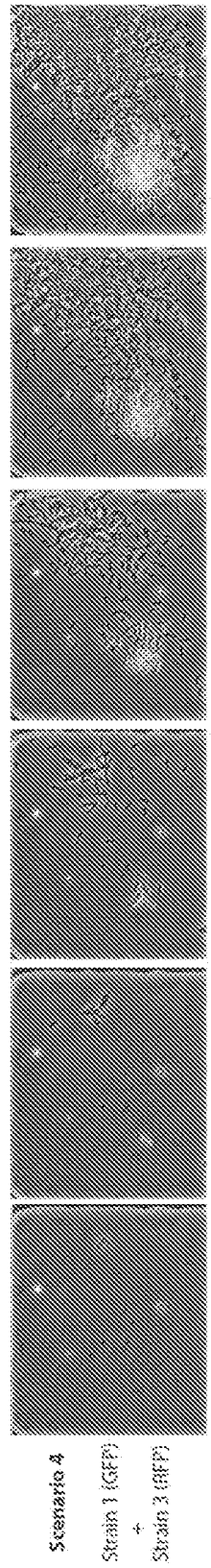
FIG. 6D is scenario 4 showing the growth of Strain 1 and Strain 3 when they are not in close proximity with each other.
Figure 6E:
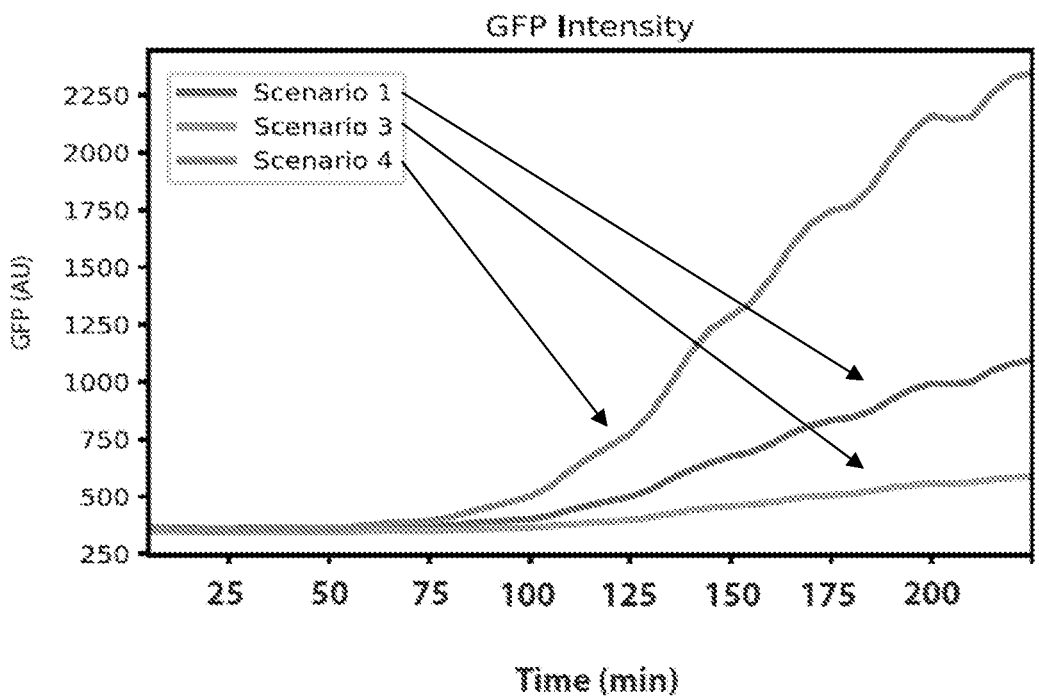
FIG. 6E and FIG. 6F shows fluorescence trajectories of the different scenarios in GFP and RFP.
Figure 6F:
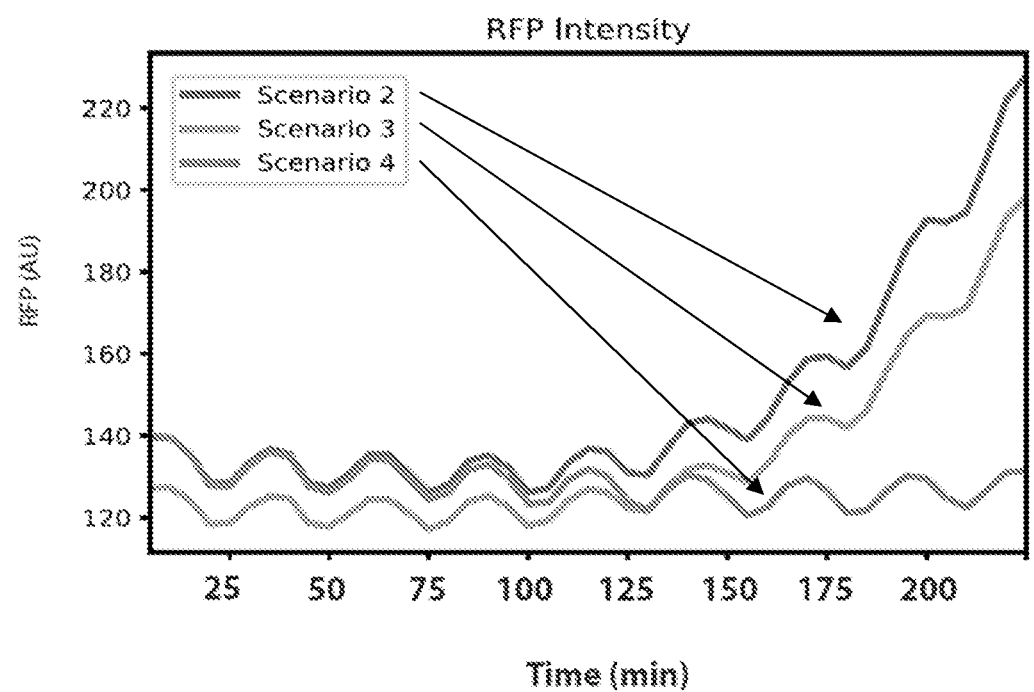
Figure 7A:
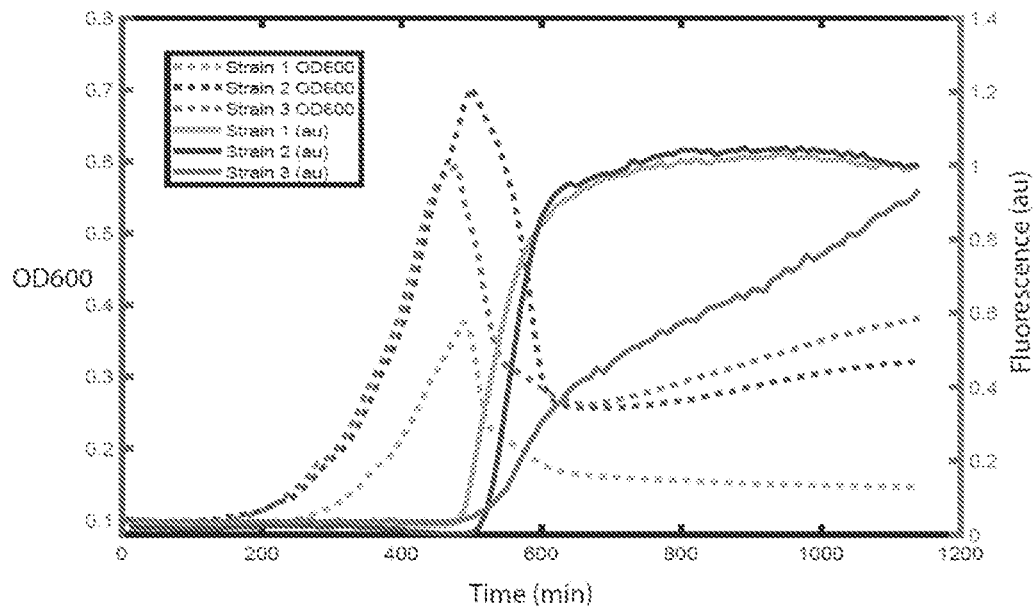
FIG. 7A shows plate reader $OD_{600}$ of Lysis for the 3 lysis strains and the corresponding expression of fluorescence (n=3).
Figure 7B:
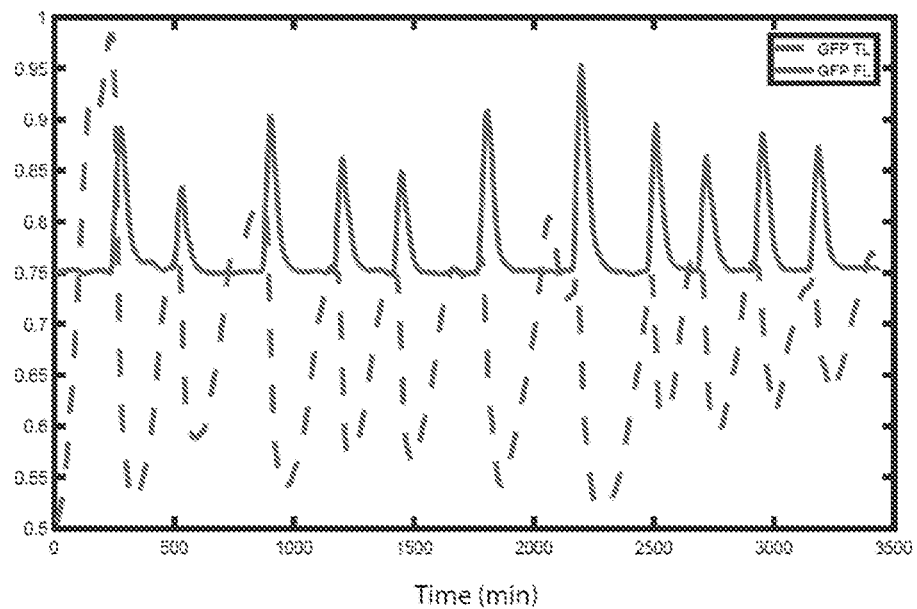
FIG. 7B shows overlay of Strain 1 fluorescence intensity normalized to max value (solid line) and transmitted light intensity normalized to max value (dashed line) of the microfluidic trap region (100× 80×2 µm).
Figure 7C:
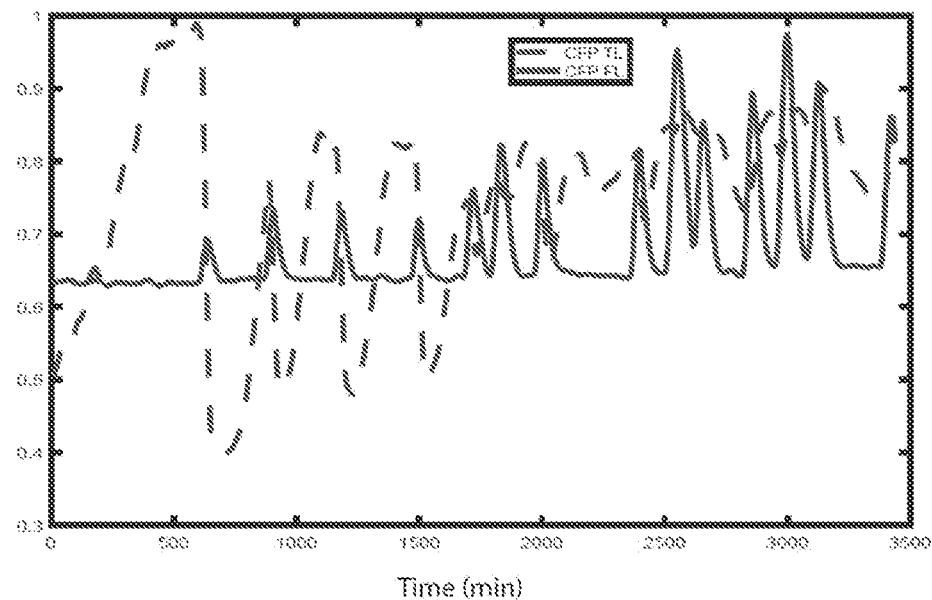
FIG. 7C shows overlay of Strain 2 fluorescence intensity normalized to max value (solid line) and transmitted light intensity normalized to max value (dashed line) of the microfluidic trap region (100×80×2 µm).
Figure 7D:
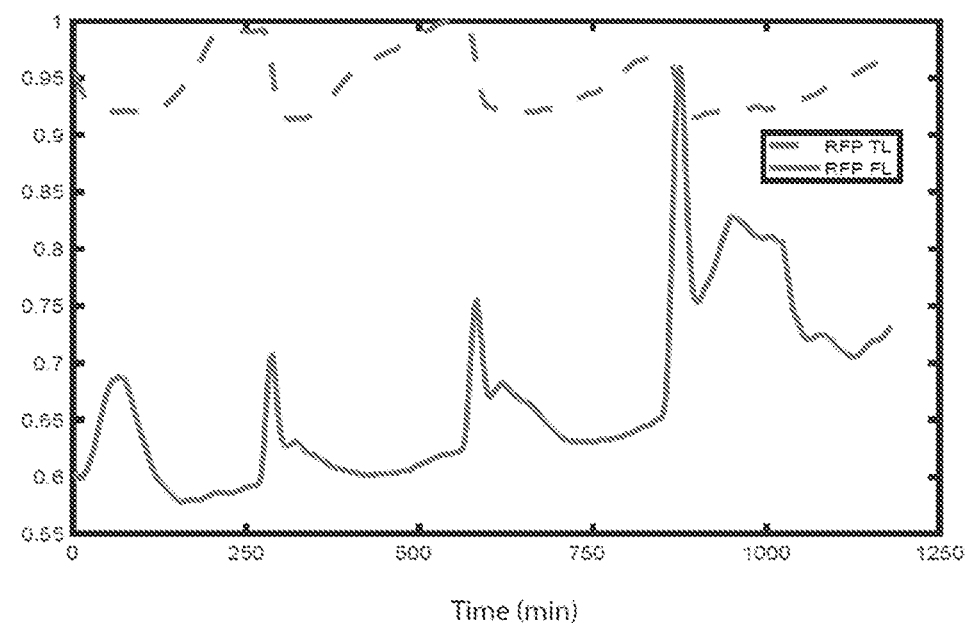
FIG. 7D shows overlay of Strain 3 fluorescence intensity normalized to max value (solid line) and transmitted light intensity normalized to max value (dashed line) of the microfluidic trap region (100×80×2 µm).
Figure 13H:
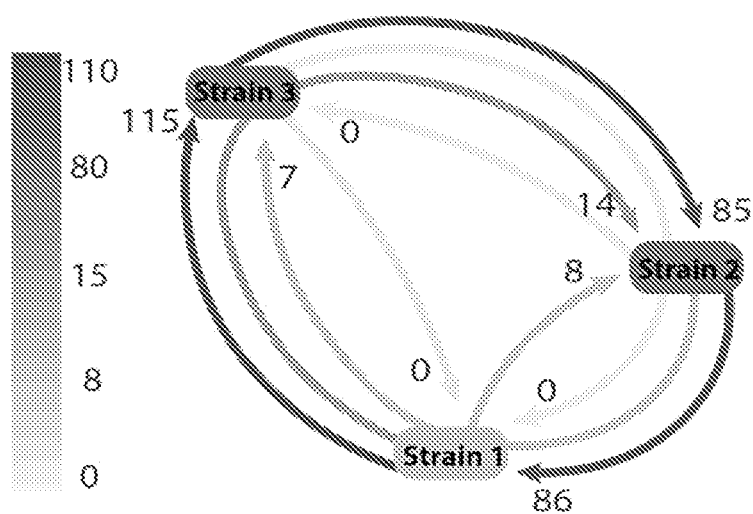
FIG. 13H is a diagram representing strain takeover events observed when all three engineered strains are cultured simultaneously. Arrows represent each possible transition event between the three strains, arrow shading indicates the number of observed transitions for each arrow.
Figure 20A:
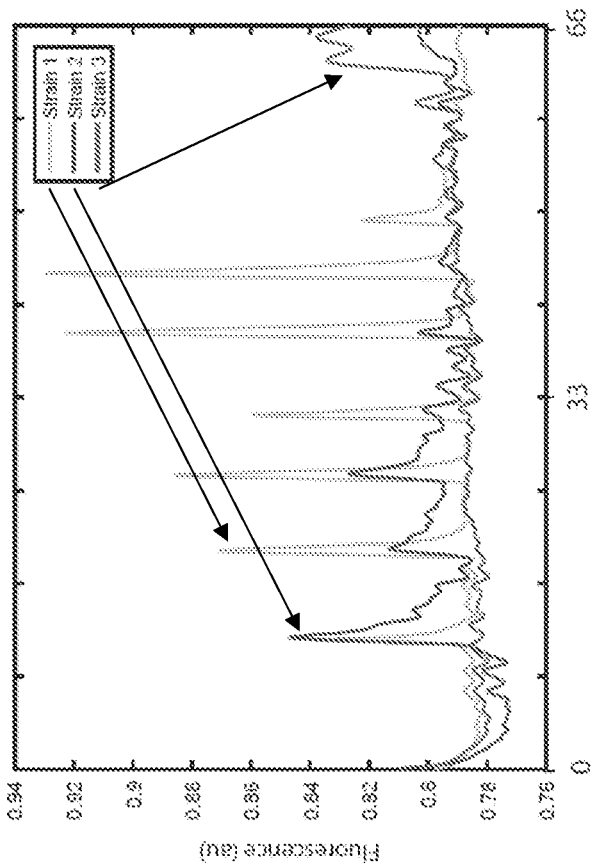
FIG. 20A is a time trace of GFP, CFP, and RFP fluorescence expression of a single trap from a 3-strain co-culture experiment in which all three strains are loaded at roughly equal ratios.
Figure 20B:
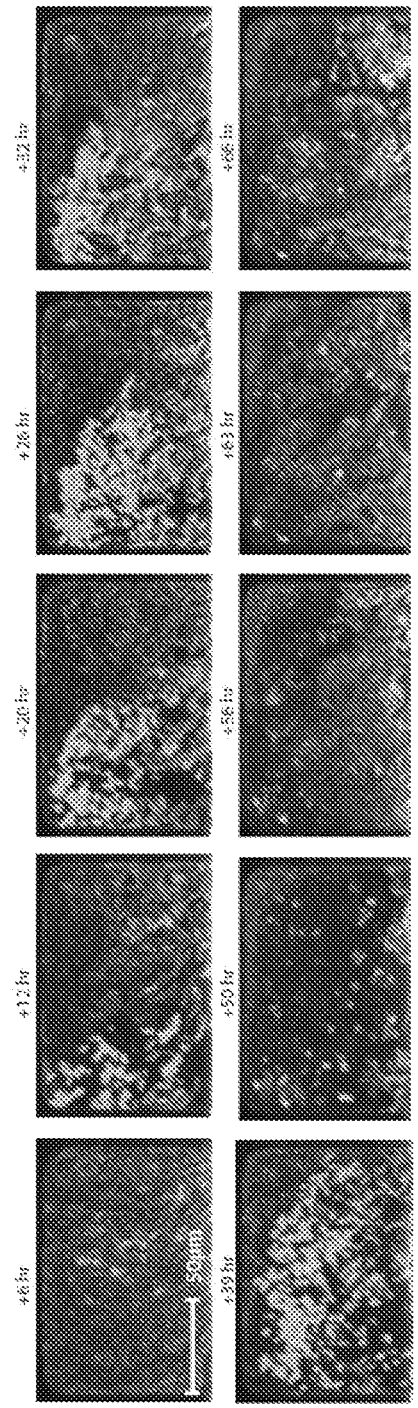
FIG. 20B shows video stills of phase contrast, GFP, CFP, and RFP for the microfluidic chamber shown in FIG. 20A.

Four separate microfluidic experiments totaling 1582 individual microfluidic traps were analyzed. Three different dynamics were observed. Four separate microfluidic experiments were analyzed, totaling 1582 individual microfluidic culture regions and it was observed that the system exhibited cyclical behavior between the three strains such as strain 2 to strain 1 to strain 3 (FIG. 20A-20B). The dynamics for ~75% of the traps consisted of a single strain out-competing the others before the first lysis event occurred. The single strain dominated the trap for the duration of the experiment. In the second case (~20%) traps cycled between two strains, for example strain 1 to strain 2. In the third case (~5%) of traps cycled through three strains, for example strain 1 to strain 2 to strain 3. By aggregating all transition events from the four experiments it is observed that the experimental results align well with the theoretical trajectories (FIG. 3F). As predicted by the model, the three strains competed until two were eliminated and a single strain survived (FIG. 3F, FIG. 13H).

Under ideal experimental conditions, a constant supply of the next strain was provided in the cycle. However, due to experimental constraints, strain cycling was dependent on cells being washed into the trap from the upstream traps and channel. It was demonstrated that under variable conditions containing all 3 strains and all 3 colicins, strains cycle sequentially. However, due to trap geometry, as duration of the experiment increases, the buildup of cell lysates within the microfluidic traps prevents new cells from being washed in upstream, reducing the ability for strain cycling to continue. Due to the limitations of these microfluidic experiments, a full cycle of the system in a single run cannot be shown. However, several instances were shown where the strains cycle from Strain 2 to Strain 1 then Strain 3 as well as other scenarios (FIG. 3D-3E, FIG. 13G). Nevertheless, by aggregating the data of four experiments and 1,600 microfluidic traps, it was demonstrated that variations of the initial conditions of the system (i.e., what the concentrations of each strain begin at initially) do not prevent oscillations between the three-strain system from reaching stability, cycling through the strains one at a time, sequentially (FIG. 3C, FIG. 19A-19B, FIG. 9). This demonstrates the robustness of the system in that variations in the initial conditions would not perturb the steady state of the system. For in-vivo applications this means that achieving the desired strain cycling will not be too sensitive to the initial conditions (e.g., concentration of dosing, time of dosing, etc.).

The consistent convergence of the RPS ecology to the expected behavior supports the feasibility of engineering ecologies to exhibit predictable and precise dynamics. The potential for synthetic microbial communities to enable new biotechnological applications has long been known (see, e.g., B. Kerr, M. A. Riley, M. W. Feldman, B. J. Bohannan, Nature 418, 171 (2002); L. R. Lynd, et al., Nature biotechnology 26, 169 (2008); T. Großkopf, O. S. Soyer, Current opinion in microbiology 18, 72 (2014); K. Zhou, K. Qiao, S. Edgar, G. Stephanopoulos, Nature biotechnology 33, 377 (2015)). Engineered ecologies exhibit complex functions that can be difficult to engineer into single populations (see, e.g., J. Shong, M. R. J. Diaz, C. H. Collins, Current Opinion in Biotechnology 23, 798 (2012); K. Brenner, L. You, F. H. Arnold, Trends in biotechnology 26, 483 (2008)).

Example 4—Plasmid Stability

A RPS synthetic ecology strategy allows external control over the evolution and composition of the ecology, enabling displacement of undesired strains through manual input without interrupting circuit function. In order to demonstrate this concept and prolong the functional stability of the SLC using the RPS system, dynamic expression in the absence of the selective antibiotic (kanamycin) was attempted. In this case, selective pressure against the SLC activator plasmid should result in rapid loss of function.

Figure 14A:
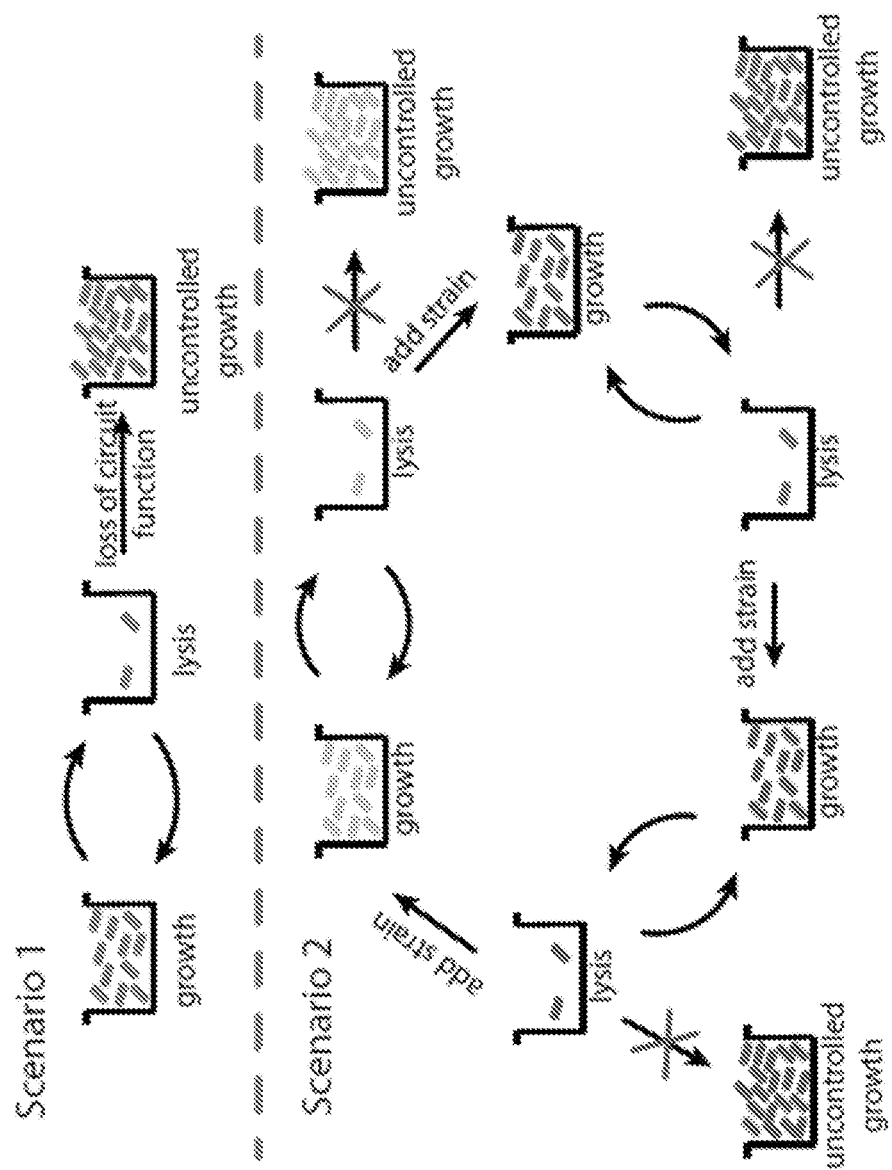
FIG. 14A is a schematic of scenario 1 depicting a system in which oscillations between growth phase and lysis transition to uncontrolled growth due to loss of circuit function. Scenario 2 depicts a cycle composed of the three-strain system in which the transition to the uncontrolled growth is prevented through the addition of the next strain of the system.
Figure 14B:
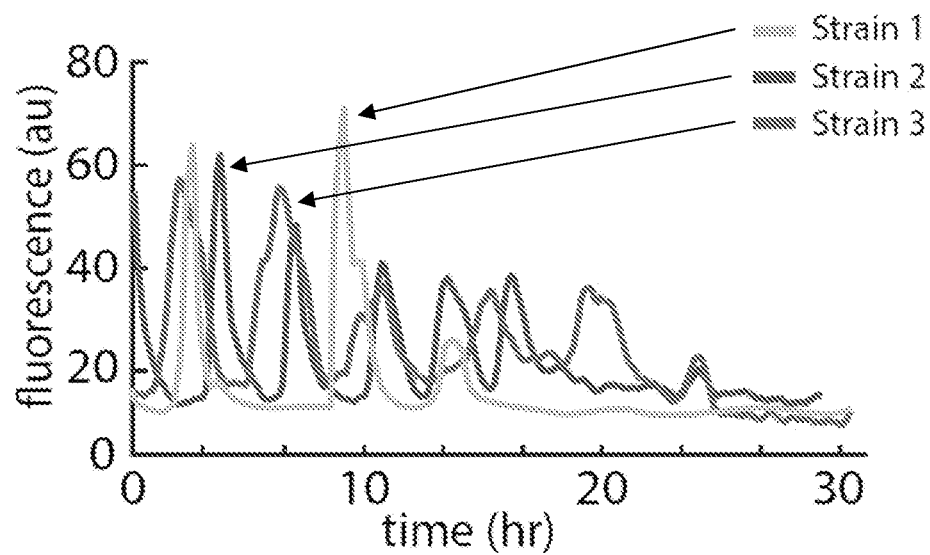
FIG. 14B is a time trace of fluorescence expression for each of the strains shows the loss of circuit function over time. In accordance with scenario 1 from FIG. 14A, each strain was cultured in the absence of kanamycin for a duration of 32 hours.
Figure 14C:
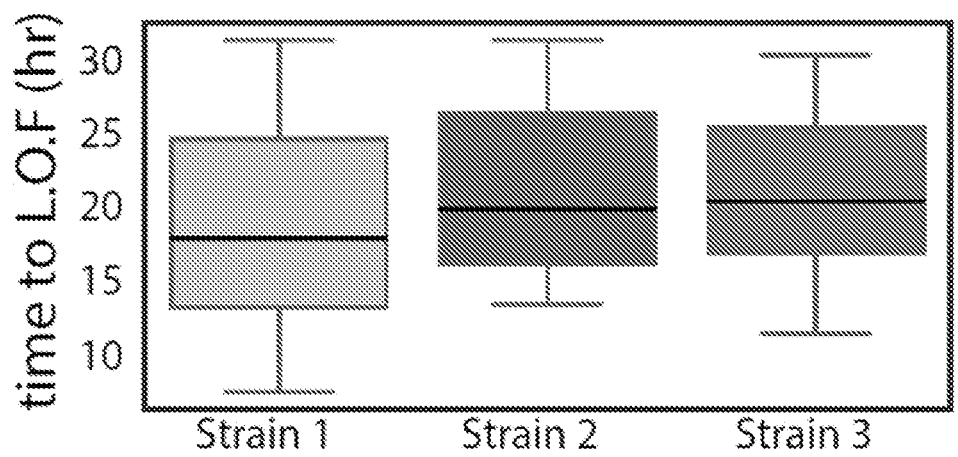
FIG. 14C is boxplots depicting the time to loss of function for each strain (n=16).
Figure 14D:
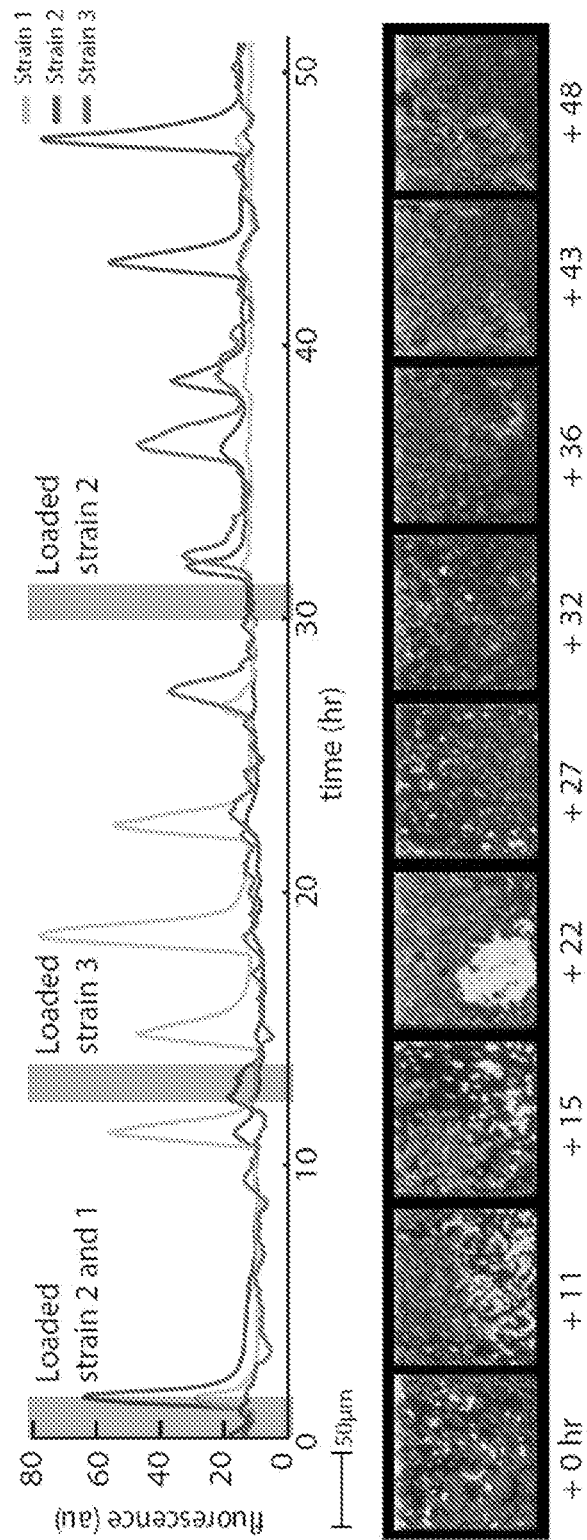
FIG. 14D In accordance with scenario 2 from FIG. 14A, strains were loaded sequentially, starting with strain 2 and strain 1. Top—time trace of GFP, CFP, and RFP fluorescence expression of a single trap that demonstrates cycling through all 3 strains in a single continuous uninterrupted run. Bottom—video stills show a composite of phase contrast and fluorescence at the indicated time points. AU, arbitrary fluorescence units (background subtracted).
Figure 16A:
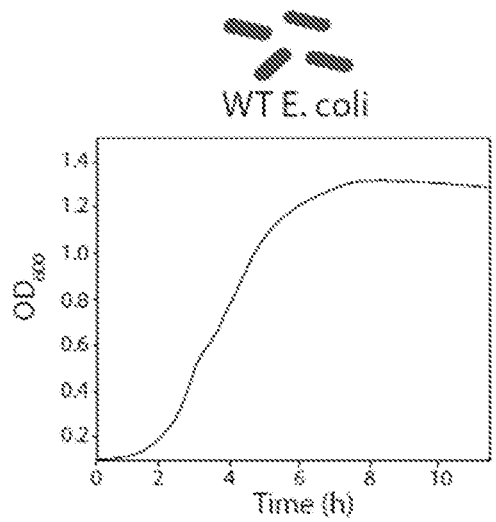
FIG. 16A is a time course trace of $OD_{600}$ for MG1655 wild-type *E. coli*.
Figure 16B:
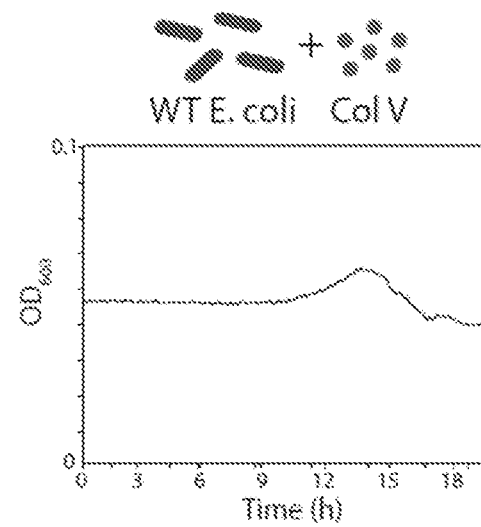
FIG. 16B is a time course trace of $OD_{600}$ for MG1655 wild-type *E. coli* co-incubated with filtered lysate of Colicin V producing strain.
Figure 16C:
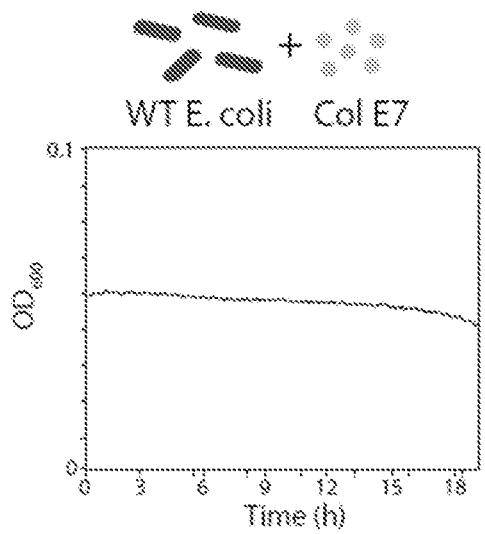
FIG. 16C is a time course trace of $OD_{600}$ for MG1655 wild-type *E. coli* co-incubated with filtered lysate of Colicin E7 producing strain.
Figure 16D:
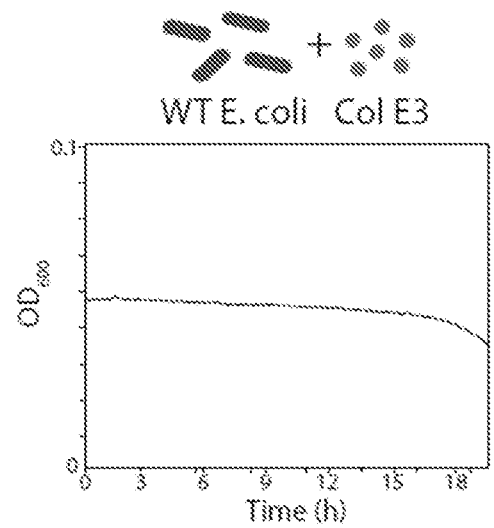
FIG. 16D is a time course trace of $OD_{600}$ for MG1655 wild-type *E. coli* co-incubated with filtered lysate of Colicin E3 producing strain.
Figure 17A:
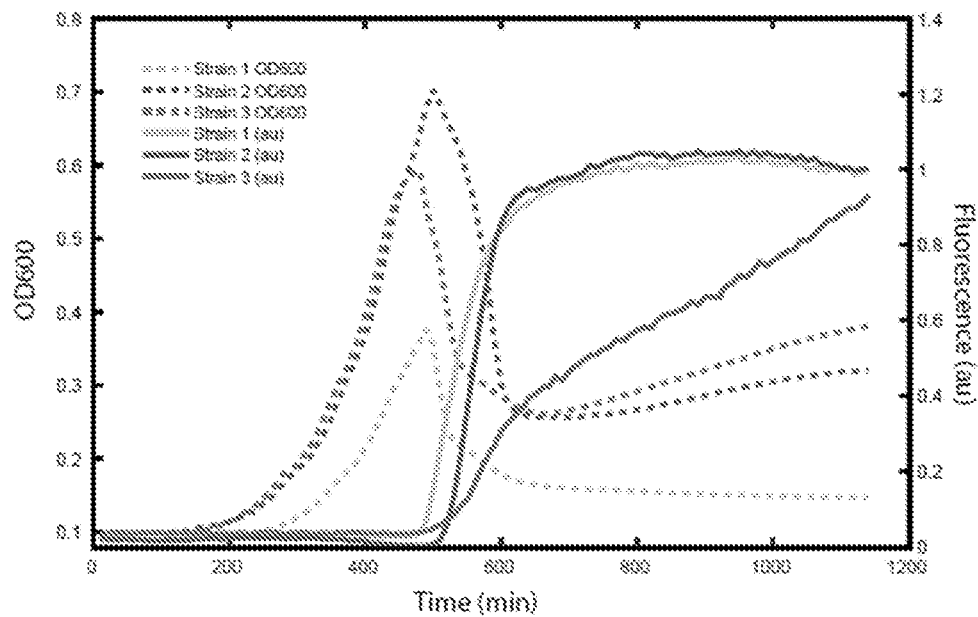
FIG. 17A is a plot of plate reader $OD_{600}$ of lysis for the 3 lysis strains and the corresponding expression of fluorescence (n=3).
Figure 17B:
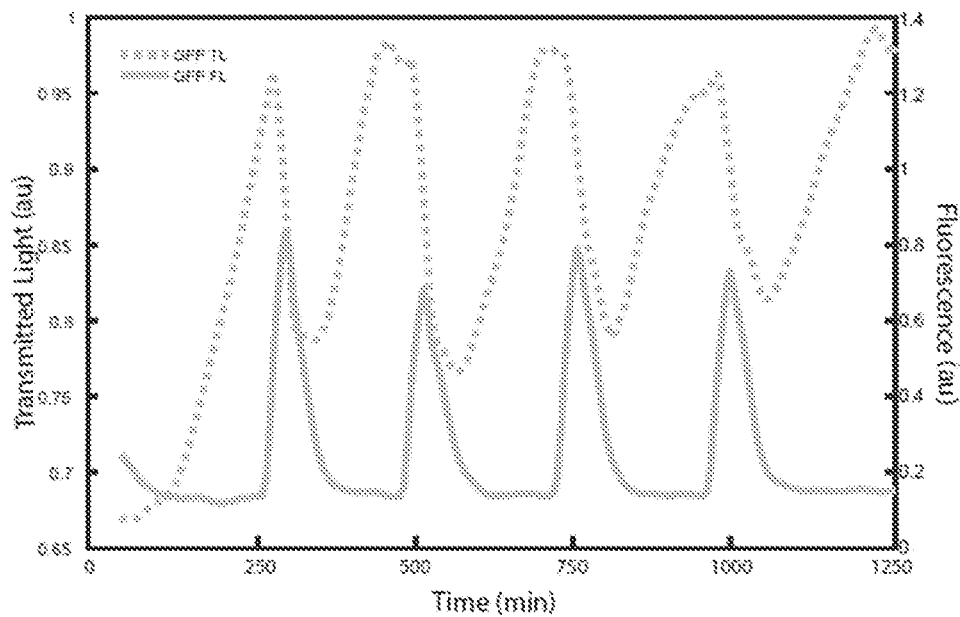
FIG. 17B is a plot overlaying Strain 1 fluorescence intensity normalized to max value (solid line) and transmitted light intensity normalized to max value (dashed line) of the microfluidic trap region (100×80×1.2 μm).
Figure 17C:
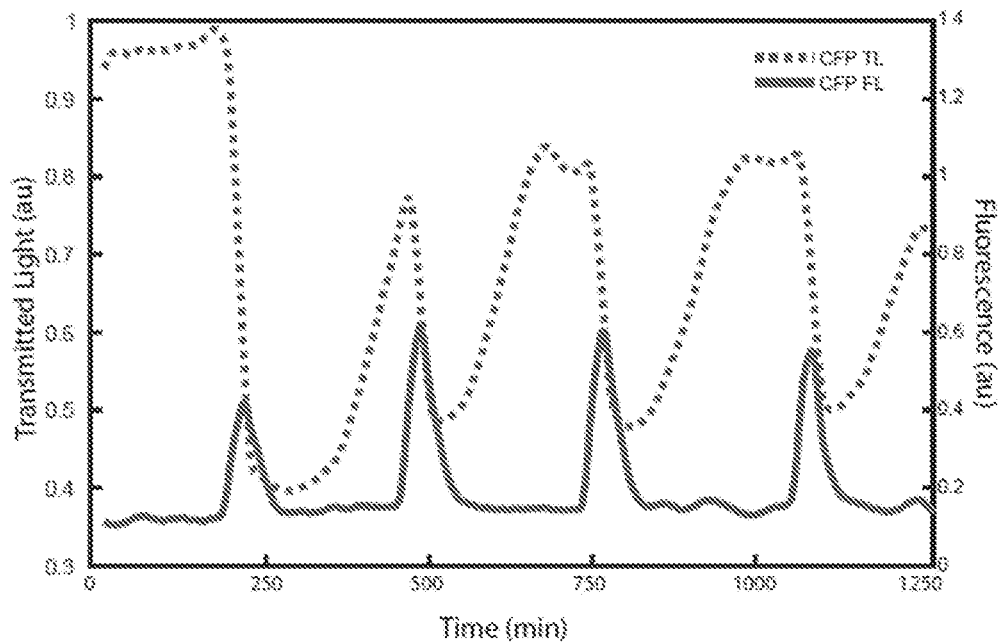
FIG. 17C is a plot overlaying Strain 2 fluorescence intensity normalized to max value (solid line) and transmitted light intensity normalized to max value (dashed line) of the microfluidic trap region (100×80×1.2 μm).
Figure 17D:
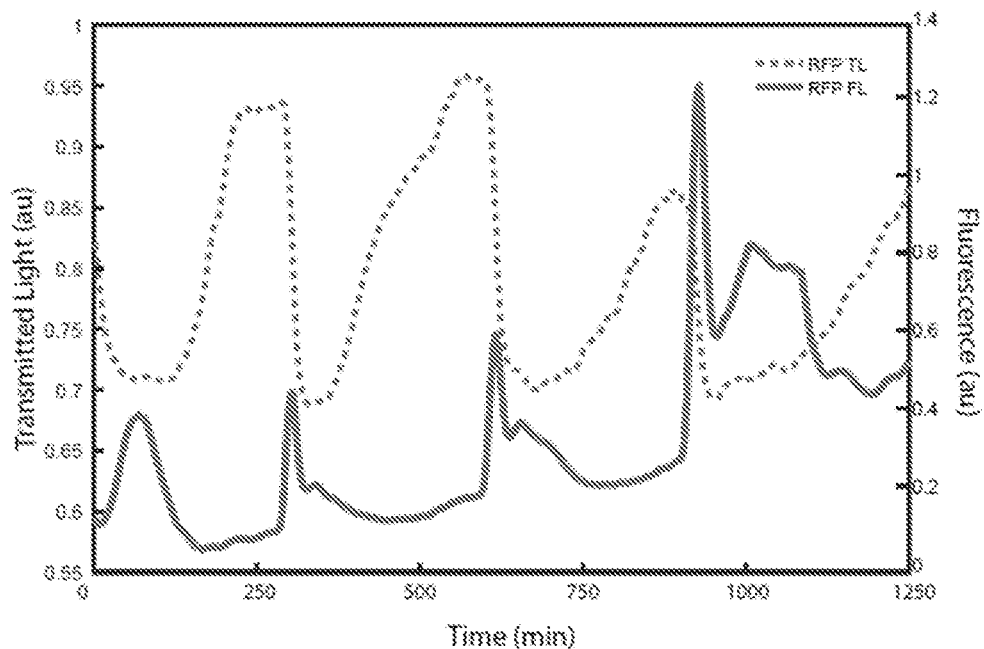
FIG. 17D is a plot overlaying Strain 3 fluorescence intensity normalized to max value (solid line) and transmitted light intensity normalized to max value (dashed line) of the microfluidic trap region (100×80× 1.2 μm).

Two scenarios (FIG. 14A) were investigated. In scenario 1, each strain was cultured individually in LB medium lacking kanamycin. In the absence of selective antibiotic, loss of circuit function was universal and resulted in the loss of fluorescence expression and synchronized lysis dynamics. The elapsed time before synchronized lysis was lost (n=16) was recorded, and it was found that between 80 to 90% of plasmid loss occurred within 32 hours, after which the strains grew uncontrollably (FIG. 14B, 14C, where L.O.F. stands for "loss of function"). In scenario 2, the experiment was started with a co-culture of strain 2 and strain 1, allowing strain 1 to take over the trap. After 12 hours, strain 3 was added to displace strain 1, and at 30 hours strain 2 was re-introduced to displace strain 3. Therefore, starting with strain 2, a full cycle was completed in a way that would likely be maintained over an indefinite period. By manually adding subsequent strains before the previous strain mutated, the duration of circuit stability was able to be prolonged without interrupting circuit function (FIG. 14D).

To further explore the effect of the RPS system on a mutable genetic circuit a batch passage experiment was conducted to compare two scenarios (FIG. 15A). In the first scenario, culture medium containing antibiotics was inoculated with Strain 1 and passaged the culture into fresh growth medium every 12 hours. In scenario 2, a culture was also inoculated with Strain 1 and passaged every 12 hours, however every 3 passages, the next strain in the RPS cycle was also added. It was observed that in scenario 1, mutations began at passage 4 and once the loss of synchronized lysis occurred, it was never recovered. However, in scenario 2 it was observed that a delay in the loss of synchronized lysis as well as recovery of lysis function even after it had been lost in previous passages (FIG. 15B). Sanger sequencing of a 1-kilobase pair region containing the X174E lysis gene and Lux cassette revealed that the RPS strategy reduced the occurrence of mutations over the same duration. In this way, by shifting the challenge of eliminating individual mutated cells to the elimination of an entire population, it was demonstrated the ability of the RPS system to prevent loss of function of a circuit, whether by mutation or plasmid loss.

As an expandable and modular platform to ensure genetic stability, the RPS system provides an additional layer of control allowing it to be combined with other traditional strategies to maintain plasmid stability. This approach may enable synthetic biologists to engineer systems that can be maintained long-term in the absence of selective antibiotics, impacting applications ranging from therapeutics to bioremediation, production, and sensing technologies. These applications will require the development of new RPS strains that are armed with different natural or synthetic toxin-antitoxin systems due to the prevalence of colicin resistance that can appear relatively quickly depending on environmental conditions. In a broader scope, the use of an engineered "synthetic ecology" to control the stability of genetic constructs creates possibilities for applied dynamical synthetic ecosystems through the programmed manipulation and interaction of individual sub-populations.

Example 3—Models

These observations were integrated into a computational model to visually show how this three-strain lysis-based system may behave with respect to a wide range of parameters. Under the assumptions that each strain could be completely killed by the other, it was found that each of the three strains would cycle once, and the strain that started initially at a higher concentration would dominate the trap (FIG. 3A). All three strains were simultaneously loaded into a single microfluidic device. All three strains were cultured to the same approximate OD then mixed together. The mixture of cells was then loaded into the microfluidic device. The system was able to cycle through the three strains, for example strain 2 to strain 1 to strain 3 (FIG. 3B-C). No instance was observed where the strains cycled back to the first strain to complete a full cycle. Due to the lethal effects of one strain on another, the three strains could compete until a single champion remained.

It was hypothesized that to achieve persistent switching in the model, adding a small (epsilon) representing a constant seed of cells is useful to avoid complete elimination of either strain (FIG. 3D). This c term represents the continuous addition of the next strain in the system to provide a constant supply of each cell type. Furthermore, the trajectory of the three-strain system converges to a stable limit cycle which is robust with respect to a wide range of initial conditions and system parameters (FIG. 8).

Three bacterial strains are considered with densities p, q, r that in the absence of colicins grow exponentially with the same nominal growth rate which can be scaled out without loss of generality. These three strains produce three types of colicins. The concentrations of these colicins in extracellular media are $C_p$, $C_q$, $C_r$, respectively. The role of these colicins is that they slow down the growth of each other in a circular manner: $C_p$ slows down the growth of q, so it grows with rate $(1+C_p)^{-1}$, $C_q$ similarly slows down r, and $C_r$ slows down p. Furthermore, all strains produce quorum-sensing molecules AHL, and the extracellular concentration of AHL is denoted A. The colicins that cells produce remain conned to the respective cells and do not affect other strains until released into the extracellular media during lysis events. The lysis of all strains occurs if A is greater than or equal to $A_c$ during which most cells get lysed, but a small fraction δ survives. The AHL in extracellular space is constantly diluted with rate $\gamma_A$, while colicins are diluted with the rate $\gamma_C$.

Suppose that at time $t_i$ right after lysis event i, the values of all 7 concentrations are $p_i$, $q_i$, $r_i$, $C_p^i$, $C_r^i$, $C_q^i$, $A_i$, respectively. Note that by assumption $A_i = A_c$ (the lysis event is short, and the concentration of AHL does not have a chance to change). The subsequent evolution of these dynamical variables is governed by the following equations:

$$\dot{p} = \frac{p}{1+C_r} \quad (1)$$

$$\dot{q} = \frac{q}{1+C_p} \quad (2)$$

$$\dot{r} = \frac{r}{1+C_q} \quad (3)$$

$$\dot{C}_p = -\gamma_C C_p \quad (4)$$

$$\dot{C}_q = -\gamma_C C_q \quad (5)$$

$$\dot{C}_r = -\gamma_C C_r \quad (6)$$

$$\dot{A} = \alpha(p+q+r) - \gamma_A A \quad (7)$$

After the lysis event i, the concentrations of p, q, r are small, and the concentration of AHL initially goes down due to dilution. But as the total bacterial density p+q+i grows sufficiently large, the concentration of AHL begins to grow back. When A reaches $A_c$ again at time $t_{i+1}$, new lysis event occurs. At this moment, the concentrations of the three strains that were equal to $P_{i+1}$, $Q_{i+1}$, $R_{i+1}$, respectively, are instantly reduced by the fraction δ, $$|p_{i+1} = \delta P_{i+1} + \epsilon \quad (8)$$

$$q_{i+1} = \delta Q_{i+1} + \epsilon \quad (9)$$

$$r_{i+1} = \delta R_{i+1} + \epsilon \quad (10)$$

[NOTE: a small ε was added to avoid complete elimination of either strain. Seemingly minor, but crucial, persistent switching does not seem to occur without it]. At the same time, colicins are released from the lysed cells into the extracellular space and added to the colicins that were there before:

$$C_p^{i+1} = C_p(t_{i+1}^-) + \beta(1-\delta)P_{i+1} \quad (11)$$

$$C_q^{i+1} = C_q(t_{i+1}^-) + \beta(1-\delta)Q_{i+1} \quad (12)$$

$$C_r^{i+1} = C_r(t_{i+1}^-) + \beta(1-\delta)R_{i+1} \quad (13)$$

Here $P_{i+1} = p(t_{i+1}^-)$ is the density of strain p immediately before the i+1-st lysis event, and similarly for Q and R. Parameter β characterizes the release rate of colicins by bacteria during lysis (assumed to be the same for all three strains).

Simulations of Eqs. (1)-(13) show robust switching dynamics of dominant stain densities in a broad range of parameter values (FIGS. 24A, 24B, 25A, 25B, 26A, and 26B).

Analytics.

Equations for colicin dynamics between lysis events are linear, so they can be trivially integrated, $$C_{p,q,r}(t) = C_{p,q,r}^i e^{-\gamma_c(t-t_i)} \quad (14)$$

Now, since the colicin concentrations as functions of time are known, equations for the strain concentrations can be integrated:

$$p(t) = p_i \exp\left[\int_{t_1}^{t} \frac{dt'}{1+C_r^i e^{-\gamma_c(t'-t_i)}}\right] = \quad (15)$$

$$p_i \exp\left[\gamma_c^{-1} \log \frac{C_r^i + e^{\gamma_c(t-t_i)}}{C_r^i + 1}\right] = p_i \left[\frac{C_r^i + e^{\gamma_c(t-t_i)}}{C_r^i + 1}\right]^{\frac{1}{\gamma_c}}$$

$$q(t) = q_i \exp\left[\int_{t_1}^{t} \frac{dt'}{1+C_p^i e^{-\gamma_c(t'-t_i)}}\right] = \quad (16)$$

$$q_i \exp\left[\gamma_c^{-1} \log \frac{C_p^i + e^{\gamma_c(t-t_i)}}{C_p^i + 1}\right] = q_i \left[\frac{C_p^i + e^{\gamma_c(t-t_i)}}{C_p^i + 1}\right]^{\frac{1}{\gamma_c}}$$

$$r(t) = r_i \exp\left[\int_{t_1}^{t} \frac{dt'}{1+C_q^i e^{-\gamma_c(t'-t_i)}}\right] = \quad (17)$$

$$r_i \exp\left[\gamma_c^{-1} \log \frac{C_q^i + e^{\gamma_c(t-t_i)}}{C_q^i + 1}\right] = r_i \left[\frac{C_q^i + e^{\gamma_c(t-t_i)}}{C_q^i + 1}\right]^{\frac{1}{\gamma_c}}$$

Finally, the concentration of AHL between lysis events was computed as $$A(t) = e^{-\gamma_A(t-t_i)}[A(t_i) + \alpha \int_{t_i}^{t}(p+q+r)e^{\gamma_A t'} dt'] \quad (18)$$

The time of the next lysis event is found from the transcendental equation $$A_c = e^{-\gamma_A(t_{i+1}-t_i)}[A_c + \alpha \int_{t_i}^{t_{i+1}} (p+q+r)e^{\gamma_A t'} dt'] \quad (19)$$

or $$\alpha \int_{t_i}^{t_{i+1}} (p+q+r)e^{\gamma_A t'} dt' = A_c[e^{\gamma_A(t_{i+1}-t_i)} - 1] \quad (20)$$

From here on it was assumed that the dynamics of AHL is much faster than population dynamics (i.e. $\gamma_A \gg 1$). Then AHL concentration tracks the total amount of cells in the chamber, and the expression for A can be simplified, $$A(t) = \alpha \gamma_A^{-1} [p(t) + q(t) + r(t)] \quad (21)$$

so the condition for the next lysis event becomes $$P_i + Q_i + R_i = \gamma_A A_c \alpha^{-1} \quad (22)$$

If colicins also degrade sufficiently fast, so they have time to degrade to negligibly small values by the end of each lysis cycle, as in examples shown in FIGS. 25A, 25B, 26A, and 26B, then the values of $C_p^i$, $C_q^i$, $C_r^i$, don't depend on the colicin concentrations during the previous lysis cycle, and are directly proportional to $P_i$, $Q_i$, $R_i$, according to Eqs. (23)-(25):

$$C_p^i = \beta(1-\delta)P_i \quad (23)$$

$$C_q^i = \beta(1-\delta)Q_i \quad (24)$$

$$C_r^i = \beta(1-\delta)R_i \quad (25)$$

Substituting these expressions and (8)-(10) in Eqs.(15)-(17) at the time of the next lysis event, $t = t_i + 1$ the following implicit mapping is achieved $$P_{i+1} = (\delta P_i + \epsilon)\left[1 + \frac{e^{\gamma_c T_i} - 1}{1 + \beta(1-\delta)R_i}\right]^{1/\gamma_c}, \quad (26)$$

$$Q_{i+1} = (\delta Q_i + \epsilon)\left[1 + \frac{e^{\gamma_c T_i} - 1}{1 + \beta(1-\delta)P_i}\right]^{1/\gamma_c}, \quad (27)$$

$$R_{i+1} = (\delta R_i + \epsilon)\left[1 + \frac{e^{\gamma_c T_i} - 1}{1 + \beta(1-\delta)Q_i}\right]^{1/\gamma_c}, \quad (28)$$

where the notation $T_i = t_{i+1} - t_i$ is introduced for the time interval between ith and (i+1)-st lysis events. The mapping is still implicit because the value $T_i$ is still undetermined. If $\delta \ll$ $$P_{i+1} = \frac{(\delta P_i + \epsilon)e^{T_i}}{(1 - \beta R_i)^{1/\gamma_c}}, \quad (29)$$

$$Q_{i+1} = \frac{(\delta Q_i + \epsilon)e^{T_i}}{(1 - \beta P_i)^{1/\gamma_c}}, \quad (30)$$

$$R_{i+1} = \frac{(\delta R_i + \epsilon)e^{T_i}}{(1 - \beta Q_i)^{1/\gamma_c}}, \quad (31)$$

1, i.e. the density of cells increases significantly between the lysis events, one can simplify expressions in the square brackets by dropping 1's:

Now $T_i$ can be computed by summing up these tree equations and using Eq. (22):

$$e^{T_i}\left[\frac{\delta P_i + \epsilon}{(1 + \beta R_i)^{1/\gamma_c}} + \frac{\delta Q_i + \epsilon}{(1 + \beta P_i)^{1/\gamma_c}} + \frac{\delta R_i + \epsilon}{(1 + \beta Q_i)^{1/\gamma_c}}\right] = \gamma_A A_c \alpha^{-1} \quad (32)$$

In the end, the following explicit 3-dimensional mapping for $P_i$, $Q_i$, $R_i$ is achieved:

$$P_{i+1} = \frac{\gamma_A A_c \alpha^{-1} X_i}{X_i + Y_i + Z_i}, \quad (33)$$

$$Q_{i+1} = \frac{\gamma_A A_c \alpha^{-1} Y_i}{X_i + Y_i + Z_i}, \quad (34)$$

$$R_{i+1} = \frac{\gamma_A A_c \alpha^{-1} Z_i}{X_i + Y_i + Z_i}, \quad (35)$$

$$(36)$$

where $$X_i = \frac{\delta P_i + \epsilon}{(1 + \beta R_i)^{1/\gamma_c}}, \quad (37)$$

$$Y_i = \frac{\delta P_i + \epsilon}{(1 + \beta P_i)^{1/\gamma_c}}, \quad (38)$$

$$Z_i = \frac{\delta P_i + \epsilon}{(1 + \beta Q_i)^{1/\gamma_c}}. \quad (39)$$

The interval between the lysis events, from Eq. (32), is given by $$T_i = \log\left[\frac{\gamma_A A_c \alpha^{-1}}{X_i + Y_i + Z_i}\right]. \quad (40)$$

Fixed Point and Hopf Bifurcation.

The fixed point of the mapping (33)-(33) in which all three strains are equal, $P_i = Q_i = R_i = P_0 = \gamma_A A_c/3\alpha$ is considered. In this regime, the period between lysis events is given by $$T_{fp} = \quad (41)$$

$$\log\left[\frac{\gamma_A A_c \alpha^{-1}(1 + \beta P_0)^{1/\gamma_c}}{3(\delta P_0 + \epsilon)}\right] = \log\left[\frac{\gamma_A A_c \alpha^{-1}(1 + \beta \gamma_A A_c/3\alpha)^{1/\gamma_c}}{\delta \gamma_A A_c/\alpha + 3\epsilon}\right].$$

$$\tilde{P}_{i+1} = \frac{P_0(2x_i - y_i - z_i)}{3X_0}, \quad (42)$$

$$\tilde{Q}_{i+1} = \frac{P_0(2y_i - x_i - z_i)}{3X_0}, \quad (43)$$

$$\tilde{R}_{i+1} = \frac{P_0(2z_i - x_i - y_i)}{3X_0}, \quad (44)$$

$$(45)$$

To study the stability of this fixed point, the map near it was linearized, where $X_0 = (\delta P_0 + \beta)(1 + \beta P_0)^{-1/\gamma_c}$ and $$x_i = \frac{\delta}{(1 + \beta P_0)^{1/\gamma_c}} \tilde{P}_i - \frac{\beta(\delta P_0 + \epsilon)}{\gamma_c(1 + \beta P_0)^{1+1/\gamma_c}} \tilde{R}_i, \quad (46)$$

$$y_i = \frac{\delta}{(1 + \beta P_0)^{1/\gamma_c}} \tilde{Q}_i - \frac{\beta(\delta P_0 + \epsilon)}{\gamma_c(1 + \beta P_0)^{1+1/\gamma_c}} \tilde{P}_i, \quad (47)$$

$$z_i = \frac{\delta}{(1 + \beta P_0)^{1/\gamma_c}} \tilde{R}_i - \frac{\beta(\delta P_0 + \epsilon)}{\gamma_c(1 + \beta P_0)^{1+1/\gamma_c}} \tilde{Q}_i. \quad (48)$$

Substituting these expressions, the following linear map was achieved $$\tilde{P}_{i+1} = A(2\tilde{P}_i - \tilde{Q}_i - \tilde{R}_i) - B(2\tilde{R}_i - \tilde{P}_i - \tilde{Q}_i) \quad (49)$$

$$\tilde{Q}_{i+1} = A(2\tilde{Q}_i - \tilde{P}_i - \tilde{R}_i) - B(2\tilde{P}_i - \tilde{R}_i - \tilde{Q}_i), \quad (50)$$

$$\tilde{R}_{i+1} = A(2\tilde{R}_i - \tilde{P}_i - \tilde{Q}_i) - B(2\tilde{Q}_i - \tilde{P}_i - \tilde{R}_i), \quad (51)$$

where $$A = \frac{\delta P_0}{3(\delta P_0 + \epsilon)} = \frac{1}{3(1 + 3\alpha\epsilon/\delta\gamma_A A_c)}, \quad (52)$$

$$B = \frac{\beta P_0}{3\gamma_c(1 + \beta P_0)} = \frac{1}{3\gamma_c(1 + 3/\beta\gamma_A A_c)} \quad (53)$$

The stability of the fixed point was determined by the eigenvalues of the characteristic matrix $$M = \begin{pmatrix} 2A+B & B-A & -A-2B \\ -A-2B & 2A+B & B-A \\ B-A & -A-2B & 2A+B \end{pmatrix} \quad (54)$$

This matrix has three eigenvalues: $\lambda_1 = 0$; $\lambda_{2,3} = 3A + 3B/2 \pm i3\sqrt{3}B/2$. The first eigenvalue is zero and corresponds to super-stability. The second and third eigenvalues are complex and can correspond to exponentially growing solutions if their absolute values $|\lambda_{2,3}|$, are greater than 1, $\sqrt{(3A+3B/2)^2 + 27B^2/4} > 1$, or $$A^2 + B^2 + AB > 1/9$$

Figure 8A:
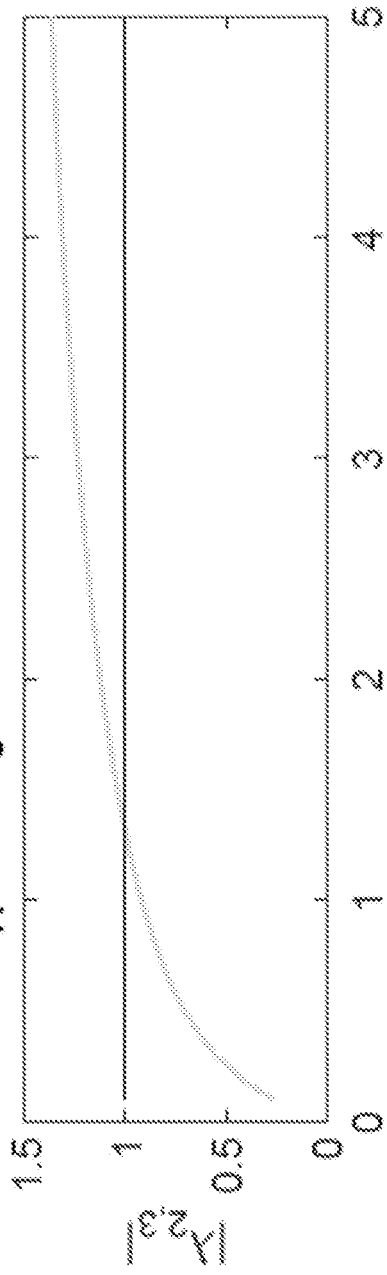
FIG. 8A shows magnitude of the non-zero eigenvalues of the map mode as a function of $A_c$. The transition to oscillations occurs at $A_c$=1.25 when $\lambda$ 23=1.
Figure 8B:
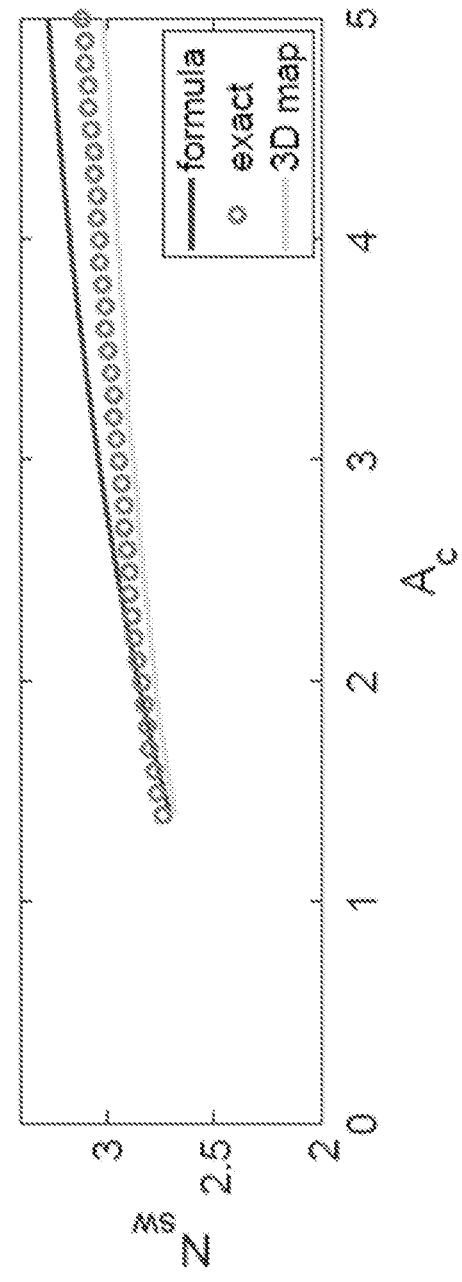
FIG. 8B shows number of lysis events per switching cycle near the Hopf bifurcation.
Figure 8C:
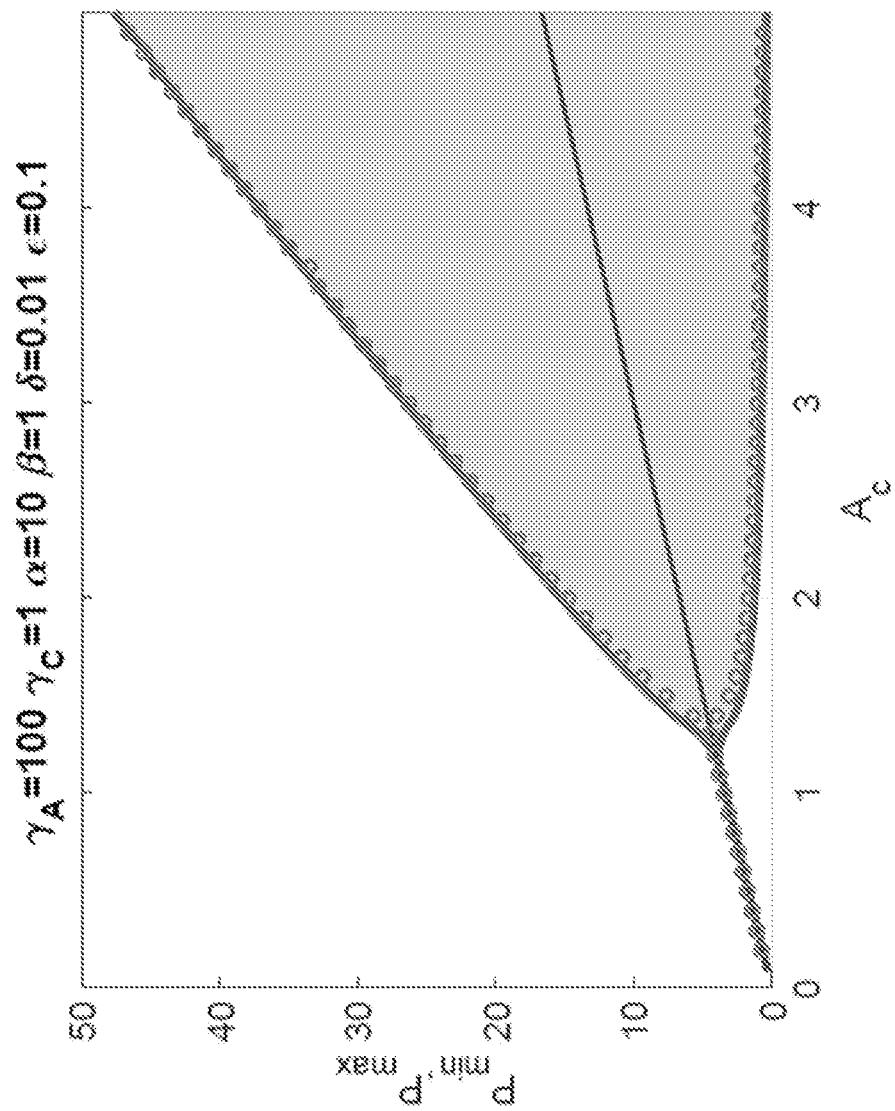
FIG. 8C shows Hopf bifurcation diagram for the map model.
Figure 8D:
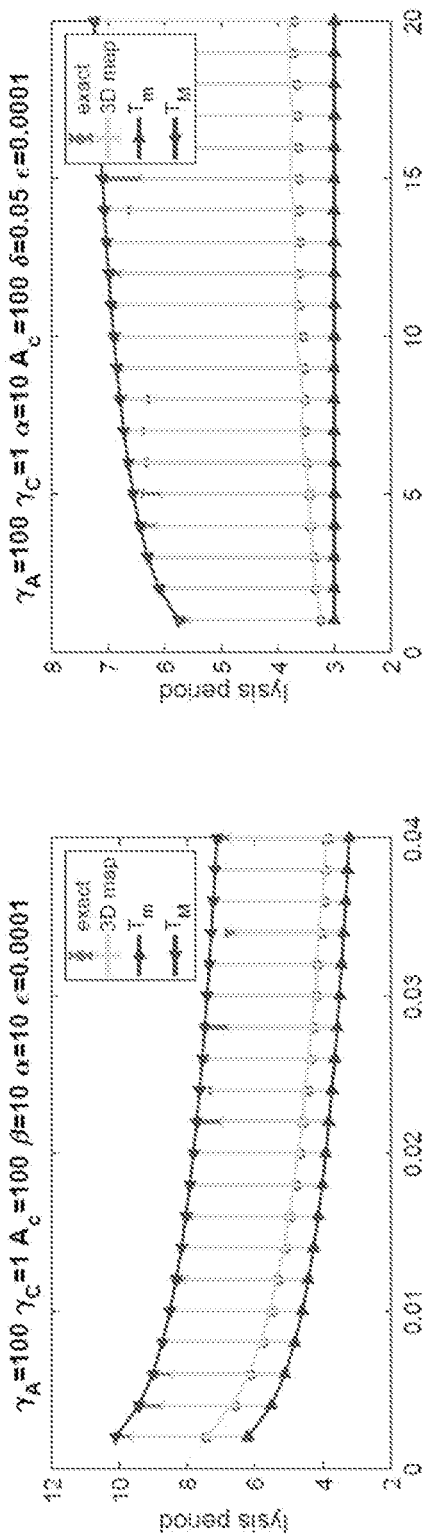
FIGS. 8D, 8E, 8F, and 8G each show parameter sweeps evaluating dependences of the intervals between lysis events and the number of lysis events per switching cycle on system parameters in the oscillatory regime.
Figure 8E:
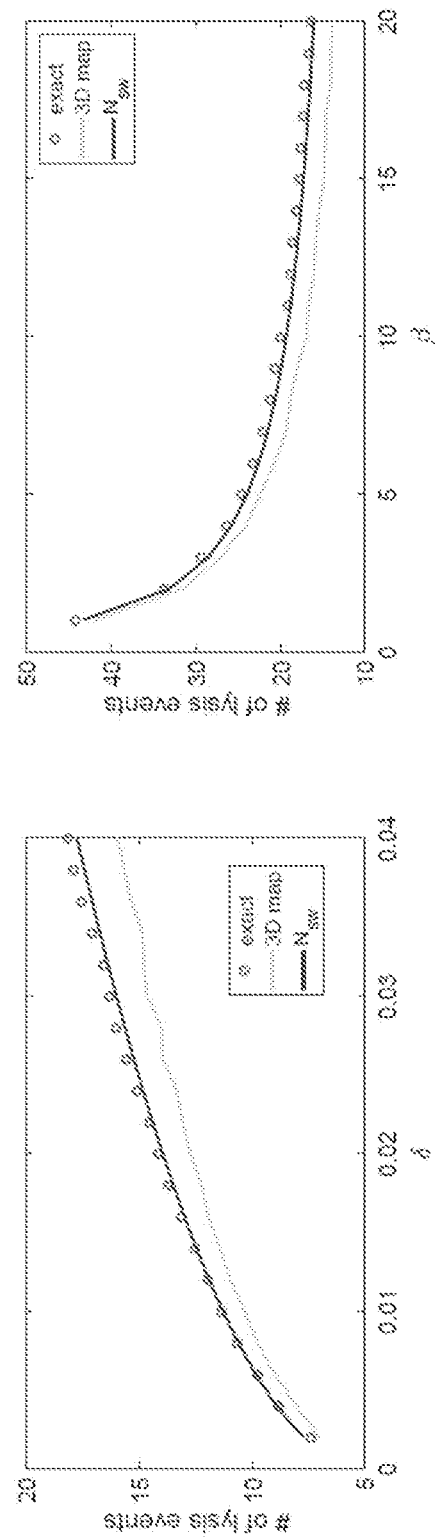
Figures 8F, 8G:
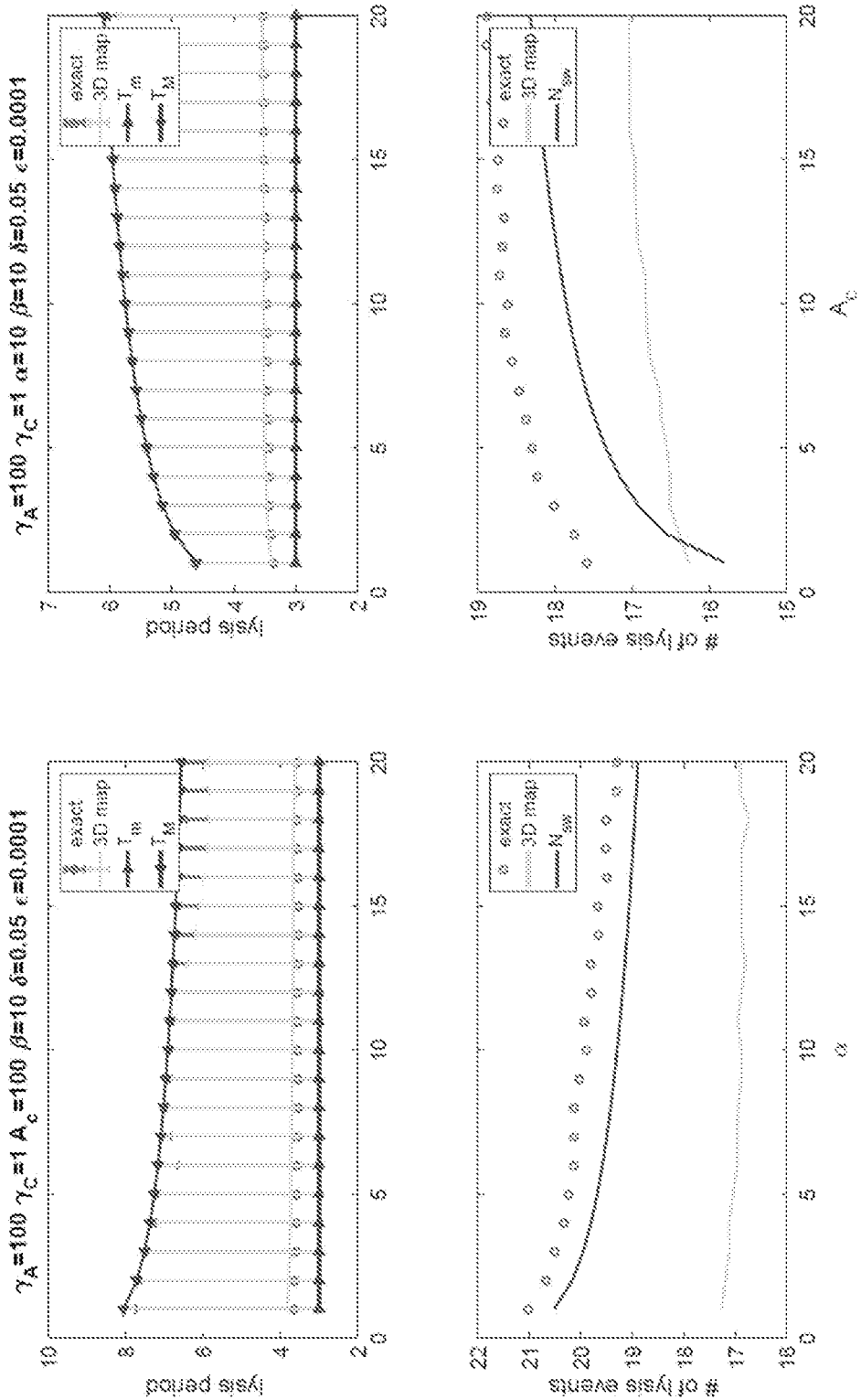
Figure 9A:
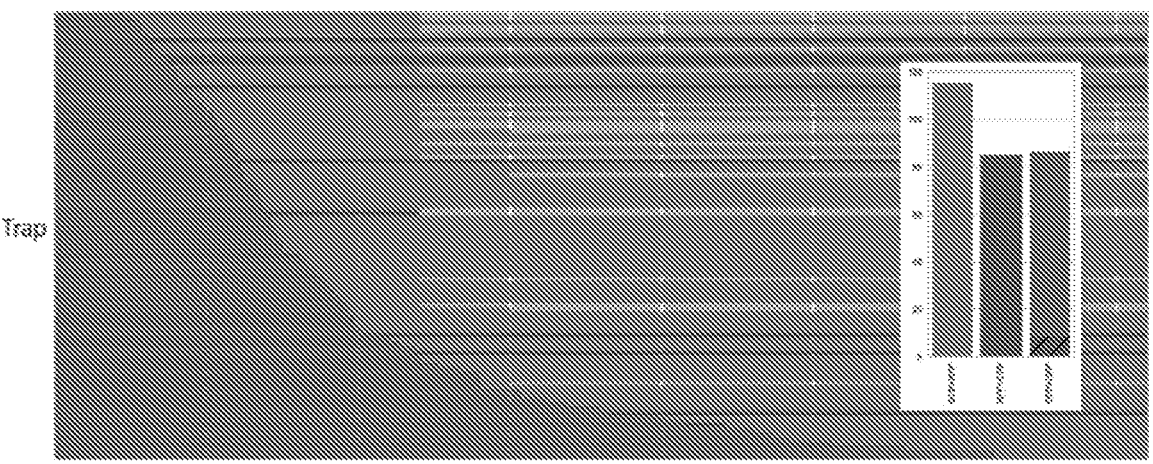
FIG. 9A shows transition events from Strain 1 (gray) to Strain 3 (light grey) over time.
Figure 9B:
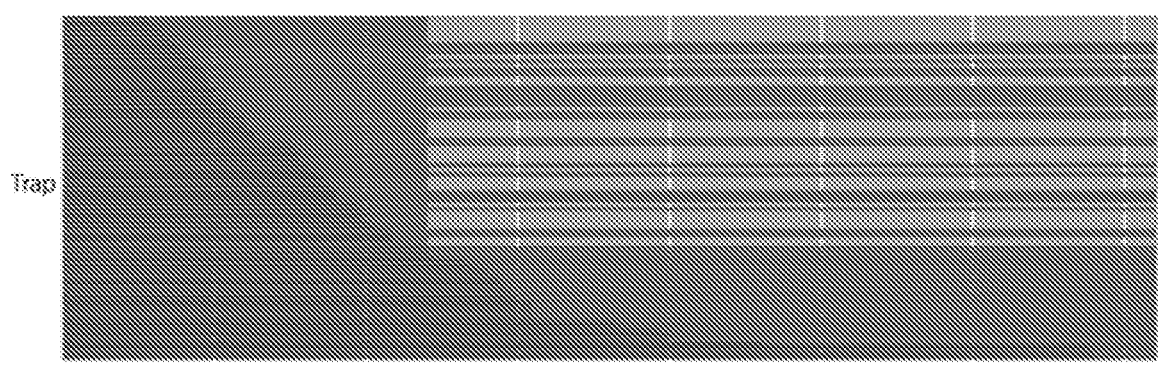
FIG. 9B shows transition events from Strain 2 (black) to Strain 1 (gray) over time.
Figure 9C:
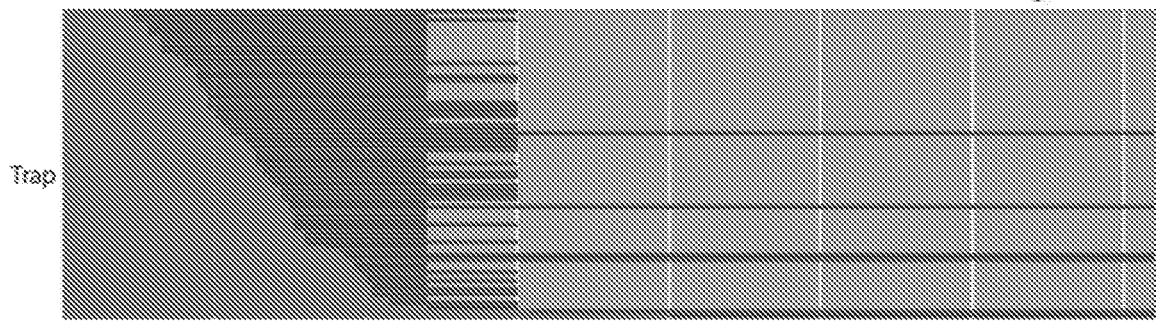
FIG. 9C shows transition events from Strain 3 (light grey) to Strain 2 (black) over time.
Figure 9D:
FIG. 9D shows transition events from Strain 1 (gray) to Strain 3 (light grey) to Strain 2 (black) over time.
Figure 9E:
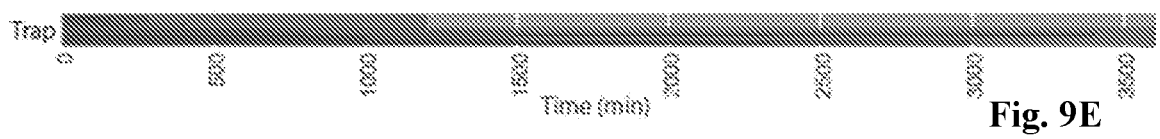
FIG. 9E shows transition events from Strain 2 (black) to Strain 1 (gray) to Strain 3 (light grey) over time.

This is the condition for the Hopf bifurcation in this model. It is easy to see that for small $A_c$, the left hand side is small, but it monotonically increases with $A_c$ to asymptotic value that is $$N_{sw} = \frac{2\pi}{3\arcsin(3\sqrt{3}B/2)} = \frac{2\pi}{3\arcsin\left[\frac{\sqrt{3}}{2\gamma_c\left(1 + \frac{3\alpha}{\beta\gamma_A A_c}\right)}\right]} \quad (55)$$

greater than 1/9, so the Hopf bifurcation always occurs at some finite $A_c$ (see FIG. 8A). At the Hopf bifurcation, where $|\lambda_{2,3}| = 1$, the number of lysis events per one switching cycle (⅓ of a period) is FIGS. 8B and 8C show the number of lysis pulses and bifurcation diagram for the map and the underlying full model.

Strongly switching regime.

Far away from the Hopf bifurcation point, the switching becomes strongly nonlinear, when one strain dominates the dynamics for many lysis periods before rapidly switching to the next strain domination, and so on (FIGS. 25, 26). To characterize the dynamics in this regime, the time interval between lysis events and the duration of switching cycles was computed.

The lysis intervals vary within a switching cycle. They are smallest in the middle of the cycle, when one strain is strongly dominating, and are somewhat longer between the cycles, when two of the strains are nearly equal.

Minimum lysis interval. In the bulk of each switching cycle, one of the strains grows to high concentration at which the lysis occurs, while the other two remain much smaller (it is assumed that $\epsilon \ll \gamma_A A/\alpha$). In this regime, the map became nearly one-dimensional and trivial (without loss of generality p was chosen to be the dominating strain and $Q_i = R_i = 0$ was $$P_i = \gamma_A A_c \alpha^{-1} = P_M, \quad (56)$$

assumed):

[it was assumed that we assume that $\epsilon \ll \delta\gamma_A A/\alpha$. The interval between lysis events during this phase is as expected.

Maximum lysis interval. Maximum lysis interval occurs during the switch from one strain $$T_m = \log\left[\frac{P_M}{\delta P_M + 3\epsilon}\right] = -\log\left[\delta + \frac{3\epsilon\alpha}{\gamma_A A_c}\right] \approx -\log\delta. \quad (57)$$

dominance to the next strain. During this switch, two of the concentrations briefly become equal at a certain $i = k+1$ (suppose, for definitiveness, $P_{k+1} = Q_{k+1}$, $R_{k+1} = 0$). It is easy to see that the condition of equality $P_{k+1} = Q_{k+1}$ is $$\frac{P_k}{(1+\beta R_k)^{1/\gamma_c}} = R_k \quad (58)$$

(small $\epsilon$ was neglected here). For sufficiently sharp switch, the magnitude $P_k$ is still close to $P_M = \gamma_A A_c/\alpha$. That allowed solving for $R_k$ which can then be used to find $T_k$. If $\beta R_k \gg 1$ (to be verified a posteriori) 1 can be neglected and the equation can be solved explicitly, $$R_k \approx \beta^1 (\beta P_0)^{\frac{\gamma_c}{\gamma_c+1}} \quad (59)$$

From here, the condition of validity of this expression for $\gamma_c \sim 1$ is $\beta\gamma_A A_c \alpha \gg 1$. The maximum lysis interval was then computed explicitly $$T_M = \log\left(\frac{P_M}{2\delta\beta^{-1}(P_M\beta)^{\gamma_c/(\gamma_c+1)}}\right) = \quad (60)$$
$$-\log\delta - \log 2 - (\gamma_c + 1)^{-1}\log(\beta\gamma_A A_c/\alpha).$$

The average lysis interval $T_a$ is somewhere between $T_m$ and $T_M$, but progressively approaches $T_m$ as the switching intervals become longer.

Switching interval duration. To estimate the duration of the switching cycles, in which one strain dominates, it was observed that that it consists of two sub-intervals. In the first sub-interval, one of the strains (p, for specificity) is dominating and remains close to $P_M$ before the lysis events, while the other two strains (q and r) are small. One of them (q) remains very small ($O(\epsilon)$) throughout the whole sub-interval since its growth is strongly suppressed by large p, while the other strain (r) is not suppressed and steadily grows from small initial level to $O(P_M)$ to eventually reach amplitudes comparable with $P_M$. Once this happens, the second sub-interval commences during which the amplitude of the first strain (p) gets quickly reduced to small ($O(\epsilon)$) because its growth is now suppressed by large r. To obtain the duration of the first sub-interval, the mapping for $R_i$ was considered, assuming that $Q_i \approx 0$, $P_i$ $$R_{i+1} = \delta e^{T_i}(R_i + \epsilon/\delta) \tag{61}$$

$\approx P_M$

According to Eq. (32), $$e^{T_i} \frac{\delta P_M}{(1+\beta R_i)^{1/\gamma_c}} \approx P_M \tag{62}$$

Using this expression in Eq. (31), the following 1D mapping was obtained $$R_{i+1} = (R_i + \epsilon/\delta)(1+\beta R_i)^{1/\gamma_c} \tag{63}$$

To find the duration of the first sub-interval, the number of iterations in which $R_i$ reaches the value of the order of $P_M$ starting from $R_0 = 0$ was determined. This sub-interval itself can be broken into two parts. While $\beta R_i \ll 1$, the second bracket was expanded to obtain the following quadratic map $$R_{i+1} = |(R_i + \epsilon/\delta)(1+\beta\gamma_c^{-1} R_i) \tag{64}$$

or introducing new variable $\hat{R}_i = \beta\gamma_c^{-1} R_i$ $$\hat{R}_{i+1} = (\hat{R}_i + \alpha)(1+\hat{R}_i) \tag{65}$$

with $a = \epsilon\beta/\delta\gamma_c$ and initial condition $\hat{R}_0 = 0$. For small $a \ll 1$, the number of iterations n to reach $\hat{R}_n = 1/\gamma c$. is large and can be estimated by taking a continuous limit and integrating the following differential equation
from $\hat{R} = 0$ to $\hat{R} = 1$, which for small a yields Of course, the last few iterations the condition $\beta R_i \ll 1$ is violated, but this expression still $$\frac{d\hat{R}}{dt} = a + a\hat{R} + \hat{R}^2 \tag{66}$$

$$n \approx \frac{\tan^{-1}(\gamma_c^{-1}/\sqrt{a})}{\sqrt{a}} \tag{67}$$

gave a good estimation of the number of iteration needed to reach $R_n = \beta^{-1}$. Next was $$\overline{R}_{i+1} \approx \overline{R}_i (1+\overline{R}_i)^{1/\gamma_c} \tag{68}$$

estimated the number of additional iterations for $R_i$ to go from $R_n = \beta^{-1}$ to $P_M$. Since by assumption $\beta \gg \epsilon/\delta$ in this range of $R_i$ the latter was neglected from the map (63) and it was simplified to
where $\overline{R}_i = \beta R_i$, with initial condition $\overline{R}_n = 1$. The first several iterates of this map were as follows: $\overline{R}_{n+1} = 2^{1/\gamma_c}$, $\overline{R}_{n+2} = [2(1+2^{1/\gamma_c})]^{1/\gamma_c}$, $\overline{R}_{n+3} = [2(1+2^{1/\gamma_c})(1+[2(1+2^{1/\gamma_c})]^{1/\gamma_c})]^{1/\gamma_c}$, etc. For $\gamma_c = O(1)$, this sequence rapidly (super-exponentially) grows with i, and so already after i=n+2, 1 was neglected in the brackets of Eq.(68) and written simply as $$\overline{R}_{i+1} \approx \overline{R}_i^{1/\gamma_c + 1} \tag{69}$$

Thus, at $N_1$ iteration, $$\overline{R}_{N_1} = [\overline{R}_{n+2}]^{(1+\gamma_c^{-1})^{N_c-n+2}} = [2(1+2^{1/\gamma_c})]^{\gamma_c^{-1}(1+\gamma_c^{-1})^{N_c-n-2}}$$

Equating this expression with PM and recalling the expression for n, the following approximate formula for $N_1$ was obtained, $$N_1 \approx \frac{\tan^{-1}(\sqrt{\delta/\epsilon\beta\gamma_C})}{\sqrt{\epsilon\beta/\delta\gamma_c}} + \frac{\log\left[\frac{\gamma_c\log(\beta\gamma_A A_c \alpha)}{\log[2(1+2^{1/\gamma_c})]}\right]}{\log(1+\gamma_c^{-1})} + 2 \tag{70}$$

During the second sub-interval, the magnitude $R_i$ is already near $P_M$, and so the growth of strain P is strongly suppressed. It means that at each lysis event it is reduced by factor $\delta$, $P_{i+1} = \delta P_i$. This immediately yielded the estimate for the number of iterations needed for $P_i$ to reach the "background" level $O(\epsilon)$, $$N_2 \approx \frac{\log(\epsilon P_M^{-1})}{\log \delta}$$

Thus, the total number of lysis intervals within a single switching cycle is given by $$N_{sw} \approx \frac{\tan^{-1}(\sqrt{\delta/\epsilon\beta\gamma_c})}{\sqrt{\epsilon\beta/\delta\gamma_c}} + \frac{\log\left[\frac{\gamma_c\log(\beta\gamma_A A_c \alpha)}{\log[2(1+2^{1/\gamma_c})]}\right]}{\log(1+\gamma_c^{-1})} + 2 + \frac{\log(\epsilon P_M^{-1})}{\log \delta} \tag{71}$$

FIGS. 8D-8G show the interval between lysis events (minimal, maximal, and average) and the number of lysis events per one switching interval as functions of some model parameters, obtained from the exact model, the 3D map, and the analytical approximations. Surprisingly, the analytical approximations appeared more accurate than the 3D map results.

REFERENCES

1. Gravel, D. et al. Experimental niche evolution alters the strength of the diversity-productivity relationship. Nature 469, 89-92 (2011).
2. De Roy, K. et al. Environmental conditions and community evenness determine the outcome of biological invasion. Nature communications 4, 1383 (2013).
3. Tanouchi, Y., Smith, R. P. & You, L. Engineering microbial systems to explore ecological and evolutionary dynamics. Current opinion in biotechnology 23, 791-797 (2012).
4. Wintermute, E. H. & Silver, P. A. Emergent cooperation in microbial metabolism. Molecular systems biology 6, 407 (2010).
5. Klitgord, N. & Segre, D. Environments that induce synthetic microbial ecosystems. PLoS Comput Biol 6, e1001002 (2010).
6. Little, A. E., Robinson, C. J., Peterson, S. B. & Raffa, K. F. Rules of engagement: Interspecies interactions that regulate microbial communities 31. In The Social Biology of Microbial Communities: Workshop Summary, vol. 62, 375-401 (National Academies Press, 2012).
7. De Roy, K., Marzorati, M., Van den Abbeele, P., Van de Wiele, T. & Boon, N. Synthetic microbial ecosystems: an exciting tool to understand and apply microbial communities. Environmental microbiology 16, 1472-1481 (2014).
8. Gardner, T. S., Cantor, C. R. & Collins, J. J. Construction of a genetic toggle switch in *Escherichia coli*. Nature 403, 339-342 (2000).

9. Elowitz, M. B. & Leibler, S. A synthetic oscillatory network of transcriptional regulators. Nature 403, 335-338 (2000).
10. Hasty, J., McMillen, D. & Collins, J. J. Engineered gene circuits. Nature 420, 224-230 (2002).
11. Endy, D. Foundations for engineering biology. Nature 438, 449-453 (2005).
12. You, L., Cox, R. S., Weiss, R. & Arnold, F. H. Programmed population control by cell-cell communication and regulated killing. Nature 428, 868-871 (2004).
13. Brenner, K., Karig, D. K., Weiss, R. & Arnold, F. H. Engineered bidirectional communication mediates a consensus in a microbial biofilm consortium. Proceedings of the National Academy of Sciences 104, 17300-17304 (2007).
14. Danino, T., Mondragón-Palomino, O., Tsimring, L. & Hasty, J. A synchronized quorum of genetic clocks. Nature 463, 326-330 (2010).
15. Chen, Y., Kim, J. K., Hirning, A. J., Josic, K. & Bennett, M. R. Emergent genetic oscillations in a synthetic microbial consortium. Science 349, 986-989 (2015).
16. Din, M. O. et al. Synchronized cycles of bacterial lysis for in vivo delivery. Nature 536, 81-85 (2016).

Other Embodiments

Embodiment 1 is a method comprising:
culturing a first bacterial strain for a first period of time in a growth environment;
adding a second bacterial strain to the growth environment and culturing the second bacterial strain for a second period of time;
adding a third bacterial strain to the growth environment and culturing the third bacterial strain for a third period of time,
wherein each of the first, second, and third bacterial strains comprises a toxin system;
wherein the toxin system of the first bacterial strain produces a first toxin/first antitoxin pair and a third antitoxin from a third toxin/third antitoxin pair wherein the first bacterial strain does not produce the third toxin;
wherein the toxin system of the second bacterial strain produces a second toxin/second antitoxin pair and the first antitoxin from the first toxin/first antitoxin pair wherein the second bacterial strain does not produce the first toxin; and
wherein the toxin system of the third bacterial strain produces a third toxin/third antitoxin pair and the second antitoxin from the second toxin/second antitoxin pair wherein the third bacterial strain does not produce the second toxin, and
optionally wherein each of the first, second, and third bacterial strains comprises
a lysis plasmid having a lysis gene under the control of an activatable promoter; and
an activator plasmid having an activator gene, the expression of which promotes the accumulation of a quorum-sensing molecule,
wherein both the activatable promoter of the lysis gene and the expression of the activator gene is activated by the quorum-sensing molecule.
Embodiment 2 is the method of embodiment 1, wherein the quorum-sensing molecule is different in each of the first, second, and third bacterial strains.
Embodiment 3 is the method of embodiment 2, wherein each quorum-sensing molecule of each of the first, second, and third bacterial strains has no or substantially no effect on the activatable promoter of the lysis gene of another strain.
Embodiment 4 is the method of embodiment 1, wherein the quorum-sensing molecule is the same in each of the first, second, and third bacterial strains.
Embodiment 5 is the method of any one of embodiments 1-4, further comprising culturing or co-culturing one or more additional bacterial strains in the growth environment.
Embodiment 6 is the method of embodiment 5, wherein each of the one or more additional bacterial strains comprise:
a lysis plasmid having a lysis gene under the control of an activatable promoter; and
an activator plasmid having an activator gene, the expression of which promotes the accumulation of a quorum-sensing molecule,
wherein both the activatable promoter of the lysis gene and the expression of the activator gene is activated by the quorum-sensing molecule.
Embodiment 7 is the method of embodiment 6, wherein the quorum-sensing molecule is different in each of the first, second, third, and one or more additional bacterial strains.
Embodiment 8 is the method of embodiment 7, wherein each quorum-sensing molecule of each of the first, second, third, and one or more additional bacterial strains has no or substantially no effect on the activatable promoter of the lysis gene of another bacterial strain used in the growth environment.
Embodiment 9 is the method of embodiment 6, wherein the quorum sensing molecule is the same in each of the first, second, third, and one or more additional bacterial strains.
Embodiment 10 is the method of any one of embodiments 6-9, wherein each of the one or more additional bacterial strains comprises a toxin system.
Embodiment 11 is the method of any one of embodiments 1-10, wherein the toxin system of the first bacterial strain, the second bacterial strain, the third bacterial strain, and each of the one or more additional bacterial strains is independently encoded in the genome, on a plasmid, on multiple plasmids, or a combination thereof.
Embodiment 12 is the method of any one of embodiments 1-11, wherein the lysis plasmid and activator plasmid of each of the at least first, second, and third bacterial strains are copies of the same plasmid.
Embodiment 13 is the method of any one of embodiments 1-11, wherein the lysis plasmid and activator plasmid of each of the at least first, second, and third bacterial strains are different plasmids.
Embodiment 14 is the method of any one of embodiments 1-13, wherein at least the first, second, and third bacterial strains are metabolically competitive.
Embodiment 15 is the method of any one of embodiments 1-14, wherein at least the first, second, and third bacterial strains are selected from *E. coli, S. typhimurium*, or a bacterial variant thereof.
Embodiment 16 is the method of any one of embodiments 1-15, wherein each of the at least the first, second, and third bacterial strains does not have a growth advantage compared to another strain in the growth environment.
Embodiment 17 is the method of any one of embodiments 1-16, wherein in each of the at least the first, second, and third bacterial strains the lysis plasmid comprises a lysis gene, an activatable promoter, and optionally a reporter gene; and the activator plasmid comprises an activator gene, optionally a degradation tag, and optionally a reporter gene.

Embodiment 18 is the method of any one of embodiments 1-17, wherein the lysis gene in each of the at least the first, second, and third bacterial strains is E from a bacteriophage ΦX174.

Embodiment 19 is the method of any one of embodiments 1-18, wherein the activatable promoter in each of the at least the first, second, and third bacterial strains is a LuxR-AHL activatable luxI promoter and the activator gene is a LuxI.

Embodiment 20 is the method of embodiment 17, wherein at least one reporter gene is selected from a gene encoding a green fluorescent protein (GFP), cyan fluorescent protein (CFP), red fluorescent protein (RFP), or a variant thereof.

Embodiment 21 is the method of embodiment 17, wherein the degradation tag is an ssrA-LAA degradation tag.

Embodiment 22 is the method of any one of embodiments 1-21, wherein at least one of the plasmids is integrated into a genome of at least one of the first, second, and third bacterial strains.

Embodiment 23 is the method of any one of embodiments 1-22, wherein the culturing occurs in a microfluidic device.

Embodiment 24 is the method of any one of embodiments 1-22, wherein the culturing occurs in a bioreactor.

Embodiment 25 is the method of any one of embodiments 1-22, wherein the culturing occurs in vivo.

Embodiment 26 is the method of any one of embodiments 1-25, wherein each of the first, second, and third periods of time ranges from about 12 to about 72 hours.

Embodiment 27 is the method of any one of embodiments 1-25, wherein each of the first, second, and third periods of time is selected from at least 24 hours, at least 48 hours, at least 72 hours, and at least 96 hours.

Embodiment 28 is the method of any one of embodiments 1-25, wherein each of the first, second, and third periods of time is selected from 12 hours, 24 hours, 48 hours, 72 hours, and 96 hours.

Embodiment 29 is the method of any one of embodiments 1-25, wherein each of the first, second, and third periods of time independently ranges from about 1 hours to about 72 hours.

Embodiment 30 is the method of embodiment 29, wherein each of the first, second, and third periods of time independently ranges from about 1 hours to about 48 hours.

Embodiment 31 is the method of embodiment 29, wherein each of the first, second, and third periods of time independently ranges from about 1 hours to about 24 hours.

Embodiment 32 is the method of embodiment 29, wherein each of the first, second, and third periods of time independently ranges from about 1 hours to about 18 hours.

Embodiment 33 is the method of embodiment 29, wherein each of the first, second, and third periods of time independently ranges from about 1 hours to about 12 hours.

Embodiment 34 is the method of embodiment 29, wherein each of the first, second, and third periods of time independently ranges from about 1 hours to about 6 hours.

Embodiment 35 is the method of embodiment 29, wherein each of the first, second, and third periods of time independently ranges from about 1 hours to about 3 hours.

Embodiment 36 is the method of any one of embodiments 1-35, wherein the first, second, and third periods of time occur sequentially.

Embodiment 37 is the method of any one of embodiments 1-36, wherein the first and second, second and third, or first and third periods of time partially or completely overlap.

Embodiment 38 is the method of any one of embodiments 1-37, wherein one or more of the first, second, and third bacterial strains encodes a heterologous nucleic acid and/or a heterologous protein operably linked to a promoter.

Embodiment 39 is the method of embodiment 38, wherein the promoter is an activatable promoter.

Embodiment 40 is the method of embodiment 39, wherein the promoter is activated by the quorum sensing molecule.

Embodiment 41 is the method of embodiment 38, wherein the promoter is a constitutive promoter.

Embodiment 42 is the method of any one of embodiments 38-41, wherein the heterologous nucleic acid and/or heterologous protein is a therapeutic agent.

Embodiment 43 is the method of embodiment 42, wherein the therapeutic agent is selected from the group consisting of: an inhibitory nucleic acid, a cytokine, an enzyme, a peptide hormone, a fusion protein, a clotting factor, a toxin, an antimicrobial peptide, and an antibody or antigen-binding fragment thereof.

Embodiment 44 is the method of embodiment 43, wherein the inhibitory nucleic acid is siRNA, shRNA, miRNA, or antisense.

Embodiment 45 is a method comprising:
  providing n bacterial strains comprising at least a first bacterial strain, a second bacterial strain, and an nth bacterial strain;
  co-culturing each of the bacterial strains sequentially for an independent period of time in a growth environment;
  wherein each of the second bacterial strain to the $n^{th}$ bacterial strain has a previous bacterial strain;
  wherein n is at least 3;
  wherein each of the n strains comprises
    a lysis plasmid having a lysis gene under the control of an activatable promoter; and
    an activator plasmid having an activator gene, the expression of which promotes the accumulation of a quorum sensing molecule,
  wherein both the activatable promoter of the lysis gene and the expression of the activator gene is activated by the quorum sensing molecule,
  wherein each of the n bacterial strains comprises a toxin system;
  wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain;
  wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Embodiment 46 is the method of embodiment 45, wherein in each of the n bacterial strains, the lysis plasmid comprises a lysis gene, an activatable promoter, and optionally a reporter gene; and the activator plasmid comprises an activator gene, optionally a degradation tag, and optionally a reporter gene.

Embodiment 47 is the method of any one of embodiments 45-46, wherein the lysis gene in each of the n bacterial strains is E from a bacteriophage ΦX174.

Embodiment 48 is the method of any one of embodiments 45-47, wherein the activatable promoter in each of the n bacterial strains is a LuxR-AHL activatable luxI promoter and the activator gene is a LuxI.

Embodiment 49 is the method of embodiment 46, wherein at least one reporter gene is selected from a gene encoding a green fluorescent protein (GFP), cyan fluorescent protein (CFP), red fluorescent protein (RFP), or a variant thereof.

Embodiment 50 is the method of embodiment 46, wherein the degradation tag is an ssrA-LAA degradation tag.

Embodiment 51 is the method of any one of embodiments 45-50, wherein at least one of the plasmids is integrated into a genome of at least one of the n bacterial strains.

Embodiment 52 is the method of any one of embodiments 45-51, wherein the quorum-sensing molecule is different in each of the n bacterial strains.

Embodiment 53 is the method of embodiment 52, wherein each quorum-sensing molecule of each of the n bacterial strains has no or substantially no effect on the activatable promoter of the lysis gene of another strain.

Embodiment 54 is the method of any one of embodiments 45-51, wherein the quorum-sensing molecule is the same in each of the n bacterial strains.

Embodiment 55 is the method of any one of embodiments 45-54, wherein the lysis plasmid and activator plasmid of each of then bacterial strains are copies of the same plasmid.

Embodiment 56 is the method of any one of embodiments 45-54, wherein the lysis plasmid and activator plasmid of each of the n bacterial strains are different plasmids.

Embodiment 57 is a method comprising:
  providing n bacterial strains comprising at least a first bacterial strain, a second bacterial strain, and an nth bacterial strain;
  co-culturing each of the bacterial strains sequentially for an independent period of time in a growth environment;
  wherein each of the second bacterial strain to the $n^{th}$ bacterial strain has a previous bacterial strain;
  wherein n is at least 3;
  wherein each of the n bacterial strains comprises a toxin system;
  wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain;
  wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Embodiment 58 is the method of any one of embodiments 44-57, wherein the n bacterial strains are metabolically competitive.

Embodiment 59 is the method of any one of embodiments 44-58, wherein each of the n bacterial strains are selected from E. coli, S. typhimurium, or a bacterial variant thereof.

Embodiment 60 is the method of any one of embodiments 44-59, wherein each of the n bacterial strains does not have a growth advantage compared to another strain in the growth environment.

Embodiment 61 is the method of any one of embodiments 44-60, wherein the toxin system of the n bacterial strains is independently encoded in the genome, on a plasmid, on multiple plasmids, or a combination thereof.

Embodiment 62 is the method of any one of embodiments 44-61, wherein the culturing occurs in a microfluidic device.

Embodiment 63 is the method of any one of embodiments 44-61, wherein the culturing occurs in a bioreactor.

Embodiment 64 is the method of any one of embodiments 44-61, wherein the culturing occurs in vivo.

Embodiment 65 is the method of any one of embodiments 44-64, wherein each of the independent periods of time ranges from about 12 to about 72 hours.

Embodiment 66 is the method of any one of embodiments 44-64, wherein each of the independent periods of time is selected from at least 24 hours, at least 48 hours, at least 72 hours, and at least 96 hours.

Embodiment 67 is the method of any one of embodiments 44-64, wherein each of the independent periods of time is selected from 12 hours, 24 hours, 48 hours, 72 hours, and 96 hours.

Embodiment 68 is the method of any one of embodiments 44-64, wherein each of the periods of time independently ranges from about 1 hours to about 72 hours.

Embodiment 69 is the method of embodiment 68, wherein each of the periods of time independently ranges from about 1 hours to about 48 hours.

Embodiment 70 is the method of embodiment 68, wherein each of the periods of time independently ranges from about 1 hours to about 24 hours.

Embodiment 71 is the method of embodiment 68, wherein each of the periods of time independently ranges from about 1 hours to about 18 hours.

Embodiment 72 is the method of embodiment 68, wherein each of the periods of time independently ranges from about 1 hours to about 12 hours.

Embodiment 73 is the method of embodiment 68, wherein each of the periods of time independently ranges from about 1 hours to about 6 hours.

Embodiment 74 is the method of embodiment 68, wherein each of the periods of time independently ranges from about 1 hours to about 3 hours.

Embodiment 75 is the method of any one of embodiments 45-74, wherein one or more of the periods of time partially or completely overlap.

Embodiment 76 is the method of any one of embodiments 45-75, wherein one or more of the n bacterial strains encodes a heterologous nucleic acid and/or a heterologous protein operably linked to a promoter.

Embodiment 77 is the method of embodiment 76, wherein the promoter is an activatable promoter.

Embodiment 78 is the method of embodiment 77, wherein the activatable promoter is activated by a quorum-sensing molecule.

Embodiment 79 is the method of embodiment 76, wherein the promoter is a constitutive promoter.

Embodiment 80 is the method of any one of embodiments 76-79, wherein the heterologous nucleic acid and/or heterologous protein is a therapeutic agent.

Embodiment 81 is the method of embodiment 80, wherein the therapeutic agent is selected from the group consisting of: an inhibitory nucleic acid, a cytokine, an enzyme, a peptide hormone, a fusion protein, a clotting factor, a toxin, an antimicrobial peptide, and an antibody or antigen-binding fragment thereof.

Embodiment 82 is the method of embodiment 81, wherein the inhibitory nucleic acid is siRNA, shRNA, miRNA, or antisense.

Embodiment 83 is the method of any one of embodiments 45-82, wherein each of the second bacterial strain through the nth bacterial strain does not produce the second toxin of the toxin system of the previous strain, and the first bacterial strain does not produce the fourth toxin of the toxin system of the nth bacterial strain.

Embodiment 84 is a bacterial strain comprising a lysis plasmid and an activator plasmid; wherein the lysis plasmid comprises a lysis gene, an activatable promoter, and optionally a reporter gene; and the activator plasmid comprises an activator gene, optionally a degradation tag, and optionally a reporter gene; wherein the bacterial strain further comprises a toxin system; wherein the toxin system produces a first toxin/first antitoxin pair and a second antitoxin from a second toxin/second antitoxin pair wherein the bacterial strain does not produce the second toxin.

Embodiment 85 is the bacterial strain of embodiment 84, wherein the lysis gene is E from a bacteriophage ΦX174.

Embodiment 86 is the bacterial strain of any one of embodiments 84-85, wherein the activatable promoter is a LuxR-AHL activatable luxI promoter and the activator gene is a LuxI.

Embodiment 87 is the bacterial strain of any one of embodiments 84-86, wherein the activator gene encodes a molecule that activates, directly or indirectly, the activatable promoter.

Embodiment 88 is the bacterial strain of embodiment 87, wherein the molecule that activates, directly or indirectly, the activatable promoter is a quorum-sensing molecule.

Embodiment 89 is the bacterial strain of any one of embodiments 84-88, wherein the lysis gene is operably linked to the activatable promoter.

Embodiment 90 is the bacterial strain of any one of embodiments 84-89, wherein the reporter gene on the lysis plasmid is operably linked to the activatable promoter.

Embodiment 91 is the bacterial strain of any one of embodiments 84-90, wherein the activator plasmid further comprises an activatable promoter.

Embodiment 92 is the bacterial strain of embodiment 91, wherein the activatable promoter of the activator plasmid is a copy of the activatable promoter of the lysis plasmid.

Embodiment 93 is the bacterial strain of any one of embodiments 91-92, wherein the activator gene is operably linked to the activatable promoter of the activator plasmid.

Embodiment 94 is the bacterial strain of any one of embodiments 91-93, wherein the reporter gene of the activator plasmid is operably linked to the activatable promoter of the activator plasmid.

Embodiment 95 is the bacterial strain of any one of embodiments 91-94, wherein the degradation tag is operably linked to the activatable promoter of the activator plasmid.

Embodiment 96 is the bacterial strain of any one of embodiments 84-95, wherein the toxin system is operably linked to the activatable promoter of the lysis plasmid.

Embodiment 97 is the bacterial strain of any one of embodiments 84-96, wherein the degradation tag is an ssrA-LAA degradation tag.

Embodiment 98 is the bacterial strain of any one of embodiments 84-97, wherein the reporter gene of the lysis plasmid, the reporter gene of the activator plasmid, or both, are fluorescent proteins.

Embodiment 99 is the bacterial strain of any one of embodiments 84-97, wherein the reporter gene of the lysis plasmid and the reporter gene of the activator plasmid are different genes.

Embodiment 100 is a bacterial strain comprising a toxin system; wherein the toxin system produces a first toxin/first antitoxin pair and a second antitoxin from a second toxin/second antitoxin pair wherein the bacterial strain does not produce the second toxin.

Embodiment 101 is the bacterial strain of any one of embodiments 84-100, wherein the bacterial strain encodes a heterologous nucleic acid and/or a heterologous protein operably linked to a promoter.

Embodiment 102 is the bacterial strain of embodiment 101, wherein the promoter is an activatable promoter.

Embodiment 103 is the bacterial strain of embodiment 102, wherein the activatable promoter is activated by a quorum-sensing molecule.

Embodiment 104 is the bacterial strain of embodiment 101, wherein the promoter is a constitutive promoter.

Embodiment 105 is the bacterial strain of any one of embodiments 101-104, wherein the heterologous nucleic acid and/or heterologous protein is a therapeutic agent.

Embodiment 106 is the bacterial strain of any one of embodiments 84-105, wherein the toxin system is encoded in the genome, on a plasmid, on multiple plasmids, or a combination thereof.

Embodiment 107 is the bacterial strain of any one of embodiments 84-106, wherein the bacterial strain further comprises a nucleic acid encoding a therapeutic agent.

Embodiment 108 is the bacterial strain of embodiment 105 or embodiment 107, wherein the therapeutic agent is selected from the group consisting of: an inhibitory nucleic acid, a cytokine, an enzyme, a peptide hormone, a fusion protein, a clotting factor, a toxin, an antimicrobial peptide, and an antibody or antigen-binding fragment thereof.

Embodiment 109 is the bacterial strain of any one of embodiments 105 or embodiments 107-108, wherein the therapeutic agent is a therapeutic polypeptide.

Embodiment 110 is the bacterial strain of any one of embodiments 105 or embodiments 107-109, wherein the therapeutic agent is cytotoxic or cytostatic to a target cell.

Embodiment 111 is the bacterial strain of embodiment 110, wherein the target cell is a cancer cell or an infected cell.

Embodiment 112 is a pharmaceutical composition comprising any one or more of the bacterial strains of embodiments 84-111.

Embodiment 113 is the pharmaceutical composition of embodiment 112, wherein the pharmaceutical composition is formulated for in situ drug delivery.

Embodiment 114 is a system comprising:
  a first bacterial strain comprising a first lysis plasmid and a first activator plasmid; wherein the first lysis plasmid comprises a first lysis gene, a first activatable promoter, and optionally a first reporter gene; and the first activator plasmid comprises a first activator gene, optionally a first degradation tag, and optionally a first reporter gene; wherein the first bacterial strain further comprises a first toxin system; wherein the first toxin system produces a first toxin/first antitoxin pair and a third antitoxin from a third toxin/third antitoxin pair wherein the first bacterial strain does not produce the third toxin;
  a second bacterial strain comprising a second lysis plasmid and a second activator plasmid; wherein the second lysis plasmid comprises a second lysis gene, a second activatable promoter, and optionally a second reporter gene; and the second activator plasmid comprises a second activator gene, optionally a second degradation tag, and optionally a second reporter gene; wherein the second bacterial strain further comprises a second toxin system; wherein the second toxin system produces a second toxin/second antitoxin pair and the first antitoxin from the first toxin/first antitoxin pair wherein the second bacterial strain does not produce the first toxin; and
  a third bacterial strain comprising a third lysis plasmid and a third activator plasmid; wherein the third lysis plasmid comprises a third lysis gene, a third activatable promoter, and optionally a third reporter gene; and the third activator plasmid comprises a third activator gene, optionally a third degradation tag, and optionally a third reporter gene; wherein the third bacterial strain further comprises a third toxin system; wherein the third toxin system produces a third toxin/third antitoxin pair and a second antitoxin from a second toxin/second antitoxin pair wherein the third bacterial strain does not produce the second toxin.

Embodiment 115 is a system comprising:
a first bacterial strain comprising a first toxin system; wherein the first toxin system produces a first toxin/first antitoxin pair and a third antitoxin from a third toxin/third antitoxin pair wherein the first bacterial strain does not produce the third toxin, wherein the first bacterial strain optionally further comprises a first lysis plasmid and a first activator plasmid; wherein the first lysis plasmid comprises a first lysis gene, a first activatable promoter, and optionally a first reporter gene; and the first activator plasmid comprises a first activator gene, optionally a first degradation tag, and optionally a first reporter gene;
a second bacterial strain comprising a second toxin system; wherein the second toxin system produces a second toxin/second antitoxin pair and the first antitoxin from the first toxin/first antitoxin pair wherein the second bacterial strain does not produce the first toxin, wherein the second bacterial strain optionally further comprises a second lysis plasmid and a second activator plasmid; wherein the second lysis plasmid comprises a second lysis gene, a second activatable promoter, and optionally a second reporter gene; and the second activator plasmid comprises a second activator gene, optionally a second degradation tag, and optionally a second reporter gene; and
a third bacterial strain comprising a third toxin system produces a third toxin/third antitoxin pair and a second antitoxin from a second toxin/second antitoxin pair wherein the third bacterial strain does not produce the second toxin, wherein the third bacterial strain optionally further comprises a third lysis plasmid and a third activator plasmid; wherein the third lysis plasmid comprises a third lysis gene, a third activatable promoter, and optionally a third reporter gene; and the third activator plasmid comprises a third activator gene, optionally a third degradation tag, and optionally a third reporter gene.

Embodiment 116 is the system of embodiment 114 or embodiment 115, further comprising one or more additional bacterial strains.

Embodiment 117 is the system of any one of embodiments 114-116, wherein the first toxin system, the second toxin system, and the third toxin system are independently encoded in the genome, on a plasmid, on multiple plasmids, or a combination thereof.

Embodiment 118 is a system comprising:
n bacterial strains comprising at least a first bacterial strain, a second bacterial strain, and an nth bacterial strain;
wherein each of the second bacterial strain to the $n^{th}$ bacterial strain has a previous bacterial strain;
wherein n is at least 3;
wherein each of the n strains comprises a toxin system;
wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain;
wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Embodiment 119 is a system comprising:
n bacterial strains comprising at least a first bacterial strain, a second bacterial strain, and an nth bacterial strain;
wherein each of the second bacterial strain to the $n^{th}$ bacterial strain has a previous bacterial strain;
wherein n is at least 3;
wherein each of the n strains comprises
a lysis plasmid having a lysis gene under the control of an activatable promoter; and
an activator plasmid having an activator gene, the expression of which promotes the accumulation of a quorum sensing molecule,
wherein both the activatable promoter of the lysis gene and the expression of the activator gene is activated by the quorum sensing molecule,
wherein each of the n bacterial strains comprises a toxin system;
wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain;
wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Embodiment 120 is the system of embodiment 118 or embodiment 119, where n is 3.

Embodiment 121 is the system of embodiment 118 or embodiment 119, wherein n is 4, 5, 6, 7, 8, 9, or 10.

Embodiment 122 is the system of any one of embodiments 118-121, wherein each of the toxin systems are independently encoded in the genome, on a plasmid, on multiple plasmids, or a combination thereof.

Embodiment 123 is the system of any one of embodiments 118-122, wherein each of the second bacterial strain through the nth bacterial strain does not produce the second toxin of the toxin system of the previous strain, and the first bacterial strain does not produce the fourth toxin of the toxin system of the nth bacterial strain.

Embodiment 124 is a kit comprising:
a first pharmaceutical composition comprising a first bacterial strain comprising a first lysis plasmid and a first activator plasmid; wherein the first lysis plasmid comprises a first lysis gene, a first activatable promoter, and optionally a first reporter gene; and the first activator plasmid comprises a first activator gene, a first degradation tag, and optionally a first reporter gene; wherein the first bacterial strain further comprises a first toxin system; wherein the first toxin system produces a first toxin/first antitoxin pair and a third antitoxin from a third toxin/third antitoxin pair wherein the first bacterial strain does not produce the third toxin;
a second pharmaceutical composition comprising a second bacterial strain comprising a second lysis plasmid and a second activator plasmid; wherein the second lysis plasmid comprises a second lysis gene, a second activatable promoter, and optionally a second reporter gene; and the second activator plasmid comprises a second activator gene, a second degradation tag, and optionally a second reporter gene; wherein the second bacterial strain further comprises a second toxin system; wherein the second toxin system produces a second toxin/second antitoxin pair and the first antitoxin from the first toxin/first antitoxin pair wherein the second bacterial strain does not produce the first toxin; and a third pharmaceutical composition comprising a third bacterial strain comprising a third lysis plasmid and a third activator plasmid; wherein the third lysis plasmid comprises a third lysis gene, a third activatable promoter, and optionally a third reporter gene; and the third activator plasmid comprises a third activator gene, a third degradation tag, and optionally a third reporter gene; wherein the third bacterial strain further comprises a third toxin system; wherein the third toxin system produces a third toxin/third antitoxin pair and a second antitoxin from a second toxin/second antitoxin pair wherein the third bacterial strain does not produce the second toxin.

Embodiment 125 is a kit comprising:
a first pharmaceutical composition comprising a first bacterial strain comprising a first toxin system; wherein the first toxin system produces a first toxin/first antitoxin pair and a third antitoxin from a third toxin/third antitoxin pair wherein the first bacterial strain does not produce the third toxin, wherein the first bacterial strain optionally further comprises a first lysis plasmid and a first activator plasmid; wherein the first lysis plasmid comprises a first lysis gene, a first activatable promoter, and optionally a first reporter gene; and the first activator plasmid comprises a first activator gene, optionally a first degradation tag, and optionally a first reporter gene;

a second pharmaceutical composition comprising second bacterial strain comprising a second toxin system; wherein the second toxin system produces a second toxin/second antitoxin pair and the first antitoxin from the first toxin/first antitoxin pair wherein the second bacterial strain does not produce the first toxin, wherein the second bacterial strain optionally further comprises a second lysis plasmid and a second activator plasmid; wherein the second lysis plasmid comprises a second lysis gene, a second activatable promoter, and optionally a second reporter gene; and the second activator plasmid comprises a second activator gene, optionally a second degradation tag, and optionally a second reporter gene; and a third pharmaceutical composition comprising a third bacterial strain comprising a third toxin system produces a third toxin/third antitoxin pair and a second antitoxin from a second toxin/second antitoxin pair wherein the third bacterial strain does not produce the second toxin, wherein the third bacterial strain optionally further comprises a third lysis plasmid and a third activator plasmid; wherein the third lysis plasmid comprises a third lysis gene, a third activatable promoter, and optionally a third reporter gene; and the third activator plasmid comprises a third activator gene, optionally a third degradation tag, and optionally a third reporter gene.

Embodiment 126 is the kit of any one of embodiments 124-125, wherein the first toxin system, the second toxin system, and the third toxin system are independently encoded in the genome, on a plasmid, on multiple plasmids, or a combination thereof.

Embodiment 127 is the kit of any one of embodiments 124-125, further comprising one or more additional bacterial strains in the first, second, third, and/or one or more additional pharmaceutical compositions.

Embodiment 128 is a kit comprising:
n bacterial strains comprising at least a first bacterial strain, a second bacterial strain, and an nth bacterial strain;
wherein each of the second bacterial strain to the $n^{th}$ bacterial strain has a previous bacterial strain;
wherein n is at least 3;
wherein each of the n strains comprises a toxin system;
wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain;
wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Embodiment 129 is a kit comprising:
n bacterial strains comprising at least a first bacterial strain, a second bacterial strain, and an nth bacterial strain;
wherein each of the second bacterial strain to the $n^{th}$ bacterial strain has a previous bacterial strain;
wherein n is at least 3;
wherein each of the n strains comprises
a lysis plasmid having a lysis gene under the control of an activatable promoter; and
an activator plasmid having an activator gene, the expression of which promotes the accumulation of a quorum sensing molecule,
wherein both the activatable promoter of the lysis gene and the expression of the activator gene is activated by the quorum sensing molecule,
wherein the lysis plasmid of each of then bacterial strains comprises a toxin system;
wherein the toxin system of the lysis plasmid of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain;
wherein the toxin system of the lysis plasmid of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Embodiment 130 is the kit of embodiment 128 or embodiment 129, where n is 3.

Embodiment 131 is the kit of embodiment 128 or embodiment 129, wherein n is 4, 5, 6, 7, 8, 9, or 10.

Embodiment 132 is a drug delivery system comprising the system of embodiments 114-123 or kit of embodiments 124-131.

Embodiment 133 is a periodic drug delivery system comprising the system of embodiments 114-123 or kit of embodiments 124-131.

Embodiment 134 is a method for treating a disease in a subject in need thereof, comprising:
administering to the subject a therapeutically effective amount of each of
a first bacterial strain comprising a first lysis plasmid and a first activator plasmid; wherein the first lysis plasmid comprises a first lysis gene, a first activatable promoter, and optionally a first reporter gene; and the first activator plasmid comprises a first activator gene, optionally a first degradation tag, and optionally a first reporter gene; wherein the first bacterial strain further comprises a first toxin system; wherein the first toxin system produces a first toxin/first antitoxin pair and a third antitoxin from a third toxin/third antitoxin pair wherein the first bacterial strain does not produce the third toxin;

a second bacterial strain comprising a second lysis plasmid and a second activator plasmid; wherein the second lysis plasmid comprises a second lysis gene, a second activatable promoter, and optionally a second reporter gene; and the second activator plasmid comprises a second activator gene, optionally a second degradation tag, and optionally a second reporter gene; wherein the second bacterial strain further comprises a second toxin system; wherein the second toxin system produces a second toxin/second antitoxin pair and the first antitoxin from the first toxin/first antitoxin pair wherein the second bacterial strain does not produce the first toxin; and a third bacterial strain comprising a third lysis plasmid and a third activator plasmid; wherein the third lysis plasmid comprises a third lysis gene, a third activatable promoter, and optionally a third reporter gene; and the third activator plasmid comprises a third activator gene, optionally a third degradation tag, and optionally a third reporter gene; wherein the third bacterial strain further comprises a third toxin system; wherein the third toxin system produces a third toxin/third antitoxin pair and a second antitoxin from a second toxin/second antitoxin pair wherein the third bacterial strain does not produce the second toxin.

Embodiment 135 is a method for treating a disease in a subject in need thereof, comprising:

administering to the subject a therapeutically effective amount of each of a first pharmaceutical comprising a first bacterial strain comprising a first lysis plasmid and a first activator plasmid; wherein the first lysis plasmid comprises a first lysis gene, a first activatable promoter, and optionally a first reporter gene; and the first activator plasmid comprises a first activator gene, optionally a first degradation tag, and optionally a first reporter gene; wherein the first bacterial strain further comprises a first toxin system; wherein the first toxin system produces a first toxin/first antitoxin pair and a third antitoxin from a third toxin/third antitoxin pair wherein the first bacterial strain does not produce the third toxin;

a second pharmaceutical comprising a second bacterial strain comprising a second lysis plasmid and a second activator plasmid; wherein the second lysis plasmid comprises a second lysis gene, optionally a second activatable promoter, and optionally a second reporter gene; and the second activator plasmid comprises a second activator gene, a second degradation tag, and optionally a second reporter gene; wherein the second bacterial strain further comprises a second toxin system; wherein the second toxin system produces a second toxin/second antitoxin pair and the first antitoxin from the first toxin/first antitoxin pair wherein the second bacterial strain does not produce the first toxin; and a third pharmaceutical comprising a third bacterial strain comprising a third lysis plasmid and a third activator plasmid; wherein the third lysis plasmid comprises a third lysis gene, a third activatable promoter, and optionally a third reporter gene; and the third activator plasmid comprises a third activator gene, optionally a third degradation tag, and optionally a third reporter gene; wherein the third bacterial strain further comprises a third toxin system; wherein the third toxin system produces a third toxin/third antitoxin pair and a second antitoxin from a second toxin/second antitoxin pair wherein the third bacterial strain does not produce the second toxin.

Embodiment 136 is a method for treating a disease in a subject in need thereof, comprising:

administering to the subject a therapeutically effective amount of each of a first bacterial strain comprising a first toxin system; wherein the first toxin system produces a first toxin/first antitoxin pair and a third antitoxin from a third toxin/third antitoxin pair wherein the first bacterial strain does not produce the third toxin, wherein the first bacterial strain optionally further comprises a first lysis plasmid and a first activator plasmid; wherein the first lysis plasmid comprises a first lysis gene, a first activatable promoter, and optionally a first reporter gene; and the first activator plasmid comprises a first activator gene, optionally a first degradation tag, and optionally a first reporter gene;

a second bacterial strain comprising a second toxin system; wherein the second toxin system produces a second toxin/second antitoxin pair and the first antitoxin from the first toxin/first antitoxin pair wherein the second bacterial strain does not produce the first toxin, wherein the second bacterial strain optionally further comprises a second lysis plasmid and a second activator plasmid; wherein the second lysis plasmid comprises a second lysis gene, a second activatable promoter, and optionally a second reporter gene; and the second activator plasmid comprises a second activator gene, optionally a second degradation tag, and optionally a second reporter gene; and a third bacterial strain comprising a third toxin system produces a third toxin/third antitoxin pair and a second antitoxin from a second toxin/second antitoxin pair wherein the third bacterial strain does not produce the second toxin, wherein the third bacterial strain optionally further comprises a third lysis plasmid and a third activator plasmid; wherein the third lysis plasmid comprises a third lysis gene, a third activatable promoter, and optionally a third reporter gene; and the third activator plasmid comprises a third activator gene, optionally a third degradation tag, and optionally a third reporter gene.

Embodiment 137 is a method for treating a disease in a subject in need thereof, comprising:

administering to the subject a therapeutically effective amount of each of a first pharmaceutical composition comprising a first bacterial strain comprising a first toxin system; wherein the first toxin system produces a first toxin/first antitoxin pair and a third antitoxin from a third toxin/third antitoxin pair wherein the first bacterial strain does not produce the third toxin, wherein the first bacterial strain optionally further comprises a first lysis plasmid and a first activator plasmid; wherein the first lysis plasmid comprises a first lysis gene, a first activatable promoter, and optionally a first reporter gene; and the first activator plasmid comprises a first activator gene, optionally a first degradation tag, and optionally a first reporter gene;

a second pharmaceutical composition comprising second bacterial strain comprising a second toxin system; wherein the second toxin system produces a second toxin/second antitoxin pair and the first antitoxin from the first toxin/first antitoxin pair wherein the second bacterial strain does not produce the first toxin, wherein the second bacterial strain optionally further comprises a second lysis plasmid and a second activator plasmid; wherein the second lysis plasmid comprises a second lysis gene, a second activatable promoter, and optionally a second reporter gene; and the second activator plasmid comprises a second activator gene, optionally a second degradation tag, and optionally a second reporter gene; and a third pharmaceutical composition comprising a third bacterial strain comprising a third toxin system produces a third toxin/third antitoxin pair and a second antitoxin from a second toxin/second antitoxin pair wherein the third bacterial strain does not produce the second toxin, wherein the third bacterial strain optionally further comprises a third lysis plasmid and a third activator plasmid; wherein the third lysis plasmid comprises a third lysis gene, a third activatable promoter, and optionally a third reporter gene; and the third activator plasmid comprises a third activator gene, optionally a third degradation tag, and optionally a third reporter gene.

Embodiment 138 is the method of any one of embodiments 134-137, wherein administering comprises administering sequentially each of the first, second, and third bacterial strains or first second and third pharmaceutical compositions to the subject.

Embodiment 139 is the method of embodiment 138, wherein administering comprises administering each of the first, second, and third pharmaceutical compositions simultaneously and wherein each of the first, second, and third pharmaceutical compositions has a different release profile for releasing the first second and third bacterial strains.

Embodiment 140 is the method of any one of embodiments 134-139, wherein each of the first, second, and third bacterial strains expresses a different therapeutic agent.

Embodiment 141 is a method for treating a disease in a subject in need thereof, comprising:
administering to the subject a therapeutically effective amount of each of n bacterial strains comprising at least a first bacterial strain, a second bacterial strain, and an nth bacterial strain;
wherein each of the second bacterial strain to the $n^{th}$ bacterial strain has a previous bacterial strain;
wherein n is at least 3;
wherein each of the n strains comprises a toxin system;
wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain;
wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Embodiment 142 is a method for treating a disease in a subject in need thereof, comprising:
administering to the subject a therapeutically effective amount of each of n bacterial strains comprising at least a first bacterial strain, a second bacterial strain, and an nth bacterial strain;
wherein each of the second bacterial strain to the $n^{th}$ bacterial strain has a previous bacterial strain;
wherein n is at least 3;
wherein each of the n strains comprises
a lysis plasmid having a lysis gene under the control of an activatable promoter; and
an activator plasmid having an activator gene, the expression of which promotes the accumulation of a quorum sensing molecule,
wherein both the activatable promoter of the lysis gene and the expression of the activator gene is activated by the quorum sensing molecule,
wherein the lysis plasmid of each of then bacterial strains comprises a toxin system;
wherein the toxin system of the lysis plasmid of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain;
wherein the toxin system of the lysis plasmid of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Embodiment 143 is the method of embodiment 141 or embodiment 142, where n is 3.

Embodiment 144 is the method of embodiment 141 or embodiment 142, wherein n is 4, 5, 6, 7, 8, 9, or 10.

Embodiment 145 is a method for treating a disease in a subject in need thereof, comprising:
administering to the subject a therapeutically effective amount of each of m pharmaceutical compositions, each comprising at least one of n bacterial strains, wherein the n bacterial strains comprise at least a first bacterial strain, a second bacterial strain, and an nth bacterial strain;
wherein each of the second bacterial strain to the $n^{th}$ bacterial strain has a previous bacterial strain;
wherein n is at least 3;
wherein each of the n strains comprises a toxin system;
wherein the toxin system of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain;
wherein the toxin system of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Embodiment 146 is a method for treating a disease in a subject in need thereof, comprising:
administering to the subject a therapeutically effective amount of each of m pharmaceutical compositions, each comprising at least one of n bacterial strains, wherein the n bacterial strains comprise at least a first bacterial strain, a second bacterial strain, and an nth bacterial strain;
wherein each of the second bacterial strain to the $n^{th}$ bacterial strain has a previous bacterial strain;

wherein n is at least 3;
wherein each of the n strains comprises
  a lysis plasmid having a lysis gene under the control of an activatable promoter; and
  an activator plasmid having an activator gene, the expression of which promotes the accumulation of a quorum sensing molecule,
wherein both the activatable promoter of the lysis gene and the expression of the activator gene is activated by the quorum sensing molecule,
wherein the lysis plasmid of each of then bacterial strains comprises a toxin system;
wherein the toxin system of the lysis plasmid of each of the second through $n^{th}$ bacterial strain independently produces a first toxin/first antitoxin pair, wherein the first toxin is effective against the previous bacterial strain, and a second antitoxin from a second toxin/second antitoxin pair produced by the previous bacterial strain;
wherein the toxin system of the lysis plasmid of the first bacterial strain produces a third toxin/third antitoxin pair, wherein the third toxin is effective against the nth bacterial strain, and a fourth antitoxin from a fourth toxin/antitoxin pair produced by the $n^{th}$ bacterial strain.

Embodiment 147 is the method of embodiment 145 or embodiment 146, where n is 3.

Embodiment 148 is the method of embodiment 145 or embodiment 146, wherein n is 4, 5, 6, 7, 8, 9, or 10.

Embodiment 149 is the method of any one of embodiments 145-146, wherein m=n.

Embodiment 150 is the method of any one of embodiments 141-149, wherein each of the toxin systems are independently encoded in the genome, on a plasmid, on multiple plasmids, or a combination thereof.

Embodiment 151 is the method of any one of embodiments 141-150, wherein each of the second bacterial strain through the nth bacterial strain does not produce the second toxin of the toxin system of the previous strain, and the first bacterial strain does not produce the fourth toxin of the toxin system of the nth bacterial strain.

Embodiment 152 is the method of any one of embodiments 145-151, wherein administering comprises administering sequentially each of the n bacterial strains or m pharmaceutical compositions to the subject.

Embodiment 153 is the method of embodiment 152, wherein administering comprises administering each of the m pharmaceutical compositions simultaneously and wherein each of the m pharmaceutical compositions has a different release profile for releasing the first second and third bacterial strains.

Embodiment 154 is the method of any one of embodiments 141-153, wherein each of the first, second, and third bacterial strains expresses a different therapeutic agent.

Embodiment 155 is the method of any one of embodiments 141-154, wherein the disease is cancer or an infection.

Embodiment 156 is the method of embodiment 155, wherein the infection is caused by an infectious agent selected from the group consisting of: *Camphylobacter jejuni, Clostridium botulinium, Escherichia coli, Listeria monocytogenes* and *Salmonella*.

Embodiment 157 is the method of embodiment 155, wherein the cancer is selected from the group consisting of: glioblastoma, squamous cell carcinoma, breast cancer, colon cancer, hepatocellular cancer, melanoma, neuroblastoma, pancreatic cancer, and prostate cancer.

Embodiment 158 is the method of any one of embodiments 1-83 or 134-157, the bacterial strain of any one of embodiments 84-111, the pharmaceutical compositions of any one of embodiments 112-113, the systems of any one of embodiments 114-123, 132, or 133, or the kits of any one of embodiments 124-131, wherein one or more of the bacterial strains expresses a therapeutic agent.

Embodiment 159 is the method of any one of embodiments 1-83 or 134-157, the bacterial strain of any one of embodiments 84-111, the pharmaceutical compositions of any one of embodiments 112-113, the systems of any one of embodiments 114-123, 132, or 133, or the kits of any one of embodiments 124-131, wherein one or more of the bacterial strains expresses a therapeutic agent selected from the group consisting of: an inhibitory nucleic acid, a cytokine, an enzyme, a peptide hormone, a fusion protein, a clotting factor, a toxin, an antimicrobial peptide, and an antibody or antigen-binding fragment thereof.

Embodiment 160 is a method comprising:
  culturing a first bacterial strain for a first period of time in a growth environment;
  adding a second bacterial strain to the growth environment and culturing the second bacterial strain for a second period of time;
  adding a third bacterial strain to the growth environment and culturing the third bacterial strain for a second period of time,
  wherein each of the first, second, and third bacterial strains comprises a toxin system;
  wherein the toxin system of the first bacterial strain produces a first toxin/first antitoxin pair and a third antitoxin from a third toxin/third antitoxin pair wherein the first bacterial strain does not produce the third toxin;
  wherein the toxin system of the second bacterial strain produces a second toxin/second antitoxin pair and the first antitoxin from the first toxin/first antitoxin pair wherein the second bacterial strain does not produce the first toxin; and
  wherein the toxin system of the third bacterial strain produces a third toxin/third antitoxin pair and the second antitoxin from the second toxin/second antitoxin pair wherein the third bacterial strain does not produce the second toxin,
  wherein the toxin system is encoded on a plasmid, multiple plasmids, integrated into the host genome, or a combination thereof.

Embodiment 161 is the method of embodiment 160, wherein each of the first, second, and third bacterial strains comprises:
  a lysis plasmid having a lysis gene under the control of an activatable promoter; and
  an activator plasmid having an activator gene, the expression of which promotes the accumulation of a quorum sensing molecule,
  wherein both the activatable promoter of the lysis gene and the expression of the activator gene is activated by the quorum sensing molecule,
  wherein the quorum sensing molecule may or may not be different in each of the first, second, and third bacterial strains;
  wherein each quorum-sensing molecule of each of the first, second, and third bacterial strains may or may not have any effect on the activatable promoter of the lysis gene of another strain.

Embodiment 162 is the method of embodiment 161, wherein each of the lysis plasmids of the first, second, and third bacterial strains is the plasmid containing the toxin system for such bacterial strain, or wherein each of the activator plasmids of the first, second, and third bacterial strains is the plasmid containing the toxin system for such bacterial strain, or wherein the toxin system for each bacterial strain is integrated into the genome.

Embodiment 163 is a method of culturing n bacterial strains comprising:
  culturing a first bacterial strain of n bacterial strains for a first period of time in a culture;
  adding a second bacterial strain of the n bacterial strains to the culture and culturing the second bacterial strain for a second period of time;
  adding each of the other of the n bacterial strains to the culture and culturing each such bacterial strain for a period of time,
  wherein n is three or a greater whole number and
  wherein a plasmid of each of the n bacterial strains comprises a toxin system;
  wherein the toxin system of the plasmid of the first bacterial strain produces a first toxin/first antitoxin pair and a nth antitoxin from an nth toxin/nth antitoxin pair wherein the first bacterial strain does not produce the nth toxin;
  wherein the toxin system of the plasmid of each mth, where m is an element of the set $\{2, 3, \ldots, n\}$, of the other bacterial strains in the n bacterial strains produces a mth toxin/mth antitoxin pair and the (m−1)th antitoxin from the (m−1)th toxin/(m−1)th antitoxin pair.

Embodiment 164 is the method of embodiment 163, wherein each of the n bacterial strains comprises:
  a lysis plasmid having a lysis gene under the control of an activatable promoter; and
  an activator plasmid having an activator gene, the expression of which promotes the accumulation of a quorum sensing molecule,
  wherein both the activatable promoter of the lysis gene and the expression of the activator gene is activated by the quorum sensing molecule,
  wherein the quorum sensing molecule may or may not be different in each of the n bacterial strains;
  wherein each quorum-sensing molecule of each of the n bacterial strains may or may not have an effect on the activatable promoter of the lysis gene of another strain of the n bacterial strains.

Embodiment 165 is the method of embodiment 164, wherein each of the lysis plasmids of the n strains is the plasmid containing the toxin system for such bacterial strain.

Embodiment 166 is the method of any one of embodiments 163-164, wherein each of the n bacterial strains produces a payload.

Embodiment 167 is the method of any one of embodiments 163-165, wherein each of the n bacterial strains produces a different payload.

Embodiment 168 is the method of any one of embodiments 163-165, wherein each of the n bacterial strains produces the same payload.

Embodiment 169 is the method of any one of embodiments 166-168, wherein each payload is a therapeutic.

Embodiment 170 is the method of embodiment 167, wherein the payload of the mth bacterial strain produces an mth substrate by directly or indirectly acting upon the substrate of the (m−1)th bacterial strain, and wherein the payload of the first bacterial strain acts upon a substrate present in the environment where the n bacterial strains are cultured.

Embodiment 171 is the method of any one of embodiments 163-170, wherein n is four.

Embodiment 172 is the method of any one of embodiments 163-170, wherein n is five.

Embodiment 173 is the method of any one of embodiments 163-170, wherein n is six.

Embodiment 174 is the method of any one of embodiments 160-162, further comprising culturing or co-culturing one or more additional bacterial strains in the culture.

Embodiment 175 is the method of embodiment 174, wherein each of the one or more additional bacterial strains comprise:
  a lysis plasmid having a lysis gene under the control of an activatable promoter; and
  an activator plasmid having an activator gene, the expression of which promotes the accumulation of a quorum sensing molecule,
  wherein both the activatable promoter of the lysis gene and the expression of the activator
  gene is activated by the quorum sensing molecule,
  wherein the quorum sensing molecule is different in each of the first, second, third, and
  one or more additional bacterial strains;
  wherein each quorum-sensing molecule of each of the first, second, third, and one or more additional bacterial strains has no or substantially no effect on the activatable promoter of
  the lysis gene of another bacterial strain used in the culture.

Embodiment 176 is the method of embodiment 175, wherein the lysis plasmid of each of the one or more additional bacterial strains comprises a toxin system.

Embodiment 177 is the method of any one of embodiments 160-162 or 174-176, wherein the lysis plasmid and activator plasmid of each of the at least first, second, and third bacterial strains is the same plasmid.

Embodiment 178 is the method of any one of embodiments 160-162 or 174-176, wherein the lysis plasmid and activator plasmid of each of the at least the first, second, and third bacterial strains are separate plasmids.

Embodiment 179 is the method of any one of embodiments 160-162 or 174-178, wherein at least the first, second, and third bacterial strains are metabolically competitive.

Embodiment 180 is the method of any one of embodiments 160-162 or 174-179, wherein at least the first, second, and third bacterial strains are selected from *E. coli*, *S. typhimurium*, or a bacterial variant thereof.

Embodiment 181 is the method of any one of embodiments 160-162 or 174-180, wherein each of the at least the first, second, and third bacterial strains does not have a growth advantage compared to another strain in the culture.

Embodiment 182 is the method of any one of embodiments 160-162 or 174-181, wherein in each of the at least the first, second, and third bacterial strains the lysis plasmid comprises a lysis gene, an activatable promoter, and optionally a reporter gene; and the activator plasmid comprises an activator gene, a degradation tag, and optionally a reporter gene.

Embodiment 183 is the method of any one of embodiments 160-162 or 174-182, wherein the lysis gene in each of the at least the first, second, and third bacterial strains is E from a bacteriophage ΦX174.

Embodiment 184 is the method of any one of embodiments 160-162 or 174-183, wherein the activatable promoter in each of the at least the first, second, and third bacterial strains is a LuxR-AHL activatable luxI promoter and the activator gene is a LuxI.

Embodiment 185 is the method of embodiment 182, wherein at least one reporter gene is selected from a gene encoding a green fluorescent protein (GFP), cyan fluorescent protein (CFP), red fluorescent protein (RFP), or a variant thereof.

Embodiment 186 is the method of embodiment 182, wherein the degradation tag is an ssrA-LAA degradation tag.

Embodiment 187 is the method of any one of embodiments 160-162 or 174-186, wherein at least one of the plasmids is integrated into a genome of at least one of the first, second, and third bacterial strains.

Embodiment 188 is the method of any one of embodiments 160-162 or 174-187, wherein the culturing occurs in a designated growth environment.

Embodiment 189 is the method of any one of embodiments 160-162 or 174-188, wherein the culturing occurs in a microfluidic device.

Embodiment 190 is the method of any one of embodiments 160-162 or 174-188, wherein the culturing occurs in a bio reactor.

Embodiment 191 is the method of any one of embodiments 160-162 or 174-188, wherein the culturing occurs in in vivo.

Embodiment 192 is the method of any one of embodiments 160-191, wherein each of the bacterial strains produce therapeutic payloads and the culturing occurs in a human or animal patient in need of the therapeutic payloads.

Embodiment 193 is the method of any one of embodiments 160-162 or 174-191, wherein each of the first, second, and third periods of time ranges from about 12 to about 72 hours.

Embodiment 194 is the method of any one of embodiments 160-162, 174-191, or 193, wherein each of the first, second, and third periods of time ranges from about 1 hours to about n hours.

Embodiment 195 is the method of any one of embodiments 160-162, 174-191, or 193, wherein each of the first, second, and third periods of time is selected from at least 24 hours, at least 48 hours, at least 72 hours, and at least 96 hours.

Embodiment 196 is the method of any one of embodiments 163-173, wherein each of the n periods of time partially or completely overlap.

Embodiment 197 is the method of any one of embodiments 163-173 or 196, wherein the n bacterial strains are cultured together.

Embodiment 198 is the method of any one of embodiments 163-173, 196, or 197, wherein each of the n bacterial strains are added to the culture sequentially such that each mth bacterial strain is added to the culture after the passage of the (m−1)th period of time.

Embodiment 199 is the method of any one of embodiments 160-162, 174-191, or 193-195, wherein each of the first, second, and third periods of time is selected from 12 hours, 24 hours, 48 hours, 72 hours, and 96 hours.

Embodiment 200 is a method of maintaining a co-culture, the method comprising:
  co-culturing at least three bacterial strains;
  wherein each of the at least three bacterial strains comprises a lysis plasmid having a lysis gene under the control of an activatable promoter; and
  an activator plasmid having an activator gene, the expression of which promotes the accumulation of a quorum sensing molecule,
  wherein both the activatable promoter of the lysis gene and the expression of the activator gene is activated by the quorum sensing molecule,
  wherein the quorum sensing molecule is different in each of the at least three bacterial strains;
  wherein each quorum-sensing molecule of each of the at least three bacterial strains has no or substantially no effect on the activatable promoter of the lysis gene of another strain;
  wherein the lysis plasmid comprises a toxin/antitoxin system.

Embodiment 201 is the method of embodiment 200, wherein the toxin/antitoxin system produces a toxin/antitoxin pair and a different antitoxin of another strain.

Embodiment 202 is the method of embodiment 200 or 201, wherein the lysis plasmid and activator plasmid of each of the at least three bacterial strains is the same plasmid.

Embodiment 203 is the method of any one of embodiments 200-202, wherein the lysis plasmid and activator plasmid of each of the at least three bacterial strains are separate plasmids.

Embodiment 204 is the method of any one of embodiments 200-203, wherein the at least the three strains are metabolically competitive.

Embodiment 205 is the method of any one of embodiments 200-204, wherein the at least three strains are selected from E. coli, S. typhimurium, or a bacterial variant thereof.

Embodiment 206 is the method of any one of embodiments 200-205, wherein each of the at least three strains does not have a growth advantage compared to another strain.

Embodiment 207 is the method of any one of embodiments 200-206, wherein in each of the at least three strains the lysis plasmid comprises a lysis gene, an activatable promoter, and optionally a reporter gene; and the activator plasmid comprises an activator gene, optionally a degradation tag, and optionally a reporter gene.

Embodiment 208 is the method of any one of embodiments 200-207, wherein the lysis gene in the at least three strains is E from a bacteriophage ΦX174.

Embodiment 209 is the method of any one of embodiments 200-208, wherein the activatable promoter is a LuxR-AHL activatable luxI promoter and the activator gene is a LuxI.

Embodiment 210 is the method of embodiment 207, wherein at least one reporter gene is selected from a gene encoding a green fluorescent protein (GFP), cyan fluorescent protein (CFP), red fluorescent protein (RFP), or a variant thereof.

Embodiment 211 is the method of embodiment 207, wherein the degradation tag is an ssrA-LAA degradation tag.

Embodiment 212 is the method of any one of embodiments 200-211, wherein the co-culture is inoculated at a ratio of 1:1:1 of each of the at least three bacterial strains.

Embodiment 213 is the method of any one of embodiments 200-212, wherein at least one of the plasmids is integrated into a genome of at least one of the at least three strains.

Embodiment 214 is the method of any one of embodiments 200-213, wherein the culturing occurs in a microfluidic device.

Embodiment 215 is the method of any one of embodiments 200-214, wherein the period of time is 12 to 72 hours.

Embodiment 216 is the method of any one of embodiments 200-214, wherein the period of time is selected from at least 24 hours, at least 48 hours, at least 72 hours, and at least 96 hours.

Embodiment 217 is the method of any one of embodiments 200-214, wherein the period of time is selected from 12 hours, 24 hours, 48 hours, 72 hours, and 96 hours.

Embodiment 218 is the method of any one of embodiments 200-217, wherein the co-culturing of the at least three strains is in a constant lysis state; wherein the constant lysis state is characterized by a steady-state balance of growth and lysis of the at least three bacterial strains.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of maintaining a bacterial co-culture, the method comprising:
   culturing a first bacterial strain for a first period of time in a growth environment;
   adding a second bacterial strain to the growth environment and culturing the second bacterial strain for a second period of time;
   adding a third bacterial strain to the growth environment and culturing the third bacterial strain for a third period of time,
   wherein each of the first, second, and third bacterial strains comprises a toxin system;
   wherein the toxin system of the first bacterial strain produces a first toxin/first antitoxin pair and a third antitoxin from a third toxin/third antitoxin pair wherein the first bacterial strain does not produce the third toxin;
   wherein the toxin system of the second bacterial strain produces a second toxin/second antitoxin pair and the first antitoxin from the first toxin/first antitoxin pair wherein the second bacterial strain does not produce the first toxin; and
   wherein the toxin system of the third bacterial strain produces a third toxin/third antitoxin pair and the second antitoxin from the second toxin/second antitoxin pair wherein the third bacterial strain does not produce the second toxin, and
   wherein each of the first, second, and third bacterial strains comprises
      a lysis plasmid having a lysis gene under the control of an activatable promoter; and
      an activator plasmid having an activator gene, the expression of which promotes the accumulation of a quorum-sensing molecule,
   wherein both the activatable promoter of the lysis gene and the expression of the activator gene is activated by the quorum-sensing molecule.

2. The method of claim 1, wherein the quorum-sensing molecule is the same in each of the first, second, and third bacterial strains.

3. The method of claim 1, wherein the toxin system of the first bacterial strain, the second bacterial strain, and the third bacterial strain is independently encoded in a genome of at least one of the first, second, and third bacterial strains, on a plasmid integrated into the genome of at least one of the first, second, and third bacterial strains, on multiple plasmids integrated into the genome of at least one of the first, second, and third bacterial strains, or a combination thereof.

4. The method claim 1, wherein in each of the at least the first, second, and third bacterial strains the lysis plasmid comprises a lysis gene, an activatable promoter, and a reporter gene; and the activator plasmid comprises an activator gene, a degradation tag, and a reporter gene.

5. The method claim 1, wherein the lysis gene in each of the at least the first, second, and third bacterial strains is E from a bacteriophage ΦX174.

6. The method claim 1, wherein the activatable promoter in each of the at least the first, second, and third bacterial strains is a LuxR-AHL activatable luxI promoter and the activator gene is a LuxI.

7. The method of claim 1, wherein one or more of the first, second, and third bacterial strains encodes a heterologous nucleic acid and/or a heterologous protein operably linked to a promoter.

8. The method of claim 7, wherein the heterologous nucleic acid and/or heterologous protein is a therapeutic agent.

9. The method of claim 8, wherein the therapeutic agent is selected from the group consisting of: an inhibitory nucleic acid, a cytokine, an enzyme, a peptide hormone, a fusion protein, a clotting factor, a toxin, an antimicrobial peptide, and an antibody or antigen-binding fragment thereof.

10. A method of maintaining a bacterial co-culture, the method comprising:
    providing n bacterial strains comprising at least a first bacterial strain, a second bacterial strain, and an $n^{th}$ bacterial strain that are distinct from each other;
    co-culturing each of the bacterial strains sequentially for one or more independent periods of time in a growth environment;
    wherein n is at least 3;
    wherein each of the n bacterial strains comprises a toxin system;
    wherein the toxin system of the first bacterial strain produces a first toxin/first antitoxin pair and an $n^{th}$ antitoxin from an $n^{th}$ toxin/$n^{th}$ antitoxin pair, wherein the first toxin is effective against the $n^{th}$ bacterial strain;
    wherein the toxin system of the second bacterial strain produces a second toxin/second antitoxin pair and the first antitoxin from the first toxin/first antitoxin pair, wherein the second toxin is effective against the first bacterial strain; and
    wherein the toxin system of the first bacterial strain produces an $n^{th}$ toxin/$n^{th}$ antitoxin pair and an $n-1^{th}$ antitoxin from an $n-1^{th}$ toxin/$n-1^{th}$ antitoxin pair, wherein the $n^{th}$ toxin is effective against the $n-1^{th}$ bacterial strain.

11. The method of claim 10, wherein the toxin system of the n bacterial strains is independently encoded in a genome of at least one of the first, second, and $n^{th}$ bacterial strains, on a plasmid integrated into the genome of at least one of the first, second, and $n^{th}$ bacterial strains, on multiple plasmids integrated into the genome of at least one of the first, second, and $n^{th}$ bacterial strains, or a combination thereof.

12. The method claim 10, wherein one or more of the periods of time partially or completely overlap.

13. The method claim 10, wherein one or more of the n bacterial strains encodes a heterologous nucleic acid and/or a heterologous protein operably linked to a promoter.

14. The method of claim 13, wherein the heterologous nucleic acid and/or heterologous protein is a therapeutic agent.

15. The method of claim 14, wherein the therapeutic agent is selected from the group consisting of: an inhibitory nucleic acid, a cytokine, an enzyme, a peptide hormone, a fusion protein, a clotting factor, a toxin, an antimicrobial peptide, and an antibody or antigen-binding fragment thereof.

16. The method claim 10, wherein each of the second bacterial strain through the nth bacterial strain does not produce the second toxin of the toxin system of the $n-1^{th}$ strain, and the first bacterial strain does not produce the $n^{th}$ toxin of the toxin system of the $n^{th}$ bacterial strain.

* * * * *

UNITED STATES PATENT AND TRADEMARK OFFICE
CERTIFICATE OF CORRECTION

PATENT NO. : 11,896,626 B2
APPLICATION NO. : 16/972405
DATED : February 13, 2024
INVENTOR(S) : Jeff Hasty, Michael Julius Liao and Muhammad Omar Din It is certified that error appears in the above-identified patent and that said Letters Patent is hereby corrected as shown below:

On the Title Page

Column 2 Item (56) (Other Publications), Line 12, Delete "4839" and insert -- 483 --.

In the Specification

Column 1, Line 7, Delete "071" and insert -- § 371 --.

In the Claims

Column 87, Line 50, in Claim 4, after "method" insert -- of --.

Column 87, Line 55, in Claim 5, after "method" insert -- of --.

Column 87, Line 58, in Claim 6, after "method" insert -- of --.

Column 87, Line 62, in Claim 7, after "method" insert -- of --.

Column 88, Line 45, in Claim 12, after "method" insert -- of --.

Column 88, Line 47, in Claim 13, after "method" insert -- of --.

Column 88, Line 59, in Claim 16, after "method" insert -- of --.

Signed and Sealed this
Twenty-sixth Day of March, 2024

Katherine Kelly Vidal
*Director of the United States Patent and Trademark Office*